United States Patent [19]

Bigge et al.

[11] Patent Number: 6,124,323
[45] Date of Patent: Sep. 26, 2000

[54] 4-SUBSTITUTED PIPERIDINE ANALOGS AND THEIR USE AS SUBTYPE SELECTIVE NMDA RECEPTOR ANTAGONISTS

[75] Inventors: Christopher F. Bigge; Po-Wai Yuen, both of Ann Arbor, Mich.; Sui Xiong Cai, Foothill, Calif.; Eckard Weber, Laguna Beach, Calif.; Richard Woodward, Aliso Viejo, Calif.; Nancy C. Lan, South Pasadena, Calif.; Zhang-Lin Zhou, Irvine, Calif.; John F. W. Keana; Anthony P. Guzikowski, both of Eugene, Oreg.

[73] Assignees: Warner-Lambert Company, Morris Plains, N.J.; Cocensys, Incorporated, Irvine, Calif.

[21] Appl. No.: 09/091,598

[22] PCT Filed: Dec. 20, 1996

[86] PCT No.: PCT/US96/20872

§ 371 Date: Sep. 16, 1998

§ 102(e) Date: Sep. 16, 1998

[87] PCT Pub. No.: WO97/23216

PCT Pub. Date: Jul. 3, 1997

Related U.S. Application Data

[60] Provisional application No. 60/009,184, Dec. 22, 1995.
[51] Int. Cl.[7] .......................... A01N 43/40; C07D 211/26; C07D 211/60; C07D 211/18; C07D 211/20
[52] U.S. Cl. .......................... 514/327; 546/229; 546/230; 546/232; 546/237; 546/236; 546/240; 514/327; 514/331
[58] Field of Search .................................. 546/236, 240, 546/237, 232, 217, 229, 230; 514/327, 331

[56] References Cited

U.S. PATENT DOCUMENTS

| | | | |
|---|---|---|---|
| 3,225,052 | 12/1965 | Janssen | 260/293.4 |
| 3,255,196 | 6/1966 | Debarre et al. | |
| 3,311,624 | 3/1967 | Ohnacker et al. | |
| 3,632,767 | 1/1972 | Gray et al. | 424/267 |
| 3,686,187 | 8/1972 | Cole et al. | |
| 4,482,560 | 11/1984 | Banno et al. | 424/258 |
| 4,567,186 | 1/1986 | Lesher et al. | 514/300 |
| 4,567,187 | 1/1986 | Banno et al. | 514/312 |
| 4,577,020 | 3/1986 | Gall | 544/366 |
| 4,643,995 | 2/1987 | Engel et al. | 514/210 |
| 4,902,695 | 2/1990 | Ornstein | 514/307 |
| 4,942,169 | 7/1990 | Sagimoto et al. | 514/318 |
| 5,011,834 | 4/1991 | Weber et al. | 514/212 |
| 5,036,077 | 7/1991 | Van Broeck et al. | 514/317 |
| 5,169,855 | 12/1992 | Cain et al. | 514/319 |
| 5,192,751 | 3/1993 | Thor | 514/82 |
| 5,192,799 | 3/1993 | Tomino et al. | 514/469 |
| 5,202,346 | 4/1993 | Butera et al. | 514/326 |
| 5,273,977 | 12/1993 | Glase et al. | 514/277 |
| 5,352,683 | 10/1994 | Mayer et al. | 514/289 |
| 5,364,867 | 11/1994 | DeHaven-Hudkins et al. | 514/326 |
| 5,428,038 | 6/1995 | Chatterjee et al. | 514/253 |
| 5,466,698 | 11/1995 | Glase et al. | 514/318 |
| 5,534,511 | 7/1996 | Mouithys-Mickalad et al. | 514/212 |
| 5,620,988 | 4/1997 | Glase et al. | 514/307 |

FOREIGN PATENT DOCUMENTS

| | | |
|---|---|---|
| 43438/85 | 6/1985 | Australia . |
| 860701 | 5/1978 | Belgium . |
| 696999 | 11/1964 | Canada . |
| 149088 | 7/1985 | European Pat. Off. . |
| 0235463 | 9/1987 | European Pat. Off. . |
| 235463 | 9/1987 | European Pat. Off. . |
| 0308328 | 3/1989 | European Pat. Off. . |
| 337136 | 10/1989 | European Pat. Off. . |
| 0351282 | 1/1990 | European Pat. Off. . |
| 0398578 | 11/1990 | European Pat. Off. . |
| 0481853 | 4/1991 | European Pat. Off. . |
| 0445701 | 9/1991 | European Pat. Off. . |
| 0449186 | 10/1991 | European Pat. Off. . |
| 488959A | 6/1992 | European Pat. Off. . |
| 0524846 | 1/1993 | European Pat. Off. . |
| 572952 | 12/1993 | European Pat. Off. . |
| 0648744 | 4/1995 | European Pat. Off. . |
| 649838 | 4/1995 | European Pat. Off. . |
| 2681319 | 3/1993 | France . |
| 2939292 | 4/1981 | Germany . |
| 3034237 | 4/1981 | Germany . |
| 3703435 | 8/1988 | Germany . |
| 4111861 | 10/1992 | Germany . |
| 4410822 | 9/1995 | Germany . |
| 61-115068 | 6/1986 | Japan . |
| 61-227565 | 10/1986 | Japan . |
| 04217945 | 8/1992 | Japan . |
| 4-312572 | 11/1992 | Japan . |
| 1055548 | 1/1967 | United Kingdom . |
| 2056435 | 3/1981 | United Kingdom . |
| 91/06297 | 5/1971 | WIPO . |
| 88/02365 | 4/1988 | WIPO . |
| 91/17156 | 11/1991 | WIPO . |
| 92/02502 | 2/1992 | WIPO . |
| 92/07831 | 10/1992 | WIPO . |

(List continued on next page.)

OTHER PUBLICATIONS

Chemical Abstracts, vol. 120, No. 19, May 9, 1994, Abstract No. 244970.

(List continued on next page.)

*Primary Examiner*—Alan L. Rotman
*Assistant Examiner*—Rita Desai
*Attorney, Agent, or Firm*—Fitzpatrick, Cella, Harper & Scinto

[57] ABSTRACT

Novel 4-substituted piperidine analogs, pharmaceutical compositions containing the same and the method of using 4-substituted piperidine analogs are selective active antagonists of N-methyl-D-aspartate (NMDA) receptor subtypes for treating conditions such as stroke, cerebral ischemia, central nervous system trauma, hypoglycemia, psychosis, anxiety, migraine headaches, glaucoma, CMV retinitis, aminoglycoside antibiotics-induced hearing loss, convulsions, chronic pain, opioid tolerance or withdrawal, urinary incontinence or neurodegenerative disorders, such as lathyrism, Alzheimer's Disease, Parkinsonism and Huntington's Disease are described.

22 Claims, 1 Drawing Sheet

FOREIGN PATENT DOCUMENTS

| | | |
|---|---|---|
| 92/18127 | 10/1992 | WIPO . |
| 93/00313 | 1/1993 | WIPO . |
| 93/15052 | 2/1993 | WIPO . |
| 93/11107 | 6/1993 | WIPO . |
| 93/02052 | 8/1993 | WIPO . |
| 94/10166 | 5/1994 | WIPO . |
| 94/13275 | 6/1994 | WIPO . |
| 94/18172 | 8/1994 | WIPO . |

OTHER PUBLICATIONS

Chemical Abstracts, vol. 91, No. 21, Nov. 19, 1979, Abstract No. 168329.
J. H. Arundel et al., "Activity of a Series of Piperdines against *Haemonchus contortus* Larvae", Journal of Medicinal Chemistry, vol. 9, No. 4, Jul. 1966, pp. 555–558.
A.F. Casy and H. Birnbaum, "Synthesis and Reactions of Some Azacycloheptan–4–ols", Journal of the Chemical Society, Dec. 1964, pp. 5130–34.
Costall, Brenda et al., "Dopamine Antagonistic Effects of a Series of Analogs of Oxiperomide and Spiroxatrine Measured Behaviourally in the Rodent", J. Pharm. Pharmac., 1978, vol. 30, 693–98.
Saxena, Anil K. et al., "Synthesis and QSAR Studies on Hypotensive N–[3–aryl(thio/sulfono)propyl]–piperazines/piperidines", Indian J. Chem., Sect. B, Dec. 1993, vol. 32B(12), pp. 1249–57.
Moriyoshi, et al. Nature 354, 31–37 (1991).
Kutsuwada et al., Nature 358, 36–41 (1992).
Basile, et al., Nature Medicine, 2, 1338–1343, (1996).
Herman et al., Neuropsychopharmacology 13 269–293 (1995).
Dickenson and Aydar, Neuroscience Lett. 121, 263–266 (1991).
Vera and Nadelhaft, Neuroscience Lett. 134, 135–138 (1991).
S.A. Lipton, P.A. Rosenberg, New Eng. J. Med. 330 (9), 613–622 (1994).
Org. Reactions 6, 151–206 (1951).
Dubuisson and Dennis, Pain 4, 161–174 (1977).
M. Fieser, L.F. Fieser, Reagents for Organic Synthesis 6, 183 (1977).
Kornetsky et al., Science 162, 1011–1012 (1968).
Sansalla et al., Science 243, 398–400 (1989).
Trujillo et al., Science 251, 85–87 (1991).
Monyer et al., Science 256, 1217–1221 (1992).
R.A. Sharma, W. Korytnyk, Tetrahedron Lett. 573–576 (1977).
D.L. Comins, et al., Tetrahedron Lett. 29, 773–776 (1988).
D.L. Comins, et al., Tetrahedron Lett. 32, 5697–5700 (1991).
S. Lipton, TINS 16(12), 527–532 (1993).
Carlsson et al., Trends Neurosci. 13, 272–276 (1990).
Tepley et al., *Biomagnetism,* eds. S. Williamson, L. Kaufmann, pp. 327–330, Plenum Press, New York (1990).
S.A. Glase et al., J. Med. Chem. 39, 3179–3187 (1996).
B.L. Chenard et al., J. Med. Chem. 34, 3085–3090 (1991).
M. Lauritzen, Acta. Neurol. Scand. 76 (Suppl. 113), 4–40 (1987).
De Lean et al., Am. J. Physiol. 235, E97–102 (1978).
W.U. Schmidt, et al., Amino Acids 1, 225–237 (1991).
T. Klockgether, L. Turski, Ann. Neurol. 34, 585–593 (1993).
Annu. Rev. Neurosci. 17, 31–108 (1994).
R.W. Gifford, et al., Arch. Intern. Med. 153, 154–183, (1993).
Harper and Powers, Biochemistry 24, 7200–7213 (1985).
Sugihara et al., Biochem. Biophys Res. Commun. 185, 826–832 (1992).
C.F. Bigge, Biochem. Pharmacol. 45, 1547–1561 (1993).
M. Lauritzen et al., Brian Res. 475, 317–327 (1988).
J.E. Haley, et al., Brain Res. 518, 218–226 (1990).
Shaw et al., Brain Research 539, 164–168 (1991).
Marek et al., Brain Res. 547, 77–81 (1991).
Lutfy et al., Brain Res. 616, 83–88 (1993).
P.H. Hutson, et al., Br. J. Pharmacol. 103, 2037–2044 (1991).
L.J. Bristow, et al., Br. J. Pharmacol. 108, 1156–1163 (1993).
Chemical Abstracts, vol. 94, No. 15, 94:121260j.
Chemical Abstracts, vol. 115, No. 23, 115:247459b.
D. Lonsdale, Dev. Pharmacol. Ther. 4, 28–36 (1982).
B.V. Clineschmidt et al., Drug. Dev. Res. 2, 147–163 (1982).
Rojas et al. Drug Dev. Res. 29, 222–226 (1993).
J.H. Kehne et al., Eur. J. Pharmacol. 193, 283–292 (1991).
J. Winslow et al., Eur. J. Pharmacol. 190, 11–21 (1990).
R. Dunn et al., Eur. J. Pharmacol. 214, 207–214 (1992).
E.W. Anthony, Eur. J. Pharmacol. 250, 317–324 (1993).
Ikeda et al., FEBS Lett. 313, 34–38 (1992).
D.L. Comins et al., J. Am. Chem. Soc. 116, 4719–4728 (1994).
DeGroat et al., J. Auton. Nerv. Sys. 3, 135–160 (1981).
Ishii et al., J. Biol. Chem. 268, 2836–2843 (1993).
Decker et al., J. Immunol. Methods 15, 61–69 (1988).
Harbert et al., J. Med. Chem. 23, 635–643 (1980).
Abou–Gharbia et al., J. Med. Chem. 30, 1818–1823 (1987).
N. Iwasaki et al., J. Med. Chem. 38, 496–507 (1995).
Kerrigan et al., J. Med. Chem. 38, 544–552 (1995).
Cook et al., J. Med. Chem. 38, 753–763 (1995).
J.N. Dumont, J. Morphol. 136, 153–179 (1972).
P.T. Francis, N.R. Sims, A.W. Procter, D.M. Bowen, J. Neurochem. 60(5), 1589–1604 (1993).
W. Danysz, et al., J. Neural Trans. 7, 155–166, (1994).
A.A.P.J. Leaó, Neurophysiol. 7, 359–390 (1944).
D.W. Choi et al., J. Neuroscience 7, 357–368 (1987).
S.R. Skilling et al, J. Neuro Sci. 10, 1309–1318 (1990).
D.L. Comins et al., J. Org. Chem. 55, 2574–2576 (1990).
Way et al., J. Pharmacol. Exp. Ther. 167, 1–8 (1969).
Huidobro et al., J. Pharmacol. Exp. Ther. 198, 318–329 (1976).
L.D. Snell et al., J. Pharmacol. Exp. Ther. 235, 50–57 (1985).
Lutfy et al., J. Pharmacol. Exp. Ther. 256, 575–580 (1991).
Tiseo et al., J. Pharmacol. Exp. Ther. 264, 1090–1096 (1993).
Miledi and Parker, J. Physiol. 357, 173–183 (1984).
Miledi and Woodward, J. Physiol. 416, 601–621 (1989).
Landon and Robbins, Methods in Enzymology 124, 412–425 (1986).
Woodward et al., Mol. Pharmacol. 41, 89–103 (1992).
Curtis et al., Nature 191, 1010–1011 (1961).
J.H. Arundel, et al., J. Med. Chem. 9, 555–558 (1966).
B.L. Chenard, et al., J. Med. Chem. 34, 3085–3090 (1991).
A.K. Saxena, et al., Chem. Abstracts, vol. 120, No. 19, 120:244964e (1994).
B. Costall, et al., Chem. Abstracts, vol. 91, No. 21, 91:168329s (1979).

4-SUBSTITUTED PIPERIDINE ANALOGS AND THEIR USE AS SUBTYPE SELECTIVE NMDA RECEPTOR ANTAGONISTS

CROSS-REFERENCE

This application is a 371 of PCT/US96/20872 filed Dec. 20, 1996, and provisional application Ser. No. 60/009,184 filed Dec. 22, 1995, now abandoned.

BACKGROUND OF THE INVENTION

1. Field of the Invention

This invention is related to 4-substituted piperidine analogs, including hydroxypiperidine and tetrahydropyridine analogs. The analogs are selectively active as antagonists of N-methyl-D-aspartate (NMDA) receptor subtypes. The invention is also directed to the use of 4-substituted piperidine analogs as neuroprotective agents for treating conditions such as stroke, cerebral ischemia, central nervous system trauma, hypoglycemia, anxiety, psychosis, glaucoma, CMV retinitis, urinary incontinence, aminoglycoside antibiotics-induced hearing loss, convulsions, migraine headache, chronic pain, opioid tolerance or withdrawal, or neuro-degenerative disorders such as lathyrism, Alzheimer's Disease, Parkinsonism and Huntington's Disease.

2. Related Background Art

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-Aspartate (NMDA) receptor. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's Disease, Parkinson's Disease and Huntington's Disease.

Various classes of substituted piperidine analogs are known. For example, EP 0648744 generically discloses phenylalkanol derivatives described by the formula

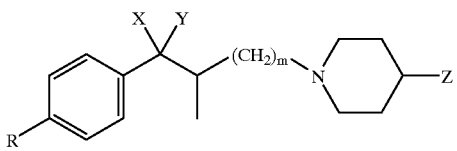

wherein R is hydrogen, hydroxy, or aryl lower alkyloxy; X is hydrogen; Y is hydroxy or hydrogen; or both X and Y taken together are oxygen; Z is aryl lower alkyl; and m is an integer from 1 to 4. The phenylalkanol derivatives of this reference are indicated to be NMDA receptor antagonists that are useful to reduce toxic injury to central neurons and may be used to treat ischemia, stroke or hypoxia. This reference does not disclose or suggest the 4-substituted piperidine analogs of this invention or their use as selective NMDA receptor subtype antagonists.

Other piperidine derivatives having aryl alkanol functionality are disclosed by PCT International Publication No. WO 93/11107 (for treating hypoxia and ischaemia), International Publication No. WO 94/10166 (for treating stroke, addiction, pain, epilepsy, psychosis, traumatic brain injury and CNS degenerative diseases), EP 0398578 (for treating stroke or CNS degenerative diseases, Alzheimer's disease, Huntington's disease and Parkinson's disease) and PCT International Publication No. WO 93/02052 (for treating stroke, traumatic injury to the brain and spinal cord, and neuronal degenerative diseases). Similar to EP 0648744, each of these references requires a piperidine derivative having an alkyl hydroxy or keto group alpha to the aryl group of the N-1 substituent. The 4-substituted piperidine analogs of this invention differ in kind from the piperidine derivatives of these references.

EP 0445701 generically discloses tetrahydropyridine a derivatives described by the formula

wherein Ar is phenyl or thienyl which may have identically or differently one or two substituents selected from the group consisting of lower alkyl, lower alkoxy, halogen, substituted or unsubstituted phenyl, trifluoromethyl and hydroxy; n is an integer of from 2 to 6; R is hydroxy or a group of the formula:

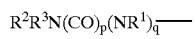

or

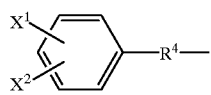

wherein $R^1$ is hydrogen or lower alkyl; $R^2$ and $R^3$ each is hydrogen or lower alkyl or taken together with the adjacent nitrogen atom may form a 5- or 6-membered heterocyclic group, which may be condensed with a benzene ring, where the heterocyclic group may identically or differently have 1 to 3 substituents selected from the group consisting of lower alkyl, halogen, oxo, pyrimidine, and substituted or unsubstituted phenyl; $R^4$ is NH, O, or a single bond; $X^1$ and $X^2$ each is hydrogen, lower alkyl, halogen, or hydroxy; p and q each is an integer of 0 or 1, except that p is 0 when q is 1. These tetrahydropyridines are said to have high affinity and specificity to σ receptors and thus may be effective for treating depression, mania and acute and chronic schizophrenia, and cerebral ischemic disease. There is no disclosure or suggestion of NMDA receptor subtype selectivity.

FR 2681319 discloses 1-(phenoxy-alkyl)piperidine derivatives represented generically by the formula

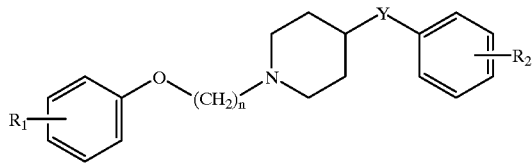

wherein $R_1$ and $R_2$ are independently selected from hydrogen, halogen, methoxy or trifluoromethyl, n is 3 or 4 and Y is —$CH_2$—, —$CH_2CH_2$—, —$OCH_2$— or —$CH_2O$—. The reference indicates that these piperidine derivatives are useful for treating cerebral disorders, dementia and other neurodegenerative disorders. The 4-substituted piperidine analogs of this invention or their use as selective NMDA receptor subtype antagonists is not disclosed or suggested.

PCT International Publication No. WO 94/18172 generically discloses imidazolybenzene compounds. represented by the formula

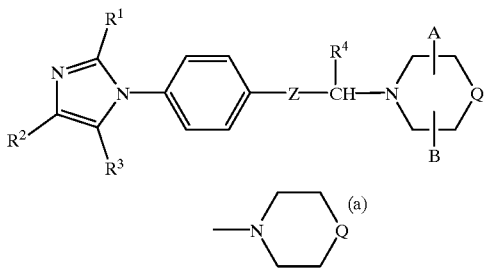

wherein $R^1$, $R^2$ and $R^3$ are independently selected from hydrogen, halogen, nitro, cyano, amino, alkyl, acyl, phenyl or alkoxy; $R^4$ is hydrogen, alkyl or cycloalkyl; Z is —$CH_2$—, —CH(OH)— or —CO—; the ring (a) is piperidyl or 1-piperazinyl; A is hydrogen, hydroxy or alkyl; and B is cycloaklyl, cycloalkylalkyl, acyl, aryl, aralkyl, heteroaryl or heteroarylalkyl. The imidazolylbenzene compound is said to be useful as an NMDA antagonist and cranial nerve cell death inhibitor. However, their is no disclosure of NMDA subtype receptor selectivity.

PCT International Publication Number WO 92/02502 generically discloses N-hydrocarbyl 4-substituted piperidines described by the formula:

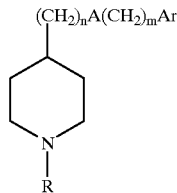

in which
R is $C_{1-8}$alkyl (phenyl)p, $C_{2-8}$alkenyl (phenyl)p, $C_{2-8}$alkynyl (phenyl)p, $C_{3-8}$cycloalkyl;
p is 0 to 2;
n is 0 to 6;
A is a bond, oxygen, sulphur or $NR^1$;
$R^1$ is hydrogen, $C_{1-8}$alkyl or phenyl$C_{1-4}$alkyl;
m is 0 to 3; and
Ar is aryl or heteroaryl, each of which may be optionally substituted; and salts thereof. This reference exemplifies 4-aryloxyalkyl piperidines. The substituted piperidines are said to be calcium channel blockers expected to be useful in the treatment of anoxia, ischemia including stroke, migraine, epilepsy, traumatic head injury, AIDS-related dementia, neurodegenerative disorders and drug addiction. The reference does not disclose or suggest the particular 4-substituted piperidine analogs of this invention or their use as selective NMDA receptor subtype antagonists for the treatment of disorders responsive thereto.

PCT International Publication Number WO 93/15052 generically describes compounds that are said to be calcium channel antagonists broadly represented by the formula:

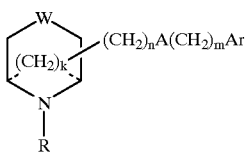

and the salts thereof, wherein W is —$CH_2$—, a bond, O or S; k is 0, or when W represents —$CH_2$— k may also be 2, in which case the dotted lines represent single bonds;

R is $C_{1-8}$alkyl(phenyl)p, $C_{2-8}$alkenyl(phenyl)p, $C_{2-8}$alkynyl(phenyl)p, $C_{3-8}$cycloalkyl or $C_{1-8}$alkyl$C_{3-8}$cycloalkyl, or R may also represent hydrogen when k is 2; p is 0 to 2 n is 0 to 6;

m is 0 to 6; and

A is a bond, —CH=CH—, —C≡C—, oxygen, sulphur or $NR^1$;

$R^1$ is hydrogen, $C_{1-8}$alkyl or phenyl$C_{1-4}$alkyl; and

Ar is aryl or heteroaryl, each of which may be optionally substituted; provided that: when W is a bond the side chain is a to the ring nitrogen atom; when W is $CH_2$, k is zero, the side chain is at the 3- or 4-position of the piperidine ring and A is a bond, oxygen, sulphur or $NR^1$ then Ar is aryl substituted by phenoxy or substituted phenoxy or is a tricyclic heteroaryl group as hereinafter defined; and when W is $CH_2$ and k is 2 the side chain —$(CH_2)_nA(CH_2)_m$Ar is not α to the nitrogen atom. This reference exemplifies mostly 2 and 3 substituted piperidines. In addition, the particular group of 3 and 4 substituted piperidines described by the reference requires A to be —CH=CH— or —C≡C—. This reference does not disclose or suggest the 4-substituted piperidine analogs of this invention. Moreover, there is no suggestion of employing 4-substituted piperidine analogs as selective NMDA receptor subtype antagonists.

European Patent Application No. 235,463 generically discloses calcium antagonists represented by the formula

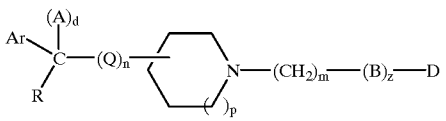

wherein;

p is zero, one or two;

A is hydrogen,

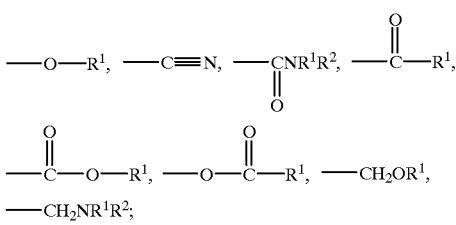

m is zero to six inclusive;

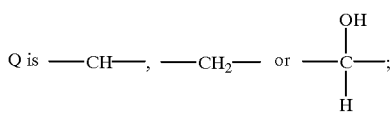

d and n are selected from zero or one and the dotted lines represent double bonds which may form consistent with the valence of carbon;

Ar, D and R are selected from the group consisting of

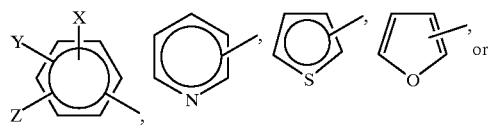

and in addition, R may have the values:

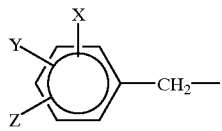

cycloalkyl or loweralkyl, and

D may have additionally the values:

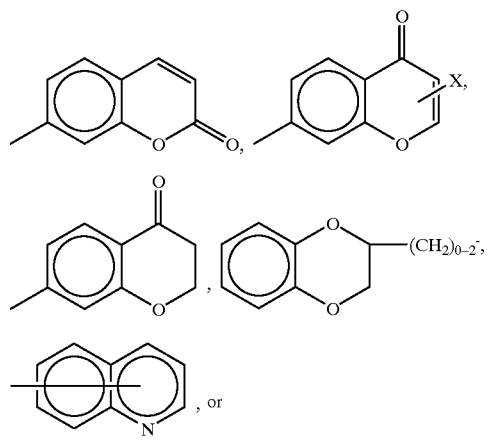

Ar(CH$_2$)1-4

X, Y and Z are selected from the group consisting of hydrogen, lower alkyl, halogen,

—NO$_2$, —O—R$^1$,

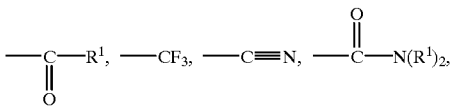

—N(R$^1$)$_2$, —C(O)OR$^1$, SO$_2$R$^2$, —SR$^2$, —S(O)R$^2$,

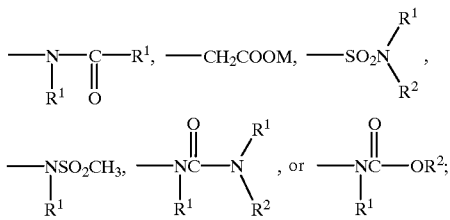

B is selected from

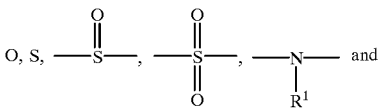

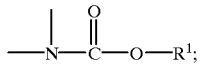

z is one or zero with the proviso that z cannot be zero at the same time n is zero when one of the following occurs at the same time that D is phenyl or substituted phenyl: (A)$_d$ is hydrogen, (A)$_d$ is cyano, (A)$_d$ is aminocarbonyl, or a double bond forms between the α carbon and a carbon of the central heterocyclic amine-ring; R$^1$ is selected from hydrogen, loweralkyl, phenyl and phenylloweralkyl; R$^2$ is selected from loweralkyl, phenyl and phenylloweralkyl; M is a pharmaceutically acceptable metal ion and the pharmaceutically acceptable salts thereof, including acid addition salts, quaternary salts, and hydrates and alcoholates thereof. This reference discloses that such compounds may be useful as coronary vasodilators, antihypertensives, antiarrhythmic, antiallergy, antihistamic and antisecretory agents. There is no suggestion or disclosure of the 4-substituted piperidines of this invention or their use as selective NMDA receptor subtype antagonists.

U.S. Pat. No. 5,202,346 generically discloses a compound represented by the formula

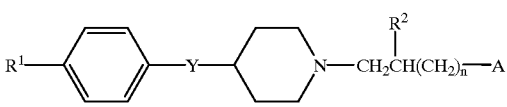

wherein R$^1$ is alkylsulfonamido of 1 to 6 carbon atoms, arylsulfonamide of 6 to 10 carbon atoms, —NO$_2$, —CN, 1-imidazolyl or 1,2,4-triazol-1-yl; Y is

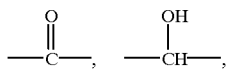

—CH$_2$—, —O—, —S—, or —SO$_2$—;

R$^2$ is hydrogen when n is 0, otherwise it is hydrogen or —OH; n is one of the integers 0, 1, 2, 3, 4, 5 or 6; A is

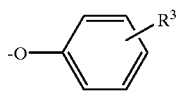

where R$^3$ is alkylsulfonamide of 1 to 6 carbon atoms, arylsulfonamido of 6 to 10 carbon atoms, —NO$_2$, —CN, 1-imidazoyl or 1,2,4-triazol-1-yl. These compounds are said to be Class III antiarrhythmic agents. JP 61-115068 discloses 4-benzylpiperidinylpropoxyaniline derivatives, such as 2-(3-(4-benzyl-1-piperidinyl)propoxy)aniline, also said to have antiarrhythmic, as well as local anesthetic action. No mention is made of NMDA antagonists, let alone selective subtype receptor antagonists.

U.S. Pat. No. 5,036,077 generically discloses piperidine derivatives described by the formula:

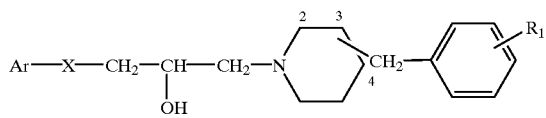

wherein Ar represents a phenyl group substituted by R$_2$, R$_3$ and R$_4$ or a naphth-1-yl or naphth-2-yl group, substituted or unsubstituted by 1 or 2 halogen atoms; X represents an oxygen atom or sulfur atom; R$_1$ represents H or a halogen atom; R$_2$ represents a halogen atom, a trifluoromethyl group, a phenyl group which is unsubstituted or substituted by 1 to 3 halogen atoms, a phenoxy group which is unsubstituted or substituted by 1 to 3 halogen atoms, or a C$_1$–C$_4$ alkyl group and the benzyl group substitutes the piperidine radical in the 2, 3 or 4 position. The piperidines are said to be useful as antimicrobial agents, but there is no disclosure or suggestion of treating disorders responsive to selective NMDA receptor subtype antagonists.

European patent application No. 649838 generically disclosed cyclized amines described by the formula:

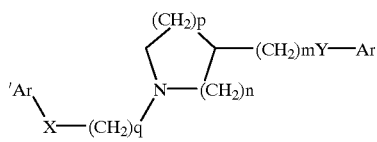

wherein the nitrogen heterocycles can be 3–8 member rings and substituted in the 2–4 positions. Ar and Ar' are opt. mono or disubstituted phenyl. The compounds are said to be useful to treat arrhythmia and tachycardia. But there is no disclosure or suggestion of treating disorders responsive to selective NMDA receptor subtype antagonists.

DE patent application No. 4410822 generically disclosed cyclized amines described by the formula:

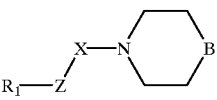

in which

R$_1$ is Ph, pyridine and other heterocycles;

Z is O, S, SO and SO$_2$;

X is (CH$_2$)$_m$CR$_2$R$_3$—(CH$_2$)$_p$ and (CH$_2$)$_m$—CHR$_2$—(CH$_2$)$_g$—CHR$_3$(CH$_2$)$_p$;

m, p and g is 0–3;

R$_2$ and R$_3$ is H, OH 1–4C alkyl or 1–4C alkoxy;

B is CHR$_4$ or NR$_4$;

R$_4$ is H, 1–6C alkyl, or ph, Benzyl, benzoyl, α-hydroxybenzyl or pyridine.

The compounds are said to be used in the treatment and therapy of diseases which are relieved by changing the function of the AMPA receptor complex. But there is no disclosure or suggestion of treating disorders responsive to selective NMDA receptor subtype antagonists.

U.S. Pat. No. 4,942,169 generically disclosed substituted piperidines described by the formula:

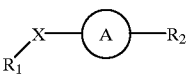

in which

R$_1$ is substituted or unsusbstituted Ph or heterocycles;

X denotes a group of formula including —(CH$_2$)$_n$—, —O(CH$_2$)$_n$—, —S(CH$_2$)$_n$— and —NH(CH$_2$)$_n$—;

n is 1–7;

the ring A denotes a group of the formula

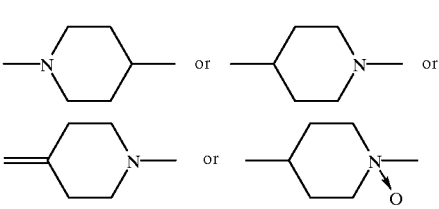

R$_2$ denotes a H, a lower alkyl group, a substituted or unsubstituted benzyl, benzoyl, pyridyl, 2-hydroxyethyl and pyridylmethyl.

The compounds are said to have antiacetylcholinesterase activities. But there is no disclosure or suggestion of treating disorders responsive to selective NMDA receptor subtype antagonists.

U.S. Pat. No. 5,169,855 generically discloses disubstituted piperidine ether derivatives for use as antipsychotic agents selective for sigma receptors. Similarly, PCT International Publication No. WO 92/18127 and PCT International Publication No. WO 91/06297 generically disclose N-phthalimidoalkyl piperidines which are useful as antipsychotic agents and which are selective for sigma receptors. However, the 4-substituted piperidine analogs of this invention are not disclosed by these references and there is no mention of NMDA receptor activity.

Numerous references have disclosed additional piperidine derivatives substituted at the 4 and 3 position for use in a variety of treatments. Such references include, for example, U.S. Pat. No. 3,255,196 (3 and 4-substituted piperidines that are active antitussives and possess analgesic, antiemetic and local anaesthetic properties); PCT International Publication No. WO 88/02365 (3 and 4-substituted piperidines that may be useful for treatment of mental disorders accompanying cerebrovascular disease); BE 860701 (4-substituted piperidines for use as vasodilators and β-adrenergic inhibitors); JP 04-312572 (4-substituted piperidines, such as 4-(4-(N,N-dimethylaminocarbonyl)phenylmethyl)piperidine, for treatment of cerebral ischemia); JP 61-227565 (4 substituted piperidine derivatives for treating diseases requiring the isolation of serotonin); EP 0449186 (4-substituted N-aralkyl piperidines which are selective sigma receptor antagonists for treating physiological or drug induced psychosis or dyskinesia); and DE 2939292 (4-substituted piperidines for use as antiallergenic and antiinflammatory agents). None of these references disclose or suggest the 4-substituted piperidine analogs of the present invention or their use as selective NMDA receptor subtype antagonists.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

Expression cloning of the first NMDA receptor subunit, NMDAR1 (NR1) in Nakanishi's lab in 1991 provided an initial view of the molecular structure of the NMDA receptor [Nature 354, 31–37 (1991)]. There are several other structurally related subunits (NMDAR2A through NMDAR2D) that join NR1 in heteromeric assemblies to form the functional ion channel complex of the receptor [Annu. Rev. Neurosci. 17, 31–108 (1994)]. The molecular heterogeneity of NMDA receptors implies a future potential for agents with subtype selective pharmacology.

Many of the properties of native NMDA receptors are seen in recombinant homomeric NR1 receptors. These properties are altered by the NR2 subunits. Recombinant NMDA receptors expressed in Xenopus oocytes have been studied by voltage-clamp recording, as has developmental and regional expression of the mRNAs encoding NMDA receptor subunits. Electrophysiological assays were utilized to characterize the actions of compounds at NMDA receptors expressed in Xenopus oocytes. The compounds were assayed at four subunit combinations of cloned rat NMDA receptors, corresponding to three putative NMDA receptor subtypes [Moriyoshi, et al. Nature 1991, 354, 31–37; Monyer et al, Science 1992, 256, 1217–1221; Kutsuwada et al, Nature 1992, 358, 36–41; Sugihara et al, Biochem. Biophys Res. Commun. 1992, 185, 826–832].

An object of this invention is to provide novel 4-substituted piperidine analogs which function as subtype-selective NMDA receptor antagonists.

A further object of this invention is to provide a pharmaceutical composition containing an effective amount of the 4-substituted piperidine analogs to treat cerebrovascular disorders responsive to the selective blockade of NMDA receptor subtypes.

Another object of this invention is to provide a method of treating disorders responsive to the subtype-selective NMDA receptor antagonists in an animal by administering a pharmaceutically effective amount of 4-substituted piperidine analogs.

SUMMARY OF THE INVENTION

This invention relates to novel 4-substituted piperidine analogs represented by the formula (I):

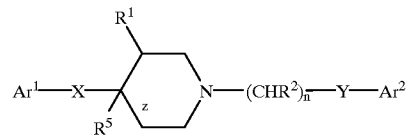

I or a pharmaceutically acceptable salt thereof wherein $Ar^1$ and $Ar^2$ are independently aryl or a heteroaryl group, either of which may be independently substituted by hydrogen, hydroxy, alkyl, halogen, nitro, cyano, carboxaldehyde, aldehyde oxime, lower alkoxy carbonylmethyl, hydroxy lower alkyl, amino carbonylmethyl, hydrazinocarbonylmethyl, acetamido, aryl, aralkyl, amino, a halogenated alkyl group, a lower alkyl amino group or a lower alkoxy group;

z is a single or double bond;

X is $-(CHR^3)_m-$, O, S or $NR^4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2, provided that when z is a double bond then X is not O or $NR^4$;

$R^1$ is hydrogen or hydroxy;

each $R^2$ is independently hydrogen, hydroxy or a lower alkyl group having 1 to 6 carbon atoms;

n is 0, 1, 2, 3 or 4;

Y is O, S, $NR^4$ or a single bond; and $R^5$ is hydrogen or hydroxy when z is a single bond preferably provided that: (i) $R^2$ cannot be hydroxy in a position alpha to $Ar^2$; (ii) if X is a single bond, z is a double bond or $R^5$ is hydroxy and $Ar^2$ is phenyl then Y cannot be O; (iii) if Y is O, n is 3 or 4, $R^2$ is exclusively hydrogen, z is a single bond, $R^1$ and $R^5$ are hydrogen and $Ar_2$ is phenyl, or halogen, methoxy, or trifluoromethyl substituted phenyl then X cannot be methylene or ethylene; (iv) if X is $-(CHR^3)_m-$, m is 2 and $R^3$ is exclusively hydrogen then $Ar^1$ cannot be imidazolyl substituted; (v) if Y is O, n is 2, 3 or 4, $R^2$ is hydrogen or hydroxy, z is a single bond, $R^1$ and $R^5$ are hydrogen, and $Ar^2$ is phenyl, or $NO_2$, CN, 1-imidazoyl, or 1,2,4-triazol-1-yl substituted phenyl then X cannot be methylene, hydroxymethylene, or O; (vi) if Y is O or S, $R^1$ and $R^5$ are hydrogen and $R^2$ is hydroxy then X is not methylene or a single bond; or (vii) if Y is a single bond, $R^2$ is exclusively hydrogen and $Ar^2$ is phenyl, then either $R^1$ or $R^5$ must be hydroxy.

The compounds of the present invention may exist as optical isomers and the inventive compounds include both the racemic mixtures of such optical isomers as well as the individual entantiomers.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate.

Halogen is fluorine, chlorine, bromine, or iodine; fluorine, chlorine, and bromine are preferred groups.

Alkyl means a straight or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Aryl means a monocyclic or bicyclic carbocyclic aromatic ring system which can be substituted or unsubstituted, for example, but not limited to phenyl, naphthyl or the like.

Heteroaryl means a monocyclic or bicyclic carbocyclic aromatic ring system substituted by one or more hetero atoms, which can be the same or different, and includes, for example, thienyl, benzo[b]thienyl, naphtho[2,3[b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbozolyl, carbozolyl, β-carbolinyl, phenanthridinyl; acrindinyl, perimidinyl, phenanthrolinyl, phenazinyl, isothiazolyl, phenothiazinyl, isoxazolyl, furazanyl, phenoxazinyl, quinoxalinyl, 2,3-dioxoquinoxalinyl, benzimidazolyl, 2-oxobenzimidazolyl, 2-oxindolyl, 2-thioxobenzimidazole, pyrazolo[3,4-d]pyrimidinyl, 4-hydroxypyrazolo[3,4-d]pyrimidinyl, and 2-methylbenzimidazolyl groups.

Aralkyl means any of the alkyl groups defined herein substituted by any of the aryl groups as defined herein.

Halogenated alkyl means any of the alkyl groups defined herein substituted by one or more halogens as defined herein.

Lower alkyl amino means any of the alkyl groups defined herein substituted by an amino group.

Lower alkoxy means an alkoxy group containing an alkyl group as defined herein.

The instant invention is also related to a pharmaceutical composition containing the compound defined by formula I in an amount effective to treat cerebrovascular disorders responsive to the selective blockade of NMDA receptor subtypes and a pharmaceutically acceptable carrier. Exemplary disorders responsive to such treatment include cerebral ischemia caused by cerebral trauma, stroke, hypoglycemia, heart attack, and surgery; anxiety-psychosis, schizophrenia; glaucoma; CMV retinitis; aminoglycoside antibiotics-induced hearing loss; urinary incontinence; opioid tolerance or withdrawal; and chronic neurodegenerative disorders such as Huntington's disease, ALS, Parkinsonism and Alzheimer's disease. The pharmaceutical composition of this invention may also be employed as an analgesic or for the treatment of epilepsy or migraine headaches.

The invention further relates to a method for treating disorders responsive to the selective blockade of N-methyl-D-aspartate receptor subtypes in an animal suffering thereof which comprises administering in unit dosage form at least one compound represented by the formula (I):

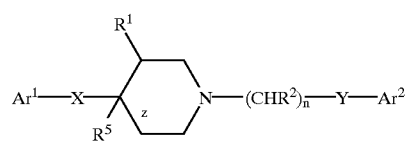

or a pharmaceutically acceptable salt thereof wherein $Ar^1$ and $Ar^2$ are independently aryl or a heteroaryl group, either of which may be independently substituted by hydrogen, hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

z is a single or double bond;

X is —$(CHR^3)_m$—, O, S or $NR^4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2, provided that when z is a double bond then X is not O or $NR^4$;

$R^1$ is hydrogen or hydroxy;

each $R^2$ is independently hydrogen, hydroxy or a lower alkyl group having 1 to 6 carbon atoms;

n is 0, 1, 2, 3 or 4;

Y is O, S, $NR^4$ or is a single bond; and $R^5$ is hydrogen or hydroxy when z is a single bond.

DETAILED DESCRIPTION OF THE INVENTION

Figure 1:
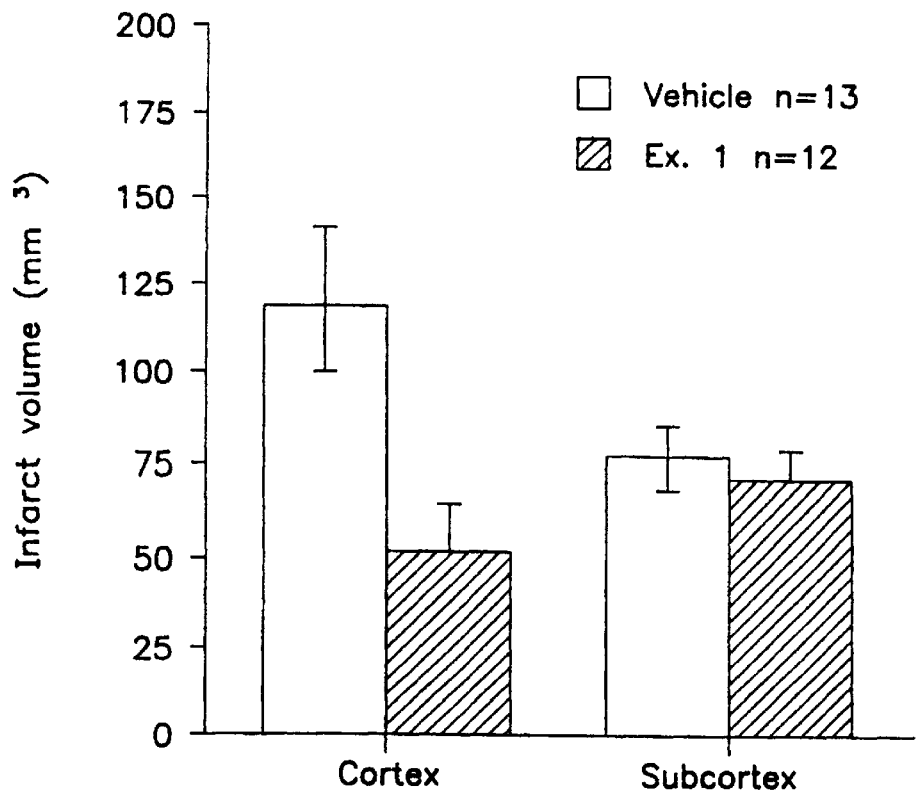
FIGS. 1 and 2 are bar graphs illustrating the mean infarct volume in the cortex and subcortex after in vivo administration of compounds of this invention to rodents.

The novel 4-substituted piperidine analogs of this invention are represented by previously defined formula (I). Generally, Y is O or a single bond. Preferably, $R^1$ or $R^5$ is hydroxy. In addition, $Ar_2$ is preferably a heteroaryl group, e.g., a benzimidazol-2-one, indol-2-one, or a quinoxaline-2,3-dione group.

Preferred embodiments of the novel 4-substituted piperidine analogs of this invention are represented by formula (II–XI). In particular, a first embodiment is represented by formula (II) as follows:

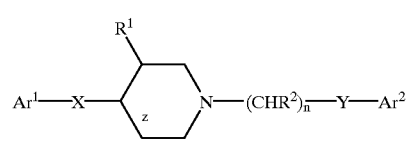

or a pharmaceutically acceptable salt thereof wherein:

$Ar^1$ and $Ar^2$ are independently the same as previously defined for formula (I);

z is a single or double bond;

X is —$(CHR^3)_m$—, O, S or $NR_4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2, provided that when z is a double bond then X is not O or $NR_4$;

$R^1$ is hydrogen or hydroxy;

each $R^2$ is independently hydrogen, hydroxy or a lower alkyl group having 1 to 6 carbon atoms;

n is 0, 1, 2, 3 or 4; and

Y is O, S, $NR^4$ or is a single bond, preferably provided that: (i) $R^2$ cannot be hydroxy in a position alpha to $Ar^2$; (ii) if X is a single bond, z is a double bond and $Ar^2$ is phenyl then Y cannot be O; (iii) if Y is O, n is 3 or 4, $R^2$ is exclusively hydrogen, $R^1$ is hydrogen and $Ar^2$ is phenyl, or halogen, methoxy, or trifluoromethyl substituted phenyl then X cannot be methylene or ethylene; (iv) if X is —$(CHR^3)_m$—, m is 2 and $R^3$ is exclusively hydrogen then $Ar^1$ cannot be imidazolyl substituted; (v) if Y is O, n is 2, 3 or 4, $R^2$ is hydrogen or hydroxy, $R^1$ is hydrogen and $Ar^2$ is phenyl, or $NO_2$, CN, 1-imidazoyl, or 1,2,4-triazol-1-yl substituted phenyl then X cannot be methylene, hydroxymethylene, or O; (vi) if Y is O or S, $R^1$ is hydrogen and $R^2$ is hydroxy then X is not methylene or a single bond; or (vii) if Y is a single bond, $R^2$ is exclusively hydrogen and $Ar^2$ is phenyl then $R^1$ must be hydroxy.

Another embodiment of the novel 4-substituted piperidines of this invention is represented by formula (III) as follows:

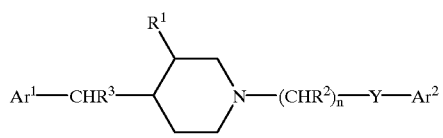

(III)

or a pharmaceutically acceptable salt thereof wherein;

$Ar^1$ and $Ar^2$ are independently the same as described for formula (I);

$R^1$ is hydrogen or hydroxy;

each $R^2$ and $R^3$ are independently hydrogen, hydroxy or a lower alkyl group having 1 to 6 carbon atoms;

n is 0, 1, 2, 3 or 4; and

Y is O, S, $NR_4$ or is a single bond, preferably provided that: (i) $R^2$ cannot be hydroxy in a position alpha to $Ar^2$; (ii) if Y is O, n is 3 or 4, $R^2$ is exclusively hydrogen, $R^1$ is hydrogen and $Ar^2$ is phenyl, or halogen, methoxy or trifluoromethyl substituted phenyl then X cannot be methylene or ethylene; (iii) if Y is O, n is 2, 3 or 4, $R^2$ is hydrogen or hydroxy, $R^1$ is hydrogen and $Ar^2$ is phenyl, or $NO_2$, CN, 1-imidazoyl, or 1,2,4-triazol-1-yl substituted phenyl then $R^3$ cannot be hydrogen; (iv) if Y is O or S, $R^1$ is hydrogen and $R^2$ is hydroxy then $R^3$ cannot be hydrogen; or (v) if Y is a single bond, $R^2$ is exclusively hydrogen and $Ar^2$ is phenyl then $R^1$ must be hydroxy.

An additional embodiment of the novel 4-substituted piperidines of this invention is represented by formula (IV) as follows:

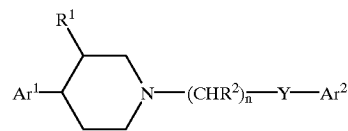

(IV)

or a pharmaceutically acceptable salt thereof, $Ar^1$ and $Ar^2$ are independently the same as described for formula (I);

$R^1$ is hydrogen or hydroxy;

each $R^2$ is independently hydrogen, hydroxy or a lower alkyl group having 1 to 6 carbon atoms;

n is 1, 2, 3 or 4; and

Y is O, S, $NR^4$ or is a single bond, preferably provided that: (i) $R^2$ cannot be hydroxy in a position alpha to $Ar^2$; or (ii) if Y is a single bond, O or S then $R^2$ is not hydroxy.

Yet another embodiment of the invention is represented by the formula (V):

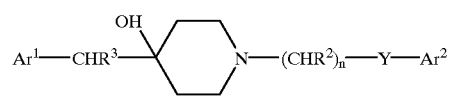

(V)

or a pharmaceutically acceptable salt thereof wherein:

$Ar^1$ and $Ar^2$ are independently the same as described for formula (I);

each $R^2$ and $R^3$ are independently hydrogen, hydroxy or a lower alkyl group having 1 to 6 carbon atoms;

n is 0, 1, 2, 3 or 4; and

Y is O, S, $NR_4$ or is a single bond, preferably provided that $R^2$ cannot be hydroxy in a position alpha to $Ar^2$.

Yet another embodiment of the invention is represented by the formula (VI):

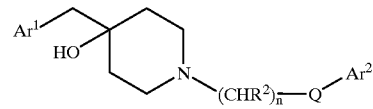

(VI)

or a pharmaceutically acceptable salt thereof wherein:

$Ar^1$ and $Ar^2$ are independently the same as described for formula (I);

each $R^2$ is independently hydrogen, hydroxy or a lower alkyl group having 1 to 6 carbon atoms;

n is 0, 1,2,3 or 4;

Q is O, S, $NR_4$ or is a single bond.

Yet another embodiment of the invention is represented by the formula (VII):

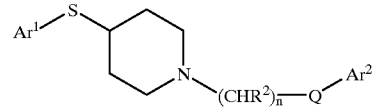

(VII)

or a pharmaceutically acceptable salt thereof wherein:

Ar¹ and Ar² are independently the same as described for formula (I);

each $R^2$ is independently hydrogen, hydroxy or a lower alkyl group having 1 to 6 carbon atoms;

n is 0, 1,2,3 or 4; and

Q is O, S, $NR_4$ or is a single bond.

Yet another embodiment of the invention is represented by the formula (VIII):

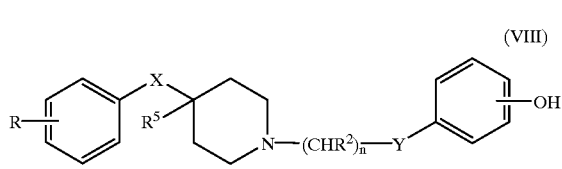

(VIII)

or a pharmaceutically acceptable salt thereof wherein:

n is 0, 1,2,3 or 4;

$R^5$ is hydrogen or hydroxy;

R is hydrogen, hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ is independently hydrogen, hydroxy or a lower alkyl group having 1 to 6 carbon atoms;

X is —$(CHR^3)_m$—O, S or $NR_4$;

Y is O, S, $NR^4$ or is a single bond;

$R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2; and $R^5$ is hydrogen or hydroxy.

Yet another embodiment of the invention is represented by the formula (IX):

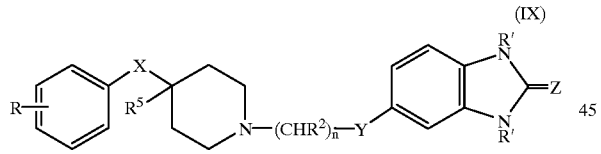

(IX)

or a pharmaceutically acceptable salt thereof wherein:

n is 0, 1,2,3 or 4;

$R^5$ is hydrogen or hydroxy;

R is hydrogen, hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ is independently hydrogen, hydroxy or a lower alkyl group having 1 to 6 carbon atoms;

Y is O, S, $NR_4$ or is a single bond;

Z is O or S.

$R^5$ is hydrogen or hydroxy;

X is —$(CHR^3)_m$—, O, S or $NR_4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2; and R' is indepenently hydrogen or alkyl.

Yet another embodiment of the invention is represented by the formula (X):

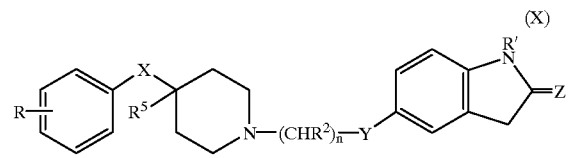

(X)

or a pharmaceutically acceptable salt thereof wherein:

n is 0, 1,2,3 or 4;

$R^5$ is hydrogen or hydroxy;

R is hydrogen, hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ is independently hydrogen, hydroxy or a lower alkyl group having 1 to 6 carbon atoms;

Y is O, S, $NR_4$ or is a single bond;

Z is O or S;

X is —$(CHR^3)_m$—, O, S or $NR_4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2;

$R^5$ is hydrogen or hydroxy; and

R' is hydrogen or alkyl.

Yet another embodiment of the invention is represented by the formula (XI):

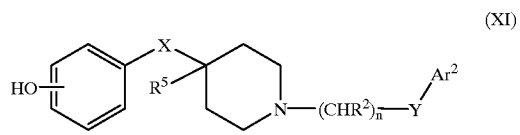

(XI)

or a pharmaceutically acceptable salt thereof wherein:

n is 0, 1,2,3 or 4;

$Ar^2$ is the same as previously defined for formula (I);

each $R^2$ is independently hydrogen, hydroxy or a lower alkyl group having 1 to 6 carbon atoms;

X is —$(CHR^3)_m$—, O, S or $NR^4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2;

Y is O, S, $NR^4$ or is a single bond; and $R^5$ is hydrogen or hydroxy.

Exemplary preferred compounds of formula I include, without limitation:

4-Phenoxy-1-[(4-fluorophenoxy)propyl]piperidine;

1-(3-Phenoxypropyl)-4-phenylpiperidine;

1-(2-Phenoxyethyl)-4-phenylpiperidine;

1-(4-Phenoxybutyl)-4-phenylpiperidine;

1-(4-(3-(Trifluoromethyl)phenoxy)butyl)-4-phenylpiperidine;

1-(2-(4-Aminophenoxy)ethyl)-4-benzylpiperidine;
3-((2-(4-Benzylpiperidin-1-yl)ethyl)oxy)benzaldehyde;
3-((2-(4-Benzylpiperidin-1-yl)ethyl)oxy)benzaldehyde oxime;
4-Benzyl-1-(2-(3-(ethoxycarbonylmethyl)phenoxy)ethyl) piperidine;
4-Benzyl-1-[2-(3-(2-hydroxyethyl)phenoxy) ethyl) piperidine;
1-(2-(3-(Aminocarbonylmethyl)phenoxy)ethyl)-4-benzylpiperidine;
4-Benzyl-1-(2-(3-(hydrazinocarbonylmethyl)phenoxy) ethyl)piperidine;
4-Benzyl-1-(1-methyl-2-phenoxyethyl)piperidine;
4-(4-Chlorobenzyl)-1-(2-(4-fluorophenoxy)ethyl) piperidine;
4-(4-Chlorobenzyl)-1-(2-(4-chlorophenoxyethyl)piperidine;
1-(2-(4-Aminophenoxy)ethyl)-4-(4-chlorobenzyl) piperidine;
4-(4-Chlorobenzyl)-1-(2-(3-(2-hydroxyethyl)phenoxy) ethyl)piperidine;
4-(4-Fluorobenzyl)-1-(2-(4-fluorophenoxy)ethyl)piperidine;
4-(4-Fluorobenzyl)-1-(2-(4-chlorophenoxy)ethyl) piperidine;
1-(2-(4-Fluorophenoxy)ethyl)-4-(4-methoxybenzyl) piperidine;
1-(2-(4-Fluorophenoxy)ethyl)-4-(4-nitrobenzyl)piperidine;
4-Benzyl-1-(1-methyl-3-phenoxypropyl)piperidine;
1-(2-Phenoxyethyl)-4-phenylpiperidine;
3-Hydroxy-1-(2-phenoxyethyl)-4-(3-trifluoromethylphenyl) piperidine;
3-Hydroxy-1-(3-phenoxypropyl)-4-(3-trifluoromethylphenyl)piperidine;
4-Benzyl-1-[2-(6-quinolinoxy)ethyl)]piperidine;
4-Benzyl-1-[2-(8-quinolinoxy)ethyl]piperidine;
4-Benzyl-1-[2-(2-amino-3-nitrophenoxy)ethyl]-piperidine;
4-Benzyl-1-[2-(2,3-diaminophenoxy)ethyl]-piperidine;
4-Benzyl-1-[2-(2,3-dioxoquinoxalin-5-oxy)ethyl] piperidine;
4-Benzyl-1-[2-(2-oxobenzimidazol-4-oxy)ethyl]piperidine;
4-Benzyl-1-[2-(4-amino-3-nitrophenoxy)ethyl]piperidine;
4-Benzyl-1-[2-(3,4-diaminophenoxy)ethyl]piperidine;
4-Benzyl-1-[2-(2,3-dioxoquinoxalin-6-oxy)ethyl] piperidine;
4-Benzyl-1-[2-(2-oxobenzimidazol-5-oxy)ethyl]piperidine;
4-Benzyl-1-[2-(2-aminophenoxy)ethyl]piperidine;
4-Benzyl-1-[2-(3-aminophenoxy)ethyl]piperidine;
4-Benzyl-1-[2-(4-aminophenoxy)ethyl]piperidine;
4-[2-(4-Benzylpiperidinoethoxy)quinazoline;
4-[2-(4-Benzylpiperidino)ethoxy]pyrazolo-[3,4-d] pyrimidine;
1-[2-(4-Benzylpiperidino)ethyl]-4-hydroxypyrazolo[3,4-d] pyrimidine;
4-Benzyl-1-[2-(2-methoxyphenoxy)ethyl]piperidine;
4-Benzyl-1-[2-(3-methoxyphenoxy)ethyl]piperidine;
4-Benzyl-1-[2-(4-methoxyphenoxy)ethyl]piperidine;
4-Benzyl-1-[2-(3,4-bisacetamidophenoxy)ethyl]piperidine;
4-Benzyl-1-[2-(2-methylbenzimidazol-6-oxy)ethyl] piperidine;
4-Benzyl-1-[2-(2-methylbenzimidazol-5-oxy)ethyl] piperidine;
4-Benzyl-1-[2-(3-trifluoromethylphenoxy)ethyl]piperidine;
4-(4-Chlorobenzyl)-1-[2-(2-nitrophenoxy)ethyl]piperidine;
4-(4-Chlorobenzyl)-1-[2-(2-aminophenoxy)ethyl] piperidine;
4-(4-Chlorobenzyl)-1-[2-(2-amino-3-nitrophenoxy)ethyl] piperidine;
4-(4-Chlorobenzyl)-1-[2-(2,3-diaminophenoxy)ethyl] piperidine;
4-(4-Chlorobenzyl)-1-[2-(2-oxobenzimidazol-4-oxy)ethyl]-piperidine;
4-(4-Chlorobenzyl)-1-[2-(4-amino-3-nitrophenoxy)ethyl] piperidine;
4-(4-Chlorobenzyl)-1-[2-(3,4-diaminophenoxy)ethyl] piperidine;
4-(4-Chlorobenzyl)-1-[2-(2-oxobenzimidazol-5-oxy)ethyl] piperidine;
4-(4-Fluorobenzyl)-1-[2-(2-oxobenzimidazol-5-oxy)ethyl] piperidine;
4-(4-Chlorophenyl)-4-hydroxy-1-(3-phenylpropyl) piperidine;
4-(4-Chlorophenyl)-4-hydroxy-1-(4-phenylbutyl) piperidine;
3-Hydroxy-1-(4-phenylbutyl)-4-(3-trifluoromethylphenyl)-piperidine;
4-Benzyl-4-hydroxy-1-(2-phenylethyl)piperidine;
1,4-Dibenzyl-4-hydroxypiperidine;
1-Benzyl-4-(4-fluorobenzyl)-4-hydroxypiperidine;
4-(4-Fluorobenzyl)-1-[2-(4-fluorophenyl)ethyl]-4-hydroxypiperidine;
4-(2-Keto-1-benzimidazolinyl)-1-(3-phenoxypropyl) piperidine;
4-Benzyl-4-hydroxy-1-(2-phenoxyethyl)piperidine;
4-Benzyl-4-hydroxy-1-(3-phenylpropyl)piperidine;
4-Benzyl-4-hydroxy-1-(3-phenoxypropyl)piperidine;
4-Benzyl-1-[(2-hydroxy-4-phenyl)butyl]piperidine;
3-Hydroxy-4-(3-trifluoromethylphenyl)-1-[3-(3-aminophenoxy)propyl]piperidine;
3-Hydroxy-4-(4-fluorophenyl)-1-[3-(3-amino-1-naphthyloxy)propyl]piperidine;
4-Benzyl-1-(2-(4-hydroxyphenoxy)ethyl)piperidine;
4-(4-Chlorobenzyl)-1-(2-(4-hydroxyphenoxy)ethyl) piperidine;
4-(4-Fluorobenzyl)-1-(2-(4-hydroxyphenoxy)ethyl) piperidine;
4-(4-Hydroxybenzyl)-1-(2-(4-fluorophenoxy)ethyl) piperidine;
4-Benzyl-1-(3-(4-hydroxyphenyl)propyl)piperidine;
4-(4-Chlorobenzyl)-1-(3-(4-hydroxyphenyl)propyl) piperidine;
4-Benzyl-1-(2-(4-hydroxyphenyl)ethyl)piperidine;
4-(3-Fluorobenzyl)-1-(2-(4-hydroxyphenoxy)ethyl) piperidine;
4-(3-Fluorobenzyl)-1-(2-(4-fluorophenoxy)ethyl)piperidine;
4-(4-Methylbenzyl)-1-(2-(4-hydroxyphenoxy)ethyl) piperidine;
4-(4-Ethylbenzyl)-1-(2-(4-hydroxyphenoxy)ethyl) piperidine;
4-(4-Methoxybenzyl)-1-(2-(4-hydroxyphenoxy)ethyl) piperidine;
4-(3,4-Difluorobenzyl)-1-(2-(4-hydroxyphenoxy)ethyl) piperidine;
4-(4-Fluorobenzyl)-4-hydroxy-1-(2-(4-hydroxyphenoxy) ethyl)piperidine;
4-(2-Fluorobenzyl)-1-(2-(4-hydroxyphenoxy)ethyl) piperidine;
4-(4-Trifluoromethylbenzyl)-1-(2-(4-hydroxyphenoxy) ethyl)piperidine;
4-(4-Isopropylbenzyl)-1-(2-(4-hydroxyphenoxy)ethyl) piperidine;
4-(4-t-Butylbenzyl)-1-(2-(4-hydroxyphenoxy)ethyl) piperidine;
4-(2-Fluoro-4-methylbenzyl)-1-(2-(4-hydroxyphenoxy) ethyl)piperidine;
4-((5,6,7,8-Tetrahydro-2-naphthyl)methyl)-1-(2-(4-hydroxyphenoxy)ethyl)piperidine;

4-((2-Naphthyl)methyl)-1-(2-(4-hydroxyphenoxy)ethyl) piperidine;
4-Benzyl-1-(2-(N-methylanilino)ethyl)piperidine;
4-Benzyl-1-(2-(thiophenoxy)ethyl)piperidine;
4-(4-Chlorobenzyl)-1-(2-(2-chloro-4-(2-hydroxyethyl) phenoxy)ethyl)piperidine;
4-(2,6-Difluorobenzyl)-1-(2-(4-hydroxyphenoxy)ethyl) piperidine;
4-(2-Fluoro-4-methylbenzyl)-1-(2-(4-hydroxy-3-methylphenoxy)ethyl)piperidine;
4-Benzyl-1-(2-(3,4-methylenedioxyphenoxy)ethyl) piperidine;
4-(2-Fluoro-4-methylbenzyl)-1(2-(3-fluoro-4-hydroxyphenoxy)ethyl)piperidine;
4-(4-Fluorobenzyl)-1-(2-(3-fluoro-4-hydroxyphenoxy) ethyl)piperidine;
4-(4-Methylbenzyl)-1-(2-(3-fluoro-4-hydroxyphenoxy) ethyl)piperidine;
4-(4-Fluorobenzyl)-1-(2-(4-hydroxy-3-methylphenoxy) ethyl)piperidine;
4-(4-Methylbenzyl)-1-(2-(4-hydroxy-3-methylphenoxy) ethyl)piperidine;
4-Hydroxy-4-(4-methylbenzyl)-1-(2-(4-hydroxyphenoxy) ethyl)piperidine;
4-Hydroxy-4-(4-methylbenzyl)-1-(2-(4-hydroxy-3-methylphenoxy)ethyl)piperidine;
4-Benzyl-1-(2-(2-hydroxyphenoxy)ethyl)piperidine;
4-Benzyl-1-(2-(3-hydroxyphenoxy)ethyl)piperidine;
4-(4-Fluorobenzyl)-1-(2-(2-hydroxyphenoxy)ethyl) piperidine;
4-(4-Fluorobenzyl)-1-(2-(3-hydroxyphenoxy)ethyl) piperidine;
4-(4-Methylbenzyl)-1-(2-(2-hydroxyphenoxy)ethyl) piperidine;
4-(4-Methylbenzyl)-1-(2-(3-hydroxyphenoxy)ethyl) piperidine;
4-Benzyl-1-(2-(N-methyl-4-hydroxyanilino)ethyl) piperidine;
4-Benzyl-4-hydroxy-1-(2-(4-hydroxyphenoxy)ethyl) piperidine;
4-(4-Fluorobenzyl)-1-(2-(4-hydroxythiophenoxy)ethyl) piperidine;
4-(4-Hydroxyphenyl)-1-(4-phenylbutyl)piperidine;
4-Benzyl-1-(3-(2-oxobenzimidazol-5-oxy)propyl) piperidine;
4-Benzyl-1-(2-(2-thioxobenzimidazol-5-oxy)ethyl) piperidine;
4-Benzyl-1-(2-(2-iminobenzimidazol-5-oxy)ethyl) piperidine;
4-(4-Methylbenzyl)-1-(2-(2-thioxobenzimidazol-5-oxy) ethyl)piperidine;
4-(4-Fluorobenzyl)-1-(2-(2-thioxobenzimidazol-5-oxy) ethyl)piperidine;
4-(4-Chlorobenzyl)-1-(2-(2-thioxobenzimidazol-5-oxy) ethyl)piperidine;
4-Benzyl-1-(2-(2-oxobenzoxazol-5-oxy)ethyl)piperidine;
4-Benzyl-1-(2-(2-oxobenzoxazol-6-oxy)ethyl)piperidine;
4-Benzyl-1-(2-(2-hydroxynaphth-6-oxy)ethyl)piperidine;
4-Benzyl-1-(2-(3-hydroxynaphth-6-oxy)ethyl)piperidine;
4-(4-Fluorobenzyl)-1-(2-(2-hydroxynaphth-6-oxy)ethyl) piperidine;
4-(4-Methylbenzyl)-1-(2-(2-hydroxynaphth-6-oxy)ethyl) piperidine;
4-Benzyl-1-(2-(3-methyl-2-oxobenzimidazol-5-oxy)ethyl) piperidine;
4-Benzyl-1-(2-(2-oxo-1,3-dihydroindol-5-oxy)ethyl) piperidine;
4-(4-Fluorobenzyl)-1(2-(2-oxo-1,3-dihydroindol-5-oxy) ethyl)piperidine; and
pharmaceutically acceptable salts thereof.

The invention is also directed to a method for treating disorders responsive to the selective blockade of NMDA receptor subtypes in animals suffering thereof. Particular preferred embodiments of the 4-substituted piperidine analogs for use in the method of this invention are represented by previously defined formulae (II–XI).

Exemplary preferred selective NMDA receptor subtype antagonist compounds that may be employed in the method of this invention include, without limitation:
1-(2-Phenoxyethyl)-4-phenylpiperidine;
1-(4-(3-(Trifluoromethyl)phenoxy)butyl)-4-phenylpiperidine;
4-Benzyl-1-(2-(4-chlorophenoxy)ethyl)piperidine;
4-Benzyl-1-(2-(4-nitrophenoxy)ethyl)piperidine;
1-(2-(4-Aminophenoxy)ethyl)-4-benzylpiperidine;
4-Benzyl-1-(2-(4-cyanophenoxy)ethyl)piperidine;
3-((2-(4-Benzylpiperidin-1-yl)ethyl)oxy)benzaldehyde;
3-((2-(4-Benzylpiperidin-1-yl)ethyl)oxy)benzaldehyde oxime;
4-Benzyl-1-(2-(3-(ethoxycarbonylmethyl)phenoxy)ethyl) piperidine;
4-Benzyl-1-(2-(3-(2-hydroxyethyl)phenoxy)ethyl) piperidine;
1-(2-(3-(Aminocarbonylmethyl)phenoxy)ethyl)-4-benzylpiperidine;
4-Benzyl-1-(2-(3-(hydrazinocarbonylmethyl)phenoxy) ethyl)piperidine;
4-Benzyl-1-(1-methyl-2-phenoxyethyl)piperidine;
4-Benzyl-1-(3-(3-fluorophenoxy)propyl)piperidine;
4-Benzyl-1-(4-(3-fluorophenoxy)butyl)piperidine;
4-(4-Chlorobenzyl)-1-(2-phenoxyethyl)piperidine;
4-(4-Chlorobenzyl)-1-(2-(4-fluorophenoxy)ethyl) piperidine;
4-(4-Chlorobenzyl)-1-(2-(4-chlorophenoxyethyl)piperidine;
4-(4-Chlorobenzyl)-1-(2-(4-nitrophenoxy)ethyl)piperidine;
1-(2-(4-Aminophenoxy)ethyl)-4-(4-chlorobenzyl) piperidine;
4-(4-Chlorobenzyl)-1-(2-(3-(2-hydroxyethyl)phenoxy) ethyl)piperidine;
4-(4-Chlorobenzyl)-1-(3-phenoxypropyl)piperidine;
4-(4-Chlorobenzyl)-1-(3-(3-fluorophenoxy)propyl) piperidine;
4-(4-Fluorobenzyl)-1-(2-(4-fluorophenoxy)ethyl)piperidine;
4-(4-Fluorobenzyl)-1-(2-(4-chlorophenoxy)ethyl) piperidine;
1-(2-(4-Fluorophenoxy)ethyl)-4-(4-methoxybenzyl) piperidine;
1-(2-(4-Fluorophenoxy)ethyl)-4-(4-nitrobenzyl)piperidine;
4-(4-Nitrobenzyl)-1-(3-phenoxypropyl)piperidine;
4-Benzyl-1-(1-methyl-3-phenoxypropyl)piperidine;
4-(4-Chlorophenyl)-4-hydroxy-1-(2-phenoxyethyl) piperidine;
1-(2-Phenoxyethyl)-4-phenylpiperidine;
4-(4-Chlorophenyl)-4-hydroxy-1-(3-phenoxypropyl) piperidine;
3-Hydroxy-1-(2-phenoxyethyl)-4-(3-trifluoromethylphenyl) piperidine;
3-Hydroxy-1-(3-phenoxypropyl)-4-(3-trifluoromethylphenyl)piperidine;
4-Benzyl-1-[2-(6-quinolinoxy)ethyl)]piperidine;
4-Benzyl-1-[2-(8-quinolinoxy)ethyl]piperidine;
4-Benzyl-1-[2-(2-amino-3-nitrophenoxy)ethyl]piperidine;
4-Benzyl-1-[2-(2,3-diaminophenoxy)ethyl]piperidine;
4-Benzyl-1-[2-(2,3-dioxoquinoxalin-5-oxy)ethyl] piperidine;

4-Benzyl-1-[2-(2-oxobenzimidazol-4-oxy)ethyl]piperidine;
4-Benzyl-1-[2-(4-amino-3-nitrophenoxy)ethyl]piperidine;
4-Benzyl-1-[2-(3,4-diaminophenoxy)ethyl]piperidine;
4-Benzyl-1-[2-(2,3-dioxoquinoxalin-6-oxy)ethyl] piperidine;
4-Benzyl-1-[2-(2-oxobenzimidazol-5-oxy)ethyl]piperidine;
4-Benzyl-1-[2-(2-nitrophenoxy)ethyl]piperidine;
4-Benzyl-1-[2-(2-aminophenoxy)ethyl]piperidine;
4-Benzyl-1-[2-(3-nitrophenoxy)ethyl]piperidine;
4-Benzyl-1-[2-(3-aminophenoxy)ethyl]piperidine;
4-Benzyl-1-[2-(4-nitrophenoxy)ethyl]piperidine;
4-Benzyl-1-[2-(4-aminophenoxy)ethyl]piperidine;
4-[2-(4-Benzylpiperidinoethoxy)quinazoline;
4-[2-(4-Benzylpiperidino)ethoxy]pyrazolo-[3,4-d] pyrimidine;
1-[2-(4-Benzylpiperidino)ethyl]-4-hydroxypyrazolo[3,4-d] pyrimidine;
4-Benzyl-1-[2-(2-methoxyphenoxy)ethyl]piperidine;
4-Benzyl-1-[2-(3-methoxyphenoxy)ethyl]piperidine;
4-Benzyl-1-[2-(4-methoxyphenoxy)ethyl]piperidine;
4-Benzyl-1-[2-(3,4-bisacet amidophenoxy)ethyl]piperidine;
4-Benzyl-1-[2-(2-methylbenzimidazol-6-oxy)ethyl] piperidine;
4-Benzyl-1-[2-(2-methylbenzimidazol-5-oxy)ethyl ]piperidine;
4-Benzyl-1-[2-(3-trifluoromethylphenoxy)ethyl]piperidine;
4-(4-Chlorobenzyl)-1-[2-(2-nitrophenoxy)ethyl]piperidine;
4-(4-Chlorobenzyl)-1-[2-(2-aminophenoxy)ethyl] piperidine;
4-(4-Chlorobenzyl)-1-[2-(2-amino-3-nitrophenoxy)ethyl] piperidine;
4-(4-Chlorobenzyl)-1-[2-(2,3-diaminophenoxy)ethyl] piperidine;
4-(4-Chlorobenzyl)-1-[2-(2-oxobenzimidazol-4-oxy)ethyl]- piperidine;
4-(4-Chlorobenzyl)-1-[2-(4-amino-3-nitrophenoxy)ethyl] piperidine;
4-(4-Chlorobenzyl)-1-[2-(3,4-diaminophenoxy)ethyl] piperidine;
4-(4-Chlorobenzyl)-1-[2-(2-oxobenzimidazol-5-oxy)ethyl]- piperidine;
4-(4-Fluorobenzyl)-1-[2-(2-oxobenzimidazol-5-oxy)ethyl]- piperidine;
4-Benzyl-1-(2-phenylethyl)piperidine;
1,4-Dibenzylpiperidine;
4-(4-Chlorophenyl)-4-hydroxy-1-(3-phenylpropyl) piperidine;
4-(4-Chlorophenyl)-4-hydroxy-1-(4-phenylbutyl) piperidine;
3-Hydroxy-1-(4-phenylbutyl)-4-(3-trifluoromethylphenyl)- piperidine;
4-Benzyl-4-hydroxy-1-(2-phenylethyl)piperidine;
1,4-Dibenzyl-4-hydroxypiperidine;
1-Benzyl-4-(4-fluorobenzyl)-4-hydroxypiperidine;
4-(4-Fluorobenzyl)-1-[2-(4-fluorophenyl)ethyl]-4-hydroxypiperidine;
4-(2-Keto-1-benzimidazolinyl)-1-(3-phenoxypropyl) piperidine;
4-Benzyl-1-(2-phenoxyethyl)piperidine;
4-Benzyl-1-(3-phenoxypropyl)piperidine;
4-Benzyl-1-(3-phenylpropyl)piperidine;
4-Benzyl-4-hydroxy-1-(2-phenoxyethyl)piperidine;
4-Benzyl-1-[2-hydroxy-3-(1-naphthyloxy)propyl] piperidine;
4-Benzyl-4-hydroxy-1-(3-phenylpropyl)piperidine;
4-Benzyl-4-hydroxy-1-(3-phenoxypropyl)piperidine;
4-Benzyl-1-[(2-hydroxy-4-phenyl)butyl]piperidine;
1-(3-Phenoxypropyl)-4-phenylpiperidine;
1-(4-Phenoxybutyl)-4-phenylpiperidine;
4-Phenoxy-1-[3-(4-fluorophenoxy)propyl]piperidine;
4-(2-Methoxyphenoxy)-1-(4-phenylbutyl)piperidine;
4-Benzyl-1-(4-phenylbutyl)piperidine;
4-[(3-Trifluoromethylphenyl)methyl]-1-[2-(3-aminophenoxy)ethyl]piperidine;
4-[(3-Trifluoromethylphenyl)methyl]-1-[3-(3-aminophenoxy)propyl]piperidine;
3-Hydroxy-4-(3-trifluoromethylphenyl)-1-[3-(3-aminophenoxy)propyl]piperidine;
3-Hydroxy-4-(4-fluorophenyl)-1-[3-(3-amino-1-naphthyloxy)propyl]piperidine;
4-Benzyl-1-(2-(4-hydroxyphenoxy)ethyl)piperidine;
4-(4-Chlorobenzyl)-1-(2-(4-hydroxyphenoxy)ethyl) piperidine;
4-(4-Fluorobenzyl)-1-(2-(4-hydroxyphenoxy)ethyl) piperidine;
4-(4-Hydroxybenzyl)-1-(2-(4-fluorophenoxy)ethyl) piperidine;
4-Benzyl-1-(3-(4-hydroxyphenyl)propyl)piperidine;
4-(4-Chlorobenzyl)-1-(3-(4-hydroxyphenyl)propyl) piperidine;
4-Benzyl-1-(2-(4-hydroxyphenyl)ethyl)piperidine;
4-(3-Fluorobenzyl)-1-(2-(4-hydroxyphenoxy)ethyl) piperidine;
4-(3-Fluorobenzyl)-1-(2-(4-fluorophenoxy)ethyl)piperidine;
4-(4-Methylbenzyl)-1-(2-(4-hydroxyphenoxy)ethyl) piperidine;
4-(4-Ethylbenzyl)-1-(2-(4-hydroxyphenoxy)ethyl) piperidine;
4-(4-Methoxybenzyl)-1-(2-(4-hydroxyphenoxy)ethyl) piperidine;
4-(3,4-Difluorobenzyl)-1-(2-(4-hydroxyphenoxy)ethyl) piperidine;
4-(4-Fluorobenzyl)-4-hydroxy-1-(2-(4-hydroxyphenoxy) ethyl)piperidine;
4-(2-Fluorobenzyl)-1-(2-(4-hydroxyphenoxy)ethyl) piperidine;
4-(4-Trifluoromethylbenzyl)-1-(2-(4-hydroxyphenoxy) ethyl)piperidine;
4-(4-Isopropylbenzyl)-1-(2-(4-hydroxyphenoxy)ethyl) piperidine;
4-(4-t-Butylbenzyl)-1-(2-(4-hydroxyphenoxy)ethyl) piperidine;
4-(2-Fluoro-4-methylbenzyl)-1-(2-(4-hydroxyphenoxy) ethyl)piperidine;
4-((5,6,7,8-Tetrahydro-2-naphthyl)methyl)-1-(2-(4-hydroxyphenoxy)ethyl)piperidine;
4-((2-Naphthyl)methyl)-1-(2-(4-hydroxyphenoxy)ethyl) piperidine;
4-Benzyl-1-(2-(N-methylanilino)ethyl)piperidine;
4-Benzyl-1-(2-(thiophenoxy)ethyl)piperidine;
4-(4-Chlorobenzyl)-1-(2-(2-chloro-4-(2-hydroxyethyl) phenoxy)ethyl)piperidine;
4-(2,6-Difluorobenzyl)-1-(2-(4-hydroxyphenoxy)ethyl) piperidine;
4-(2-Fluoro-4-methylbenzyl)-1-(2-(4-hydroxy-3-methylphenoxy)ethyl)piperidine;
4-Benzyl-1-(2-(3,4-methylenedioxyphenoxy)ethyl) piperidine;
4-(2-Fluoro-4-methylbenzyl)-1-(2-(3-fluoro-4-hydroxyphenoxy)ethyl)piperidine;
4-(4-Fluorobenzyl)-1-(2-(3-fluoro-4-hydroxyphenoxy) ethyl)piperidine;
4-(4-Methylbenzyl)-1-(2-(3-fluoro-4-hydroxyphenoxy) ethyl)piperidine;

4-(4-Fluorobenzyl)-1-(2-(4-hydroxy-3-methylphenoxy)ethyl)piperidine;
4-(4-Methylbenzyl)-1-(2-(4-hydroxy-3-methylphenoxy)ethyl)piperidine;
4-Hydroxy-4-(4-methylbenzyl)-1-(2-(4-hydroxyphenoxy)ethyl)piperidine;
4-Hydroxy-4-(4-methylbenzyl)-1-(2-(4-hydroxy-3-methylphenoxy)ethyl)piperidine;
4-Benzyl-1-(2-(2-hydroxyphenoxy)ethyl)piperidine;
4-Benzyl-1-(2-(3-hydroxyphenoxy)ethyl)piperidine;
4-(4-Fluorobenzyl)-1-(2-(2-hydroxyphenoxy)ethyl)piperidine;
4-(4-Fluorobenzyl)-1-(2-(3-hydroxyphenoxy)ethyl)piperidine;
4-(4-Methylbenzyl)-1-(2-(2-hydroxyphenoxy)ethyl)piperidine;
4-(4-Methylbenzyl)-1-(2-(3-hydroxyphenoxy)ethyl)piperidine;
4-Benzyl-1-(2-(N-methyl-4-hydroxyanilino)ethyl)piperidine;
4-Benzyl-4-hydroxy-1-(2-(4-hydroxyphenoxy)ethyl)piperidine;
4-(4-Fluorobenzyl)-1-(2-(4-hydroxythiophenoxy)ethyl)piperidine;
4-(4-Hydroxyphenyl)-1-(4-phenylbutyl)piperidine;
4-Benzyl-1-(3-(2-oxobenzimidazol-5-oxy)propyl)piperidine;
4-Benzyl-1-(2-(2-thioxobenzimidazol-5-oxy)ethyl)piperidine;
4-Benzyl-1-(2-(2-iminobenzimidazol-5-oxy)ethyl)piperidine;
4-(4-Methylbenzyl)-1-(2-(2-thioxobenzimidazol-5-oxy)ethyl)piperidine;
4-(4-Fluorobenzyl)-1-(2-(2-thioxobenzimidazol-5-oxy)ethyl)piperidine;
4-(4-Chlorobenzyl)-1-(2-(2-thioxobenzimidazol-5-oxy)ethyl)piperidine;
4-Benzyl-1-(2-(2-oxobenzoxazol-5-oxy)ethyl)piperidine;
4-Benzyl-1-(2-(2-oxobenzoxazol-6-oxy)ethyl)piperidine;
4-Benzyl-1-(2-(2-hydroxynaphth-6-oxy)ethyl)piperidine;
4-Benzyl-1-(2-(3-hydroxynaphth-6-oxy)ethyl)piperidine;
4-(4-Fluorobenzyl)-1-(2-(2-hydroxynaphth-6-oxy)ethyl)piperidine;
4-(4-Methylbenzyl)-1-(2-(2-hydroxynaphth-6-oxy)ethyl)piperidine;
4-Benzyl-1-(2-(3-methyl-2-oxobenzimidazol-5-oxy)ethyl)piperidine;
4-Benzyl-1-(2-(2-oxo-1,3-dihydroindol-5-oxy)ethyl)piperidine;
4-(4-Fluorobenzyl)-1-(2-(2-oxo-1,3-dihydroindol-5-oxy)ethyl)piperidine; and pharmaceutically acceptable salts thereof.

The compounds of this invention may be prepared using methods well known to those skilled in the art. Exemplary reaction schemes I, II, and III illustrate methods for preparing the compounds of this invention. The starting materials employed in Schemes I, II and III are readily available or can be prepared by known methods.

Scheme I.

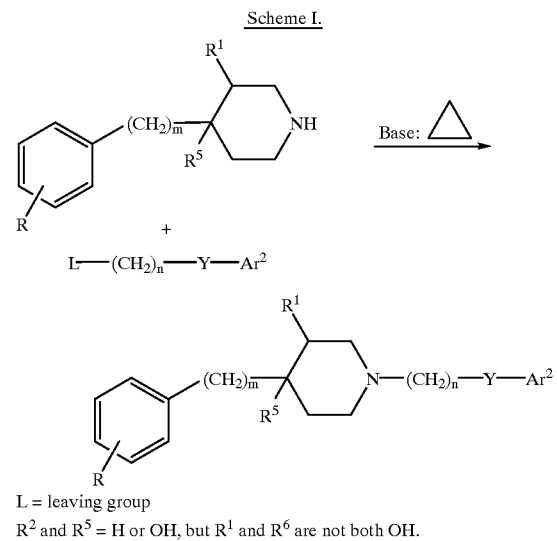

L = leaving group
$R^2$ and $R^5$ = H or OH, but $R^1$ and $R^6$ are not both OH.

Scheme II.

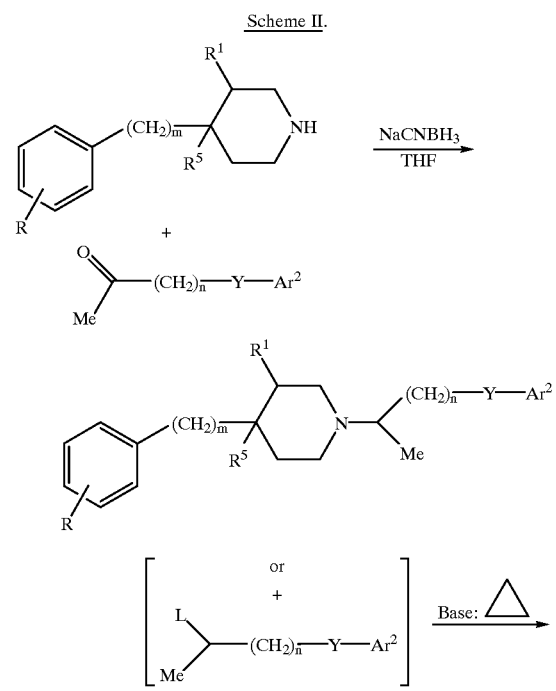

Scheme III.

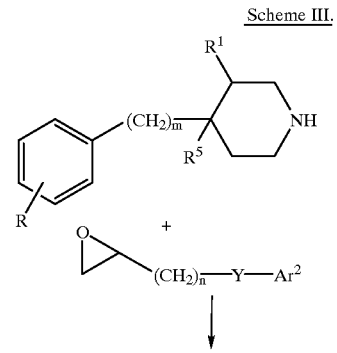

-continued

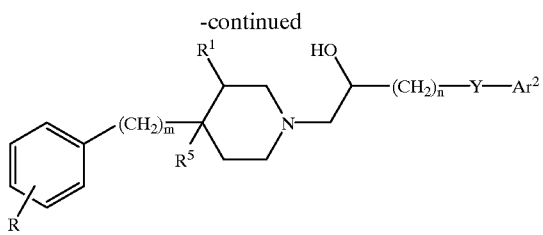

The compounds of the present invention are useful in treating or preventing neuronal loss, neurodegenerative diseases and chronic pain. They are also useful as anticonvulsants and for inducing anesthesia, as well as for treating epilepsy and psychosis. The therapeutic and side effect profiles of subtype-selective NMDA receptor subtype antagonists and agonists should be markedly different from the more non-subtype selective NMDA receptor inhibitors. The subtype-selective analogs of the present invention are expected to exhibit little or no untoward side effects caused by non-specific binding with other receptors, particularly, the PCP and glutamate bindings sites associated with the NMDA receptor. In addition, selectivity for different NMDA receptor subtypes will reduce side effects such as sedation that are common to non-subtype-selective NMDA receptor antagonists. The compounds of the present invention are effective in treating or preventing the adverse consequences of the hyperactivity of the excitatory amino acids, e.g. those which are involved in the NMDA receptor system, by preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease, Parkinson's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier which makes them particularly useful for treating or preventing conditions involving the central nervous system.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The selective NMDA receptor subtype antagonists, agonists and modulators may be tested for in vivo anticonvulsant activity after intraperitoneal or intravenous injection using a number of anticonvulsant tests in mice (audiogenic seizure model in DBA-2 mice, pentylenetetrazol-induced seizures in mice, maximum electroshock seizure test (MES) or NMDA-induced death). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the rodent. It is expected that such results will suggest that the selective NNDA receptor subtype antagonists and agonists of the present invention do not show the PCP-like behavioral side effects that are common to NMDA channel blockers such as MK-801 and PCP or to competitive NMDA antagonists such as CGS 19755.

The selective NMDA receptor subtype antagonists and agonists are also expected to show potent activity in vivo after intraperitoneal or intravenous injection suggesting that these compounds can penetrate the blood/brain barrier.

Elevated levels of glutamate has been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment of glaucoma. Preferably, the invention is directed to the treatment of patients which have primary open-angle glaucoma, chronic closed-angle glaucoma, pseudo doexfoliation, or other types of glaucoma or ocular hypertension. Preferably, the compound is administered over an extended period (e.g. at least six months and preferably at least one year), regardless of the changes in the patient's intraocular pressure over the period of administration. The compounds of the present invention are also useful in treating CMV retinitis, particularly in combination with antiviral agents. CMV afflicts the ganglion cell layer which may result in higher levels of glutamate. Thus, NMDA receptor antagonists could block retinitis by blocking the toxicity effect of high levels of glutamate.

Aminoglycoside antibiotics have been used successfully in the treatment of serious Gram-negative bacterial infections. However, prolonged treatment with these antibiotics will result in the destruction of sensory hearing cells of the inner ear and consequently, induce permanent loss of hearing. A recent study of Basile, et al. (Nature Medicine, 2:1338–1344, 1996) indicated that amioglycosides produce a polyamine-like enhancement of glutamate excitotoxicity through their interaction with the NMDA receptor. Thus, compounds of the present invention with NMDA receptor antagonist activity will be useful in preventing aminoglycoside antibiotics-induced hearing loss by antagonizing their interaction with the receptor.

The compounds of the present invention are useful in treating headaches, in particular, migraine headaches. During migraine attack, a sensory disturbance with unique changes of brain blood flow will result in the development of characteristic migraine auras. Since this unique phenomena has been replicated in animal experiments with cortical-spreading depression (CSD) of Leaó, A.A.P.J., Neurophysiol. 7:359–390 (1944), CSD is considered an important phenomena in the pathophysiology of migraine with aura (Tepley et al., In: Biomagnetism, eds. S. Williamson, L. Kaufmann, pp. 327–330, Plenum Press, New York (1990)). The CSD is associated with the propagation (2~6 mm/s) of transient changes in electrical activity which relate to the failure of ion homoestatis in the brain, efflux of excitatory amino acids from the neurons and increased energy metabolism (Lauritzen, M., Acta Neurol. Scand. 76 (Suppl. 113) :4–40 (1987)). It has been demonstrated that the initiation of CSD in a variety of animals, including humans, involved the release of glutamate and could be triggered by NMDA (Curtis et al., Nature 191:1010–1011 (1961); and Lauritzen et al., Brain Res. 475:317–327 (1988)). Subtype selective NMDA antagonists will be therapeutically useful for migraine headache because of their expected low side effects, their ability to cross the blood brain barrier and their systemic bioavailability.

Bladder activity is controlled by parasympathetic preganglionic neurons in the sacral spinal cord (DeGroat et al., J. Auton. Nerv. Sys. 3:135–160(1981)). In humans, it has been shown that the highest density of NMDA receptors in the spinal cord are located at the sacral level, including those areas that putatively contain bladder parasympathetic preganglionic neurons (Shaw et al., Brain Research 539:164–168 (1991)). Because NMDA receptors are excitatory in nature, pharmacological blockade of these receptors would suppress bladder activity. It has been shown that the noncompetitive NMDA receptor antagonist MK801 increased the frequency of micturition in rat (Vera and Nadelhaft, Neuroscience Letters 134:135–138(1991)). In addition, competitive NMDA receptor antagonists have also been shown to produce a dose-dependent inhibition of bladder and of urethral sphincter activity (U.S. Pat. No. 5,192,751). Thus, it is anticipated that subtype-selective NMDA receptor antagonists will be effective in the treatment of urinary incontinence mediated by their modulation on the receptor channel activity.

Non-competitive NMDA receptor antagonist MK801 has been shown to be effective in a variety of animal models of anxiety which are highly predictive of human anxiety (Clineschmidt, B. V. et al., Drug Dev. Res. 2:147–163 (1982)). In addition, NMDA receptor glycine site antagonists are shown to be effective in the rat protentiated startle test (Anthony, E. W., Eur. J. Pharmacol. 250:317–324 (1993)) as well as several other animal anxiolytic models (Winslow, J. et al, Eur. J. Pharmacol. 190:11–22 (1990); Dunn, R. et al., Eur. J. Pharmacol. 214:207–214 (1992); and Kehne, J. H. et al, Eur. J. Pharmacol. 193:283–292 (1981)).

Glycine site antagonists, (+) HA-966 and 5,7-dichlorokynurenic acid were found to selectively antagonize d-amphetamine induced stimulation when injected into rat nucleus accumbens but not in striatum (Hutson, P. H. et al., Br. J. Pharmacol. 103:2037–2044 (1991)). Interestingly, (+) HA-966 was also found to block PCP and MK801-induced behavioral arousal (Bristow, L. J. et al., Br. J. Pharmacol, 108:1156–1163 (1993)). These findings suggest that a potential use of NMDA receptor channel modulators, but not channel blockers, as atypical neuroleptics.

It has been shown that in an animal model of Parkinson's disease—MPP$^+$ or methamphetamine-induced damage to dopaminergic neurons—can be inhibited by NMDA receptor antagonists (Rojas et al., Drug Dev. Res. 29:222–226 (1993); and Sonsalla et al, Science 243:398–400 (1989)). In addition, NMDA receptor antagonists have been shown to inhibit haloperidol-induced catalepsy (Schmidt, W. J. et al., Amino Acids 1:225–237 (1991)), increase activity in rodents depleted of monoamines (Carlsson et al., Trends Neurosci. 13:272–276 (1990)) and increase ipsilateral rotation after unilateral substantia nigra lesion in rats (Snell, L. D. et al., J. Pharmacol. Exp. Ther. 235:50–57 (1985)). These are also experimental animal models of Parkinson's disease. In animal studies, the antiparkinsonian agent amantadine and memantine showed antiparkinsonian-like activity in animals at plasma levels leading to NMDA receptor antagonism (Danysz, W. et al., J. Neural Trans. 7:155–166, (1994)). Thus, it is possible that these antiparkinsonian agents act therapeutically through antagonism of an NMDA receptor. Therefore, the balance of NMDA receptor activity maybe important for the regulation of extrapyramidal function relating to the appearance of parkinsonian symptoms.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., Science 162:1011–1012 (1968); Way et al., J. Pharmacol. Exp Ther. 167:1–8 (1969); Huidobro et al., J. Pharmacol. Exp Ther. 198:318–329 (1976); Lutfy et al., J. Pharmacol. Exp Ther. 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block toleranfce without interference with analgesia is an active area of research.

Recent studies have suggested a modulatory role for the NMDA receptor in morphine tolerance. (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993); Herman et al., Neuropsychopharmacology 12:269–294 (1995).) Further, it has been reported that NMDA receptor antagonists are useful for inhibiting opioid tolerance and some of the symptoms of opioid withdrawal. Thus, the present invention is also directed to the administration of the compounds described herein to inhibit opiate tolerance and to treat or ameliorate the symptoms of opiate withdrawal by blocking the glycine co-agonist site associated with the NMDA receptor.

Thus, the present invention is directed to compounds having high affinity to a particular NMDA receptor subtype and low affinity to other sites such as dopamine and other catecholamine receptors. According to the present invention, those compounds having high binding to a particular NMDA subunit exhibit an $IC_{50}$ of about 100 $\mu$M or less in an NMDA subunit binding assay (see Table 1). Preferably, the compounds of the present invention exhibit a selective subunit $IC_{50}$ of 10 $\mu$M or less. Most preferably, the compounds of the present invention exhibit a selective subunit $IC_{50}$ of about 1.0 $\mu$M or less.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder and post traumatic stress disorders. Preferably, about 0.01 to about 10 mg/kg is orally administered to treat or prevent such disorders or for schizophrenia or other psychoses. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, to treat or prevent glaucoma or urinary incontinence, as well as for the treatment of Alzheimer's disease, amyotrophic lateral sclerosis, Huntington's disease, Parkinson's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, either as an acute intravenous injection, intravenous infusion, or on a regimen of 1–4 times per day. When used to treat chronic pain, migraine headache, to induce anesthesia, to treat or prevent opiate tolerance or to treat opiate withdrawal, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular selective NMDA receptor subtype antagonist or agonist of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of NMDA subunit binding sites in vitro has been difficult because of the lack of selective drug ligands. Thus, the compounds of the present invention may be used to characterize the NMDA subunits and their distribution. Particularly preferred subtype-selective NMDA receptor antagonists and agonists of the present invention which may be used for this purpose are isotopically radio-labelled derivatives, e.g., where one or more of the atoms are replaced with $^3H$, $^{11}C$, $^{14}C$, $^{15}N$, or $^{18}F$.

Electrophysiological Assays at NMDA Receptor Subunits

Preparation of RNA. cDNA clones encoding the NR1A, NR2A, NR2B, NR2C and NR2D rat NMDA receptor subtypes were provided by Dr. P. H. Seeburg (see, Moriyoshi et al., *Nature* (Lond.) 354:31–37 (1991); Kutsuwada et al., *Nature* (Lond.) 358:36–41 (1992) Monyer et al., *Science* (Washington, D.C.) 256:1217–1221 (1992); Ikeda et al., *FEBS Lett*. 313:34–38 (1992); Ishii et al., *J. Biol. Chem*. 268:2836–2843 (1993) for details of these clones or their mouse homologs). The clones were transformed into appropriate host bacteria and plasmid preparations were made with conventional DNA purification techniques. A sample of each clone was linearized by restriction enzyme digestion and cRNA was synthesized with T3 RNA polymerase. The cRNA was diluted to 400 ng/μl and stored in 1 μl aliquots at −80° C. until injection.

The Xenopus oocyte expression system. Mature female *Xenopus laevis* were anaesthetized (20–40 min) using 0.15% 3-aminobenzoic acid ethyl ester (MS-222) and 2–4 ovarian lobes were surgically removed. Oocytes at developmental stages IV–VI (Dumont, J. N., *J. Morphol*. 136:153–180 (1972)), were dissected from the ovary still surrounded by enveloping ovarian tissues. Follicle-enclosed oocytes were micro-injected with 1:1 mixtures of cRNA:NR1A+NR2A, 2B, 2C or 2D; injecting ~2,5, or 20 ng of RNA encoding each receptor subunit. NR1A encoding cRNA was injected alone at ~20 ng. Oocytes were stored in Barth's medium containing (in mM):NaCl, 88; KCl, 1; CaCl$_2$, 0.41; Ca(NO$_3$)$_2$, 0.33; MgSO$_4$, 0.82 NaHCO$_3$, 2.4; HEPES 5, pH 7.4, with 0.1 mg/ml gentamicin sulphate. While oocytes were still surrounded by enveloping ovarian tissues the Barth's medium was supplemented with 0.1% bovine serum. Oocytes were defolliculated 1–2 days following injections by treatment with collagenase (0.5 mg/ml Sigma Type I for 0.5–1 hr) (Miledi and Woodward, *J. Physiol*. (Lond.) 416:601–621 (1989)) and subsequently stored in serum-free medium.

Electrical recordings were made using a conventional two-electrode voltage clamp (Dagan TEV-200) over periods ranging between 3–21 days following injection. (Woodward et al., *Mol. Pharmacol*. 41: 89–103 (1992)). Oocytes were placed in a 0.1 ml recording chamber continuously perfused (5–15 ml min$^{-1}$) with frog Ringer's solution containing (in mM):NaCl, 115; KCl, 2; CaCl$_2$, 1.8; HEPES, 5; pH 7.4. Drugs were applied by bath perfusion. Using oocytes expressing different subunit combinations of NMDA receptor, NMDA currents were activated by co-application of glutamate (100 μm) and glycine (1–100 μm). Inhibitory potency of the novel antagonists was assessed on responses elicited by fixed concentrations of glutamate and glycine, by measuring reductions in current induced by progressively increasing concentrations of antagonist. Concentration-inhibition curves were fit with equation 1.

$$I/I_{control}=1/(1+([antagonist]/10^{-pIC50})^n) \quad \text{Eq. 1}$$

in which $I_{control}$ is the current evoked by agonists alone, $pIC_{50}=-\log IC_{50}$, $IC_{50}$ is the concentration of antagonist that produces half maximal inhibition, and n is the slope factor. (De Lean et al., *Am. J. Physiol*. 235:E97–102 (1978)). For incomplete curves analysis by fitting was unreliable and $IC_{50}$ values were calculated by simple regression over linear portions of the curves (Origin: Microcal Software).

Induction of Focal Ischemia

Rats were intubated and maintained under anesthesia with 2% of halothane. Body temperature was maintained at 37.5° C. during surgery by means of a warming pad and a rectal probe connected to the control unit. The common carotid arteries (CCA) were isolated, and a loose silk ligature was placed around each CCA. A vertical skin incision was made between the left orbit and the auditory canal. The posterior part of the zygoma was removed and a small opening (2.0–2.5 mm) was drilled dorsorostrally to the foramen ovale under constant saline irrigation. The dura was opened with a microsurgical hook and the brain gently retracted to expose the bifurcation of the internal carotid artery and the middle cerebral artery (MCA). The ipsilateral CCA was ligated and the MCA coagulated from its origin to the olfactory tract. The contralateral CCA was occluded with an arterial clip. All cuts were sutured and an i.v. line was connected to an infusion pump for delivery of the compound of the invention. Two hours after MCA occlusion, the clip on the contralateral CCA was removed. Rectal temperature was measured 2 hours after MCA occlusion (MCA-0).

Maximal Electroshock-induced Seizures

Seizures were induced by application of current (50 mA, 60 pulses/sec, 0.8 sec pulse width, 1 sec duration, d.c.) through saline-coated corneal electrodes using a Ugo Basile ECT device (Model 7801). Mice were restrained by gripping the loose skin on their dorsal surface, electrodes were held lightly against the two cornea, then current was applied and mice were observed for a period of up to 30 sec for the occurrence of a tonic hindlimb extensor response. A tonic seizure was defined as a hindlimb extension in excess of 90 degrees from the plane of the body. Results were treated in a quantal manner.

The examples which follow are intended as an illustration of certain preferred embodiments of the invention, and no limitation of the invention is implied.

EXAMPLE 1

4-Benzyl-1-(2-phenoxyethyl)piperidine

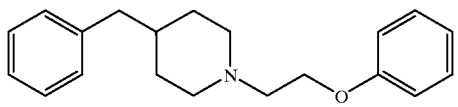

4-Benzylpiperidine was treated with 1-bromo-2-phenoxyethane and excess potassium carbonate as a solution in methylethylketone and heated at reflux for 12 hours. Standard workup and chromatography gave the title compound.

EXAMPLE 2

4-Benzyl-1-(3-phenoxypropyl)piperidine

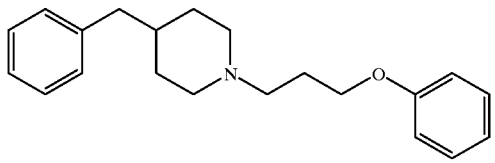

A solution of 4-benzylpyridine and 1-bromo-3-phenoxypropane in acetone was stirred at room temperature overnight. After removal of the solvent, the residue was dissolved in ethanol and treated with sodium borohydride to give the tetrahydropyridine adduct. Reduction of the double bond was accomplished in MeOH under a hydrogen atmosphere (50 psi) using 10% Pd-C as a catalyst to give the title compound.

EXAMPLE 3

4-Benzyl-1-[2-hydroxy-3-(1-naphthyloxy)propyl]piperidine

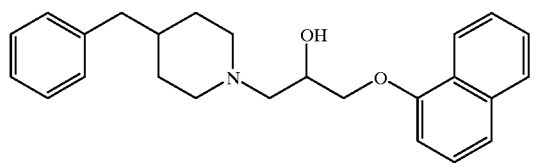

A mixture of 1-naphthyl alcohol, chloromethyloxirane, potassium carbonate and methylethylketone was heated at reflux for 5 hours to give 2-(1-naphthyloxy)methyloxirane. This intermediate was treated with 4-benzylpiperidine to give the title compound.

EXAMPLE 4

4-Benzyl-1-[(2-hydroxy-4-phenyl)butyl]piperidine

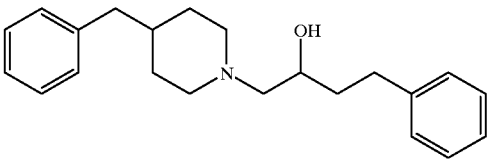

A solution of 4-phenyl-1-butene in chloroform was treated with m-chloroperbenzoic acid and stirred for 1.5 hours. Standard workup and chromatography gave the epoxide. Condensation of the epoxide and 4-benzylpiperidine in refluxing toluene gave the title compound.

EXAMPLE 5

4-Phenoxy-1-[(4-fluorophenoxy)propyl]piperidine

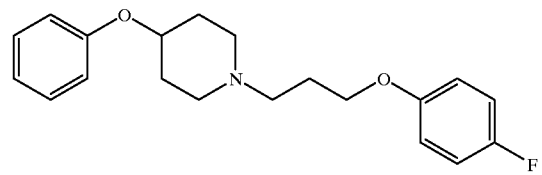

A mixture of 4-phenoxypyridine and benzylbromide in acetone was stirred overnight at room temperature. After removal of the solvent, the residue was dissolved in methanol, cooled to −20° C. and treated portionwise with sodium borohydride, and warmed to 0° C. After a standard workup and purification, the resulting tetrahydropyridine adduct was dissolved in methanol and hydrogenated using 20% Pd-C as a catalyst to provide 4-phenoxypiperidine. A mixture of 4-phenoxypiperidine and 1-bromo-3-(4-fluorophenoxy)propane in acetone with excess potassium carbonate was heated at reflux for 12 hours to give the title compound.

EXAMPLE 6

4-(2-Methoxyphenoxy)-1-(4-phenylbutyl)piperidine

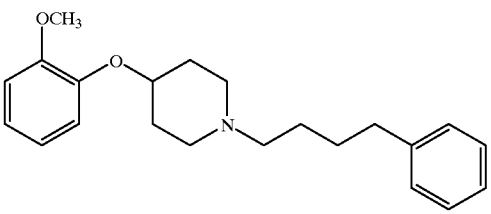

A solution of 4-(2-methoxyphenoxy)pyridine was treated with 1-bromo-4-phenylbutane in acetone to give the pyridinium salt. Sequential reduction with sodium borohydride in ethanol and catalytic hydrogenation using 10% Pd-C as a catalyst in methanol gave the title compound.

EXAMPLE 7

1-(3-Phenoxypropyl)-4-phenylpiperidine

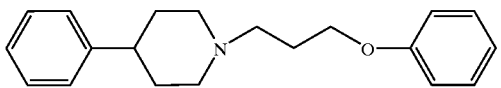

A mixture of 3-phenoxypropyl bromide (224 mg, 1.04 mmol), 4-phenylpiperidine (140 mg, 0.870 mmol) and $K_2CO_3$ (264 mg, 1.91 mmol) in 15 mL of EtOH was refluxed under $N_2$ for 12 hr. The inorganic salt was removed through a short column of silica gel and washed with EtOAc (3×15 mL). The filtrate was evaporated in vacuo to give a residue, which was purified by flash chromatography giving the title as a pale yellow oil (165 mg, 64%): $^1$H NMR (CDCl$_3$) 1.90 (m, 4 H), 2.10 (m, 4 H), 2.55 (m, 1H), 2.70 (bs, 2 H), 3.20 (bs, 2 H), 4.05 (m, 2 H), 6.92 (m, 4 H), 7.29 (m, 6 H).

EXAMPLE 8

1-(2-Phenoxyethyl)-4-phenylpiperidine

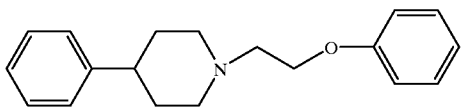

The compound was prepared in a manner similar to example 7. From 2-phenoxyethyltosylate (380 mg, 1.30 mmol) and 4-phenylpiperidine (167 mg, 1.04 mmol) there was obtained the amine as a pale yellow oil (224 mg, 77%): $^1$H NMR (CDCl$_3$) 1.91 (m, 4 H), 2.40 (bs, 2 H), 2.60 (m, 1H), 3.00 (bs, 2 H), 3.25 (bs, 2 H), 4.25 (m, 2 H), 6.94 (m, 4 H), 7.30 (m, 6 H).

EXAMPLE 9

1-(4-Phenoxybutyl)-4-phenylpiperidine

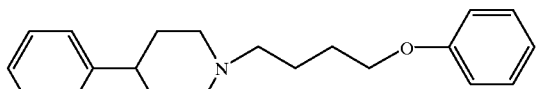

The compound was prepared in a manner similar to example 7. From 4-phenoxybutyl bromide (256 mg, 1.12 mmol) and 4-phenylpiperidine (150 mg, 0.930 mmol) there was obtained the amine as a pale yellow oil (solidified after standing overnight, 196 mg, 68%): $^1$H NMR (CDCl$_3$) 1.88 (m, 10 H), 2.10 (m, 1 H), 3.00 (bs, 2 H), 3.20 (bs, 2 H), 4.00 (m, 2 H), 6.91 (m, 4 H), 7.26 (m, 6 H).

EXAMPLE 10

1-(4-(3-(Trifluoromethyl)phenoxy)butyl)-4-phenylpiperidine hydrobromide

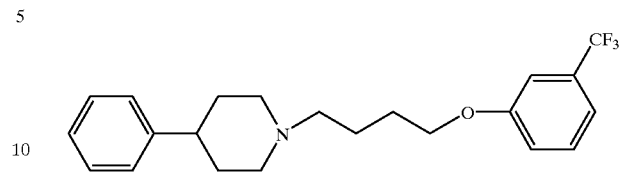

The compound was prepared in a manner similar to example 7. From 1-bromo-4-(3-(trifluoromethyl) phenoxy) butane (387 mg, 1.30 mmol) and 4-phenylpiperidine (140 mg, 0.870 mmol) there was obtained the amine as a pale yellow oil (82 mg, 25%). The oil was dissolved in 2 mL of EtOH. To this solution was added 4 mL of 1.2 M HBr in MeOH. The resulting solution was allowed to stir at rt for 2 hr. The MeOH was evaporated in vacuo to dryness. Ether (15 mL) was added to the residue and was stirred overnight. The solid was collected by filtration and dried to give the product (110 mg, 100%): mp 134–136° C.; $^1$H NMR (CDCl$_3$) 1.94 (m, 2 H), 2.08 (m, 2 H), 2.22 (bs, 2 H), 2.75–2.86 (m, 5 H), 3.10 (m, 2 H), 3.76 (m, 2 H), 4.04 (m, 2 H), 7.10–7.41 (m, 9 H), 11.52 (bs, 1 H). Anal. Calcd for $C_{22}H_{27}NBrF_3O$: C, 57.65; H, 5.94; N, 3.06. Found: C, 57.37; H, 5.65; N, 3.10.

EXAMPLE 11

4-Benzyl-1-(2-(4-chlorophenoxy)ethyl)piperidine hydrochloride

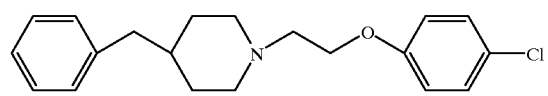

The compound was prepared in a manner similar to example 7. From 4-benzylpiperidine (500 mg, 2.85 mmol, Aldrich) and 2-(4-chlorophenoxy)ethyl bromide (704 mg, 2.99 mmol) there was obtained the amine as a pink oil which solidified upon scratching with a glass rod (835 mg, 89%): mp 72–73° C.; The hydrochloride salt was prepared in a manner similar to example 10 as a fluffy, colorless, crystalline solid, mp 177–178° C.; $^1$H NMR (CDCl$_3$) 1.55–2.17 (m, 5 H), 2.50–2.82 (m, 4 H), 3.20–3.55 (m, 2 H), 3.65 (d, J=12 Hz, 2 H), 4.53 (t, J=4.2 Hz, 2 H), 6.80 (d, J=8.7 Hz, 2 H), 7.00–7.18 (m, 7 H), 12.68 (bs, 1 H). Anal. Calcd for $C_{20}H_{25}Cl_2NO$: C, 65.57; H, 6.88; N, 3.82. Found: C,65.45, H.7.08, N,3.80

EXAMPLE 12

4-Benzyl-1-(2-(4-nitrophenoxy)ethyl)piperidine hydrobromide

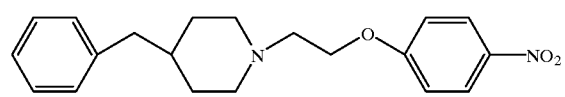

The compound was prepared in a manner similar to example 10. From 4-benzylpiperidine (1.00 g, 5.70 mmol) and 1-bromo-2-(4-nitrophenoxy)ethane (1.47 g, 5.98 mmol)

there was obtained the title compound as a colorless solid (1.82 g, 76%): mp 155–157° C.; $^1$H NMR (CDCl$_3$) 1.16–2.21 (m, 5 H), 2.58–2.89 (m, 4 H), 3.25–3.78 (m, 4 H), 4.74 (t, J=4.2 Hz, 2 H), 6.90–7.35 (m, 7 H), 8.20 (d, J=9.0 Hz, 2 H). Anal. Calcd for C$_{20}$H$_{25}$BrN$_2$O$_3$: C, 57.01; H, 5.98; N, 6.65. Found: C, 57.15; H, 6.03; N, 6.61.

EXAMPLE 13

1-(2-(4-Aminophenoxy)ethyl)-4-benzylpiperidine dihydrobromide

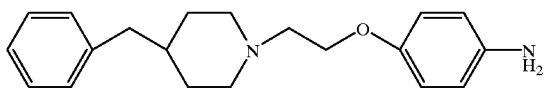

A mixture of 4-benzyl-1-(2-(4-nitrophenoxy)ethyl) piperidine hydrobromide (900 mg, 2.14 mmol) and Pd/C (10%; 100 mg) in MeOH (50 mL) was shaken under H$_2$ (20–30 psi, Parr) for 2.25 h at 25° C. The catalyst was removed by filtration (Celite). The resulting solution was acidified with a dilute solution of HBr in MeOH. The MeOH was removed in vacuo (rotoevap) to give a syrup. Ether (45 mL) was added and the resulting mixture was vigorously stirred at 25° C. for 48 h. A gray suspension was obtained. The solid was collected, washed with ether (3×3 mL) and dried in vacuo (0.005 Torr, 56° C.) to give a beige powder (606 mg, 60%): mp>130° C.; $^1$H NMR (DMSO-d$_6$) 1.33–1.88 (m, 5 H), 2.38–3.75 (m, 8 H), 4.25–4.45 (m, 2 H), 7.04–7.38 (m, 9 H), 9.49–10.30 (m, 4 H).

EXAMPLE 14

4-Benzyl-1-(2-(4-cyanophenoxy)ethyl)piperidine

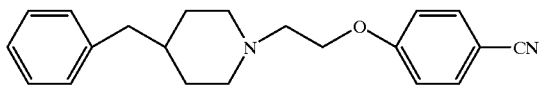

The compound was prepared in a manner similar to example 7. From 2-(4-cyano-phenoxy)ethyl bromide (2.26 g, 10.0 mmol) and 4-benzylpiperidine (1.75 g, 10.0 mmol) there was obtained the amine as a solid (2.2 g, 69%): mp 83–85° C.; $^1$H NMR (CDCl$_3$) 1.37 (m, 2 H), 1.60 (m, 1 H), 1.63 (m, 2 H), 2.08 (m, 2 H), 2.53 (d, J=6.6 Hz, 2 H), 2.81 (m, 2 H), 3.00 (d, J=10.8 Hz, 2 H), 4.15 (t, J=4.8 Hz, 2 H), 6.92 (d, J=8.4 Hz, 2 H), 7.15 (m, 5 H), 7.55 (d, J=8.7 Hz, 2 H).

EXAMPLE 15

3-((2-(4-Benzylpiperidin-1-yl)ethyl)oxy) benzaldehyde hydrochloride

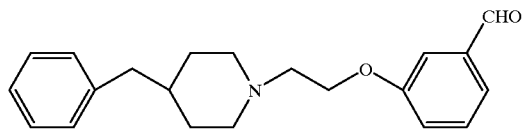

A) 3-((2-Bromoethyl)oxy)benzaldehyde. A mixture of 3-hydroxybenzaldehyde (4.88 g, 40.0 mmol), 1,2-dibromoethane (75.2 g, 400 mmol) and K$_2$CO$_3$ (13.8 g, 100 mmol) in 50 mL of acetonitrile was allowed to reflux under N$_2$ for 2 days. The inorganic salt was removed through a short column of silica gel and washed with EtOAc (3×50 mL). Evaporation of solvent gave a residue, which was purified by flash chromatography giving the product as a pale yellow oil (7.65 g, 84%): $^1$H NMR (CDCl$_3$) 3.67 (t, J=6.3 Hz, 2 H), 4.36 (t, J=6.3 Hz, 2 H), 7.20–7.49 (m, 4 H), 9.98 (s, 1 H).

B) 3-((2-Bromoethyl)oxy)benzaldehyde ethylene acetal. To a solution of 3-((2-bromoethyl)oxy)benzaldehyde (2.29 g, 10.0 mmol) in 50 mL of dry benzene were added ethylene glycol (1.22 mL, 22.0 mmol) and of p-toluenesulfonic acid (50 mg). The resulting solution was allowed to reflux for 2 days. The solution was washed with saturated NaHCO$_3$ solution (2×20 mL) and dried over Na$_2$SO$_4$. Evaporation of solvent gave the product as pale yellow oil (2.24 g, 82%): $^1$H NMR (CDCl$_3$) 3.64 (t, J=6.3 Hz, 2 H), 4.03 (m, 2 H), 4.13 (m, 2 H), 4.31 (t, J=6.3 Hz, 2 H), 5.98 (s, 1 H), 6.91–7.31 (m, 4 H).

C) 3-((2-(4-Benzylpiperidin-1-yl)ethyl)oxy) benzaldehyde ethylene acetal. The compound was prepared in a manner similar to example 7. From 3-((2-bromoethyl) oxy)benzaldehyde ethylene acetal (2.24 g, 8.20 mmol) and 4-benzylpiperidine (1.75 g, 10.0 mmol) there was obtained the amine as a colorless oil (2.9 g, 94%): $^1$H NMR (CDCl$_3$) 1.32 (m, 2 H), 1.60 (m, 1 H), 1.62 (d, J=12.9 Hz, 2 H), 2.05 (m, 2 H), 2.53 (d, J=6.6 Hz, 2 H), 2.78 (m, 2 H), 2.96 (d, J=12 Hz, 2 H), 4.02 (m, 2 H), 4.11 (s, 4 H), 5.79 (s, 1 H), 6.88–7.25 (m, 9H).

D) 3-((2-(4-Benzylpiperidin-1-yl)ethyl)oxy) benzaldehyde hydrochloride. To a solution of 3-((2-(4-benzylpiperidin-1-yl)ethyl)oxy)benzaldehyde ethylene acetal (1.1 g, 3.0 mmol) in 10 mL of EtOH was added 9 mL of 2 N HCl solution. The resulting solution was allowed to stir at 70° C. for 3 hr. The solution was neutralized with saturated NaHCO$_3$ solution to pH 7 and extracted with EtOAc (3×30 mL). The combined extracts were dried over Na$_2$SO$_4$. Evaporation of solvents gave the product as a pale yellow oil (0.87 g, 90%). To a solution of this oil (200 mg, 0.62 mmol) in 5 mL of MeOH was added dropwise 3 mL of 1 M HCl in MeOH. The resulting solution was allowed to stir at rt for 10 min. Evaporation of solvent gave an oil, to which was added 45 mL of ether. The mixture was allowed to stir at rt for 2 days. The solid was collected by filtration and dried in vacuo giving the product as a solid (110 mg, 50%): mp 145–147° C. (dec.); $^1$H NMR (CDCl$_3$) 1.72 (m, 2 H), 1.88 (m, 2 H), 2.06 (m, 2 H), 2.62 (d, J=6.30 Hz, 2 H), 2.75 (m, 2 H), 3.41 (s, 2 H), 3.67 (m, 2 H), 4.64 (s, 2 H), 7.11–7.51 (m, 9 H), 9.97 (s, 1 H), 12.71 (s, 1 H).

EXAMPLE 16

3-((2-(4-Benzylpiperidin-1-yl)ethyl)oxy) benzaldehyde oxime

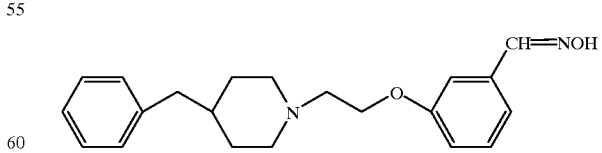

To a solution of 3-((2-(4-benzylpiperidin-1-yl)ethyl)oxy) benzaldehyde (200 mg, 0.620 mmol) in 6 mL of 50% aqueous EtOH was added a solution of hydroxylamine hydrochloride (110 mg, 1.55 mmol) and sodium acetate (246 mg, 2.77 mmol) in 50% aqueous EtOH (10 mL). The resulting solution was allowed to stir at room temperature for 3 days. The EtOH was evaporated and a colorless solid was collected by filtration and dried to give the product (160 mg, 70%): mp 141–143° C.; $^1$H NMR (CDCl$_3$) 1.40 (m, 2 H), 1.50 (m, 1 H), 1.64 (m, 2 H), 2.12 (m, 2 H), 2.54 (m, 2 H), 2.85 (s, 2 H), 3.08 (m, 2 H), 4.21 (m, 2 H), 6.88–7.28 (m, 9 H), 8.04 (s, 1 H), 10.00 (bs, 1 H).

EXAMPLE 17

4-Benzyl-1-(2-(3-(ethoxycarbonylmethyl)phenoxy) ethyl)piperidine

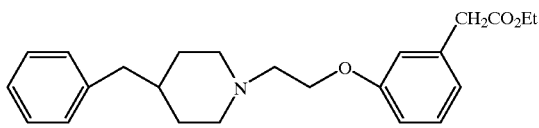

A) Ethyl 3-hydroxyphenylacetate. To a solution of 3-hydroxyphenylacetic acid (10 g, 66 mmol) in 200 mL of EtOH was added 4 mL of H$_2$SO$_4$. The resulting solution was allowed to reflux for 3 days. The solvent was evaporated in vacuo, water (50 mL) added to the residue, and the resulting mixture was extracted with EtOAc (3×30 mL). The combined organic extract was dried over Na$_2$SO$_4$. The solvent was evaporated in vacuo to give the product as a colorless oil (11.5 g, 97%): $^1$H NMR (CDCl$_3$) 1.26 (t, J=7.2 Hz, 3 H), 3.57 (s, 3 H), 4.15 (q, J=7.2 Hz, 2 H), 6.75 (m, 3 H), 7.16 (m, 1 H).

B) Ethyl 3-((2-bromoethyl)oxy)phenylacetate. From ethyl 3-hydroxyphenylacetate (3.6 g, 20 mmol), 1,2-dibromoethane (37.6 g, 200 mmol) was obtained the title compound as a pale yellow oil (4.68 g, 82%): $^1$H NMR (CDCl$_3$) 1.26 (t, J=7.2 Hz, 3 H), 3.59 (s, 3 H), 3.63 (t, J=6.3 Hz, 2 H), 4.14 (q, J=7.2 Hz, 2 H), 4.29 (t, J=6.3 Hz, 2 H), 6.84 (m, 3 H), 7.24 (m, 1 H).

C) 4-Benzyl-1-(2-(3-(ethoxycarbonylmethyl)phenoxy) ethyl)piperidine. The compound was prepared in a manner similar to example 7. From ethyl 3-((2-bromoethyl)oxy) phenylacetate (2.18 g, 7.60 mmol) and 4-benzylpiperidine (1.58 g, 9.00 mmol) there was obtained the amine as a pale yellow oil (2.32 g, 80%): $^1$H NMR (CDCl$_3$) 1.26 (t, J=7.2 Hz), 1.45 (m, 2 H), 1.61 (m, 1 H), 1.64 (m, 2 H), 2.06 (m, 2 H), 2.54 (d, J=6.9 Hz, 2 H), 2.78 (m, 2 H), 3.00 (d, J=11.4 Hz, 2 H), 3.64 (s, 3 H), 6.86 (m, 3 H), 7.29 (m, 6 H).

EXAMPLE 18

4-Benzyl-1-(2-(3-(2-hydroxyethyl)phenoxy) ethyl) piperidine

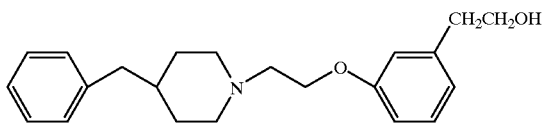

To a suspension of lithium aluminum hydride (150 mg, 4.0 mmol) in 10 mL of anhydrous THF was added dropwise a solution of 4-benzyl-1-(2-(3-(ethoxycarbonylmethyl) phenoxy)ethyl)piperidine (0.382 g, 1.00 mmol) in 2 mL of THF at −78° C. The resulting mixture was allowed to warm to room temperature and was stirred for 12 hr. Water (0.2 mL), 15% NaOH aqueous solution (0.2 mL) and water (1 mL) were added successively. The colorless solid was removed by filtration and washed with EtOAc (3×20 mL). The filtrate was dried over Na$_2$SO$_4$. Evaporation of solvents gave a residue, which was purified by flash chromatography giving the title product as colorless oil (223 mg, 66%) $^1$H NMR (CDCl$_3$) 1.37 (m, 2 H), 1.60 (m, 1 H), 1.63 (m, 2 H), 2.05 (m, 2 H), 2.36 (d, J=6.6 Hz, 2 H), 2.76 (m, 2 H), 2.82 (m, 2 H), 2.95 (m, 3 H), 3.81 (t, J=6.9 Hz, 2 H), 4.08 (t, J=6.9 Hz, 2 H), 6.80 (m, 3 H), 7.17–7.29 (m, 6 H).

EXAMPLE 19

1-(2-(3-(Aminocarbonylmethyl)phenoxy)ethyl)-4-benzylpiperidine

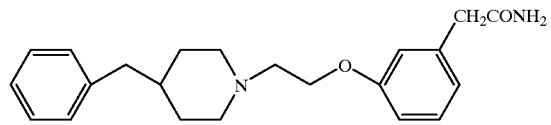

To a solution of 4-benzyl-1-(2-(3-(ethoxycarbonylmethyl) phenoxy)ethyl)piperidine (0.382 g, 1.00 mmol) in 5 mL of MeOH was added 5 mL of 30% NH$_4$OH solution. The resulting solution was allowed to stir at rt for 12 hr. The MeOH was evaporated in vacuo and water (10 mL) was added. A colorless solid precipitated. The solid was collected by filtration and dried in vacuo giving the title product (218 mg, 62%): mp 100–101° C.; $^1$H NMR (CDCl$_3$) 1.31 (m, 2 H), 1.60 (m, 1 H), 1.609 (m, 2 H), 2.04 (m, 2 H), 2.53 (d, J=6.6 Hz, 2 H), 2.80 (t, J=4.8 Hz, 2 H), 2.95 (d, J=11.4 Hz, 2 H), 3.55 (s, 2 H), 4.08 (t, J=6 Hz, 2 H), 5.35 (s, 2 H), 6.82 (m, 2 H), 7.13–7.27 (m, 6 H).

EXAMPLE 20

4-Benzyl-1-(2-(3-(hydrazinocarbonylmethyl) phenoxy)ethyl)piperidine

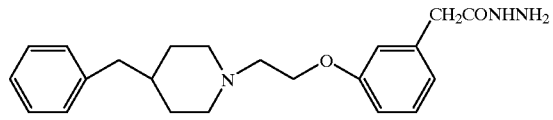

To a solution of 4-benzyl-1-(2-(3-(ethoxycarbonylmethyl) phenoxy)ethyl)piperidine (0.382 g, 1.00 mmol) in 5 mL of MeOH was added 5 mL of hydrazine hydrate. The resulting solution was allowed to stir at rt for 12 hr. The MeOH was evaporated in vacuo and water (10 mL) was added. A colorless solid precipitated. The solid was collected by filtration and dried in vacuo giving the title product (240 mg, 65%): mp 89–91° C.; $^1$H NMR (CDCl$_3$) 1.31 (m, 2 H), 1.60 (m, 1 H), 1.62 (m, 2 H), 2.04 (t, J=11.7 Hz, 2 H), 2.52 (d, J=6.9 Hz, 2 H), 2.76 (t, J=6.0 Hz, 2 H), 2.95 (d, J=11.4 Hz, 2 H), 3.53 (s, 2 H), 3.83 (bs, 2 H), 4.08 (t, J=6.3 Hz, 2 H), 6.66 (s, 1 H), 6.79 (m, 3 H), 7.12–7.27 (m, 6 H).

EXAMPLE 21

4-Benzyl-1-(1-methyl-2-phenoxyethyl)piperidine hydrobromide

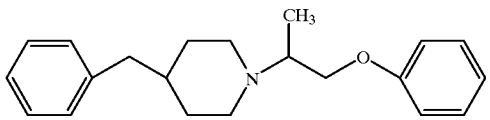

A) 1-Phenoxypropan-2-ol. To a suspension of lithium aluminum hydride (6.0 g, 0.15 mol) in 50 mL of THF was added dropwise a solution of phenoxyacetone (15 g, 0.10 mol) in 5 mL of THF at −78° C. The mixture was allowed to warm to room temperature and was stirred for an additional 2 h. Water (6.0 mL), 15% NaOH solution (6.0 mL) and water (18 mL) were added to the reaction mixture successively. The resulting mixture was extracted with EtOAc (15 mL) and ether (2×50 mL). The combined organic extract was dried over $Na_2SO_4$. The solvent was evaporated in vacuo to give a residue, which was purified by distillation giving the product as a colorless oil (12.5 g, 82%): bp 65–67° C., 0.06 Torr; $^1$H NMR (CDCl$_3$) 1.28 (d, J=7.0 Hz, 3 H), 2.35 (bs, 1 H), 3.80 (m, 1 H), 3.97 (m, 1H), 4.20 (m, 1 H), 6.93 (m, 3 H), 7.32 (m, 2 H).

B) 1-Phenoxy-2-tosylpropane. To a solution of 1-phenoxypropan-2-ol (5.0 g, 33 mmol) in 20 mL of CH$_2$Cl$_2$ and 25 mL of pyridine was added tosyl chloride (12.6 g, 66.0 mmol) in one portion at 0° C. The resulting solution was allowed to stir overnight at rt. The solution was poured into ice water (100 g) and the organic layer was separated. The aqueous layer was extracted with CH$_2$Cl$_2$ (2×50 mL). The combined organic layer was washed with 1.0 N HCl (2×50 mL) and 0.1 M NaHCO$_3$ solution (30 mL) and dried. Evaporation of solvent gave a residue, which was recrystallized from CH$_2$Cl$_2$/hexanes to give the product as a colorless solid (7.5 g, 74%): mp 92–94° C.; $^1$H NMR (CDCl$_3$) 1.42 (d, J=9.6 Hz, 3 H), 2.44 (s, 3 H), 3.90 (m, 1 H), 4.04 (m, 1 H), 4.83 (m, 1 H), 6.68 (d, J=8.1 Hz, 2 H), 6.94 (m, 1 H), 7.33 (m, 4 H), 7.79 (d, J=8.1 Hz, 2 H).

C) 4-Benzyl-1-(1-methyl-2-phenoxyethyl)piperidine hydrobromide. The compound was prepared in a manner similar to example 10. From 1-phenoxy-2-tosylpropane (550 mg, 1.80 mmol) and 4-benzylpiperidine (263 mg, 1.50 mmol) there was obtained the hydrobromide salt as a solid (290 mg, 50%): mp 151–153° C.; $^1$H NMR (CDCl$_3$) 1.60 (m, 3 H), 1.83 (m, 2 H), 2.23 (m, 2 H), 2.65 (m, 2 H), 2.93 (m, 2 H), 3.57 (m, 4 H), 4.24 (m, 1 H), 4.56 (m, 1 H), 6.87–7.27 (m, 10 H), 11.20 (bs, 1 H); Anal. Calcd for $C_{21}H_{28}NBrO$: C, 64.60; H, 7.23; N, 3.59. Found: C, 64.27; H, 7.37; N, 3.58.

EXAMPLE 22

4-Benzyl-1-(3-(3-fluorophenoxy)propyl)piperidine hydrobromide

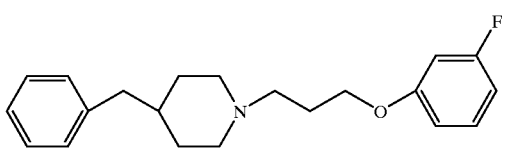

The compound was prepared in a manner similar to example 10. From 4-benzylpiperidine (500 mg, 2.85 mmol) and 1-bromo-3-(3-fluorophenoxy)propane (697 mg, 2.99 mmol) there was obtained the hydrobromide salt was as a colorless powder (838 mg, 72%): mp 155.5–157.5° C.; $^1$H NMR (CDCl$_3$) 1.60–1.94 (m, 3 H), 2.05–2.25 (m, 2 H), 2.41–2.72 (m, 6 H), 3.11–3.21 (m, 2 H), 3.63 (d, J=11 Hz, 2 H), 4.05 (t, J=5.4 Hz, 2 H), 6.52–6.71 (m, 3 H), 7.09–7.34 (m, 6 H), 11.40 (bs, 1 H). Anal. Calcd for $C_{21}H_{27}BrFNO$: C, 61.77; H, 6.66; N, 3.43. Found: C, 61.86; H, 6.80; N, 3.40.

EXAMPLE 23

4-Benzyl-1-(4-(3-fluorophenoxy)butyl)piperidine hydrobromide

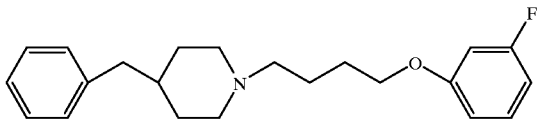

The compound was prepared in a manner similar to example 10. From 4-benzylpiperidine (500 mg, 2.85 mmol) and 1-bromo-4-(3-fluorophenoxy)butane (1.06 g, 4.28 mmol) there was obtained the hydrobromide salt as a colorless powder (240 mg, 88%): mp 124.5–127.5° C.; $^1$H NMR (CDCl$_3$) 1.70–1.94 (m, 5 H), 2.05–2.23 (m, 4 H), 2.51–2.60 (m, 4 H), 2.93–3.08 (m, 2 H), 3.60 (d, J=11 Hz, 2 H), 3.97 (t, J=5.7 Hz, 2 H), 6.52–6.70 (m, 3 H), 7.12–7.30 (m, 6 H), 11.35 (bs, 1 H). Anal. Calcd for $C_{22}H_{29}BrFNO$: C, 62.56; H, 6.92; N, 3.32. Found: C, 62.54; H, 7.15; N, 3.42.

EXAMPLE 24

4-(4-Chlorobenzyl)-1-(2-phenoxyethyl)piperidine hydrochloride

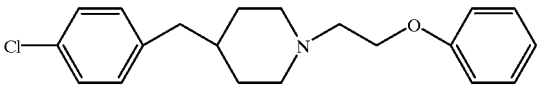

The compound was prepared in a manner similar to example 10. From 4-(4-chlorobenzyl)piperidine hydrochloride (500 mg, 2.03 mmol) and 2-phenoxyethyl tosylate (623 mg, 2.13 mmol) there was obtained the hydrochloride salt as a colorless powder (455 g, 62%), mp 200–202° C.; $^1$H NMR (CDCl$_3$) 1.55–1.89 (m, 3 H), 2.06 (q, J=12 Hz, 2 H), 2.50–2.89 (m, 4 H), 3.20–3.55 (m, 2 H), 3.66 (d, J=12 Hz, 2 H), 4.54 (bs, 2 H), 6.86 (d, J=7.8 Hz, 2 H), 6.95–7.09 (m, 3 H), 7.22–7.34 (m, H), 12.64 (bs, 1 H). Anal. Calcd for $C_{20}H_{25}Cl_2NO$: C, 65.57; H, 6.88; N, 3.82. Found: C, 65.42; H, 6.65; N, 3.57.

EXAMPLE 25

4-(4-Chlorobenzyl)-1-(2-(4-fluorophenoxy)ethyl)piperidine hydrobromide

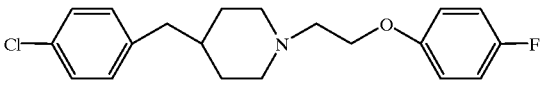

A) 2-(4-Fluorophenoxy)ethyl bromide. From 4-fluorophenol (10.0 g, 89.2 mmol) and 1,2-dibromoethane (38.4 mL, 83.8 g, 446 mmol) was obtained a colorless liquid (8.90 g, 46%): $^1$H NMR (CDCl$_3$) 3.62 (t, J=6.3 Hz, 2 H), 4.25 (t, J=6.3 Hz, 2 H), 6.82–6.91 (m, 2 H), 6.92–7.03 (m, 2 H).

B) 4-(4-Chlorobenzyl)-1-(2-(4-fluorophenoxy)ethyl) piperidine hydrobromide. A mixture of 4-(4-chlorobenzyl) piperidine hydrochloride (1.00 g, 4.06 mmol), 2-(4-fluorophenoxy)ethyl bromide (933 mg, 4.26 mmol) and K$_2$CO$_3$ (1.15 g, 8.32 mmol) in CH$_3$CN (30 mL) was stirred at reflux under N$_2$ for 3 d. The reaction was allowed to cool to 25° C. The reaction was then added to 100% HCl (100 mL) and extracted with CHCl$_3$ (3×50 mL). The extract was washed with 5% NH$_4$OH (2×50 mL), filtered through cotton and the solvent removed on a rotoevap to give a colorless oil. The product was purified chromatographically on silica gel (2.5×30 cm). Elution with CHCl$_3$ removed the more mobile impurities. Elution with 2% EtOH/99% CHCl$_3$ removed the product. The solvent was removed from the product fractions on a rotoevap to give a colorless solid. The solid was dissolved in warm MeOH (10 mL), filtered through Celite and the MeOH removed on a rotoevap to give an colorless solid. The solid was dried in vacuo (0.005 Torr, 25° C.) to give an colorless solid (1.23 g, 87%): mp 85–87.5° C.; $^1$H NMR (CDCl$_3$) δ 1.25–1.68 (m, 5 H), 2.04 (t, J=12 Hz, 2 H), 2.50 (d, J=6.9 Hz, 2 H), 2.76 (t, J=6.0 Hz, 2 H), 2.97 (d, J=11 Hz, 2 H), 4.05 (t, J=6.0 Hz, 2 H), 6.77–7.00 (m, 4 H), 7.06 (d, J=8.1 Hz, 2 H), 7.24 (d, J=8.1 Hz, 2 H).

The hydrobromide salt was prepared according to the following procedure. A solution of the free base (1.00 g, 2.87 mmol) in MeOH (15 mL, prepared with warming) was treated with a dilute solution of HBr in MeOH until the amine solution became permanently acidic (pH paper). The solvent was removed in vacuo to give a syrup. The syrup was stirred vigorously in ether (95 mL) for 18 h to give a yellow suspension. The solid was collected, washed with ether (3×3 mL) and dried in vacuo (0.005 Torr, 79° C.) to yield a pale yellow powder (1.14 g, 93%): mp 117.5–119.5° C.; $^1$H NMR (CDCl$_3$) δ 1.60–1.89 (m, 3 H), 2.08 (q, J=12 Hz, 2 H), 2.58 (d, J=6.9 Hz, 2 H), 2.82 (q, J=11 Hz, 2 H), 3.27–3.48 (m, 2 H), 3.70 (d, J=12 Hz, 2 H), 4.53 (t, J=3.6 Hz, 2 H), 6.77–7.10 (m, 6 H), 7.23 (d, J=8.4 Hz, 2 H), 11.48 (bs, 1 H).

An analytical sample was prepared by crystallization of the above powder from 2-butanone/ether as a fluffy crystalline solid, mp 117–118° C. Anal. Calcd for C$_{20}$H$_{24}$BrClFNO: C, 56.03; H, 5.64; N, 3.27. Found: C, 56.14; H, 5.46; N, 3.28.

EXAMPLE 26

4-(4-Chlorobenzyl)-1-(2-(4-chlorophenoxyethyl) piperidine hydrochloride

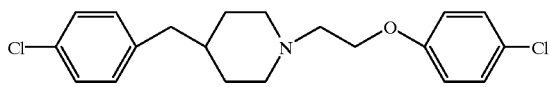

The compound was prepared in a manner similar to example 25. From 4-(4-chlorobenzyl)piperidine hydrochloride (500 mg, 2.03 mmol) and 2-(4-chlorophenoxy)ethyl bromide (502 mg, 2.13 mmol) there was obtained the hydrochloride salt as a colorless powder (641 g, 81%): mp 167–169° C.; $^1$H NMR (CDCl$_3$) 1.55–1.89 (m, 3 H), 2.06 (q, J=13 Hz, 2 H), 2.50–2.82 (m, 4 H), 3.20–3.55 (m, 2 H), 3.65 (d, J=12 Hz, 2 H), 4.53 (t, J=4.2 Hz, 2 H), 6.81 (d, J=8.7 Hz, 2 H), 7.04 (d, J=8.7 Hz, 2 H), 7.20–7.28 (m, 4 H), 12.75 (bs, 1 H); Anal. Calcd for C$_{20}$H$_{24}$Cl$_3$NO: C, 59.94; H, 6.04; N, 3.49. Found: C, 60.05; H, 5.85; N, 3.18.

EXAMPLE 27

4-(4-Chlorobenzyl)-1-(2-(4-nitrophenoxy)ethyl) piperidine hydrobromide

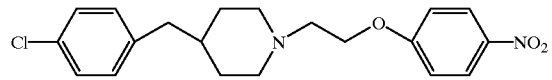

The compound was prepared in a manner similar to example 25. From 4-(4-chlorobenzyl)piperidine hydrochloride (1.00 g, 4.06 mmol) and 1-bromo-2-(4-nitrophenoxy) ethane (1.05 g, 4.26 mmol) there was obtained the hydrobromide salt as a colorless solid (1.27 g, 69%): mp 155–158° C.; $^1$H NMR (CDCl$_3$) 1.55–2.20 (m, 5 H), 2.52–2.89 (m 4 H), 3.25–3.78 (m, 4 H), 4.74 (t, J=4.5 Hz, 2 H), 6.98 (d, J=9.3 H, 2 H), 7.05 (d J=8.1 Hz, 2H), 7.25 (d, J=7.5 Hz, 2 H), 8.21 (d, J=8.7 Hz, 2 H), 11.77 (bs, 1H). Anal. Calcd for C$_{20}$H$_{24}$BrClN$_2$O$_3$: C, 52.70; H, 5.31; N, 6.15. Found: C, 52.82; H, 5.42; N, 6.09.

EXAMPLE 28

1-(2-(4-Aminophenoxy)ethyl)-4-(4-chlorobenzyl) piperidine dihydrobromide

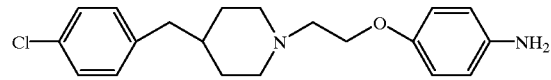

A mixture of 4-(4-chlorobenzyl)-1-(2-(4-nitrophenoxy) ethyl)piperidine hydrobromide (500 mg, 1.10 mmol) and Pd/C (10%, 50 mg) in MeOH (25 mL) was shaken under H$_2$ (20–30 psi, Parr) for 2.25 h and worked up to give a beige powder (350 mg, 63%): mp>130° C.; $^1$H NMR (DMSO-d$_6$) 1.37–1.88 (m, 5 H), 2.45–3.75 (m, 8 H), 4.30–4.42 (m, 2 H), 7.04–7.38 (m, 8 H), 9.35–10.20 (m, 4 H); HRMS Calcd for C$_{20}$H$_{25}$ClN$_2$O: 344.1655. Found: 344.1656.

EXAMPLE 29

4-(4-Chlorobenzyl)-1-(2-(3-(2-hydroxyethyl) phenoxy)ethyl)piperidine

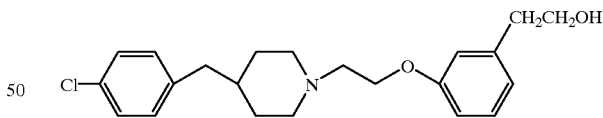

A) 4-(4-Chlorobenzyl)-1-(2-(3-(ethoxycarbonylmethyl) phenoxy)ethyl)piperidine. The compound was prepared in a manner similar to example 7. From ethyl 3-((2-bromoethyl) oxy)phenylacetate (2.26 g, 7.80 mmol) and 4-(4-chlorobenzyl)piperidine hydrochloride (2.2 g, 9.0 mmol) there was obtained the amine as a pale yellow oil (1.74 g, 55%): $^1$H NMR (CDCl$_3$) δ 1.25 (t, J=7.2 Hz, 3 H), 1.50 (m, 3 H), 1.61 (m, 2 H), 2.09 (m, 2 H), 2.50 (d, J=6.3 Hz, 2 H), 2.80 (bs, 2 H), 2.99 (m, 2 H), 3.56 (s, 2 H), 4.13 (m, 4 H), 6.83 (m, 3 H), 7.08 (d, J=8.1 Hz, 2 H), 7.22 (m, 3 H).

B) 4-(4-Chlorobenzyl)-1-(2-(3-(2-hydroxyethyl) phenoxy)ethyl)piperidine. To a suspension of lithium aluminum hydride (76 mg, 2.0 mmol) in 10 mL of anhydrous THF was added dropwise a solution of ethyl 4-(4- chlorobenzyl)-1-(2-(3-(ethoxycarbonylmethyl)phenoxy) ethyl)piperidine (0.435 g, 1.10 mmol) in 2 mL of THF at −78° C. The resulting mixture was allowed to warm to room temperature and stirred further for 12 hr. Water (0.2 mL), 15% NaOH aqueous solution (0.2 mL) and water (1 mL) were added successively. The colorless solid was removed through filtration and washed with EtOAc (3×20 mL). The filtrate was dried over $Na_2SO_4$. Evaporation of solvent gave a residue, which was purified by flash chromatography giving the title product as colorless oil (310 mg, 76%): $^1$H NMR ($CDCl_3$) 1.34 (m, 2 H), 1.63 (m, 4 H), 1.90 (m, 1 H), 2.07 (m, 2 H), 2.43 (m, 2 H), 2.83 (m, 3 H), 2.98 (m, 2 H), 3.39 (m, 2 H), 4.10 (m, 2 H), 6.78 (m, 3 H), 7.25 (m, 5 H).

EXAMPLE 30

4-(4-Chlorobenzyl)-1-(3-phenoxypropyl)piperidine hydrobromide

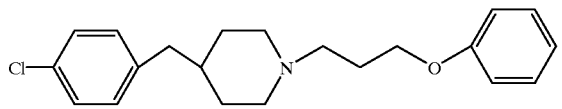

The compound was prepared in a manner similar to example 25. From 4-(4-chlorobenzyl)piperidine hydrochloride (1.00 g, 4.06 mmol) and 3-phenoxypropyl bromide (916 mg, 4.26 mmol, Aldrich) there was obtained the hydrobromide salt as a colorless powder (980 mg, 62%), mp 143.5–145.5° C.; $^1$H NMR ($CDCl_3$) 1.65–1.89. (m, 3 H), 2.15 (dd, $J_1$=12 Hz, $J_2$=13 Hz, 2 H), 2.39–2.76 (m, 6 H), 3.12–3.25 (m, 2 H), 3.63 (d, J=11 Hz, 2 H), 4.05 (t, J=5.1 Hz, 2 H), 6.80–7.10 (m, 5 H), 7.21–7.31 (m, 4 Hz), 11.32 (bs, 1 H). Anal. Calcd for $C_{21}H_{27}BrClNO$: C, 59.38; H, 6.41; N, 3.30. Found: C, 59.01; H, 6.41; N, 3.17.

EXAMPLE 31

4-(4-Chlorobenzyl)-1-(3-(3-fluorophenoxy)propyl) piperidine hydrobromide

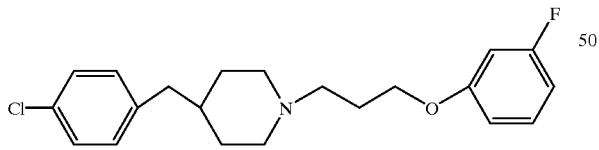

The compound was prepared in a manner similar to example 25. From 4-(4-chlorobenzyl)piperidine hydrochloride (500 mg, 2.03 mmol) and 1-bromo-3-(3-fluorophenoxy) propane (497 mg, 2.13 mmol) there was obtained the hydrobromide salt as a colorless powder (540 mg, 60%): mp 119–122° C.; $^1$H NMR ($CDCl_3$) 1.68–2.73 (m, 11 H), 3.10–3.23 (m, 2 H), 3.64 (d, J=11 Hz, 2 H), 4.05 (t, J=5.1 Hz, 2 H), 6.52–6.72 (m, 3 H), 7.03–7.33 (m, 5 H), 11.42 (bs, 1 H). Anal. Calcd for $C_{21}H_{26}ClBrFNO$: C, 56.96; H, 5.92; N, 3.16. Found: C, 57.08; H, 6.00; N, 3.15.

EXAMPLE 32

4-(4-Chlorobenzyl)-1-(4-phenoxybut-2-en-1-yl) piperidine maleic acid salt

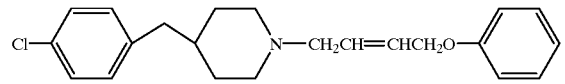

A) 1-Chloro-4-phenoxybut-2-ene. A mixture of phenol (5.00 g, 53.1 mmol), cis-1,4-dichloro-2-butene (27.9 mL, 33.2 g, 266 mmol), $K_2CO_3$ (7.71 g, 55.8 mmol) in DMF (30 mL) was stirred at 120° C. under $N_2$. After 24 h, TLC (10% $CHCl_3$/90% hexanes) indicated partial conversion of phenol to a higher $R_f$ product. A crystal of $I_2$ was added and the reaction was allowed to proceed and additional 24 h. It was worked up to give a yellow liquid (1.00 g, 10%; a mixture of isomers (cis and trans) by NMR (approximately 9:1 respectively): $^1$H NMR ($CDCl_3$, major isomer) 4.17 (d, J=6.6 Hz, 2 H), 4.66 (d, J=4.2 Hz, 2 H), 5.82–5.98 (m, 2 H), 6.91–7.05 (m, 3 H), 7.27–7.30 (m, 2 H).

B) 4-(4-Chlorobenzyl)-1-(4-phenoxybut-2-en-1-yl) piperidine maleic acid salt. The compound was prepared in a manner similar to example 7. From 4-(4-chlorobenzyl) piperidine hydrochloride (1.35 g, 5.47 mmol) and 1-chloro-4-phenoxybut-2-ene (1.00 g, 5.47 mmol) there was obtained a clear amber oil (933 mg, 48%): $^1$H NMR ($CDCl_3$, major isomer) 1.22–1.68 (m, 5 H), 1.91 (t, J=8.1 Hz, 2 H,), 2.50 (d, J=6.9 Hz, 2 H), 2.95 (d, J=11 Hz, 2 H), 3.08 (d, J=6.0 Hz, 2 H), 4.59 (d, J=5.4 Hz, 2 H), 5.76–5.92 (m, 2 H, decoupling shows that the 2 olefinic protons have J=12 Hz), 6.85–7.33 (m, 9 H). The maleic acid salt was prepared according to the following procedure. A solution of the free base (136 mg, 382 mmol) in ether (1 mL) was added to a vigorously stirred solution of maleic acid (250 mg, Aldrich) in ether (10 mL). An oil formed. Additional ether was added (total volume 45 mL) and the mixture was vigorously stirred for 24 h to give a suspension. The solid was collected, washed with ether (6×1 mL) and dried in vacuo (0.005 Torr, 56° C.) to yield a colorless powder (120 mg, 67%; 90% cis isomer by NMR): mp 84–85.5° C.; $^1$H NMR ($CDCl_3$) 1.60–1.89 (m, 5 H), 2.48–2.68 (m, 4 H), 3.58 (d, J=12 Hz, 2 H), 3.80 (d, J=7.2 Hz, 2 H), 4.59 (d, J=5.4 Hz, 2 H), 5.77–5.90 (m, 1 H), 6.12–6.24 (m, 1 H), 6.30 (s, 1 H), 6.83–7.36 (m, 10 H), 12.33 (bs, 1 H). Anal. Calcd for $C_{26}H_{30}ClNO_5$: C, 66.16; H, 6.41; N, 2.97. Found: C, 65.93; H, 6.28; N, 3.21.

EXAMPLE 33

4-(4-Fluorobenzyl)-1-(2-(4-fluorophenoxy)ethyl) piperidine hydrochloride

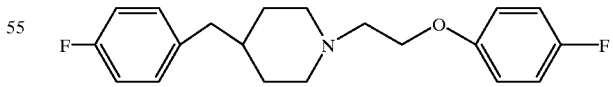

A) N-Acetylisonipecotic acid. Isonipecotic acid (25.0 g, 0.190 mol) was dissolved in acetic anhydride (100 mL) and the solution stirred at reflux for 8 h, then the solvent was removed under reduced pressure and the crude compound crystallized from MeOH/ether to afford the title compound as a colorless solid (24.4 g, 74%): mp 171° C.; $^1$H NMR (DMSO-$d_6$) 1.20–1.50 (m, 2H), 1.65–1.85 (m, 2H), 1.94 (s, 3H), 2.35–2.50 (m, 1H), 2.64 (t, J=11.7 Hz, 1H), 3.04 (t, J=11.7 Hz, 1H), 3.69 (d, J=13.5 Hz, 1H), 4.15 (d, J=13.2 Hz, 1H), 12.2 (bs, 1H).

B) N-Acetylisonipecotoyl chloride. N-acetylisonipecotic acid (0.67 g, 3.9 mmol) was added to $SOCl_2$ (4.1 mL). The acid chloride precipitated from solution and petroleum ether (60 mL) was added. The mixture was filtered and the residue was washed several times with petroleum ether to afford the title compound as a colorless solid (0.716 g, 97%): mp 133–138° C. $^1H$ NMR (DMSO-$d_6$) 1.20–1.50 (m, 2H), 1.65–2.00 (m, 2H), 1.94 (s, 3H), 2.30–2.50 (m, 1H), 2.64 (t, J=11.4 Hz, 1H), 3.04 (t, J=11.4 Hz, 1H), 3.69 (d, J=13.2 Hz, 1H), 4.14 (d, J=13.2 Hz, 1H).

C) 1-Acetyl-4-(4-fluorobenzoyl)piperidine. N-acetylisonipecotoyl chloride (2.00 g, 10.5 mmol) was slowly added to a stirred mixture of aluminum trichloride (2.80 g, 21.1 mmol) in fluorobenzene (10 mL). After addition was complete, the mixture was refluxed for 1 h. The mixture was poured into ice and the resulting layers were separated. The aqueous layer was extracted with $CH_2Cl_2$ (2×30 mL), the combined organic phase was dried and was concentrated under reduced pressure to afford the title compound as a pale yellow oil (1.30 g, 50%): $^1H$ NMR (CDCl$_3$) 1.50–1.70 (m, 1H), 1.70–2.00 (m, 3H), 2.10 (s, 3H), 2.81 (t, J=12.0 Hz, 1H), 3.15–3.30 (m, 1H), 3.40–3.55 (m, 1H), 3.90 (d, J=13.2 Hz, 1H), 4.57 (d, J=13.2 Hz, 1H), 7.14 (t, J=8.4 Hz, 2H), 7.97 (dd, J=5.7 and 8.4 Hz, 2H).

D) 4-(4-Fluorobenzoyl)piperidine hydrobromide. A solution of 1-acetyl-4-(4-fluoro-benzoyl)piperidine (1.20 g, 4.80 mmol) in HCl (6N, 15 mL) was refluxed for 2 h. The cooled solution was made basic (NaOH) and then extracted with benzene (2×40 mL). The collected organic phase was washed with brine (50 mL), dried and was concentrated under reduced pressure. The free amine was dissolved in HBr (saturated solution in MeOH, 10 mL). The precipitated hydrobromide salt was collected, washed with ether (2×4 mL) and dried in vacuo to afford the title compound as a colorless solid (1.54 g, 98%): mp 198° C.; $^1H$ NMR (CD$_3$OD) 1.80–2.00 (m, 2H), 2.05–2.18 (m, 2H), 3.12–3.28 (m, 2H), 3.40–3.50 (m, 2H), 3.70–3.85 (m, 1H), 4.85 (s, 2H), 7.24 (t, J=8.3 Hz, 2H), 8.10 (dd, J=5.7 and 8.7 Hz, 2H).

E) 4-(4-Fluorobenzyl)piperidine hydrobromide. Triethylsilyl hydride (8.40 mL, 53.0 mmol) was added dropwise to a solution of 4-(4-fluorobenzoyl)piperidine hydrobromide (1.52 g, 5.30 mmol) in trifluoroacetic acid (30 mL). The resulting solution was allowed to stir for 4 days at 25° C. then the solvent was removed in vacuo. The organic residue was made basic with NaOH (10% solution) and extracted with EtOAc (3×50 mL). The collected organic phase was dried and concentrated under reduced pressure. The crude compound was dissolved in a saturated solution of HBr in MeOH (10 mL) then after 10 min at 25° C. the solution was concentrated under reduced pressure. The crude compound was purified by trituration with acetone (10 mL) for 1 h. The solid was collected, washed with acetone (2×4 mL) and dried in vacuo to afford the title compound as a colorless solid (0.65 g, 45%): mp 176–180° C.; $^1H$ NMR (DMSO-$d_6$) 1.20–1.45 (m, 2H), 1.57–1.83 (m, 3H), 2.47 (s, 2H), 2.63–2.85 (m, 2H), 3.10–3.30 (m, 2H), 7.03–7.35 (m, 4H), 8.30 (bs, 1H), 8.55 (bs, 1H).

F) 4-(4-Fluorobenzyl)-1-(2-(4-fluorophenoxy)ethyl) piperidine hydrochloride. The compound was prepared in a manner similar to example 20. From 4-(4-fluorobenzyl) piperidine hydrobromide (600 mg, 2.19 mmol) and 2-(4-fluorophenoxy)ethyl bromide (504 mg, 2.30 mmol) there was obtained the hydrochloride salt as a fluffy, colorless, crystalline solid (315 mg, 40%): mp 153–154° C.; $^1H$ NMR (CDCl$_3$) 1.55–2.15 (m, 5 H), 2.50–2.83 (m, 4 H), 3.20–3.50 (m, 2 H), 3.66 (d, J=11 Hz, 2 H), 4.42–4.56 (m, 2 H), 6.76–7.12 (m, 8 H), 12.62 (bs, 1 H). Anal. Calcd for $C_{20}H_{24}ClF_2NO$: C, 65.30; H, 6.58; N, 3.81. Found: C, 65.08; H, 6.79; N, 3.78.

EXAMPLE 34

4-(4-Fluorobenzyl)-1-(2-(4-chlorophenoxy)ethyl) piperidine hydrochloride

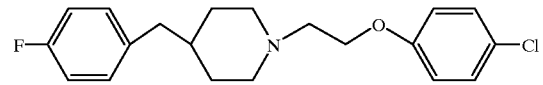

The compound was prepared in a manner similar to example 25. From 4-(4-fluorobenzyl)piperidine hydrobromide (600 mg, 2.19 mmol) and 2-(4-chlorophenoxy)ethyl bromide (542 mg, 2.30 mmol) there was obtained the hydrochloride salt was as a fluffy, colorless, crystalline solid (460 mg, 56%): mp 173–174° C.; $^1H$ NMR (CDCl$_3$) 1.55–2.15 (m, 5 H), 2.50–2.83 (m, 4 H), 3.20–3.50 (m, 2 H), 3.66 (d, J=11 Hz, 2 H), 4.45–4.60 (m, 2 H), 6.80 (d, J=9.0 Hz, 2 H), 6.91–7.12 (m, 4 H), 7.24 (d, J=8.7 Hz, 2 H), 12.60 (bs, 1 H); Anal. Calcd for $C_{20}H_{24}Cl_2FNO$: C, 62.51; H, 6.29; N, 3.64. Found: C, 62.53; H, 6.57; N, 3.63.

EXAMPLE 35

1-(2-(4-Fluorophenoxy)ethyl)-4-(4-methoxybenzyl) piperidine hydrochloride

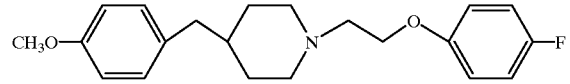

A) 4-(4-Methoxybenzyl)piperidine. The compound was prepared according to Gray, A. P.; Village, B. and Heitmeier, D. E. (U.S. Pat. No. 3,632,767, 1972) as a colorless, crystalline solid, mp 60–61° C. (Lit. 59–61° C.). $^1H$ NMR (CDCl$_3$) 1.02–1.20 (m, 2 H), 1.42–1.68 (m, 4 H), 2.45 (d, J=6.6 Hz, 2 H), 2.54 (d, J=12 Hz, 2 H), 3.02 (d, J=12 Hz, 2 H), 3.78 (s, 3 H), 6.81 (d, J=8.4 Hz, 2 H), 7.05 (d, J=8.1 Hz, 2 H).

B) 1-(2-(4-Fluorophenoxy)ethyl)-4-(4-methoxybenzyl) piperidine hydrochloride. This compound was prepared in a manner similar to example 25. From 4-(4-methoxybenzyl) piperidine (500 mg, 2.44 mmol) and 2-(4-fluorophenoxy) ethyl bromide (561 mg, 2.56 mmol) there was obtained the hydrochloride salt as colorless plates: mp 171–172° C.; $^1H$ NMR (CDCl$_3$) 1.55–2.18 (m, 5 H), 2.50–2.82 (m, 4 H), 3.25–3.70 (m, 4 H), 3.77 (s, 3 H), 4.50 (t, J=3.6 Hz, 2 H), 6.75–7.07 (m, 8 H), 12.56 (bs, 1 H). Anal. Calcd for $C_{21}H_{27}ClFNO_2$: C, 66.39; H, 7.16; N, 3.69. Found: C, 66.52; H, 7.29; N, 3.68.

EXAMPLE 36

1-(2-(4-Fluorophenoxy)ethyl)-4-(4-nitrobenzyl) piperidine hydrobromide

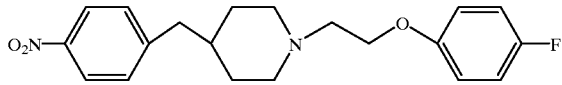

A) 4-(2- and 4-Nitrobenzyl)piperidine trifluoroacetamide. To stirred, ice bath cold TFAA (5 mL), 4-benzylpiperidine (2.00 g, 11.4 mmol) was added dropwise over 10 min. Additional TFAA was added (5 mL) and the reaction was stirred 5 min. The ice bath was removed and the reaction was allowed to stir an additional hour. This was re-cooled in an ice bath and solid $KNO_3$ (1.21 g, 12.0 mmol) was added in portions. The ice bath was removed and TFA (10 mL) was then added. After stirring at 25° C. for one hour, the reaction mixture was added to ice water (200 mL) to give a gummy mixture. This was extracted with $CHCl_3$ (3×75 mL). The extract was washed with water (200 mL), saturated $NaHCO_3$ (200 mL) and water (200 mL), filtered through cotton and the solvent removed on a rotoevap to give a yellow oil (3.6 g). The mixture was separated by chromatography on silica gel to give the ortho isomer as a pale yellow solid (371 mg, 11%): mp 74.5–76.5° C.; $^1$H NMR ($CDCl_3$) 1.20–1.40 (m, 2 H), 1.71–2.05 (m, 3 H), 2.68 (t, J=13 Hz, 1 H), 2.75–2.95 (m, 2 H), 3.05 (t, $J_1$=13 Hz, $J_2$=14 Hz, 1 H), 3.98 (d, J=14 Hz, 1 H), 4.54 (d, J=13 Hz, 1 H), 7.27 (d, J=6.6 Hz, 1 H), 7.40 (t, J=7.5 Hz, 1 H), 7.54 (t, J=7.5 Hz, 1 H), 7.96 (d, J=7.8 Hz, 1 H); and the para isomer as a yellow oil (1.03 g, 29%): $^1$H NMR ($CDCl_3$) 1.20–1.40 (m, 2 H), 1.71–1.98 (m, 3 H), 2.60–2.75 (m, 3 H), 3.06 (t, $J_1$=13 Hz, $J_2$=14 Hz, 1 H), 3.99 (d, J=14 Hz, 1 H), 4.54 (d, J=14 Hz, 1 H), 7.30 (d, J=8.4 Hz, 2 H), 8.17 (d, J=8.1 Hz, 2 H).

B) 4-(4-Nitrobenzyl)piperidine hydrochloride. To a stirred solution of 4-(4-nitrobenzyl)piperidine trifluoroacetamide (1.00 g, 3.16 mmol) in 95% EtOH, a solution of NaOH (500 mg) in water (5 mL) was added. The reaction was allowed to stir at 25° C. After 5 min, The reaction was added to water and extracted with $CHCl_3$ (3×50 mL). The extract was washed with water (100 mL), filtered through cotton and the solvent removed on a rotoevap to give a yellow oil. The oil was dissolved in MeOH (5 mL) and concd HCl was added until the amine solution was permanently acidic. The solvent was removed on a rotoevap and the resulting solid was dried on a rotoevap at 70° C. (750 mg, 92%): mp 191–194° C. $^1$H NMR ($D_2O$) 1.35–1.57 (m, 2 H), 1.78–2.05 (m, 3 H), 2.71 (d, J=6.9 Hz, 2 H), 2.94 (t, J=13 Hz, 2 H), 3.40 (d, J=13 Hz, 2 H), 7.39 (d, J=8.4 Hz, 2 H), 8.10 (d, J=8.4 Hz, 2 H).

C) 1-(2-(4-Fluorophenoxy)ethyl)-4-(4-nitrobenzyl) piperidine hydrobromide. This compound was prepared in a manner similar to example 25. From 4-(4-nitrobenzyl) piperidine hydrochloride (427 mg, 1.66 mmol) and 2-(4-fluorophenoxy)ethyl bromide (381 mg, 1.74 mmol) there was obtained the hydrobromide salt as a pale beige powder (510 mg, 94%): mp 147–148° C.; $^1$H NMR ($CDCl_3$) 1.65–1.89. (m, 3 H), 2.20 (q, J=12 Hz, 2 H), 2.69–2.90 (m, 4 H), 3.35–3.45 (m, 2 H), 3.73 (d, J=12 Hz, 2 H), 4.55 (t, J=3.6 Hz, 2 H), 6.77–7.04 (m, 4 H), 7.30 (d, J=8.4 Hz, 2 H), 8.16 (d, J=8.4 Hz, 2 H), 11.75 (bs, 1 H). Anal. Calcd for $C_{20}H_{24}BrFN_2O_3$: C, 54.68; H, 5.51; N, 6.38. Found: C, 54.67; H, 5.36; N, 6.29.

EXAMPLE 37

4-(4-Nitrobenzyl)-1-(3-phenoxypropyl)piperidine hydrobromide

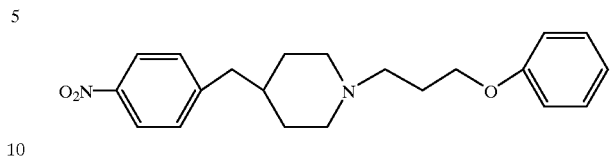

This compound was prepared in a manner similar to example 10. From 4-(4-nitrobenzyl)piperidine hydrochloride (250 mg, 974 mmol) and 3-phenoxypropyl bromide (219 mg, 1.02 mmol) there was obtained the hydrobromide salt as a beige powder (289 mg, 94%): mp 148–150° C.; $^1$H NMR ($CDCl_3$) 1.78–2.82 (m, 11 H), 3.12–3.26 (m, 2 H), 3.66 (d, J=11 Hz, 2 H), 4.07 (t, J=5.1 Hz, 2 H), 6.84 (d, J=8.1 Hz, 2 H), 6.96 (t, J=7.5 Hz, 1 H), 7.23–7.35 (m, 4 H), 8.16 (d, J=8.4 Hz, 2 H), 11.40 (bs, 1 H). Anal. Calcd for $C_{21}H_{27}BrN_2O_3$: C, 57.94; H, 6.25; N, 6.43. Found: C, 57.72; H, 6.11; N, 6.15.

EXAMPLE 38

4-(4-Chloroanilino)-1-(2-(4-fluorophenoxy)ethyl) piperidine dihydrochloride

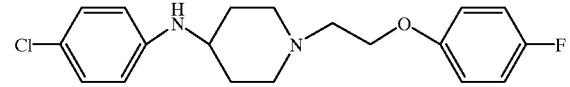

A) 1-(2-(4-Fluorophenoxy)ethyl)-4-piperidone. This compound was prepared in a manner similar to example 7. From 4-piperidone monohydrate hydrochloride (2.50 g, 16.3 mmol), 2-(4-fluorophenoxy)ethyl bromide (3.74 g, 17.1 mmol) there was obtained the amine as a pale yellow liquid which crystallized upon agitation (3.39 g, 88%): mp 71–73° C.; $^1$H NMR ($CDCl_3$) 2.48 (t, J=6.0 Hz, 4 H), 2.85–2.97 (m, 6 H), 4.10 (t, J=5.4 Hz, 2 H), 6.80–7.03 (m, 4 H).

B) 4-(4-Chloroanilino)-1-(2-(4-fluorophenoxy)ethyl) piperidine dihydrochloride. To a stirred solution of 1-(2-(4-fluorophenoxy)ethyl)-4-piperidone (1.00 g, 4.21 mmol) in MeOH (10 mL) there were added 4-chloroaniline (1.61 g, 12.6 mmol) and $NaCNBH_3$ (787 mg, 12.6 mmol). The resulting solution was allowed to stir at 25° C. under $N_2$ for 5 d. A brown solution was present. The reaction was added to 10% HCl (100 mL) and was allowed to stir at 25° C. for 20 min in order to allow the excess reducing agent to decompose. The resulting mixture was washed with ether (3×50 mL). The ether was back extracted with 10% HCl (25 mL). The combined acid portion was made basic (pH 8) with an NaOH solution. The basic solution was extracted with ether (3×50 mL). The ether extract was washed with saturated NaCl (50 mL), filtered through cotton and the ether removed on a rotoevap to give a colorless oil. This was purified chromatographically on silica gel (2.5×30 cm). $CHCl_3$ elution removed the unreacted 4-chloroaniline. Elution with 2. EtOH/98% $CHCl_3$ gave the product as a pale orange solid (398 mg, 27%): mp 66–71° C.; The hydrochloride salt was obtained as a pale yellow solid (340 mg, 72%): mp 199–207° C. (dec); $^1$H NMR (DMSO-$d_6$) 1.85–2.20 (m, 4 H), 3.00–3.80 (m, 7 H), 4.39 (t, J=3.9 Hz, 2 H), 6.92–7.36 (m, 10 H), 11.15 and 11.23 (overlapping bs, 1 H). Anal. Calcd for $C_{19}H_{24}Cl_3FN_2O$: C, 54.11; H. 5.74; N, 6.64. Found: C, 54.21; H, 5.78; N, 6.54.

EXAMPLE 39

1-(2-(4-Fluorophenoxy)ethyl)-4-(N-(4-fluoroanilino)piperidine hydrochloride

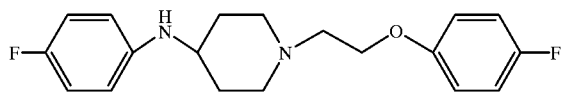

This compound was prepared in a manner similar to example 38. From 1-(2-(4-fluorophenoxy)ethyl)-4-piperidone (2.20 g, 9.27 mmol), 4-fluoroaniline (3.09 g, 27.8 mmol, Aldrich) and NaCNBH$_3$ (1.15 g, 18.5 mmol) there was obtained the hydrochloride as a pale beige solid (903 mg, 24%): mp 173–178° C. (dec); $^1$H NMR (DMSO-d$_6$) 1.75–2.20 (m, 4 H), 3.00–3.70 (m, 7 H), 4.39 (bs, 2 H), 6.70–7.20 (m, 9 H), 11.05 (bs, 1 H); $^1$H NMR (CD$_3$OD) δ 2.00–2.38 (m, 4 H), 3.18–3.80-(m, 7 H), 4.39 (t, J=4.5 Hz), 6.90–7.32 (m, 8 H). Anal. Calcd for $C_{19}H_{23}ClF_2N_2O$ 0.14 H$_2$O: C, 61.45; H, 6.32; N, 7.54. Found: C, 61.10; H, 5.92; N, 7.36.

EXAMPLE 40

4-(N-(4-Chloroanilino)-1-(3-phenoxypropyl)piperidine hydrobromide

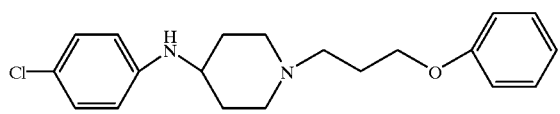

A) 1-(3-Phenoxypropyl)-4-piperidone. This compound was prepared in a manner similar to example 7. From 4-piperidone monohydrate hydrochloride (3.07 g, 20.0 mmol) and 3-phenoxypropyl bromide (4.52 g, 21.0 mmol) there was obtained the amine as a pale yellow liquid (1.48 g, 32%): $^1$H NMR (CDCl$_3$) 2.03 (p, J=6.6 Hz, 2 H), 2.46 (t, J=5.7 Hz, 4 H), 2.66 (t, J=6.9 Hz, 2 H), 2.78 (t, J=6.0 Hz, 4 H), 4.06 (t, J=6.0 Hz, 2 H), 6.88–6.99 (m, 3 H), 7.29 (t, J.=8 1 Hz, J$_2$=7.5 Hz, 2 H).

B) 4-(N-(4-Chloroanilino)-1-(3-phenoxypropyl) piperidine hydrobromide. This compound was prepared in a manner similar to example 38. From 1-(3-phenoxypropyl)-4-piperidone (1.47 g, 6.30 mmol), 4-chloroaniline (804 mg, 6.30 mmol) and NaCNBH$_3$ (1.31 g, 21 mmole) there was obtained the hydrobromide salt as a colorless solid (450 mg, 14%), mp 193–195° C. (dec); $^1$H NMR (DMSO-d$_6$) 1.60–2.25 (m, 6 H), 3.00–3.65 (m, 7 H), 4.04 (t, J=5.7 Hz, 2 H), 6. 62–6.70 (m, 2 H), 6.83–6.97 (m, 3 H), 7.10 (d, J=8.7 Hz, 2 H), 7.28 (t, J$_1$=7.8 Hz, J$_2$=7.5 Hz, 2 H), 9.64 (bs, 1 H). Anal. Calcd for $C_{20}H_{26}BrClN_2O$.0.40 H$_2$O: C, 55.47; H, 6.24; N, 6.46. Found: C, 55.64; H, 6.07; N, 6.37.

A General Procedure for Reaction of Piperidine with Alkyl Chloride or Bromide A mixture of a free base of piperidine derivative and an alkyl chloride or bromide in toluene in the presence of NaI was refluxed for 1–10 h. The reaction mixture was cooled to r.t, filtered and washed with hexane. The filtrate was evaporated, and the residue was chromatographed over silica gel to give the product. If the product is a solid, it was crystallized from hexane or hexane-ethyl acetate. If the product is an oil, it was dissolved in acetone and 4N HCl solution in 1,4-dioxane or conc. HCl was added until the mixture became strong acidic (pH<2). It was rotaevaporated, and co-evaporated until a solid residue was obtained, then the solid was recrystallized from acetone to give the hydrochloride.

EXAMPLE 41

4-Benzyl-1-(1-methyl-3-phenoxypropyl)piperidine hydrochloride

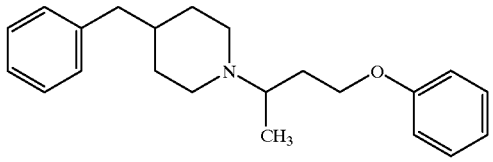

A) 1-Methyl-3-phenoxypropyl chloride. A mixture of phenol (1.546 g, 16.4 mmol) and NaOH (644 mg, 16.1 mmol) in ethanol (25 mL) was refluxed until a solution was formed (about 20 min) and it was cooled to room temperature. To the resulting solution was added 1,3-dichlorobutane (2.124 g, 16.7 mmol) and it was refluxed for 18 h, cooled to room temperature and evaporated, The residue was extracted with ethyl acetate (3×20 mL) and the extract was washed with brine, dried (MgSO$_4$) and evaporated. The residual oil was repeatedly (3 times) chromatographed over silica gel (hexane-EtOAc, 95: 5) to give 554 mg of a yellow oil, which contained about 80% of the desired product by $^1$H NMR and was used for the next reaction without further purification.

B) 4-Benzyl -1-(1-methyl -3-phenoxypropyl)piperidine hydrochloride. From the above crude 1-methyl-3-phenoxypropyl chloride (520 mg, 2.2 mmol) and 4-benzylpiperidine (750 mg, 4.23 mmol) there was obtained 220 mg (31%) of the amine as a yellow viscous oil. $^1$H NMR (CDCl$_3$), 1.299 (d, 3H, J=6), 1.48–1.55 (m, 1H), 1.61–1.92 (m, 7H), 2.35–2.48 (m, 3H), 2.528 (d, 2H, J=7.7), 2.85–2.92 (m, 2H), 4.417 (q, 1H, J=6), 6.88–6.93 (m, 2H), 7.13–7.29 (m, 8H). The hydrochloride, mp 177–8° C. Anal. Calcd. for $C_{22}H_{30}ClNO$: C 73.41, H 8.40, N 3.89; Found: C 73.35, H 8.48, N 3.66.

EXAMPLE 42

4-(4-Chlorophenyl)-4-hydroxyl-1-(2-phenoxyethyl)piperidine hydrochloride

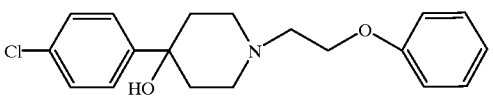

From β-bromophenetole (201 mg, 1.0 mmol) and 4-(4-chlorophenyl)-4-hydroxypiperidine (212 mg, 1.0 mmol) there was obtained 110 mg (51%) of the amine as a yellow viscous oil. $^1$H NMR (CDCl$_3$): 1.65–1.76 (m, 4H), 2.12–2.22 (m, 2H), 2.59–2.66 (m, 2H), 2.88–2.95 (m, 3H), 4.155 (t, 2H, J=5.8), 6.91–6.98 (m, 3H), 7.29–7.33 (m, 3H), 7.44–7.47 (m, 3H). The hydrochloride, mp 197–8° C. Anal. Calcd. for $C_{19}H_{23}Cl_2NO_2$: C 61.96, H 6.29, N 3.80; Found: C 61.69, H 6.13, N 3.69.

EXAMPLE 43

1-(2-Phenoxyethyl)-4-phenylpiperidine hydrochloride

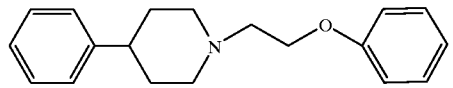

From β-bromophenetole (65 mg, 0.32 mmol) and 4-phenylpiperidine (105 mg, 0.65 mmol) there was obtained 120 mg (65%) of the amine as a yellow viscous oil. $^1$H NMR (CDCl$_3$): 1.80–1.85 (m, 4H), 2.12–2.30 (m, 2H), 2.48–2.59 (m, 1H), 2.873 (t, 2H, J=5.8), 3.13–3.17 (m, 2H), 4.155 (t, 2H, J=5.8), 6.91–6.98 (m, 4H), 7.20–7.35 (m, 6H). The hydrochloride, mp 165–6° C.

EXAMPLE 44

4-(4-Chlorophenyl)-4-hydroxy-1-(3-phenoxypropyl) piperidine

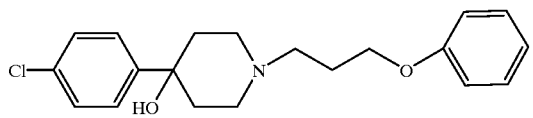

From 3-phenoxypropyl bromide (260 mg, 1.2 mmol) and 4-(4-chlorophenyl)-4-hydroxypiperidine (514 mg, 2.4 mmol) there was obtained 266 mg (63.6%) of the amine as a yellowish powder, mp 125–6° C. $^1$H NMR (CDCl$_3$): 1.56 (bs, 1H), 1.72–1.76 (m, 2H), 1.98–2.18 (m, 4H), 2.42–2.49 (m, 2H), 2.58–2.63 (m, 2H), 2.83–2.87 (m, 2H), 4.040 (t, 2H, J=6), 6.90–6.96 (m, 3H), 7.28–7.33 (m, 4H), 7.44–7.47 (d, 2H, J=8.5). Anal. Calcd. for C$_{20}$H$_{24}$ClNO$_2$: C 69.45, H 6.99, N 4.05; Found: C 69.41, H 7.03, N 4.07.

EXAMPLE 45

3-Hydroxy-1-(2-phenoxyethyl)-4-(3-trifluoromethylphenyl)piperidine hydrochloride

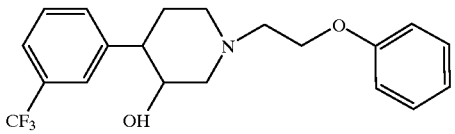

From β-bromophenetole (183 mg, 0.91 mmol) and 3-hydroxy-4-(3-trifluoromethylphenyl)piperidine (450 mg, 1.84 mmol) there was obtained 270 mg (81%) of the amine as a yellow viscous oil. $^1$H NMR (CDCl$_3$): 1.66–1.79 (m, 3H), 1.95–2.27 (m, 2H), 2.61–2.69 (m, 2H), 2.90–2.98 (m, 4H), 4.171 (t, 2H, J=5.7), 6.91–6.98 (m, 3H), 7.26–7.32 (m, 2H), 7.44–7.60 (m, 2H), 7.68–7.71 (d, 1H, J=7.7), 7.81 (s, 1H). The hydrochloride, mp 150–51° C. Anal. Calcd. for C$_{20}$H$_{23}$ClF$_3$NO$_2$: C 59.78, H 5.77, N 3.49; Found: C 59.67, H 5.69, N 3.40.

EXAMPLE 46

3-Hydroxy-1-(3-phenoxypropyl)-4-(3-trifluoromethylphenyl)piperidine hydrochloride

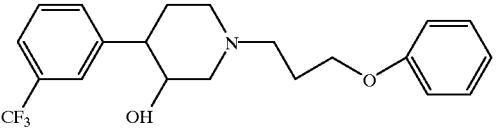

From 3-phenoxypropyl bromide (184 mg, 0.86 mmol) and 4-(3-trifluoromethylphenyl)-3-piperidinol (420 mg, 1.71 mmol) there was obtained 216 mg (67%) of the amine as a yellow viscous oil. $^1$H NMR (CDCl$_3$): 1.62–1.78 (m, 3H), 2.00–2.08 (m, 2H), 2.17–2.25 (m, 2H), 2.47–2.54 (m, 2H), 2.649 (t, 2H, J=7), 2.89–2.92 (m, 2H), 4.048 (t, 2H, J=6), 6.90–6.97 (m, 3H), 7.26–7.32 (m, 2H), 7.44–7.60 (m, 2H), 7.69 (d, 1H, J=7.7), 7.81 (s, 1H). The hydrochloride, mp 176–8° C. Anal. Calcd. for C$_{21}$H$_{25}$ClF$_3$NO$_2$: C 60.65, H 6.06, N 3.37; Found: C 60.65, H 6.01, N 3.25.

EXAMPLE 47

4-Benzyl-4-hydroxy-1-(2-phenoxyethyl)piperidine hydrochloride

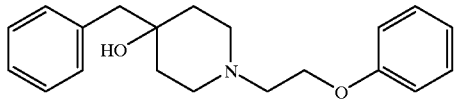

From β-bromophenetole (303 mg, 1.5 mmol) and 4-benzyl-4-hydroxypiperidine (607 mg, 3.05 mmol) there was obtained 320 mg (68%) of the amine as a yellow viscous oil. $^1$H NMR (CDCl$_3$): 1.198 (bs, 1H, OH), 1.52–1.56 (m, 2H), 1.67–1.83 (m, 4H), 2.41–2.49 (m, 2H), 2.76–2.84 (m, 4H), 4.105 (t, 2H, J=6), 6.89–6.96 (m, 3H), 7.19–7.34 (m, 7H). The hydrochloride, mp 175–6° C. Anal. Calcd. for C$_{20}$H$_{26}$ClNO$_2$: C 69.05, H 7.53, N 4.03; Found: C 69.00, H 7.55, N 3.96.

EXAMPLE 48

4-Benzyl-4-hydroxy-1-(3-phenoxypropyl)piperidine

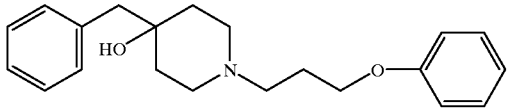

From 3-phenoxypropyl bromide (338 mg, 1.57 mmol) and 4-benzyl-4-hydroxypiperidine (628 mg, 3.16 mmol) there was obtained 320 mg (62%) of the amine as a yellowish powder, mp 87–8° C. $^1$H NMR (CDCl$_3$): 1.200 (bs, 1H), 1.52–1.56 (m, 2H), 1.71–1.81 (m, 2H), 1.96–2.05 (m, 2H), 2.29–2.36 (m, 2H), 2.546 (t, 2H, J=7), 2.68–2.72 (m, 2H), 2.764 (s, 2H), 4.00 (t, 2H, J=6), 6.88–6.95 (m, 3H), 7.19–7.34 (m, 7H). Anal. Calcd. for C$_{21}$H$_{27}$NO$_2$: C 77.50, H 8.36, N 4.30; Found: 77.06, H 8.39, N 4.04.

EXAMPLE 49

4-Benzyl-1-(2-chloroethyl)piperidine

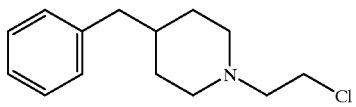

From 1-bromo-2-chloroethane (14.35 g, 0.1 mol) and 4-benzylpiperidine (17.53 g, 0.1 mol) there was obtained 2.5 g (11%) of the title compound as a yellowish oil. $^1$H NMR (CDCl$_3$): 1.25–1.38 (m, 2H), 1. 45–1.57 (m, 1H), 1.61–1.66 (m 2H), 1.96–2.05 (m, 2H), 2.537 (d, 2H, J=7), 2.690 (t, 2H, J=7), 2.87–2.91 (m, 2H), 3.574 (t, 2H, J=7), 7.12–7.30 (m, 5H). It was used without further purification.

EXAMPLE 50

4-Benzyl-1-[2-(6-quinolinoxy)ethyl)]piperidine

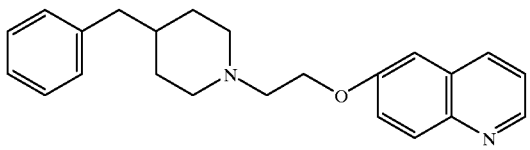

A mixture of NaOH (58 mg, 1.45 mmol), 6-hydroxyquinoline (204 mg, 1.4 mmol) in EtOH (15 mL) was refluxed for 0.5 h. The resulting solution was cooled to r.t, and 4-benzyl-1-(2-chloroethyl)piperidine (615 mg, 2.8 mmol) was added. It was refluxed for 16 h, cooled to r.t, and filtered. The filtrate was evaporated, and the residue was chromatographed over silica gel (EtOAc: EtOH, 7:3) to give 305 mg (71%) of the amine as a yellow viscous oil. $^1$H NMR (CDCl$_3$): 1.34–1.47 (m, 2H), 1.50–1.63 (m, 1H), 1.66–1.71 (m 2H), 2.10–2.18 (m, 2H), 2.558 (d, 2H, J=7), 2.897 (t, 2H, J=6), 3.04–3.08 (m, 2H), 4.255 (t, 2H, J=6), 7.07–7.39 (m, 8H). 7.989 (d, 1H, J=9), 8.01–8.05 (m, 1H), 8.758 (dd, 1H, J=4; 1.2). The hydrochloride, mp 202–204° C. Anal. Calcd. for (C$_{23}$H$_{26}$N$_2$O+2HCl): C 65.87, H 6.73, N 6.68; Found: C 65.78, H 6.65, N 6.58.

EXAMPLE 51

4-Benzyl-1-[2-(8-quinolinoxy)ethyl]piperidine

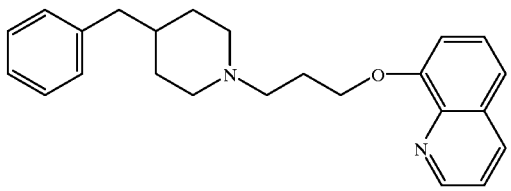

The compound was prepared in a manner similar to example 50. From 8-hydroxyquinoline (330 mg, 2.27 mmol) and 4-benzyl-1-(2-chloroethyl)piperidine (423 mg, 1.92 mmol) there was obtained 284 mg (43.6%) of the amine as a yellow viscous oil. $^1$H NMR (CDCl$_3$): 1.36–1.44 (m, 2H), 1.50–1.60 (m, 1H), 1.65–1.69 (m 2H), 2.08–2.15 (m, 2H), 2.545 (d, 2H, J=7), 3.00–3.07 (m, 4H), 4.371 (t, 2H, J=7), 7.13–7.47 (m, 9H), 8.11–8.14 (m, 1H), 8.92–8.94 (m, 1H).

Anal. for the hydrochloride, Calcd. for (C$_{23}$H$_{26}$N$_2$O+2HCl+H$_2$O): C 63.16, H 6.91, N 6.40; Found: C 63.16, H 7.13, N 6.26.

EXAMPLE 52

4-Benzyl-1-[2-(2-amino-3-nitrophenoxy)ethyl]piperidine

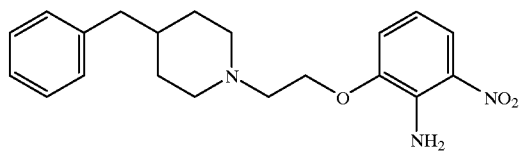

The compound was prepared in a manner similar to example 50. From 2-amino-3-nitrophenol (310 mg, 2.0 mmol) and 4-benzyl-1-(2-chloroethyl)piperidine (445 mg, 2.0 mmol) there was obtained 590 mg (89.6%) of the amine as a yellow viscous oil. $^1$H NMR (CDCl$_3$): 1.25–1.37 (m, 2H), 1.50–1.60 (m, 1H), 1.65–1.70 (m, 2H), 2.02–2.10 (m, 2H), 2.554 (d, 2H, J=7), 2.768 (t, 2H, J=5.5), 2.94–2.98 (m, 2H), 4.110 (t, 2H, J=5.5), 6.570 (t, 1H, J=8), 6.750 (bs, 2H), 6.947 (d, 1H, J=8), 7.14–7.31 (m, 5H). 7.770 (d, 1H, J=8).

EXAMPLE 53

4-Benzyl-1-[2-(2,3-diaminophenoxy)ethyl]piperidine

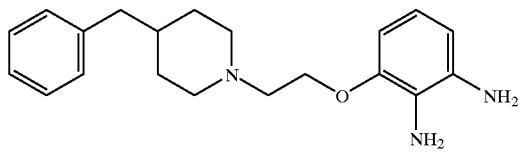

A mixture of the nitro compounds (580 mg, 76 mmol), 5% Pd/C (70 mg) and EtOH (20 mL) was shaken under H$_2$ (30 psi) for 2 h. The mixture was filtered, and the filtrate was evaporated to give 478 mg (90%) of the diamine as a yellow powder, mp 88–90° C. $^1$H NMR (CDCl$_3$): 1.35–1.43 (m, 2H), 1.50–1.60 (m, 1H), 1.65–1.69 (m, 2H), 2.06–2.14 (m, 2H), 2.552 (d, 2H, J=7), 2.813 (t, 2H, J=6), 3.00–3.04 (m, 2H), 3.420 (bs, 4H), 4.131 (t, 2H, J=6), 6.39–6.42 (m, 2H), 6.636 (t, 1H, J=8), 7.13–7.30 (m, 5H). Anal. Calcd. for C$_{20}$H$_{27}$N$_3$O: C, 73.81, H, 8.36, N, 12.91; Found: C, 74.02, H, 8.27, N, 12.70.

EXAMPLE 54

4-Benzyl-1-[2-(2,3-dioxoquinoxalin-5-oxy)ethyl]piperidine

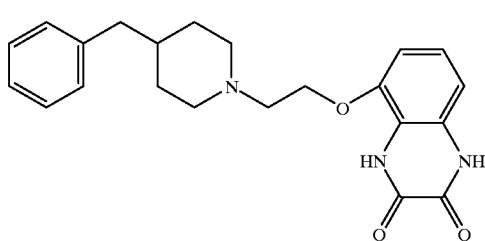

A solution of the diamine (465 mg, 1.55 mmol) and oxalic acid (270 mg, 3.0 mmol) in 2N HCl (10 mL) was refluxed for 3 h, then cooled to r.t. The mixture was neutralized to pH 7 with 1N aq NaOH. The mixture was heated to boil with stirring, then cooled to r.t. The precipitate was filtered, washed with H$_2$O (3×5 mL) and dried. The dry brown solid was stirred vigorously with EtOAc (10 mL) for 0.5 h at r.t, then filtered, washed with EtOAc (2×5 mL), and dried to give 352 mg (60%) of the title compound as a cream powder, mp 244–5° C. $^1$H NMR (DMSO-d$_6$): 1.27–1.34 (m, 2H), 1.50–1.54 (m, 3H), 1.961 (t, 2H, J=10.6), 2.500 (d, 2H, J=5.5), 2.678 (t, 2H, J=5.5), 2.90–2.94 (m, 2H), 4.115 (t, 2H, J=5.5), 6.775 (d, 1H, J=8), 6.834 (d, 1H, J=8), 7.020 (t, 1H, J=8), 7.14–7.30 (m, 5H), 11.87 (bs, 2H). Anal. Calcd. for (C$_{22}$H$_{25}$N$_3$O$_3$+0.25H$_2$O): C, 68.82, H, 6.69, N, 10.94; Found: C, 68.76, H, 6.42, N, 10.83.

EXAMPLE 55

4-Benzyl-1-[2-(2-oxobenzimidazol-4-oxy)ethyl]piperidine

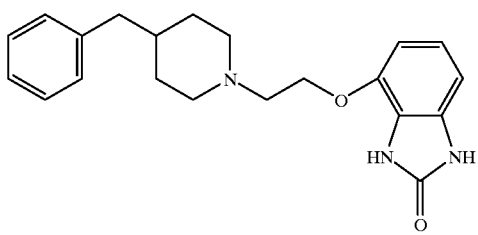

A solution of the diamine (150 mg, 0.5 mmol), 1,1'-carbonyldiimidazole (CDI, 100 mg, 0.62 mmol) in toluene (5 mL) was refluxed under N$_2$ for 18 h, then evaporated. The residual solid was dissolved in EtOAc (20 mL) and washed with H$_2$O (3×10 mL). The EtOAc solution was evaporated, and the residual solid was heated with 15 mL of hexane-ethyl acetate (10:1) to boil, then cooled to rt. The precipitate was filtered, and dried to give 122 mg (60%) of the title compound as a cream powder, mp 153–4° C. $^1$H NMR (CDCl$_3$): 1.56–1.70 (m, 4H), 2.00–2.12 (m, 3H), 2.613 (d, 2H, J=5), 2.728 (t, 2H, J=5), 3.043 (d, 2H, J=10.5), 4.164 (t, 2H, J=5), 6.655 (d, 1H, J=8), 6.748 (d, 1H, J=8), 6.918 (t, 1H, J=8), 7.16–7.30 (m 5H), 9.199 (s, 1H), 10.856 (s, 1H).

EXAMPLE 56

4-Benzyl-1-[2-(4-amino-3-nitrophenoxy) ethyl]piperidine

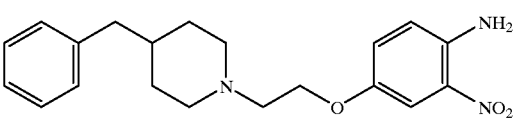

This compound was prepared in a manner similar to example 50. From 4-amino-3-nitrophenol (306 mg, 2. mmol) and 4-benzyl-1-(2-chloroethyl)piperidine (440 mg, 2.0 mmol) there was obtained 450 mg of the amine as a yellowish powder, mp 89–90° C. $^1$H NMR (CDCl$_3$): 1.30–1.41 (m, 2H), 1.50–1.55 (m, 1H), 1.62–1.67 (m 2H), 2.96–2.07 (m, 2H), 2.535 (d, 2H, J=7), 2.757 (t, 2H, J=7), 2.95–2.99 (m, 2H), 4.054 (t, 2H, J=7), 5.868 (bs, 2H), 6.739 (d, 1H, J=9), 7.080 (dd, 1H, J=9; 3), 7.13–7.30 (m, 5H), 7.560 (d, 1H, J=3).

EXAMPLE 57

4-Benzyl-1-[2-(3,4-diaminophenoxy)ethyl]piperidine

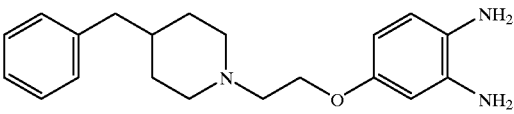

The hydrogenation of the nitro compound (500 mg, 1.40 mmol) was carried out under the same condition as that for example 53, followed by crystallization from hexane to give the diamine (296 mg, 65%) as a yellowish crystalline solid, mp 78–9° C. $^1$H NMR (CDCl$_3$): 1.26–1.39 (m, 2H), 1.45–1.57 (m, 1H), 1.61–1.65 (m, 2H), 1.98–2.06 (m, 2H), 2.530 (d, 2H, J=7), 2.727 (t, 2H, J=6), 2.94–3.10 (m, 3H), 3.495 (bs, 2H), 4.003 (t, 2H, J=6), 6.245 (dd, 1H, J=8; 2.5), 6.317 (d, 1H, J=2.5), 6.612 (d, 1H, J=8), 7.12–7.29 (m, 5H).

EXAMPLE 58

4-Benzyl-1-[2-(2,3-dioxoquinoxalin-6-oxy)ethyl]piperidine

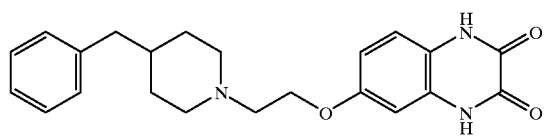

This compound was prepared in a manner similar to example 54. From the diamine (104 mg, 0.32 mmol) and oxalic acid (50 mg, 0.55 mmol) there was obtained the title compound as a cream powder, mp 176–180° C. $^1$H NMR (DMSO-d$_6$): 1.27–1.34 (m, 2H), 1.50–1.54 (m, 3H), 1.961 (t, 2H, J=10.6), 2.500 (d, 2H, J=5.5), 2.678 (t, 2H, J=5.5), 2.90–2.94 (m, 2H), 4.115 (t, 2H, J=5.5), 6.775 (d, 1H, J=8), 6.834 (d, 1H, J=8), 7.020 (t, 1H, J=8), 7.14–7.30 (m, 5H), 11.87 (bs, 2H). Anal. For the hydrochloride, Calcd. for (C$_{22}$H$_{25}$N$_3$O$_3$+1.4 HCl): C, 61.38, H, 6.18, N, 9.76; Found: C, 61.51, H, 5.85, N, 9.77.

EXAMPLE 59

4-Benzyl-1-[2-(2-oxobenzimidazol-5-oxy)ethyl]piperidine

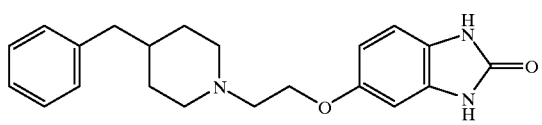

This compound was prepared in a manner similar to example 55. From the diamine (148 mg, 0.46 mmol) and CDI (88 mg, 0.54 mmol) there was obtained 144 mg (92%) of the title compound as an off-white powder, mp 224–5° C. $^1$H NMR (DMSO-$d_6$): 1.16–1.24 (m, 2H), 1.40–1.54 (m, 3H), 1.90–1.97 (m, 2H), 2.487 (d, 2H, J=7), 2.610 (t, 2H, J=6), 2.86–2.90 (m, 2H), 3.968 (t, 2H, J=6), 6.48–6.51 (m, 2H), 6.770 (d, 1H, J=9), 7.14–7.29 (m 5H), 10.355 (s, 1H), 10.485 (s, 1H).

EXAMPLE 60

4-Benzyl-1-[2-(2-nitrophenoxy)ethyl]piperidine

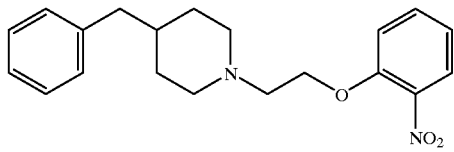

This compound was prepared in a manner similar to example 50. From 2-nitrophenol (200 mg, 1.44 mmol) and 4-benzyl-1-(2-chloroethyl)piperidine (320 mg, 1.45 mmol) there was obtained 340 mg (72.6%) of the amine as a yellow viscous oil. $^1$H NMR (CDCl$_3$): 1.24–1.37 (m, 2H), 1.49–1.59 (m, 1H), 1.63–1.67 (m, 2H), 2.05–2.13 (m, 2H), 2.535 (d, 2H, J=7), 2.835 (t, 2H, J=5.5), 2.95–2.99 (m, 2H), 4.230 (t, 2H, J=5.5), 7.00–7.30 (m, 7H), 7.510 (t, 1H, J=8), 7.820 (d, 1H, J=8). Anal. for the hydrochloride, Calcd. for (C$_{20}$H$_{24}$N$_2$O$_3$+1.45 HCl): C 60.77, H 6.49, N 7.09; Found: C 61.05, H 6.53, N 7.07.

EXAMPLE 61

4-Benzyl-1-[2-(2-aminophenoxy)ethyl]piperidine

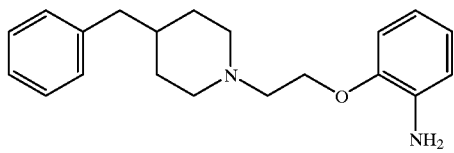

The nitro compound (310 mg, 0.9 mmol) was hydrogenated (Pd/C/H$_2$) to give 275 mg (97%) of the amine as a yellow viscous oil. $^1$H NMR (CDCl$_3$): 1.29–1.40 (m, 2H), 1.50–1.60 (m, 1H), 1.65–1.69 (m, 2H), 2.04–2.12 (m, 2H), 2.553 (d, 2H, J=7), 2.800 (t, 2H, J=6), 3.00–3.03 (m, 2H), 3.910 (bs, 2H), 4.128 (t, 2H, J=6), 6.67–6.82 (m, 2H), 7.13–7.31 (m, 5H). Anal. for the hydrochloride, Calcd. for (C$_{22}$H$_{26}$N$_2$O+2.5HCl): C 61.22, H 7.45, N 7.14; Found: C 61.05, H 7.53, N 6.78.

EXAMPLE 62

4-Benzyl-1-[2-(3-nitrophenoxy)ethyl]piperidine

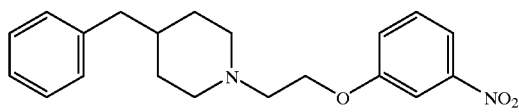

The compound was prepared in a manner similar to example 60 and obtained as a yellow viscous oil. $^1$H NMR (CDCl$_3$): 1.28–1.41 (m, 2H), 1.49–1.67 (m, 3H), 2.12–2.10 (m, 2H), 2.543 (d, 2H, J=7), 2.801 (t, 2H, J=6), 2.95–3.00 (m, 2H), 4.157 (t, 2H, J=6), 7.13–7.30 (m, 6H), 7.410 (t, 1H, J=8), 7.430 (bs, 1H), 7.806 (d, 1H, J=8).

EXAMPLE 63

4-Benzyl-1-[2-(3-aminophenoxy)ethyl]piperidine

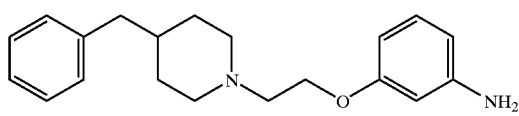

The compound was prepared in a manner similar to example 61 and obtained as a yellow viscous oil. $^1$H NMR (CDCl$_3$): 1.35–1.45 (m, 2H), 1.64–1.68 (m, 3H), 1.64–1.68 (m, 2H), 2.01–2.14 (m, 2H), 2.548 (d, 2H, J=6.5), 2.807 (t, 2H, J=5.5), 3.00–3.04 (m, 2H), 3.64 (bs, 2H), 4.093 (t, 2H, J=5.5), 6.24 (bs, 1H), 6.27–6.31 (m, 1H), 7.036 (t, 1H, J=8), 7.13–7.30 (m, 5H).

EXAMPLE 64

4-Benzyl-1-[2-(4-nitrophenoxy)ethyl]piperidine

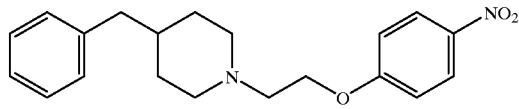

The compound was prepared in a manner similar to example 60 and obtained as a yellow viscous oil. $^1$H NMR (CDCl$_3$): 1.26–1.39 (m, 2H), 1.49–1.58 (m, 1H), 1.61–1.67 (m, 2H), 2.02–2.09 (m, 2H), 2.540 (d, 2H, J=7), 2.800 (t, 2H, J=6), 2.94–2.99 (m, 2H), 4.173 (t, 2H, J=6), 6.950 (d, 2H, J=9), 7.16–7.30 (m, 5H), 8.189 (d, 1H, J=9).

EXAMPLE 65

4-Benzyl-1-[2-(4-aminophenoxy)ethyl]piperidine

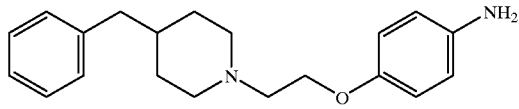

This compound was prepared in a manner similar to example 61 as a yellow viscous oil. $^1$H NMR (CDCl$_3$): 1.42–1.69 (m, 5H), 2.11–2.18 (m, 2H), 2.552 (d, 2H, J=6.5), 2.829 (t, 2H, J=5.5), 3.05–3.09 (m, 2H), 3.380 (bs, 2H), 4.087 (t, 2H, J=5.5), 6.628 (d, 2H, J=9), 6.737 (d, 2H, J=9), 7.13–7.30 (m, 5H).

EXAMPLE 66

4-[2-(4-Benzylpiperidinoethoxy)quinazoline

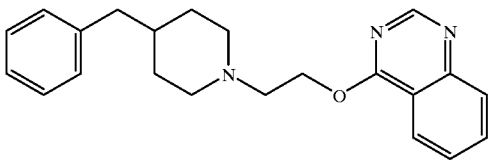

This compound was prepared in a manner similar to example 50. From 4-hydroxyquinazoline (169 mg, 1.16 mmol) and 4-benzyl-1-(2-chloroethyl)piperidine (232 mg, 0.98 mmol) there was obtained 243 mg (71.7%) of the amine as a bulk solid, mp 76–77° C. $^1$H NMR (CDCl$_3$): 1.22–1.32 (m, 2H), 1.47–1.55 (m, 1H), 1.58–1.63 (m, 2H), 1.99–2.07 (m, 2H), 2.516 (d, 2H, J=7), 2.661 (t, 2H, J=6), 2.83–2.87 (m, 2H), 4.075 (t, 2H, J=6), 7.11–7.29 (m, 4H). 7,47–7.52 (m, 2H), 7.07–7.85 (m, 2H), 8.087 (s, 1H), 8.310 (d, 1H, J=8). Anal. Calcd. for C$_{21}$H$_{25}$N$_3$O: C 75.19, H 7.51, N 12.53; Found: C 75.46, H 7.07, N 11.75.

EXAMPLE 67

4-[2-(4-Benzylpiperidino)ethoxy]pyrazolo[3,4-d]pyrimidine (A) and 1-[2-(4-Benzylpiperidino)ethyl]-4-hydroxypyrazolo[3,4-d]pyrimidine(B)

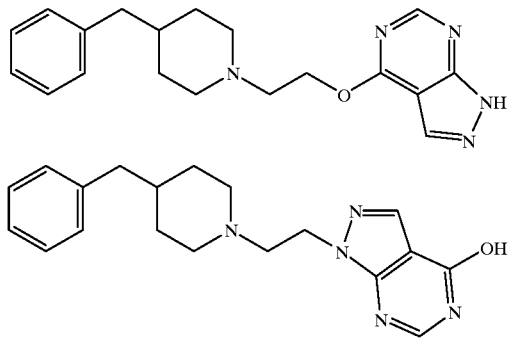

Similar treatment of 4-hydroxypyrazolo[3,4-d]-pyrimidine (204 mg, 1.50 mmol) with NaOH (70 mg, 1.75 mmol) and 4-benzyl-1-(2-chloroethyl)piperidine (357 mg, 1.50 mmol) gave 135 mg (25%) of white powder, mp 178–193° C. It was TLC (EtOAc-EtOH, 10:1) pure, but $^1$H NMR indicated that it was a mixture of the title compounds.

EXAMPLE 68

4-Benzyl-1-[2-(2-methoxyphenoxy)ethyl]piperidine

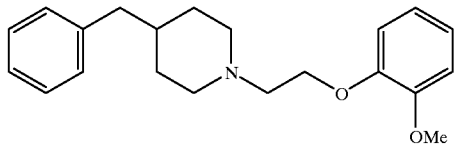

From 1-(2-Bromoethoxy)-2-methoxybenzene (515 mg, 2.23 mmol) and 4-benzylpiperidine (785 mg, 4.48 mmol) there was obtained 560 mg (85%) of the amine as a yellowish oil. $^1$H NMR (CDCl$_3$): 1.27–1.40 (m, 2H), 1.47–1.58 (m, 1H), 1.62–1.66 (m,2H), 1.99–2.06 (m, 2H), 2.543 (d, 2H, J=7), 2.745 (t, 2H, J=6), 2.95–2.99 (m, 2H), 3.760 (s, 3H), 4.041 (t, 2H, J=6), 6.79–6.85 (m, 4H), 7.13–7.30 (m, 5H). The hydrochloride, mp 165–6° C.

EXAMPLE 69

4-Benzyl-1-[2-(3-methoxyphenoxy)ethyl]piperidine

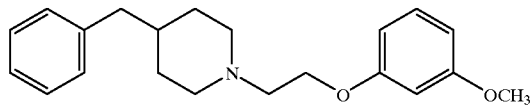

From the 1-(2-bromoethoxy)-3-methoxybenzene (1.732 g, 7.48 mmol) and 4-benzylpiperidine (1.310 g, 7.48 mmol) there was obtained 750 mg (319%) of the amine as a colorless oil. $^1$H NMR (CDCl$_3$): 1.27–1.40 (m, 2H), 1.48–1.59 (m, 1H), 1.62–1.66 (m, 2H), 2.00–2.08 (m, 2H), 2.540 (d, 2H, J=7), 2.771 (t, 2H, J=6), 2.95–2.99 (m, 2H), 3.784 (s, 3H), 4.081 (t, 2H, J=6), 6.47–6.48 (m, 2H), 6.51 (bs, 1H), 7.13–7.30 (m, H). The hydrochloride, mp 122–3° C. Anal. Calcd. for (C$_{21}$H$_{27}$NO$_2$+HCl): C, 69.69, H 7.80, N 3.87; Found: C 69.62, H 7.75, N 3.86.

EXAMPLE 70

4-Benzyl-1-12-(4-methoxyphenoxy)ethyl]piperidine

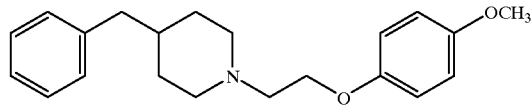

From 1-(2-bromoethoxy)-4-methoxybenzene (0.53 g, 2.3 mmol) and 4-benzylpiperidine (0.85 g, 4.86 mmol) there was obtained 600 mg (80%) of the amine as a yellowish oil. $^1$H NMR (CDCl$_3$): 1.27–1.40 (m, 2H), 1.47–1.59 (m, 1H), 1.62–1.66 (m,2H), 1.98–2.09 (m, 2H), 2.534 (d, 2H, J=7), 2.819 (t, 2H, J=6), 2.96–2.99 (m, 2H), 3.848 (s, 3H), 4.140 (t, 2H, J=6), 6.86–6.92 (m, 4H), 7.13–7.30 (m, 5H). The hydrochloride, mp 150–1° C.

EXAMPLE 71

4-Benzyl-1-[2-(3,4-bisacetamidophenoxy)ethyl] piperidine, (A) 4-Benzyl-1-[2-(2-methylbenzimidazol-6-oxy)ethyl]piperidine (B) and 4-Benzyl-1-[2-(2-methylbenzimidazol-5-oxy)ethyl]piperidine(C)

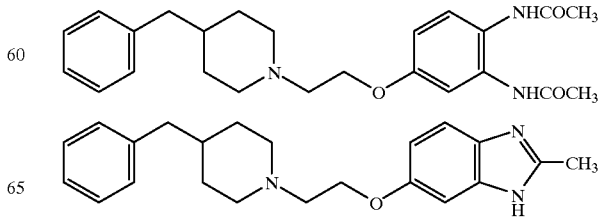

-continued

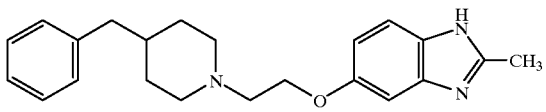

To a solution of 4-benzyl-1-[2-(3,4-diaminophenoxy)ethyl] piperidine (260 mg, 0.8 mmol) in toluene (10 mL) was added acetyl chloride (3 mL). The resulting mixture was refluxed under $N_2$ for 24 h, then cooled to r.t and evaporated. To the residue was added $H_2O$ (20 mL) and $CHCl_3$. The mixture was cooled (ice-water), and 4 N aq. NaOH was added dropwise with stirring to adjust the pH to 10–11. The $CHCl_3$ layer was separated, and the aqueous was extracted with $CHCl_3$ (2×15 mL). The $CHCl_3$ solutions were combined, washed with brine (20 mL), and evaporated. The residue was chromatographed over silica gel ($CHCl_3$:MeOH=7:3) to first give 60 mg (17%) of the diacetimide as a colorless oil. $^1H$ NMR ($CDCl_3$) 1.27–1.40 (m, 2H), 1.49–1.67 (m, 3H), 2.03–2.07 (m, 2H), 2.272 (s, 3H, 2.289 (s, 3H), 2.543 (d, 2H, J=7), 2.789 (t, 2H, J=6), 2.95–2.99 (m, 2H), 4.115 (t, 2H, J=6), 6.828 (d, 1H, J=3), 7.020 (dd, 1H, J=9, 3), 7.13–7.30 (m,6H). The benzimidizoles was then obtained (70 mg, 25) as a yellowish oil, which showed one spot on TLC ($CHCl_3$-MeOH, 7:3), and $^1H$ NMR ($CDCl_3$) indicated that it was a mixture: 1.32–1.40 (m, 2H), 1.45–1.57 (m, 1H), 1.62–1.66 (m, 2H), 2.02–2.09 (m, 2H), 2.129 (s, 3H), 2.537 (t, 2H, J=7), 2.757 (t, 2H, J=6), 2.94–2.98 (m, 2H), 4.050 (t, 2H, J=6), 6.705 (dd, 2H, J=9; 2), 6.991 (d, 1H, J=2),7.13–7.30 (m, 5H), 7.986 (bs, 0.5H, NH), 8.342 (bs, 0.5H, NH).

EXAMPLE 72

4-Benzyl-1-[2-(3-trifluoromethylphenoxy)ethyl]piperidine

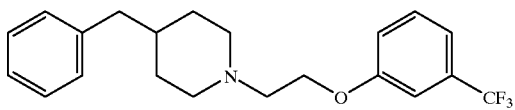

The compound was prepared in a manner similar to example 50. From 3-trifluoromethylphenol (1.626 g, 10.0 mmol) and 4-benzyl-1-(2-chloroethyl)piperidine (592 mg, 2.49 mmol) there was obtained 450 mg (50%) of the amine as an oil. $^1H$ NMR ($CDCl_3$): 1.38–1.43 (m, 2H), 1.50–1.60 (m, 1H), 1.64–1.68 (m 2H), 2.05–2.13 (m, 2H), 2.535 (d, 2H, J=7), 2.812 (t, 2H, J=5.5), 3.00–3.04 (m, 2H), 4.120 (t, 2H, J=5.5), 6.94–7.37 (m, 9H). The hydrochloride, mp 155–6° C.

EXAMPLE 73

4-(4-Chlorobenzyl)-1-[2-(2-nitrophenoxy)ethyl]piperidine

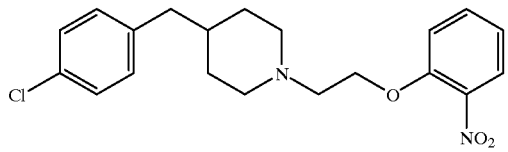

From 2-(2-nitrophenoxy)ethyl bromide (990 mg, 4.0 mmol) and 4-(4-chlorobenzyl)piperidine (840 mg, 4.0 mmol) there was obtained 190 mg (50%) of the amine as a yellow oil. $^1H$ NMR ($CDCl_3$): 1.28–1.40 (m, 2H), 1.48–1.55 (m, 1H), 1.62–1.67 (m, 2H), 2.11–2.18 (m, 2H), 2.507 (d, 2H, J=7),2.876 (t, 2H, J=6), 3.00–3.04 (m, 2H), 4.263 (t, 2H, J=6), 7.00–7.09 7 (m, 3H), 7.241 (d, 2H, J=8), 7.49–7.55 (m, 2H), 7.81–7.84 (m,1H).

EXAMPLE 74

4-(4-Chlorobenzyl)-1-[2-(2-aminophenoxy)ethyl]piperidine

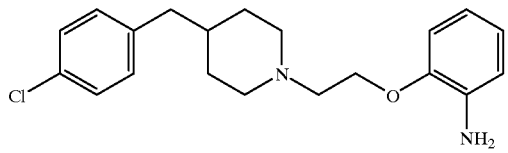

The nitro compound (100 mg, 0.27 mmol) was hydrogenated (Raney $Ni/H_2$) to give 83 mg (90%) of the amine as a gray viscous oil. The hydrochloride was obtained as a highly hygroscopic solid. $^1H$ NMR ($D_2O$): 1.45–1.57 (m, 2H), 1.85–1.91 (m, 3H), 2.578 (d, 2H, J=7), 2.97–3.05 (m, 2H), 3.58–3.68 (m, 4H), 4.479 (t, 2H, J=5), 7.09–7.20 (m, 5H), 7.31–7.47 (m, 3H).

EXAMPLE 75

4-(4-Chlorobenzyl)-1-[2-(2-amino-3-nitrophenoxy)ethyl]piperidine

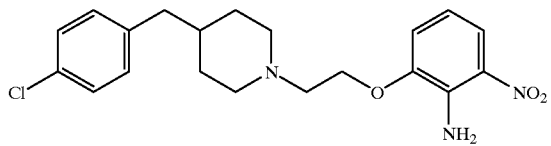

From 4-(4-chlorobenzyl)piperidine (1.22 g, 5.8 mmol) and 2-(2-amino-3-nitrophenoxy)ethyl bromide (740 mg, 3.0 mmol) there was obtained 696 mg (60%) of the amine as a solid, mp 85–6° C. $^1H$ NMR ($CDCl_3$): 1.23–1.36 (m, 2H), 1.47–1.58 (m, 1H), 1.63–1.66 (m, 2H), 2.02–2.09 (m, 2H), 2.522 (d, 2H, J=7), 2.772 (t, 2H, J=5.5), 2.95–2.98 (m, 2H), 4.112 (t, 2H, J=5.5), 6.573 (t, 1H, J=7.5), 6.740 (bs, 2H, $NH_2$), 6.947 (d, 1H, J=7.5), 7.077 (d, 2H, J=8), 7.252 (d, 2H, J=8), 7.772 (d, 1H, J=7.5).

EXAMPLE 76

4-(4-Chlorobenzyl)-1-[2-(2,3-diaminophenoxy)ethyl]piperidine

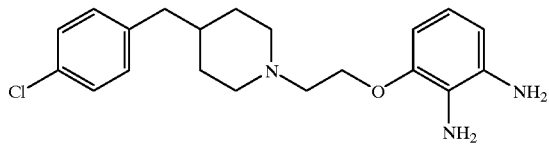

The nitro (636 mg, 1.63 mmol) was hydrogenated (Raney Ni/H$_2$) to give 617 mg (956) of the diamine as a deep purple bulk solid. $^1$H NMR (CDCl$_3$): 1.23–1.36 (m, 2H), 1.45–1.55 (m, 1H), 1.60–1.64 (m, 2H), 2.00–2.08 (m, 2H), 2.503 (d, 2H, J=7), 2.767 (t, 2H, J=6), 2.95–2.99 (m, 2H), 3.415 (bs, 2H, NH$_2$), 3.541 (bs, 2H, NH$_2$), 4.102(t, 2H, J=6), 6.402 (d, 1H, J=8), 6.408 (d, 1H, J=8), 6.636 (t, 1H, J=8), 7.065 (d, 2H, J=8.5), 7.242 (d, 2H, J=8.5).

EXAMPLE 77

4-(4-Chlorobenzyl)-1-[2-(2-oxobenzimidazol-4-oxy)ethyl]piperidine

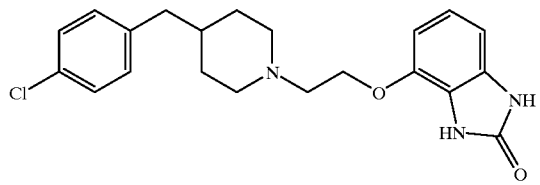

The compound was prepared in a manner similar to example 55. From the diamine (610 mg, 1.7 mmol) and CDI (405 mg, 2.5 mmol) there was obtained 380 mg (58%) of the title compound as a cream-colored powder, mp 147–8° C. $^1$H NMR (DMSO-d$_6$): 1.15–1.24 (m, 2H), 1.41–1.52 (m, 3H), 1.92–1.99 (m, 2H), 2.488 (d, 2H, J=7), 2.653 (t, 2H, J=5.5), 2.88–2.92 (m, 2H), 4.105 (t, 2H, J=5.5), 6.561 (d, 1H, J=8), 6.615 (d, 1H, J=8), 6.836 (t, 1H, J=8), 7.182 (d, 2H, J=8), 7.320 (d, 2H, J=8), 10.544 (s, 1H), 10.689 (s, 1H). The hydrochloride, mp 175–5° C.

EXAMPLE 78

4-(4-Chlorobenzyl)-1-[2-(4-amino-3-nitrophenoxy)ethyl]piperidine

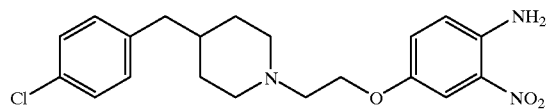

From 4-(4-chlorobenzyl)piperidine (1.25 g, 5.95 mmol) and 2-(4-amino-3-nitrophenoxy)ethyl bromide (738 mg, 3.0 mmol) there was obtained 826 mg (70%) of the amine as a yellow solid, mp 93–4° C. $^1$H NMR (CDCl$_3$): 1.26–1.39 (m, 2H), 1.44–1.65 (m, 3H), 2.00–2.07 (m, 2H), 2.512 (d, 2H, J=7), 2.761 (t, 2H, J=6), 2.95–2.99 (m, 2H), 4.059 (t, 2H, J=6), 5.872 (bs, 2H, NH$_2$), 6.746 (d, 1H, J=9), 7.06–7.08 (m, 3H), 7.23–7.27 (m, 2H), 7.568 (d, 1H, J=2.5).

EXAMPLE 79

4-(4-Chlorobenzyl)-1-[2-(3,4-diaminophenoxy)ethyl]piperidine

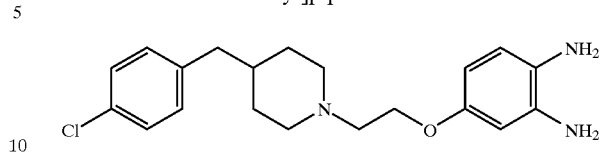

The nitro (690 mg, 1.77 mmol) was hydrogenated (Raney Ni/H$_2$) to give 600 mg (94%) of the diamine as a brown viscous oil. $^1$H NMR (CDCl$_3$): 1.26–1.37 (m, 2H), 1.45–1.55 (m, 1H), 1.59–1.63 (m, 2H), 1.98–2.06 (m, 2H), 2.501 (d, 2H, J=7), 2.728 (t, 2H, J=6), 2.94–2.98 (m, 2H), 3.069 (bs, 2H, NH$_2$), 3.503 (bs, 2H, NH$_2$), 4.005(t, 2H, J=6), 6.250 (dd, 1H, J=8; 2), 6.321 (d, 1H, J=2), 6.618 (d, 1H, J=8), 7.066 (d, 2H, J=8), 7.240 (d, 2H, J=8).

EXAMPLE 80

4-(4-Chlorobenzyl)-1-[2-(2-oxobenzimidazol-5-oxy)ethyl]piperidine

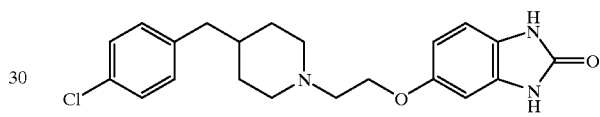

The compound was prepared in a manner similar to example 55. From the diamine (570 mg, 1.59 mmol) and CDI (324 mg, 2.0 mmol) there was obtained 365 mg (60%) of the title compound as an off-white powder, mp 211–2° C. $^1$H NMR (DMSO-d$_6$): 1.14–1.22 (m, 2H), 1.40–1.52 (m, 3H), 1.89–1.97 (m, 2H), 2.487 (d, 2H, J=7), 2.590 (t, 2H, J=6), 2.86–2.89 (m, 2H), 3.965 (t, 2H, J=5.5), 6.561 (d, 1H, J=8), 6.48–6.51 (m 2H), 6.776 (d, 1H, J=8), 7.182 (d, 2H, J=8), 7.318 (d, 2H, J=8), 10.358 (s, 1H), 10.488 (s, 1H). The hydrochloride, mp. 277–9° C.

EXAMPLE 81

2-(2-Oxobenzimidazol-5-oxy)ethyl bromide

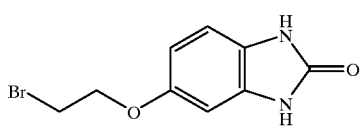

A solution of 2-(4-amino-3-nitrophenoxy)ethyl bromide (980 mg, 7.59 mmol) in dry THF (20 mL) was shaken over 5% Pd/C (80 mg) under H$_2$ (20–30 psi) for 5 h, then filtered. To the filtrate was added CDI (2.4 g, 14.8 mmol). The mixture was stirred at room temperature under N$_2$ for 4 h, then refluxed for 14 h. The mixture was evaporated, then the residual solid was washed with CHCl$_3$ (3×15 mL), and dried to give 407 mg (21%) of the title compound as an off-white powder, mp 225–6° C. $^1$H NMR (DMSO-d$_6$): 3.747 (t, 2H, J=5.5), 4.234 (t, 2H, J=5.5), 6.52–6.54 (m, 2H), 6.792 (d, 1H, J=9), 10.399 (s, 1H), 10.521 (s, 1H).

EXAMPLE 82

4-(4-fluorobenzyl)-1-[2-(2-oxobenzimidazol-5-oxy)ethyl]piperidine

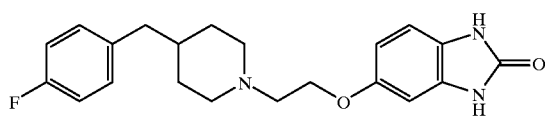

A mixture 2-(2-oxobenzimidazol-5-oxy)ethyl bromide (125 mg, 0.5 mmol), 4-(4-fluorobenzyl)piperidine (200 mg, 1.0 mmol) and NaI (50 mg) in THF (15 mL) was refluxed for 16 h, then cooled to room temperature. The mixture was filtered and the filter cake was washed with THF (2×5 mL). The filtrate and the washings were combined and evaporated. The residual solid was washed with EtOAc (2×10 mL) and CHCl$_3$ (2×5 mL), then dried to give 120 mg of crude product as an off-white powder.

The $^1$H NMR indicated that the desired product was contaminated by the starting material and the salt of the piperidine.

EXAMPLE 83

4-Benzyl-1-(2-phenylethyl)piperidine hydrochloride

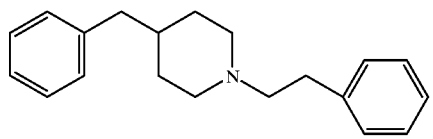

From (2-bromoethyl)benzene (380 mg, 2.05 mmol) and 4-benzylpiperidine (724 mg, 4.13 mmol) there was obtained 400 mg (70%) of the amine as a yellow viscous oil. $^1$H NMR (CDCl$_3$): 1.31–1.41 (m, 2H), 1.43–1.60 (m, 1H), 1.66–1.69 (m, 3H), 1.91–1.99 (m, 2H), 2.53–2.58 (m, 3H), 2.77–2.83 (m, 2H), 2.982 (m, 2H), 7.14–7.30 (m, 10H). The hydrochloride, mp 251–252° C. Anal. Calcd. for C$_{20}$H$_{26}$ClN: C 76.05, H 8.30, N 4.43; Found: C 75.95, H 8.48, N 4.39.

EXAMPLE 84

4-Benzyl-1-(3-phenylpropyl)piperidine hydrochloride

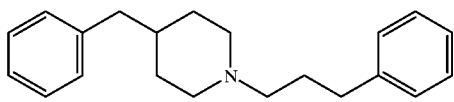

From 1-bromo-3-phenylpropane (402 mg, 2.02 mmol) and 4-benzylpiperidine (715 mg, 4.08 mmol) there was obtained 500 mg (84%) of the amine as a yellow viscous oil, $^1$H NMR (CDCl$_3$): 1.26–1.37 (m, 2H), 1.41–1.56 (m, 1H), 1.60–1.66 (m, 2H), 1.76–1.87 (m, 4H), 2.326 (t, 2H, J=8), 2.525 (d, 2H, J=7), 2.608 (t, 2H, J=8), 2.87–2.91 (m, 2H), 7.12–7.29 (m, 10H). The hydrochloride, mp 191–193° C. Anal. Calcd. for C$_{21}$H$_{28}$ClN: C 76.45, H 8.55, N 4.25; Found: 76.41, H 8.69, N 4.08.

EXAMPLE 85

4-Dibenzylpiperidine

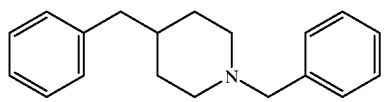

From benzyl bromide (351 mg, 3.1 mmol) and 4-benzylpiperidine (1.103 g, 6.3 mmol) there was obtained 540 mg (65%) of the amine as a yellowish powder, mp 60–61° C. $^1$H NMR (CDCl$_3$): 1.22–1.37 (m, 2H), 1.43–1.56 (m, 1H), 1.58–1.64 (m, 2H), 1.85–1.93 (m, 2H), 2.526 (t, 2H, J=6.6), 2.84–2.87 (m, 2H), 3.470 (s, 2H), 7.12–7.30 (m, 10H). Anal. Calcd. for C$_{19}$H$_{27}$N: C 85.99, H 8.73, N 5.28; Found: 85.95, H 8.83, N 5.24.

EXAMPLE 86

4-(4-Chlorophenyl)-4-hydroxyl-1-(3-phenylpropyl)piperidine

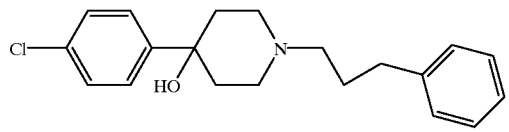

From 3-phenylpropyl bromide (200 mg, 1.0 mmol) and 4-(4-chlorophenyl)-4-hydroxypiperidine (212 mg, 1.0 mmol) there was obtained 100 mg (30%) of the amine as a yellowish powder, mp 107–8° C. $^1$H NMR (CDCl$_3$): 1.52–1.75(m, 5H), 1.84–1.96 (m, 2H), 2.12–2.19 (m, 2H), 2.40–2.49 (m, 2H), 2.661 (t, 2H, J=7.6), 2.83–2.86 (m, 2H), 7.19–7.33 (m, 6H), 7.43–7.46 (m, 3H). Anal. Calcd. for C$_{20}$H$_{24}$ClNO: C 72.82, H 7.33, N 4.25; Found: C 72.54, H 7.18, N 4.23.

EXAMPLE 87

4-Benzyl-1-(4-phenylbutyl)piperidine hydrochloride

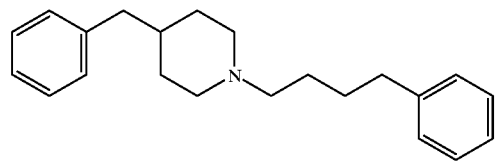

From 1-chloro-4-phenylbutane (338 mg, 2.0 mmol) and 4-benzylpiperidine (708 mg, 4.0 mmol) there was obtained 420 mg (68%) of the amine as a yellow viscous oil. $^1$H NMR (CDCl$_3$): 1.22–1.37 (m, 2H), 1.52–1.70 (m, 7H), 1.79–1.87 (m, 2H), 2.28–2.33 (m, 2H), 2.525 (d, 2H, J=27), 2.59–2.64 (m, 2H), 2.87–2.90 (m, 2H), 7.12–7.20 (m, 6H). 7.25–7.30 (m, 4H). The hydrochloride, mp 167–8° C.

EXAMPLE 88

4-(4-Chlorophenyl)-4-hydroxyl-1-(4-phenylbutyl) piperidine

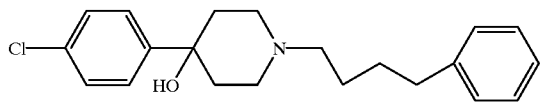

From 1-chloro-4-phenylbutane (203 mg, 1.2 mmol) and 4-(4-chlorophenyl)-4-hydroxypiperidine (514 mg, 2.4 mmol) there was obtained 30 mg (7%) of the amine as a yellowish powder, mp 110–111° C. $^1$H NMR (CDCl$_3$): 1.56–1.74 (m, 7H), 2.08–2.18 (m, 2H), 2.36–2.46 ((, 4H), 2.62–2.67 (m, 2H), 2.80–2.84 (m, 2H), 7.187 (d, 2H, J=7), 7.26–7.33 (m, 5H), 7.445 (d, 2H, J=7). Anal. Calcd. for $C_{21}H_{26}ClNO$: C 73.35, H 7.62, N 4.07; Found: C 73.59, H 7.54, N 4.12.

EXAMPLE 89

3-Hydroxy-1-(4-phenylbutyl)-4-(3-trifluoromethylphenyl)piperidine hydrochloride

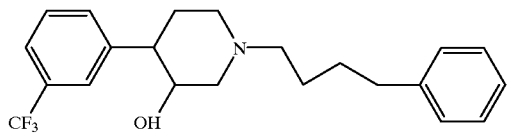

From 1-chloro-4-phenylbutane (80 mg, 0.4 7 mmol) and 4-(3-trifluoromethylphenyl)-3-piperidinol (100 mg, 0.41 mmol) there was obtained 36 mg (20%) of the amine as a yellow viscous oil. $^1$H NMR (CDCl$_3$): 1.46–1.75 (m, 7H), 2.12–2.22 (m, 2H), 2.37–2.46 (m, 4H), 2.650 (t, 2H, J=7), 2.82–2.86 (m, 2H), 7.18–7.31 (m, 4H), 7.43–7.53 (m, 3H), 7.691 (d, 1H, J=7.5), 7.81 (bs, 1H). The hydrochloride, mp 177–8° C. Anal. Calcd. for $C_{22}H_{27}ClF_3NO$: C 63.84, H 6.58, N 3.38; Found: C 64.13, H 6.60, N 3.42.

EXAMPLE 90

4-Benzyl-4-hydroxy-1-(2-phenylethyl)piperidine hydrochloride

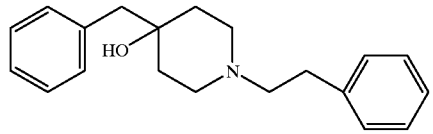

From 2-phenylethyl bromide (702 mg, 3.8 mmol) and 4-benzyl-4-hydroxypiperidine (1.51 g, 7.9 mmol) there was obtained 960 mg (83.6%) of the amine as a yellow viscous oil. $^1$H NMR (CDCl$_3$): 1.20–1.27 (m, 1H), 1.54–1.60 (m, 4H), 1.75–1.85 (m, 2H), 2.35–2.42 (m, 2H), 2.60–2.65 (m, 2H), 2.78–2.85 (m, 4H), 7.19–7.34 (m, 10H). The hydrochloride, mp 233–5° C. Anal. Calcd. for $C_{20}H_{26}ClNO$: C 72.38, H 7.90, N 4.22; Found: C 72.06, H 7.90, N 3.97.

EXAMPLE 91

4-Benzyl-4-hydroxy-1-(3-phenylpropyl)piperidine hydrochloride

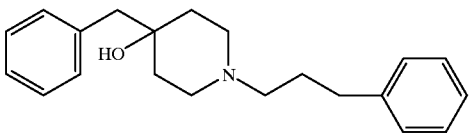

From 1-bromo-3-phenylpropane (598 mg, 3.0 mmol) and 4-benzyl-4-hydroxypiperidine (1.15 g, 6.0 mmol) there was obtained 780 mg (84%) of the amine as a yellow viscous oil. $^1$H NMR (CDCl$_3$): 1.183 (s, 1H, OH), 1.50–1.54 (m, 2H), 1.71–1.89 (m, 4H), 2.24–2.32 (m, 2H), 2.397 (t, 2H, J=8), 2.60–2.70 (m, 4H), 2.755 (s, 2H), 7.12–7.34 (m, 10H). The hydrochloride, mp 156–7° C. Anal. Calcd. for $C_{21}H_{28}ClNO$: C 72.92, H 7.87, N 4.05; Found: C 73.07, H 8.10, N 4.13.

EXAMPLE 92

1,4-Dibenzyl-4-hydroxypiperidine hydrochloride

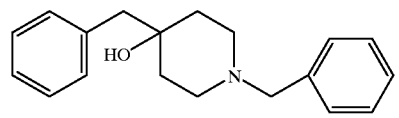

From benzyl bromide (334 mg, 1.95 mmol) and 4-benzyl-4-hydroxypiperidine (398 g, 2.0 mmol) there was obtained 150 mg (52%) of the amine as a yellow viscous oil. The hydrochloride, mp 200–1° C. $^1$H NMR (D$_2$O): 1.72–1.92 (m, 4H), 2.803 (s, 2H), 3.13–3.35 (m, 4H), 4.268 (s, 2H, 7.22–7.49 (m, 10H). Anal. Calcd. for $C_{19}H_{24}ClNO$: C 71.80, H 7.61, N 4.41; Found: C 71.94, H 7.72, N 4.25.

EXAMPLE 93

1-Benzyl-4-(4-fluorobenzyl)-4-hydroxypiperidine hydrochloride

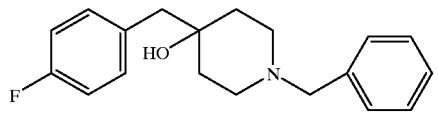

To a 250-ml three-necked round-bottomed flask was added 2.31 g of Mg turnings and 15 mL of anhydrous THF under N$_2$. To which was added dropwise a solution of 1,2-dibromoethane (0.489 g, 2.65 mmol) in 5 mL of THF at rt. After addition, THF was removed and the residue was rinsed with THF (2×5 mL). To this residue was added dropwise a solution of 4-fluorobenzyl chloride (13.4 g, 92.6 mmol) in 50 mL of THF at 0° C. After addition, the solution was allowed to stir at rt for 2 hrs. and another 50 mL of THF was added. After cooling down to −35° C.—40° C., a solution of 4-benzylpiperidone (5.0 g, 26.5 mmol) in 20 mL of THF was added dropwise. After the addition was complete, the reaction mixture was allowed to stir at rt for 3 hrs and stand overnight. To this reaction mixture was added 100 mL of saturated NH$_4$Cl aqueous solution at 0°C. and then extracted with dichloromethane (2×50 mL). The combined organic phase was evaporated in vacuo to give an oil, which was redissolved into 200 mL of dichloromethane and washed with saturated NH$_4$Cl aqueous solution (2×30 mL) and brine (50 mL), and then dried over sodium sulfate. Evaporation of solvent followed by flash chromatography (EtOAc R$_f$=0.25), giving 6.7 g (85%) of the product as a pale yellow oil. $^1$H NMR (300 MHz, CDCl$_3$) δ 1.463 (m, 2 H), 1.680 (m, 2 H), 2.174 (s, 1 H), 2.290 (m, 2 H), 2.620 (m, 2 H), 2.725 (s, 2 H), 3.510 (s, 2 H), 6.890 (m, 2 H), 7.138 (m, 2 H), 7.268 (m, 5 H). The hydrochloride, mp 225–6° C. Anal. Calcd. for C$_{19}$H$_{23}$ClFNO: C 67.95, H 6.90, N 4.17; Found: C 67.74, H 6.81, N 4.07.

EXAMPLE 94

4-(4-Fluorobenzyl)-4-hydroxypiperidine

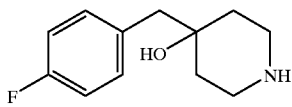

A mixture of 1-benzyl-4-(4-fluorobenzyl)-4-hydroxypiperidine (520 mg, 1.7 mmol), 5% Pd/C (150 mg) and EtOH (15 mL) was shaken under H$_2$ (30 psi) for 14 h and filtered. The filtrate was evaporated to give 350 mg (98%) of the title compound as a yellowish oil. $^1$H NMR (CDCl$_3$), 1.45–1.64 (m, 6H), 2.792 (s, 2H), 2.63–2.96 (m, 4H), 6.97–7.02 (m, 2H), 7.14–7.19 (m, 2H).

EXAMPLE 95

4-(4-Fluorobenzyl)-1-[2-(4-fluorophenyl)ethyl]-4-hydroxypiperidine hydrochloride

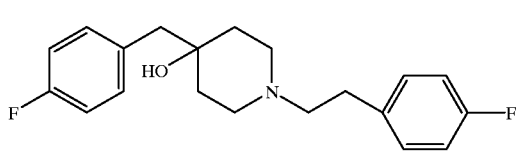

A mixture of 2-(4-fluorophenyl)ethanol tosylate 432 mg, 1.47 mmol), 4-(4-fluorobenzyl)-4-hydroxypiperidine (200 g, 0.96 mmol), K$_2$CO$_3$ (270 mg, 1.96 mmol) and EtOH (30 mL) was refluxed for 18 h, then worked up to give 146 mg (46%) of the title compound as a yellow viscous oil. $^1$H NMR (CDCl$_3$): 1.51–1.56 (m, 2H), 1.73–1.83 (m, 2H), 2.35–2.43 (m, 2H), 2.58–2.63 (m, 3H), 2.74–2.82 (m, 6H), 6.92–7.02 (m, 4H), 7.12–7.19 (m, 4H). The hydrochloride, mp 197–8° C. Anal. Calcd. for C$_{20}$H$_{24}$ClF$_2$NO: C 65.30, H 6.58, N 3.81; Found: C 65.06, H 6.44, N 3.72.

EXAMPLE 96

4-(2-Keto-1-benzimidazolinyl)-1-(3-phenoxypropyl)piperidine hydrobromide

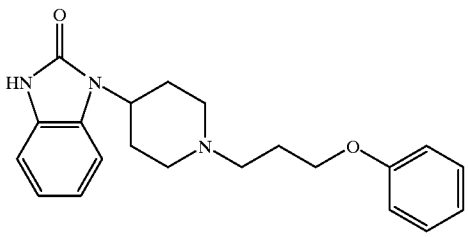

A mixture of 4-(2-keto-1-benzimidazolinyl)piperidine (980 mg. 4.51 mmol) and 3-phenoxypropyl bromide (1.02 g, 4.73 mmol) was reacted in the presence of K$_2$CO$_3$ in CH$_2$CN by refluxing under N$_2$ for about 4 h to obtain the hydrobromide as a pale beige solid (1.06 g, 54%); mp 136–138° C. (foams); $^1$H NMR (CD$_3$OD) δ 2.12 (d, J=13 Hz, 2H), 2.25–2.40 (m, 2 H), 2.81–2.99 (m, 2 H), 3.22–3.49 (m, 4 H), 3.82 (d, J=12 Hz, 2 H), 4.14 (t, J=8.4 Hz, 2 H), 4.55–4.70 (m, 1 H), 6.91–7.41 (m, 9 H).

EXAMPLE 97

Preparation of 3-Hydroxy-1-(4-phenylbutyl)-4-(3-trifluoromethylphenyl)piperidine and the hydrochloride From 1-chloro-4-phenylbutane (80 mg, 0.47 mmol), 4-(3-trifluoromethylphenyl)-3-piperidinol (100 mg, 0.41 mmol) and NaI (125 mg) in toluene (10 mL) was obtained 36 mg (20%) of the product as a yellow viscous oil. $^1$H NMR (CDCl$_3$): 1.46–1.75 (m, 7H), 2.12–2.22 (m, 2H), 2.37–2.46 (m, 4H), 2.650 (t, 2H, J=7), 2.82–2.86 (m, 2H), 7.18–7.31 (m, 4H), 7.43–7.53 (m, 3H), 7.691 (d, 1H, J=7.5), 7.81 (bs, 1H). The hydrochloride, mp 177–8° C. Analysis, Calcd. for C$_{22}$H$_{27}$ClF$_3$NO: C 63.84, H 6.58, N 3.38; Found: C 64.13, H 6.60, N 3.42.

EXAMPLE 98

1-[2-(4-Benzyloxyphenoxy)ethyl]-4-benzylpiperidine hydrochloride

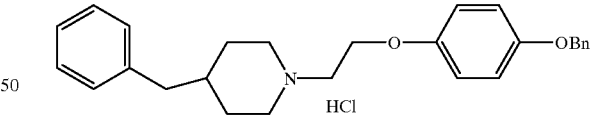

A) 2-(4-Benzyloxyphenoxy)ethyl bromide. A mixture of 4-(benzyloxy)phenol (10 g, 0.05 mol), potassium carbonate (17.3 g, 0.125 mol) in 50 mL of acetonitrile and 21.6 mL of 1,2-dibromoethane was allowed to reflux for 24 h. The inorganic salt was removed through a short column of silica gel and washed with ethyl acetate (3×25 mL). The combined flitrate was evaporated in vacuo to give a crude mixture, which was purified by flash chromatography (5% EtOAc in hexane), giving 12 g (79%) of the bromide as a white solid. mp 75–77° C. $^1$H NMR (CDCl$_3$) 3.611 (t, J=6.2 Hz, 2 H), 4.242 (t, J=6.2 Hz, 2 H), 5.021 (s, 2 H), 6.869 (m, 4 H), 7.381 (m, 5 H).

B) From a mixture of 2-(4-benzyloxyphenoxy)ethyl bromide (1.44 g, 4.7 mmol), 4-benzylpiperidne (0.876 g, 5.0 mmol), potassium carbonate (1.725 g, 12.5 mmol) in 50 mL of acetonitrile was obtained 1.62 g (86%) of the free base. It was converted to its HCl salt in 100% yield. mp 164–166° C. $^1$H NMR (CDCl$_3$) 1.509 (m, 1 H), 1.675 (d, J=12.3 Hz, 2 H), 2.460 (m, 4 H), 2.935 (m, 2 H), 3.349 (m, 2 H), 3.445 (d, J=11.7 Hz, 2 H), 4.257 (s, 2 H), 5.005 (s, 2 H), 6.892 (m, 4 H), 7.182–7.396 (m, 10 H), 10.2 (brs, 2 H).

EXAMPLE 99

1-[2-(4-hydroxyphenoxy)ethyl]-4-benzylpiperidine hydrochloride

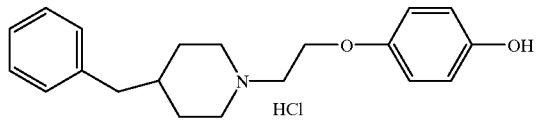

To a solution of 1-[2-(4-benzyloxyphenoxy)ethyl]-4-benzylpiperidine hydrochloride (401 mg, 1.0 mmol) in 25 mL of ethanol was added 1.0 mL of 1 M HCl in methanol and 100 mg of 10% Pd/C. The resulting mixture was hydrogenated at 30 psi of hydrogen for 2 h. The catalyst was removed through a short column of celite (5 g) and washed with methanol (3×15 mL). The combined flitrate was evaporated in vacuo to give an oil and then ether (30 mL) was added to the residue. The resulting mixture was allowed to stir at rt overnight. The white solid was collected by filtration and dried in vacuo, giving 330 mg (100%) of the title product. mp 212–215° C. $^1$H NMR (CDCl$_3$+DMSO-d$_3$) 1.656 (m, 3 H), 1.829 (m, 2 H), 2.425 (s, 2 H), 2.626 (m, 2 H), 3.187 (m, 2 H), 3.4 (brs, 1 H), 4.253 (s, 2 H), 6.549 (m, 4 H), 6.942–7.092 (m, 5 H), 12.0 (brs, 1 H).

EXAMPLE 100

1-[2-(4-Benzyloxyphenoxy)ethyl]-4-(chlorobenzyl) piperidine hydrochloride

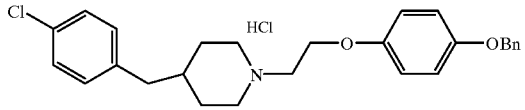

From a mixture of 2-(4-benzyloxyphenoxy)ethyl bromide (0.921 g, 3.0 mmol), 4-chlorobenzylpiperidne hydrochloride (0.74 g, 3.0 mmol), potassium carbonate (1.035 g, 7.5 mmol) in 50 mL of acetonitrile there was obtained 1.1 g (85%) of the free base. It was converted to its HCl salt in 71% yield, mp 171–173° C. $^1$H NMR (DMSO-d$_6$) 1.513 (m, 1 H), 1.656 (d, J=12.6 Hz, 2 H), 2.460 (m, 4 H), 2.972 (m, 2 H), 3.349 (m, 2 H), 3.438 (d, J=12 Hz, 2 H), 4.267 (s, 2 H), 5.004 (s, 2 H), 6.900 (m, 4 H), 7.162–7.396 (m, 9 H), 10.2 (brs, 1 H).

EXAMPLE 101

1-[2-(4-Hydroxyphenoxy)ethyl]-4-(chlorobenzyl) piperidine hydrochloride

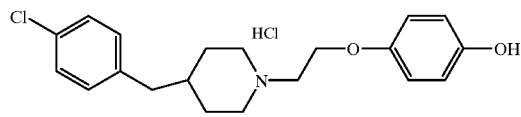

To a solution of 1-[2-(4-benzyloxyphenoxy)ethyl]-4-(4-chlorobenzyl)piperidine (200 mg, 0.46 mmol) in 5 mL of chloroform was added 330 mg (1.65 mmol) of iodotrimethylsilane. The resulting solution was allowed to stir at rt for 30 min. and then methanol (4 mL) was added and was stirred for 20 min. Evaporation of solvent gave a residue, which was purified by flash chromatography (20% methanol in chloroform) to give an oil. This oil was dissolved into 5 mL of methanol and 1 mL of 1 M HCl in methanol was added. The resulting solution was allowed to stir for 10 min. Evaporation of methanol gave a residue, to which was added ether (30 mL). The resulting mixture was allowed to stir at rt overnight. The white solid was collected by filtration and dried in vacuo, giving 91 mg (52%) of the title compound, mp 168–170° C. $^1$H NMR (CD$_3$OD) 1.536 (m, 2 H), 1.656 (d, J=12.6 Hz, 3 H), 2.615 (d, J=6.9 Hz, 2 H), 3.060 (m, 2 H), 3.499 (m, 2 H), 3.591 (m, 2 H), 4.245 (t, J=4.8 Hz, 2 H), 6.710 (m, 2 H), 6.823 (m, 2 H), 7.177 (d, J=8.4 Hz, 2 H), 7.280 (d, J=8.1 Hz, 2 H).

EXAMPLE 102

1-[2-(4-Hydroxyphenoxy)ethyl]-4-(4-fluorobenzyl) piperidine hydrochloride

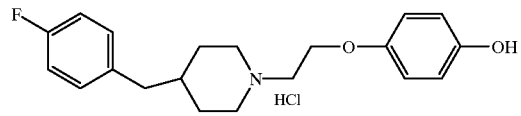

A) 4-Fluorobenzyltriphenylphosphonium bromide. To a solution of triphenylphosphine (26.2 g, 0.1 mol) in 100 mL of ether was added 4-fluorobenzyl bromide (18.9 g, 0.1 mol). The resulting solution was allowed to stir at rt overnight. The white solid was collected by filtration and dried to give 37.0 g (82%) of the bromide as a white solid. mp 280–282° C. $^1$H NMR (CDCl$_3$) 5.492 (d, J=14.4 Hz, 2 H), 6.773 (d, J=8.7 Hz, 2 H), 7.123 (m, 2 H), 7.596 (m, 6 H), 7.749 (m, 9 H).

B) 1-Benzyl-4-(4-fluorobenzylidene)piperidine. To a 250-mL three-necked round bottom flask was added 1.28 g (60% in mineral oil) of sodium hydride and 20 mL of dry DMSO under N$_2$. The mixture is heated at 80° C. for 1 h. The resulting solution was cooled in an ice-water bath. To this solution was added a suspension of 4-fluorobenzyltriphenylphosphonium bromide (16.23 g, 0.036 mol) in 120 mL of warm DMSO. The resulted solution was stirred at 0°C. for 10 min. and at rt for 15 min. Then 4-benzylpiperidone (5.67 g, 0.03 mol) was added dropwise under N$_2$. The resulting mixture was allowed to stir at 80° C. overnight. Then the mixture was poured into ice (400 g)

and extracted with ether (3×200 mL). The combined extracts was dried over sodium sulfate. The solvent was evaporated in vacuo to give a residue, which was purified by flash chromatography (eluent 5% EtOAc in hexanes), giving 7.0 g (83%) of the amine as a pale yellow oil. $^1$H NMR (CDCl$_3$) 2.359–2.545 (m, 8 H), 3.530 (s, 2 H), 6.220 (s, 1 H), 6.983 (m, 2 H), 7.135 (m, 2 H), 7.262–7.335 (m, 5 H).

C) 1-Benzyl-4-(4-fluorobenzyl)piperidine hydrochloride. To a solution of 1-benzyl-4-(4-fluorobenzylidene)piperidine (4.22 g, 15 mmol) in 100 mL of methanol was added 200 mg of PtO$_2$. The resulting mixture was hydrogenated at 40 psi for 8 h. The catalyst was removed through a short column of Celite (10 g) and was washed with methanol (3×20 mL). The filtrate was evaporated in vacuo and dissolved into 20 mL of methanol, to which was added 30 mL of 1 M HCl in methanol. The resulting solution was stirred for 10 min. Evaporation of methanol gave a residue, to which was added 60 mL of ether and stirred for overnight. An off white solid was collected by filtration and dried to give 4.6 g (96%) of the salt, mp 168–170° C. $^1$H NMR (CDCl$_3$) 1.626 (m, 2 H), 1.733 (m, 2 H), 2.089 (q, J=12.3 Hz, 2 H), 2.564 (m, 3 H), 3.414 (d, J=11.1 Hz, 2 H), 4.104 (d, J=5.1 Hz, 2 H), 6.944 (m, 2 H), 7.050 (m, 2 H), 7.431 (m, 3 H), 7.605 (m, 2 H), 12.41 (s, 1 H).

D) 4-(4-Fluorobenzyl)piperidine hydrochloride. A mixture of 1-benzyl-4-(4-fluorobenzyl)piperidine hydrochloride (4.5 g, 14 mmol) and 1.93 g of 10% Pd/C in 100 mL of 95% ethanol was hydrogenated to give 3.2 g (98%) of the title compound, mp 158–160° C. $^1$H NMR (CDCl$_3$) 1.699–1.808 (m, 5 H), 2.570 (m, 2 H), 2.792 (m, 2 H), 3.450 (m, 2 H), 6.976 (m, 2 H), 7.048 (m, 2 H), 9.451 (brs, 2 H).

E) 1-[2-(4-Benzyloxyphenoxy)ethyl]-4-(4-fluorobenzyl) piperidine. From a mixture of 2-(4-benzyloxyphenoxy)ethyl bromide (3,50 g, 11.4 mmol), 4-fluorobenzylpiperidine hydrochloride (2.6 g, 11.4 mmol), potassium carbonate (3.91 g, 28 mmol) in 60 mL of acetonitrile was obtained 4:0 g (84%) of the amine as a pale yellow solid. mp 73–75° C. $^1$H NMR (CDCl$_3$) 1.262 (m, 3 H), 1.621 (m, 2 H), 2.013 (m, 2 H), 2.470 (d, J=6.9 Hz, 2 H), 2.730 (t, J=6.0 Hz, 2 H), 2.933 (m, 2 H), 4.019 (t, J=5.7 Hz, 2 H), 4.987 (s, 2 H), 6.784–6.961 (m, 7 H), 7.067 (m, 2 H), 7.290–7.412 (m, 4 H).

F) A mixture of 1-[2-(4-benzyloxyphenoxy)ethyl]-4-(4-fluorobenzyl)piperidine (4.0 mg, 9.5 mmol) in 100 mL of methanol and 1.0 g of 5% Pd/C was hydrogenated to give 3.2 g (95%) of the title compound, mp 196–198° C. $^1$H NMR (CD$_3$OD) 1.58 (m, 2 H), 1.890 (m, 3 H), 2.602 (d, J=6.3 Hz, 2 H), 3.08 (m, 2 H), 3.49 (t, J=5.1 Hz, 2 H), 3.62 (m, 2 H), 4.250 (t, J=5.1 Hz, 2 H), 6.771 (d, J=9.3 Hz, 2 H), 7.017 (m, 2 H), 7.196 (m, 2 H). Anal. Calcd for C$_{20}$H$_{25}$ClFNO$_2$.0.15H$_2$O: C, 65.17; H, 6.92; N, 3.80. Found: C, 64.93; H, 6.80; N, 4.13.

EXAMPLE 103

4-Benzyl-1-(2-(4-fluorophenoxy)ethyl)piperidine hydrochloride

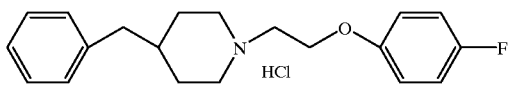

From a mixture of 4-benzylpiperidine (500 mg, 2.85 mmol), 2-(4-fluorophenoxy)ethyl bromide (655 mg, 2.99 mmol) and K$_2$CO$_3$ (413 mg, 2.99 mmol) in CH$_3$CN (20 mL) was obtained the title compound as a fluffy, colorless, crystalline solid (395 g, 79%): mp 165–167° C., $^1$H NMR (CDCl$_3$) 1.70–1.90 (m, 3H), 1.94–2.14 (m, 2H), 2.59 (d, J=7.2 Hz, 2H), 2.65–2.85 (m, 2H), 3.20–3.50 (m, 2H), 3.65 (d, J=12 Hz, 2H), 4.49 (t, J=4.5 Hz, 2H), 6.76–7.30 (m, 9H), 12.47 (bs, 1H); Anal. Calcd for C$_{20}$H$_{25}$ClFNO: C, 68.66; H, 7.20; N, 4.00. Found: C, 68.66; H, 7.11; N, 3.98.

EXAMPLE 104

1-(2-(4-Fluorophenoxy)ethyl)-1-(4-hydroxybenzyl) piperidine

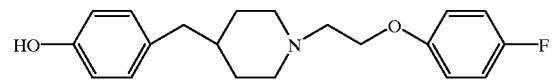

From a solution of BBr$_3$ in CH$_2$Cl$_2$ (3 mL, 1 M) and 1-(2-(4-fluorophenoxy)ethyl)-1-(4-methoxybenzyl) piperidine hydrochloride (300 mg, 790 μmol) in dry CH$_2$Cl$_2$ (20 mL) was obtained a colorless granular solid (155 mg, 60%): mp 149–150° C., $^1$H NMR (DMSO-d$_6$) 1.12–1.20 (m, 2H), 1.28–1.44 (m, 1H), 1.48 (d, J=12 Hz, 2H), 1.84–1.96 (m, 2H), 2.33 (d, J=6.6 Hz, 2H), 2.59 (t, J=6.0 Hz, 2H), 2.84 (d, J=11 Hz, 2H), 3.98 (t, J=6.0 Hz, 2H), 6.63 (d, J=2.1 Hz, 2H), 6.86–6.96 (m, 4H), 7.02–7.12 (m, 2H), 9.12 (s, 1H); Anal. Calcd for C$_{20}$H$_{24}$FNO$_2$ 0.1 H$_2$O: C, 72.52; H, 7.36; N, 4.23. Found: C, 72.44; H, 7.11; N, 4.17.

EXAMPLE 105

3-{4-[2-(4-Chlorobenzylpiperidino)ethoxy]phenyl}-2-methyl-2-propanol hydrochloride

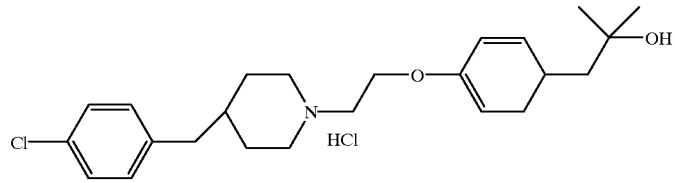

To a solution of 1-[2-(4-ethoxycarbonylmethylphenoxy) ethyl]-4-(4-chlorobenzyl)piperidine (415.5 mg, 1.0 mmol) in 10 mL of anhydrous THF was added 2 mL of 1.4 M MeMgBr in tolune/THF at −78° C. The resulting solution was allowed to warm to rt and stir at rt for another 3 h. Then the solution was poured into water (5 mL) and extracted with ethyl acetate (3×25 mL). The combined extracts were washed with brine (10 mL) and dried over sodium sulfate. Evaporation of solvent gave a residue, which was purified by flash chromatography (20% methanol in chloroform), giving 312 mg (78%) of free base. The hydrochloride, mp 55–56°

C. ¹H NMR (CD₃OD) 1.207 (s, 6 H), 1.70 (m, 2 H), 1.800 (m, 2 H), 2.056 (m, 2 H), 2.592 (d, J=6.9 Hz, 2 H), 2.703 (s, 2 H), 2.769 (s, 2 H), 3.370 (brs, 2 H), 3.647 (m, 2 H), 4.531 (brs, 2 H), 6.802 (d, J=8.4 Hz, 2 H), 7.04 (d, J=8.4 Hz, 2 H), 7.121 (d, J=8.4 Hz, 2 H), 7.261 (d, J=8.4 Hz, 2 H), 12.65 (brs, 1 H).

EXAMPLE 106

1-[3-(4-Hydroxyphenyl)propyl]-4-benzylpiperidine hydrochloride

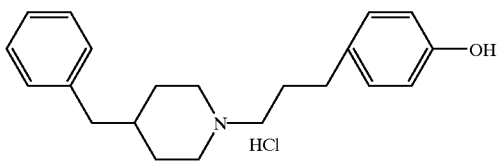

A) Ethyl 4-hydroxyphenylpropionate. From a solution of 4-hydroxyphenylpropionic acid (8.4 g, 50 mmol) in 200 mL of ethanol with 4 mL of concentrated sulfuric acid was obtained 9.7 g (100%) of the title compound as a pale oil. ¹H NMR (CDCl₃) 1.235 (t, J=6.9 Hz, 3 H), 2.584 (t, J=8.1 Hz, 2 H), 2.873 (t, J=8.1 Hz, 2 H), 4.113 (q, J=6.9 Hz, 2 H), 6.880 (d, J=8.4 Hz, 2 H), 7.135 (d, J=8.4 Hz, 2 H).

B) Ethyl 4-benzyloxyphenylpropionate. From a mixture of ethyl 4-hydroxyphenylpropionate (9.7 g, 50 mmol), benzyl bromide (8.58 g, 50 mmol), potassium carbonate (10.35 g, 75 mmol) in 100 mL of acetonitrile was obtained the title compound (85% yield) as a clear oil. ¹H NMR (CDCl₃) 1.232 (t, J=7.2 Hz, 3 H), 2.582 (t, J=8.1 Hz, 2 H), 2.892 (t, J=8.1 Hz, 2 H), 4.110 (q, J=7.2 Hz, 2 H), 5.040 (s, 2 H), 6.915 (d, J=8.4 Hz, 2 H), 7.133 (d, J=8.4 Hz, 2 H), 7.416 (m, 5 H).

C) 3-(4-Benzyloxyphenyl)propan-1-ol. To a slurry of lithium aluminium hydride (1.6 g, 42 mmol) in 50 mL of ether was added dropwise a solution of ethyl 4-benzyloxyphenylpropionate (12 g, 42 mmol) in 100 mL of ether at 0°C. After addition, the resulting mixture was allowed to stir at rt overnight. Then the reaction was quenched by the slow and dropwise addition of water (10 mL), followed by addition of 100 mL of 1 M HCl aqueous solution. The mixture was stirred for 15 min., then the organic layer was separated. The water phase as ectracted again with ether (2×50 mL). The combined extracts were washed with brine (50 mL), dried over sodium sulfate. Evaporation of solvent gave 9.76 g (960) of the title compound as a white solid. mp 60–62° C. ¹H NMR (CDCl₃) 1.863 (t, J=6.6 Hz, 2 H), 2.628 (t, J=7.5 Hz, 2 H), 3.669 (t, J=6.3 Hz, 2 H), 5.042 (s, 2 H), 6.919 (d, J=7.8 Hz, 2 H), 7.129 (d, J=7.8 Hz, 2 H), 7.420 (m, 5 H).

D) 3-(4-Benzyloxyphenyl)prop-1-yl mesylate. To a solution of 3-(4-benzyloxyphenyl)propan-1-ol (9.76 g, 40 mmol) in 75 mL of methylene dichloride and 7.8 mL of triethylamine was added dropwise methanesulfonyl chloride (9.17 g, 80 mmol) at −20° C. The resulting mixture was allowed to stir at rt for 30 min. and was diluted with 100 mL of methylene dichloride. The solution was washed with 1M HCl (2×100 mL), saturated sodium bicarbonate solution (100 mL) and brine (50 mL), then was dried over MgSO₄. Evaporation of solvent gave 12.2 g (95%) of the crude title compound as a white solid. ¹H NMR (CDCl₃) 2.042 (t, J=6.6 Hz, 2 H), 2.694 (t, J=7.5 Hz, 2 H), 2.984 (s, 3 H), 4.195 (t, J=6.0 Hz, 2 H), 5.045 (s, 2 H), 6.928 (d, J=8.4 Hz, 2 H), 7.116 (d, J=8.4 Hz, 2 H), 7.418 (m, 5 H).

E) 1-[3-(4-Benzyloxyphenyl)propyl]-4-benzylpiperidine hydrochloride. From a mixture of 3-(4-benzyloxyphenyl) prop-1-yl mesylate (0.96 g, 3.0 mmol), 4-benzylpiperidine (0.526 g, 3.0 mmol), potassium carbonate (1.035 g, 7.5 mmol) in 20 mL of acetonitrile was obtained 0.7 g (54%) of the title compound, mp 203–205° C. ¹H NMR (CDCl₃) 1.65 (m, 1 H), 1.798 (d, J=14.4 Hz, 2 H), 2.073 (m, 2 H), 2.214 (m, 2 H), 2.458 (m, 2 H), 2.635 (m, 4 H), 2.849 (m, 2 H), 3.516 (d, J=10.8 Hz, 2 H), 5.028 (s, 2 H), 6.904 (d, J=8.4 Hz, 2 H), 7.120 (d, J=8.4 Hz, 2 H), 7.225–7.406 (m, 5 H), 12.2 (s, 1 H).

F) A mixture of 1-[3-(4-benzoxyphenyl)propyl]-4-benzylpiperidine (200 mg, 0.46 mmol) in 25 mL of ethanol with 50 mg of 10% Pd/C was hydrogenated at 30 psi of hydrogen to give 135 mg (85%) of the title compound, mp 208–210° C. ¹H NMR (CD₃OD) 1.477 (m, 2 H), 1.875 (m, 2 H), 1.964 (m, 2 H), 2.579 (m, 4 H), 2.859 (m, 2 H), 3.010 (m 2 H), 3.282 (s, 2 H), 3.483 (m, 2 H), 6.697 (d, J=8.4 Hz, 2 H), 7.026 (d, J=8.4 Hz, 2 H), 7.138–7.255 (m, 5 H).

EXAMPLE 107

1-[3-(4-Hydroxyphenyl)propyl]-4-(4-chlorobenzyl) piperidine hydrochloride

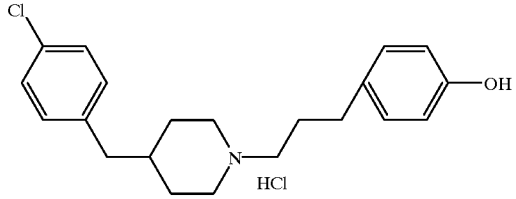

A) 1-[3-(4-Benzyloxyphenyl)propyl]-4-(4-chlorobenzyl) piperidine hydrochloride. From a mixture of 3-(4-benzyloxyphenyl)prop-1-yl mesylate (0.96 g, 3.0 mmol), 4-chlorobenzylpiperidine hydrochloride (0.74 g, 3.0 mmol), potassium carbonate (1.035 g, 7.5 mmol) in 20 mL of acetonitrile was obtained 0.68 g (48%) of the title compound, mp 202–204° C. ¹H NMR (CDCl₃) 1.645 (m, 1 H), 1.731 (m, 2 H), 2.086 (m, 2 H), 2.220 (m, 2 H), 2.465 (m, 2 H), 2.577–2.668 (m, 4 H), 2.849 (m, 2 H), 3.487 (d, J=11.7 Hz, 2 H), 5.034 (s, 2 H), 6.881 (d, J=8.7 Hz, 2 H), 7.030 (d, J=8.7 Hz, 2 H), 7.058 (d, J=10.2 Hz, 2 H), 7.238 (d, J=10.2 Hz, 2 H), 7.384 (m, 5 H), 12.25 (brs, 1 H).

B) From a solution of 1-[3-(4-benzyloxyphenyl)propyl]-4-(4-chlorobenzyl)piperidine (100 mg, 0.212 mmol) in 5 mL of chloroform with 300 mg of iodotrimethylsilane was obtained 72 mg (90%) of the title compound, mp 183–185° C. ¹H NMR (CD₃OD) 1.416 (m, 2 H), 1.860(m, 3 H), 1.983 (m, 2 H), 2.603 (m, 4 H), 2.882 (m, 2 H), 3.049 (m, 2 H), 3.505 (d, J=12.3 Hz, 2 H), 6.694 (d, J=8.4 Hz, 2 H), 7.019 (d, J=8.4 Hz, 2 H), 7.157 (d, J=8.1 Hz, 2 H), 7.264 (d, J=8.1 Hz, 2 H).

EXAMPLE 108

1-[2-(4-Hydroxyphenyl)ethyl]-4-benzylpiperidine hydrochloride

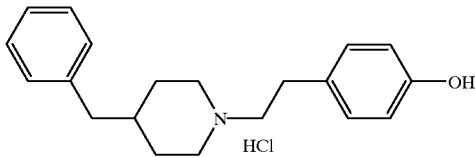

A) 2-(4-Benzyloxyphenyl)ethyl mesylate was prepared from ethyl 4-hydroxyphenylacetate and benzyl bromide in three steps as a white solid, mp 48–50° C. $^1$H NMR (CDCl$_3$) 2.828 (s, 3 H), 2.993 (t, J=6.9 Hz, 2 H), 4.377 (t, J=6.9 Hz, 2 H), 5.045 (s, 2 H), 6.921 (d, J=8.4 Hz, 2 H), 7.136 (d, J=8.4 Hz, 2 H), 7.396 (m, 5 H).

B) 1-[2-(4-Benzyloxyphenyl)ethyl]-4-benzylpiperidine hydrochloride. From a mixture of 2-(4-benzyloxyphenyl) ethyl mesylate (0.96 g, 3.5 mmol), 4-benzylpiperidine (0.526 g, 3.0 mmol), potassium carbonate (1.035 g, 7.5 mmol) in 20 mL of acetonitrile was obtained 0.5 g (40%) of the title compound, mp 183–185° C. $^1$H NMR (CDCl$_3$) 1.72 (m, 1 H), 1.805 (d, J=12.6 Hz, 2 H), 2.116 (m, 2 H), 2.573 (brs, 2 H), 2.626 (d, J=6.9 Hz, 2 H), 3.085 (m, 2 H), 3.190 (m, 2 H), 3.574 (m, 2 H), 5.030 (s, 2 H), 6.895 (d, J=8.4 Hz, 2 H), 7.117 (m, 3 H), 7.214–7.402 (m, 9 H), 12.42 (brs, 1 H).

C) 1-[2-(4-Hydroxyphenyl)ethyl]-4-benzylpiperidine hydrochloride. A mixture of 1-[2-(4-benzyloxyphenyl) ethyl]-4-benzylpiperidine (200 mg, 0.46 mmol) in 25 mL of ethanol with 50 mg of 10% Pd/C was hydrogenated at 30 psi of hydrogen to give 155 mg (98%) of the title compound, mp 222–224° C. $^1$H NMR (CD$_3$OD) 1.487 (m, 2 H), 1.897 (m, 3 H), 2.626 (d, J=6.6 Hz, 2 H), 2.908–2.963 (m, 4 H), 3.207–3.261 (m, 2 H), 3.573 (m, 2 H), 6.731 (d, J=8.4 Hz, 2 H), 7.075 (d, J=8.4 Hz, 2 H), 7.175 (m, 3 H), 7.310 (m, 2 H).

EXAMPLE 109

1-Benzyl-4-(3-fluorobenzyl)piperidine hydrochloride

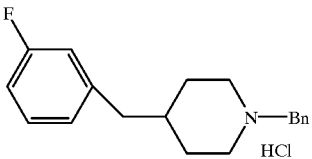

The title compound was prepared from triphenylphosphine and 3-fluorobenzyl bromide in three steps, mp 153–155° C. $^1$H NMR (CHCl$_3$) 1.647 (m, 1 H), 1.775 (m, 2 H), 2.109 (s, 2 H), 2.597 (s, 4 H), 3.450 (s, 2 H), 4.128 (s, 2 H), 6.857 (m, 3 H), 7.260 (m, 1 H), 7.434 (s, 3 H), 7.592 (s, 2 H), 12.398 (brs, 1 H). Anal. Calcd for C$_{19}$H$_{23}$ClFN: C, 71.35; H, 7.25; N, 4.38. Found: C, 71.33; H, 7.19; N, 4.60.

EXAMPLE 110

1-(2-Phenoxyethyl)-4-(3-Fluorobenzyl)piperidine hydrochloride

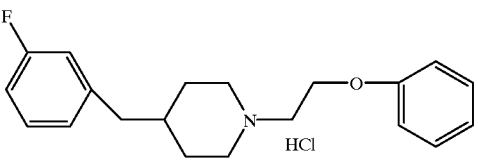

A) 4-(3-Fluorobenzyl)piperidine hydrochloride. A solution of 1-benzyl-4-(3-fluorobenzyl)piperidine hydrochloride (319 mg, 1.0 mmol) in 10 ml of methanol with 80 mg of 10% Pd/C was hydrogenated at 50 psi to give 228 mg (98%) of the title compound, mp 173–175° C. $^1$H NMR (CHCl$_3$) 1.613–1.807 (m, 5 H), 2.593 (m, 2 H), 2.785 (m, 2 H), 3.481 (m, 2 H), 6.880 (m, 3 H), 7.25 (m, 1 H), 9.363 (s, 1 H), 9.634 (s, 1 H).

B) From a mixture of 4-(3-fluorobenzyl)piperidine hydrochloride (229.5 mg, 1.0 mmol), 2-phenoxyethyl tosylate (350.4 mg, 1.2 mmol), potassium carbonate (414 mg, 3.0 mmol) in 15 mL of ethanol was 175 mg (50%) of the title compound, mp 175–177° C. $^1$H NMR (DMSO-d$_6$) 1.696 (m, 1 H), 1.582 (m, 2 H), 2.096 (m, 2 H), 2.617 (m, 2 H), 2.781 (m, 2 H), 3.395 (m, 2 H), 3.687 (m, 2 H), 4.547 (s, 2 H), 6.756–6.999 (m, 6 H), 7.288 (m, 3 H), 12.556 (s, 1 H). Anal. Calcd for C$_{20}$H$_{25}$ClFNO: C, 68.66; H, 7.20; N, 4.00. Found: C, 68.37; H, 7.09; N, 3.98.

EXAMPLE 111

1-[2-(4-Benzyloxyphenoxy)ethyl]-4-(3-fluorobenzylpiperidine hydrochloride

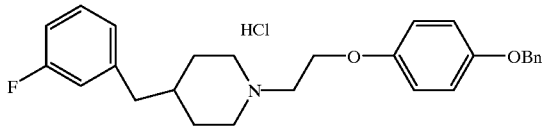

From a mixture of 2-(4-benzyloxyphenoxy)ethyl bromide (0.767 g, 2.5 mmol), 4-(3-fluorobenzyl)piperidne hydrochloride (0.459 g, 2.0 mmol), potassium carbonate (0.69 g, 5.0 mmol) in 20 mL of acetonitrile was obtained 600 mg (66%) of the title compound, mp 154–156° C. $^1$H NMR (CDCl$_3$) 1.795 (m, 3 H), 2.056 (m, 2 H), 2.613 (d, J=7.2 Hz, 2 H), 2.758 (m, 2 H), 3.354 (m, 2 H), 3.646 (d, J=7.8 Hz, 2 H), 4.485 (s, 2 H), 5.006 (s, 2 H), 6.815 (m, 4 H), 6.877 (m, 4 H), 7.736 (m, 5 H), 12.6 (brs, 1 H). Anal. Calcd for C$_{27}$H$_{31}$ClFNO$_2$.0.3H$_2$O: C, 70.28; H, 6.90; N, 3.04. Found: C, 70.28; H, 6.70; N, 3.12.

EXAMPLE 112

1-[2-(4-Hydroxyphenoxy)ethyl]-4-(3-fluorobenzylpiperidine hydrochloride

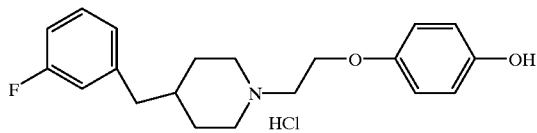

A mixture of 1-[2-(4-benzyloxyphenoxy)ethyl]-4-(3-fluorobenzylpiperidine hydrochloride (200 mg, 0.44 mmol) in 25 mL of ethanol with 60 mg of 20% Pd(OH)$_2$ was hydrogenated at 30 psi of hydrogen to give 153 mg (95%) of the title compound, mp 176–178° C. $^1$H NMR (CD$_3$OD) 1.558 (m, 2 H), 1.881 (m, 3 H), 2.640 (d, J=6.9 Hz, 2 H), 3.058 (m, 2 H), 3.506 (m, 2 H), 3.609 (d, J=7.6 Hz, 2 H), 4.256 (t, J=5.1 Hz, 2 H), 6.711 (m, 2 H), 6.823 (m, 2 H), 6.981 (m, 3 H), 7.292 (m, 1 H). Anal. Calcd for C$_{20}$H$_{25}$ClFNO$_2$: C, 65.66; H, 6.89; N, 3.83. Found: C, 65.29; H, 6.85; N, 3.79.

EXAMPLE 113

4-(3-Fluorobenzyl)-1-(2-(4-fluorophenoxy)ethyl) piperidine hydrochloride

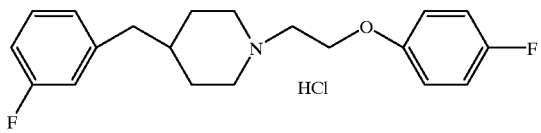

From a mixture of 4-(3-fluorobenzyl)piperidine hydrochloride (500 mg, 2.18 mmol), 2-(4-fluorophenoxy)ethyl bromide (501 mg, 2.29 mmol) and K$_2$CO$_3$ (615 mg, 4.45 mmol) in CH$_3$CN (20 mL) was obtained the title compound as a fluffy, colorless, crystalline solid (360 mg, 81%): mp 155–157° C., $^1$H NMR (CDCl$_3$) 1.65–1.90 (m, 3H), 1.98–2.16 (m, 2H), 2.62 (d, J=7.2 Hz, 2H), 2.65–2.85 (m, 2H), 3.20–3.53 (m, 2H), 3.67 (d, J=12 Hz, 2H), 4.51 (t, J=4.5 Hz, 2H), 6.78–7.10 (m, 7H), 7.19–2.28 (m, 1H), 12.64 (bs, 1H); Anal. Calcd for C$_{20}$H$_{24}$ClF$_2$NO: C, 65.30; H, 6.58; N, 3.81. Found: C, 65.35; H, 6.58; N, 3.77.

EXAMPLE 114

1-[2-(4-Benzyloxyphenoxy)ethyl]-4-(4-methylbenzyl)piperidine hydrochloride

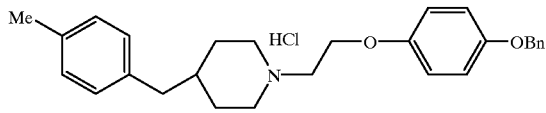

A) 4-(4-Methylbenzyl)piperidine hydrochloride was prepared in four steps from triphenylphosphine and 4-methylbenzyl bromide as a white solid, mp 209–211° C. $^1$H NMR (CHCl$_3$) 1.696 (m, 3 H), 1.817 (m, 2 H), 2.316 (s, 3 H), 2.546 (m, 2 H), 2.779 (m, 2 H), 3.437 (d, J=8.7 Hz, 2 H), 6.991 (d, J=7.8 Hz, 2 H), 7.054 (d, J=7.8 Hz, 2 H), 9.3 (brs, 1 H), 9.6 (brs, 1 H).

B) 1-[2-(4-Benzyloxyphenoxy)ethyl]-4-(4-methylbenzyl) piperidine. From a mixture of 2-(4-benzyloxyphenoxy)ethyl bromide (0.61 g, 2.0 mmol), 4-(4-methylbenzyl)piperidne hydrochloride (0.45 g, 2.0 mmol), potassium carbonate (0.69 g, 5.0 mmol) in 20 mL of acetonitrile was obtained 650 mg (72%) of the title compound, mp 194–196° C. $^1$H NMR (CDCl$_3$) 1.70 (m, 1 H), 1.803 (m, 2 H), 2.025 (m, 2 H), 2.313 (s, 3 H), 2.569 (d, J=6.9 Hz, 2 H), 2.724 (m, 2 H), 3.337 (m, 2 H), 3.629 (d, J=11.4 Hz, 2 H), 4.485 (s, 2 H), 5.006 (s, 2 H), 6.810 (d, J=10.8 Hz, 2 H), 6.875 (d, J=10.8 Hz, 2 H), 6.993 (d, J=7.8 Hz, 2 H), 7.081 (d, J=7.8 Hz, 2 H), 7.315–7.393 (m, 5 H), 12.507 (brs, 1 H).

EXAMPLE 115

1-[2-(4-Hydroxyphenoxy)ethyl]-4-(4-methylbenzyl) piperidine hydrochloride

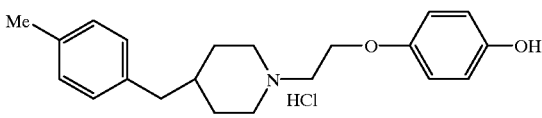

A mixture of 1-[2-(4-benzyloxyphenoxy)ethyl]-4-(4-methylbenzyl)piperidine hydrochloride (250 mg, 0.55 mmol) in 25 mL of ethanol with 60 mg of 20% Pd(OH)$_2$ was hydrogenated at 30 psi of hydrogen to give 140 mg (88%) of the title compound, mp 198–200° C. $^1$H NMR (CD$_3$OD) 1.6 (m, 2 H), 1.881–1.923 (m, 3 H), 2.288 (s, 3 H), 2.572 (d, J=6.6 Hz, 2 H), 3.06 (m, 2 H), 3.473 (m, 2 H), 3.61 (m, 2 H), 4.243 (t, J=5.1 Hz, 2 H), 6.709 (dd, J$_1$=2.4 Hz, J$_2$=6.6 Hz, 2 H), 6.830 (dd, J$_1$=2.4 Hz, J$_2$=6.6 Hz, 2 H), 7.703 (m, 4 H). Anal. Calcd for C$_{21}$H$_{28}$ClNO$_2$.0.5H$_2$O: C, 68.00; H, 7.88; N, 3.78. Found: C, 68.14; H, 7.65; N. 3.72.

EXAMPLE 116

1-(2-(4-Fluorophenoxy)ethyl)-4-(4-methylbenzyl) piperidine hydrochloride

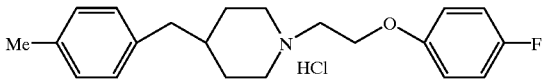

From a mixture of 4-(4-methylbenzyl)piperidine (500 mg, 2.21 mmol), 2-(4-fluorophenoxy)ethyl bromide (508 mg, 2.32 mmol) and K$_2$CO$_3$ (626 mg, 4.53 mmol) in CH$_3$CN (20 mL) was obtained the title compound as colorless plates (293 mg, 63%), mp 189–191° C., $^1$H NMR (CDCl$_3$) 1.60–2.12 (m, 5H), 2.31 (s, 3H), 2.57 (d, J=7.2 Hz, 2H), 2.62–2.82 (m, 2H), 3.20–3.55 (m, 2H), 3.65 (d, J=12 Hz, 2H), 4.51 (t, J=4.5 Hz, 2H), 6.78–6.84 (m, 2H), 6.92–7.02 (m, 6H), 7.08 (d, J=8.1 Hz, 2H), 12.56 (bs, 1H); Anal. Calcd for C$_{21}$H$_{27}$ClFNO: C, 69.31; H, 7.48; N, 3.85. Found: C, 69.49; H, 7.39; N, 3.88.

EXAMPLE 117

4-(4-Chlorobenzyl)-1-(2-(4-fluorophenoxy)-1,2,5,6-tetrahydropyridine hydrochloride

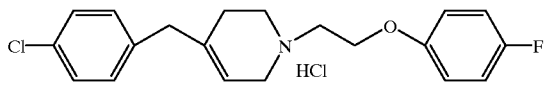

A) 4-(4-Chlorobenzyl)-1,2,5,6-tetrahydropyridine hydrochloride. A suspension of LiAlH$_4$ (3.60 g, 95.0 mmol) in dry ether (from LiAlH$_4$) was prepared under N$_2$. To this stirred suspension, a solution of AlCl$_3$ (4.00 g, 30.0 mmol) in dry ether (75 mL) was added with stirring and ice bath cooling over 10 min under N$_2$. After addition, the ice bath was removed and the suspension was allowed to stir 1 hr at 25° C. To the resulting suspension, a solution of 4-(4-chlorobenzyl)pyridine (12.2 g, 60.0 mmol) in dry ether (50 mL) was added at 25° C. over 3 min. After addition, the resulting suspension was stirred at reflux for 4 h. The reaction was allowed to cool to 25° C. The excess hydride was quenched by the very careful addition of 101 HCl (100 mL) with stirring and ice bath cooling. After addition, the layers were separated and the ether portion was extracted with 10. HCl (2×75 mL). The combined aqueous portion was made basic by the addition of concd NH$_4$OH (100 mL) to give a colorless suspension. The suspension was extracted with ether (4×100 mL). The extract was dried over Na$_2$SO$_4$, filtered and the solvent removed to give a yellow liquid (~13 g), The liquid was distilled in vacuo employing a 15 cm fractionating column. A fraction was collected between 125–133° C., 0.005 Torr to yield a colorless liquid (10.5 g, 84%): $^1$H NMR (CDC$_3$) 1.51 (s, 1H), 1.89 (s, 2H), 2.90 (t, J=5.7 Hz, 2H), 3.22 (s, 2H), 3.31 (s, 2H), 5.37–5.46 (m, 1H), 7.08 (d, J=7.8 Hz, 2H), 7.22 (d, J=7.8 Hz, 2H). The free base was converted to the hydrochloride salt as large colorless plates (7.52 g, 61%): mp 210–212° C., $^1$H NMR (D$_2$O) 2.17–2.26 (m, 2H), 3.25 (t, J=6.3 Hz, 2H), 3.34 (s, 2H), 3.61–3.66 (m, 2H), 5.47–5.54 (m, 1H), 7.20 (d, J=8.4 Hz, 2H), 7.33 (d, J=8.4 Hz, 2H).

B) From a mixture of 4-(4-chlorobenzyl)-1,2,5,6-tetrahydropyridine hydrochloride (500 mg, 2.05 mmol), 2-(4-fluorophenoxy)ethyl bromide (471 mg, 2.15 mmol) and K$_2$CO$_3$ (580 mg, 4.20 mmol) in CH$_3$CN (15 mL) was obtained the title compound as a near colorless crystalline solid (311 mg, 69%): mp 174–175° C., $^1$H NMR (CDCl$_3$) 2.21–2.35 (m, 1H), 2.72–2.88 (m, 1H), 3.03–3.17 (m, 1H), 3.27–3.65 (m, 6H), 3.99 (d, J=16 Hz, 1H), 4.48–4.62 (m, 2H), 5.38 (s, 1H), 6.80–6.86 (m, 2H), 6.94–7.01 (m, 2H), 7.10 (d, J=8.1 Hz, 2H), 7.28 (d, J=8.1 Hz, 2H), 13.00 (bs, 1H); Anal. Calcd for C$_{20}$H$_{22}$Cl$_2$FNO: C, 62.83; H, 5.80; N, 3.66. Found: C, 62.95; H, 5.68; N, 3.71.

EXAMPLE 118

4-(2-Fluorobenzyl)1-(2-(4-fluorophenoxy)ethyl) piperidine hydrochloride

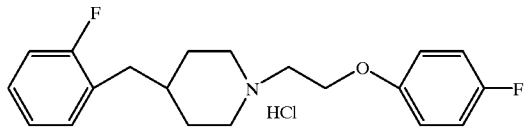

A) 4-(2-Fluorobenzoyl)pyridine. A solution of 2-bromofluorobenzene (19.2 g, 110 mmol) in dry THF (200 mL) was prepared under N$_2$ in a flame dried, 1 L, 3 neck, reaction flask. The stirred solution was cooled in a dry ice/acetone (−78° C.) bath for 5 min under N$_2$. To this cold solution a solution of n-butyl lithium in hexanes (55 mL, 2.20 M, 121 mmol) was added via a syringe with stirring over a 15 min period. After addition, the solution was allowed to stir for 5 min at 78° C. To this cold, stirred solution a solution of 4-cyanopyridine (10.4 g, 100 mmol) in dry THF (200 mL) was added from an addition funnel over a 30 min period. After addition, the cold bath was removed and the solution was stirred until the reaction temperature was estimated to be between 10 and 20° C. The reaction mixture was added to ice H$_2$O (500 mL) containing NH$_4$Cl (20 g) to give a deep red solution. The solution was extracted with ether (3×200 mL). The red ether solution was then extracted with 10% aqueous HCl (200 mL and 2×100 mL) to give a deep red aqueous solution. The pH of this solution was adjusted to ~10 with concd NH$_4$OH. The mixture was extracted with ether (3×100 mL). The extract was washed with H$_2$O (300 mL), dried over Na$_2$SO$_4$ and the solvent was removed to give a red oil (17.2 g). The oil was purified by Kugelrohr distillation (OT 80–90° C., 0.005 Torr). The collected product solidified to yield the title compound as a pale yellow solid (12.6 g, 63%): mp 59–61° C.; $^1$H NMR (CDCl$_3$) 7.10–7.36 (m, 2H), 7.50–7.70 (m, 4H), 8.10 (d, J=5.7 Hz, 2H).

B) 4-(2-fluorobenzyl)pyridine. A suspension of 4-(2-fluorobenzoyl)pyridine (12.6 g, 62.6 mmol) in ethylene glycol (50 mL) was prepared in an open 250 mL beaker. To the stirred suspension anhydrous hydrazine (8.62 g, 269 mmol) followed by solid NaOH (10.8 g, 269 mmol) were added. The beaker was placed in an oil bath (50° C.). The reaction mixture was stirred while the temperature of the oil bath was raised to 80–85° C. at which point the reaction foamed vigorously. After foaming subsided, the temperature was raised to 160° C. and was stirred an additional hour to give a pale orange mixture. The reaction mixture was allowed to cool to 25° C. to give a thick honey. The honey was dissolved in H$_2$O (200 mL) and the resulting mixture was extracted with ether (3×75 mL). The extract was washed with H$_2$O (200 mL), dried over Na$_2$SO$_4$ and the ether was removed to give a yellow liquid (11.9 g). The liquid was distilled in vacuo (0.005 Torr). A fraction was collected (78–96° C.) to yield the title compound as a pale yellow liquid (5.83 g, 50%): $^1$H NMR (CDCl$_3$) 3.99 (s, 2H), 7.00–7.30 (m, 6H), 8.49 (d, J=5.4 Hz, 2H).

C) 4-(2-Fluorobenzyl)piperidine hydrochloride. A mixture of 4-(2-fluorobenzyl)pyridine (5.83 g, 31.1 mmol) in a solution of MeOH (100 mL) and concd HCl (5.5 mL) with PtO$_2$ (150 mg) was hydrogenated at 20 to 30 psi to yield the title compound as a colorless powder (6.66 g, 93%): mp 187–188° C. $^1$H NMR (D$_2$O) 1.34–1.54 (m, 2H), 1.78–1.98 (m, 3H), 2.63 (d, J=6.6 Hz, 2H), 2.89 (td, J=13 and 3.0 Hz, 2H), 3.32–3.43 (m, 2H), 3.78 (s, 3H), 7.06–7.17 (m, 2H), 7.23–7.31 (m, 2H).

D) 4-(2-Fluorobenzyl)1-(2-(4-fluorophenoxy)ethyl) piperidine hydrochloride. From A mixture of 4-(2-fluorobenzyl)piperidine hydrochloride (500 mg, 2.18 mmol), 2-(4-fluorophenoxy)ethyl bromide (502 mg, 2.29 mmol) and K$_2$CO$_3$ (618 mg, 4.47 mmol) in CH$_3$CN (20 mL) was obtained the title compound as a colorless crystalline solid (470 mg, 64%), mp 159–160° C. $^1$H NMR (CDCl$_3$) 1.70–2.22 (m, 5H), 2.62–2.88 (m, 4H), 3.20–3.50 (m, 2H), 3.60–3.75 (m, 2H), 4.52 (t, J=4.5 Hz, 2H), 6.78–7.28 (m, 8H), 12.64 (bs, 1H); Anal. Calcd for C$_{20}$H$_{24}$ClF$_2$NO: C, 65.30; H, 6.58; N, 3.81. Found: C, 65.25; H, 6.46; N, 3.74.

EXAMPLE 119

4-Acetyl-1-(2-(4-hydroxyphenoxy)ethyl)-4-phenylpiperidine hydrochloride

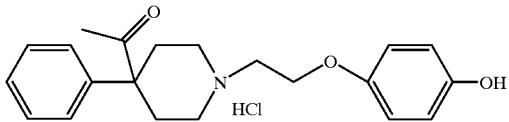

A) 4-Acetyl-1-(2-(4-methoxyphenoxy)ethyl)-4-phenylpiperidine. From a mixture of 4-acetyl-4-phenylpiperidine hydrochloride (600 mg, 2.50 mmol), 2-(4-methoxyphenoxy)ethyl bromide (605 mg, 2.62 mmol) and $K_2CO_3$ (708 mg, 5.12 mmol) in $CH_3CN$ (20 mL) was obtained a beige solid (780 mg, 88%): mp 69–70° C. $^1H$ NMR ($CDCl_3$) 1.91 (s, 3H), 2.03–2.16 (m, 2H), 2.32–2.54 (m, 4H), 2.74 (t, J=6.0 Hz, 2H), 2.78–2.90 (m, 2H), 3.76 (s, 3H), 4.04 (t, J=6.0 Hz, 2H), 8.30 (d, J=1.2 Hz, 4H), 7.22–7.38 (m, 5H).

B) From 4-acetyl-1-(2-(4-methoxyphenoxy)ethyl)-4-phenylpiperidine (770 mg, 2.18 mmol) in dry $CH_2Cl_2$ (20 mL) and $BBr_3$ in $CH_2Cl_2$ (8 mL, 1 M) was obtained the title compound as a colorless granular solid (310 mg, 38%): mp 210–212° C. $^1H$ NMR ($CD_3OD$) 1.98 (s, 3H), 2.10–2.55 (m, 2H), 2.76–3.30 (m, 4H), 3.54 (bs, 2H), 3.60–3.84 (m, 2H), 4.27 (bs, 2H), 6.74 (d, J=9.0 Hz, 2H), 6.85 (d, J=8.4 Hz, 2H), 7.32–7.50 (m, 5H). Anal Calcd for $C_{21}H_{26}ClNO_3$ 0.1 $H_2O$: C, 66.78 H, 6.99; N, 3.71. Found: C, 66.64; H, 6.71; N, 3.65.

EXAMPLE 120

1-[2-(4-Hydroxyphenyl)ethoxy]-4-(4-ethylbenzyl)piperidine hydrochloride

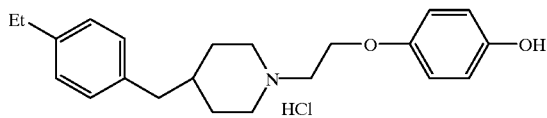

A) 4-(4-Ethylbenzyl)piperidine hydrochloride was prepared from triphenylphosphine and 4-ethylbenzyl bromide in four steps as a white solid, mp 175–177° C. $^1H$ NMR ($CHCl_3$) 1.219 (t, J=7.8 Hz, 3 H), 1.707 (m, 2 H), 1.828 (m, 3 H), 2.553–2.654 (m, 4 H), 2.775 (m, 2 H), 3.436 (d, J=11.7 Hz, 2 H), 7.017 (d, J=7.8 Hz, 2 H), 7.109 (d, J=7.8 Hz, 2 H), 9.3 (s, 1 H), 9.6 (s, 1 H). Anal. Calcd for $C_{14}H_2ClN$: C, 70.13; H, 9.25; N, 5.84. Found: C, 69.88; H, 9.48; N, 5.71.

B) 1-[2-(4-Benzyloxyphenoxy)ethoxy]-4-(4-ethylbenzyl)piperidine hydrochloride. From a mixture of 2-(4-benzyloxyphenoxy)ethyl bromide (0.46 g, 1.5 mmol), 4-ethylbenzylpiperidine hydrochloride (0.359 g, 1.5 mmol), potassium carbonate (0.52 g, 3.75 mmol) in 50 mL of acetonitrile was obtained 0.51 g (73%) of the title product. mp 186–188° C. $^1H$ NMR ($CDCl_3$) 1.218 (t, J=7.8 Hz, 3 H), 1.68 (m, 1 H), 1.805 (m, 2 H), 2.030 (m, 2 H), 2.320 (m, 3 H), 2.480 (m, 4 H), 2.730 (m, 2 H), 3.338 (m, 2 H), 3.625 (d, J=11.4 Hz, 2 H), 4.482 (s, 2 H), 5.004 (s, 2 H), 6.812 (d, J=10.8 Hz, 2 H), 6.873 (d, J=10.8 Hz, 2 H), 6.992 (d, J=7.8 Hz, 2 H), 7.083 (d, J=7.8 Hz, 2 H), 7.320–7.389 (m, 5 H), 12.62 (s, 1 H).

C) A mixture of 1-[2-(4-benzyloxyphenoxy)ethyl]-4-(4-ethylbenzyl)piperidine hydrochloride (510 mg, 1.095 mmol) in 50 mL of methanol and 128 mg of 20% $Pd(OH)_2$ was hydrogenated at 30 psi of hydrogen to give 385 mg (94%) of the title compound as white-off solid, mp 174–176° C. $^1H$ NMR ($CD_3OD$) 1.206 (t, J=7.8 Hz, 3 H), 1.564 (s, 2 H), 1.901–1.943 (m, 3 H), 2.595 (m, 4 H), 3.033 (m, 2 H), 3.501 (m, 2 H), 3.667 (m, 2 H), 4.260 (s, 2 H), 6.721 (d, J=9.0 Hz, 2 H), 6.842 (d, J=9.0 Hz, 2 H), 6.842 (d, J=9.0 Hz, 2 H), 7.124 (m, 4 H). Anal. Calcd for $C_{22}H_{30}ClNO_2$: C, 70.29; H, 8.04; N, 3.73. Found: C, 70.06; H, 8.07; N, 3.50. (HPLC>98%).

EXAMPLE 121

1-[2-(4-Hydroxyphenoxy)ethyl]-4-(4-methoxybenzyl)piperidine hydrochloride

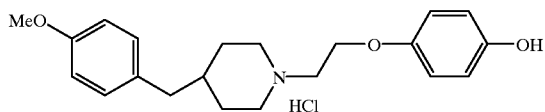

The title compound was prepared from 2-(4-benzyloxyphenoxy)ethyl bromide (0.384 g, 1.25 mmol), 4-(4-methoxybenzyl)piperidine (0.257 g, 1.25 mmol) and potassium carbonate (0.43 g, 3.12 mmol) in two steps as a white solid, mp 123–125° C. $^1H$ NMR ($CD_3OD$) 1.554 (m, 2 H), 1.891 (m, 3 H), 2.567 (m, 2 H), 3.029 (m, 2 H), 3.501 (m, 2 H), 3.637 (m, 2 H), 3.759 (s 3 H), 4.262 (s, 2 H), 6.743 (m, 2 H), 6.839 (m, 4 H), 7.111 (m, 2 H). Anal. Calcd for $C_{21}H_{28}ClNO_3 \cdot 0.3H_2O$: C, 65.80; H, 7.52; N, 3.65. Found: C, 65.56; H, 7.57; N, 3.60.

EXAMPLE 122

1-[2-(4-Hydroxyphenoxy)ethyl]-4-(3,4-difluorobenzyl)piperidine hydrochloride

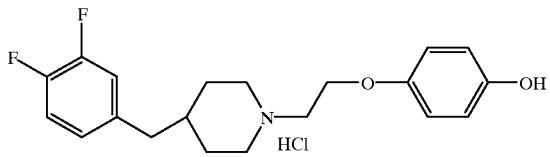

A) 4-(3,4-Difluorobenzyl)piperidine hydrochloride was prepared from triphenylphosphine and 3,4-difluorobenzyl bromide in four steps as a white solid, mp 174–175° C. $^1H$ NMR ($CHCl_3$) 1.704–1.827 (m, 5 H), 2.564 (m, 2 H), 2.798 (m, 2 H), 3.457 (d, J=8.1 Hz, 2 H), 6.833 (m, 1 H), 6.891 (m, 1 H), 7.052 (m, 1 H), 9.38 (s, 1 H), 9.60 (s, 1 H). Anal. Calcd for $C_{12}H_{16}ClF_2N$: C, 58.18; H, 6.51; N, 5.65. Found: C, 57.89; H, 6.43; N, 5.59.

B) The title compound was prepared in two steps from 2-(4-benzyloxyphenoxy)ethyl bromide, 3,4-difluorobenzylpiperidine hydrochloride and potassium carbonate in two steps as an off white solid, mp 180–182° C. $^1H$ NMR ($CD_3OD$) 1.595 (m, 2 H), 1.889 (d, J=12.0 Hz, 3 H), 2.607 (m, 2 H), 3.051 (m, 2 H), 3.513 (m, 2 H), 3.647 (d, J=10.2 Hz, 2 H), 4.272 (s, 2 H), 6.718 (d, J=8.7 Hz, 2 H), 6.841 (d, J=8.7 Hz, 2 H), 7.017 (m, 1 H), 7.170 (m, 2 H). Anal. Calcd for $C_{20}H_{24}ClF_2NO_2 \cdot 0.6H_2O$: C, 60.98; H, 6.44; N, 3.55. Found: C, 60.72; H, 6.38; N, 3.45.

EXAMPLE 123

1-[2-(4-Hydroxyphenoxy)ethyl]-4-(4-fluorobenzyl)-4-hydroxy-piperidine hydrochloride

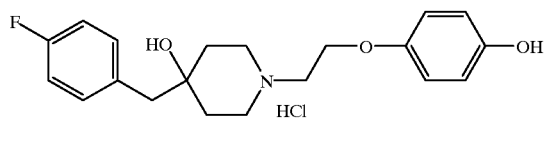

A) 1-[2-(4-Benzyloxyphenoxy)ethyl]-4-(4-fluorobenzyl)-4-hydroxypiperidine. A mixture of 2-(4-benzoxyphenoxy) ethyl bromide (1.075 g, 3.5 mmol), 4-(4-fluorobenzyl)-4-hydroxypiperidine (0.778 g, 3.7 mmol), potassium carbonate (1.28 g, 9.25 mmol) in 50 mL of acetonitrile was allowed to reflux for 12 h. The inorganic salt was removed through a short column of silica gel and washed with ethyl acetate (3×25 mL). The combined flitrate was evaporated in vacuo to give a crude product, which was purified by flash chromatography (59 methanol in ethyl acetate), giving 0.8 g (53%) of the title compound as a pale yellow oil. $^1$H NMR (CDCl$_3$) 1.544 (m, 2 H), 1.80 (m, 2 H), 2.50 (m, 2 H), 2.834 (m, 3 H), 3.484 (s, 4 H), 4.079 (t, J=4.8 Hz, 2 H), 5.008 (s, 2 H), 6.810 (d, J=9.0 Hz, 2 H), 6.878 (d, J=9.0 Hz, 2 H), 6.997 (m, 2 H), 7.135 (m, 2 H), 7.350 (m, 5 H).

B) 1-[2-(4-Hydroxyphenoxy)ethyl]-4-(4-fluorobenzyl)-4-hydroxypiperidine hydrochloride. To a solution of 1-[2-(4-benzyloxyphenoxy)ethyl]-4-(4-fluorobenzyl)-4-hydroxypiperidine (0.8 g, 1.8 mmol) in 25 mL of methanol was added 200 mg of 20% Pd(OH)$_2$. The resulting mixture was hydrogenated at 20 psi of hydrogen for 3 h. The catalyst was removed through a short column of celite (5 g) and washed with methanol (3×15 mL), to which was added 4 mL of 1 M HCl in methanol. The resulting solution was allowed to stir at rt for 10 min. and methanol was evaporated in vacuo to give a residue, to which 50 mL of ether was added. The resulting mixture was stirred overnight. A white solid was collected by filtration and dried in vacuo, giving 550 mg (80%) of the title compound, mp 128–130° C. $^1$H NMR (CD$_3$OD) 1.732 (m, 2 H), 1.935 (m, 2 H), 2.825 (m, 2 H), 3.328 (m, 2 H), 3.486 (m, 4 H), 4.265 (s, 2 H), 6.719 (m, 2 H), 6.840 (m, 2 H), 7.033 (m, 2 H), 7.238 (m, 2 H). Anal. Calcd for C$_{20}$H$_{25}$ClFNO$_3$.0.5H$_2$O: C, 61.46; H, 6.70; N, 3.58. Found: C, 61.50; H, 6.64; N, 3.59.

EXAMPLE 124

4-(2-Fluorobenzyl)-1-(2-(4-methoxyphenoxy)ethyl) piperidine hydrochloride

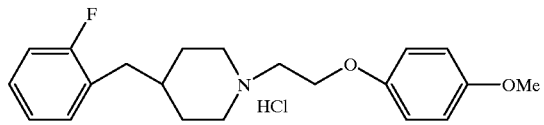

From a mixture of 4-(2-fluorobenzyl)piperidine hydrochloride (407 mg, 1.77 mmol), 2-(4-methoxyphenoxy)ethyl bromide (430 mg, 1.86 mmol) and K$_2$CO$_3$ (501 mg, 3.63 mmol) in CH$_3$CN (20 mL) was obtained the title compound as colorless flakes (387 mg): mp 151–152° C., $^1$H NMR (CDCl$_3$) 1.74–1.88 (m, 3H), 1.98–2.16 (m, 2H), 2.65 (d, J=6.9 Hz, 2H), 2.68–2.84 (m, 2H), 3.26–3.48 (m, 2H), 3.61–3.70 (m, 2H), 3.75 (s, 3H), 4.74 (t, J=4.2 Hz, 2H), 6.80 (s, 4H), 6.96–7.24 (m, 4H), 12.53 (bs, 1H); Anal. Calcd for C$_{21}$H$_{27}$ClFNO$_2$: C, 66.39; H, 7.16; N, 3.69. Found: C, 66.29; H, 6.94; N, 3.59.

EXAMPLE 125

1-(2-(4-Hydroxyphenoxy)ethyl)-4-(2-picolyl) piperidine dihydrochloride

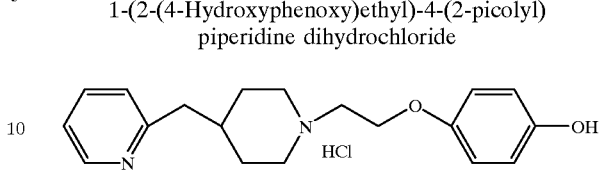

A) 1-(2-(4-Methoxyphenoxy)ethyl)isonipecotamide. From a mixture of isonipecotamide (11.1 g, 86.6 mmol), 2-(4-methoxyphenoxy)ethyl bromide (20.0 g, 86.6 mmol) and K$_2$CO$_3$ (12.0 g, 86.6 mmol) in CH$_3$CN (500 mL) was obtained the title compound as beige needles (17.2 g, 72%): mp 132–134° C., $^1$H NMR (CDCl$_3$) 1.68–1.92 (m, 4H), 2.06–2.22 (m, 3H), 2.76 (t, J=6.0 Hz, 2H), 2.98–3.08 (m, 2H), 3.76 (s, 3H), 4.03 (t, J=6.0 Hz, 2H), 5.59 (bs, 1H), 5.82 (bs, 1H), 6.83 (d, J=0.9 Hz. 4H).

B) 4-Cyano-1-(2-(4-methoxyphenoxy)ethyl)piperidine. To a stirred suspension of 1-(2-(4-methoxyphenoxy)ethyl) isonipecotamide (10.0 g, 35.9 mmol) in CHCl$_3$ (80 mL) neat SOCl$_2$ (30 mL) was added drop wise over 5 min. The resulting suspension was heated at reflux with stirring under N$_2$ for 1 h. The reaction was allowed to cool to 25° C. and the volatile portion was removed to give a yellow syrup. The syrup was partitioned between CHCl$_3$ and H$_2$O (200 mL) each. The stirred yellow mixture was made basic by the addition of concd NH$_4$OH (50 mL) to give a pink mixture. The layers were separated and the aqueous portion was extracted with CHCl$_3$ (2×50 mL). The combined organic portion was washed with 10% NH$_4$OH, H$_2$O and brine (200 mL each), was filtered through cotton and the solvent was removed to give a red oil that partially solidified upon standing. The product was purified on silica gel (3.5×25 cm) with CHCl$_3$ then 2% EtOH/98% CHCl$_3$ elution to yield the title compound as an amber oil that solidified to a beige solid upon standing (6.8 g, 73%): mp 49–51° C.; $^1$H NMR (CDCl$_3$) 1.78–2.03 (m, 4H), 2.40–2.54 (m, 2H), 2.58–2.84 (m, 5H), 3.76 (s, 3H), 4.03 (t, J=5.7 Hz, 2H), 6.83 (s, 4H).

C) 1-(2-(4-Methoxyphenoxy)ethyl)-4-(2-picoloyl) piperidine was prepared from 2-bromopyridine (1.34 g, 8.45 mmol), n-BuLi (4.2 mL, 9.30 mmol, 2.2 M solution in hexanes) and 4-cyano-1-(2-(4-methoxyphenoxy)ethyl) piperidine (2.00 g, 7.68 mmol) as an orange oil (1.40 g, 54%): $^1$H NMR (CDCl$_3$) 1.72–1.98 (m, 4H), 2.32 (td, J=12 and 2.7 Hz, 2H), 2.82 (t, J=6.0 Hz, 2H), 3.02–3.12 (m, 2H), 7.76 (s, 3H), 3.78–3.90 (m, 1H), 4.07 (t, J=6.0 Hz, 2H), 6.76–6.88 (m, 4H), 7.45 (ddd, J=7.5, 4.8 and 1.2 Hz, 1H), 7.82 (td, J=7.5 and 1.8 Hz, 1H), 8.02 (dt, J=7.8 and 0.9 Hz, 1H), 8.67 (dq, J=7.8 and 0.9 Hz, 1H).

D) 1-(2-(4-Methoxyphenoxy)ethyl)-4-(2-picolyl) piperidine. 1-(2-(4-methoxyphenoxy)ethyl)-4-(2-picoloyl) piperidine (1.40 g, 4.11 mmol) was reduced by anhydrous hydrazine (565 mg, 17.6 mmol) to yield the title compound as an amber oil (1.10 g, 82%): $^1$H NMR (CDCl$_3$) 1.30–1.46 (m, 2H), 1.63 (d, J=13 Hz, 2H), 1.72–1.88 (m, 1H), 2.06 (td, J=12 and 2.4 Hz, 2H), 2.70 (d, J=7.2 H, 2H), 2.74 (t, J=6.0 Hz, 2H), 2.90–3.00 (m, 2H), 3.75 (s, 3H), 4.03 (t, J=6.0 Hz, 2H), 6.81 (d, J=1.2 Hz, 4H), 7.05–7.12 (m, 2H), 7.56 (td, J=7.5 and 2.1 Hz, 1H), 8.53 (dd, J=5.4 and 1.8 Hz, 1H).

E) 1-(2-(4-Hydroxyphenoxy)ethyl)-4-(2-picolyl) piperidine dihydrochloride From 1-(2-(4-methoxyphenoxy)

ethyl)-4-(2-picolyl)piperidine (536 mg, 1.64 mmol) and BBr₃ in CH₂Cl₂ (6 mL, ~1 M) was obtained the title compound as a slightly hygroscopic brown powder (217 mg): mp 55–62° C.; ¹H NMR (CD₃OD) 1.70–2.01 (m, 4H), 2.14–2.40 (m, 1H), 3.04–3.28 (m, 4H), 3.54 (t, J=4.5 Hz, 2H), 3.70 (d, J=13 Hz, 2H), 4.30 (t, J=4.5 Hz, 2H), 6.73 (d, J=9.3 Hz, 2H), 6.85 (d, J=9.0 Hz, 2H), 7.98 (t, J =6.6 Hz, 1H), 8.06 (d, J=8.1 Hz, 1H), 8.58 (t, J=7.8 Hz, 1H), 8.79 (d, J=5.4 Hz, 1H).

EXAMPLE 126

1-[2-(4-Hydroxyphenoxy)ethyl]-4-hydroxy-4-phenylpiperidine hydrochloride

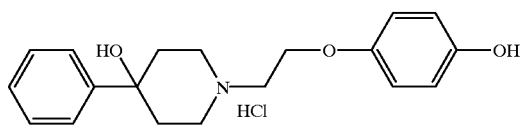

The title compound was prepared from 2-(4-benzyloxyphenoxy)ethyl bromide (0.384 g, 1.25 mmol), 4-hydroxy-4-phenylpiperidne (0.222 g, 1.25 mmol) and potassium carbonate (0.431 g, 3.12 mmol) in two steps as white solid (190 mg), mp 208–210° C. ¹H NMR (CD₃OD) 2.020 (m, 3 H), 2.420 (m, 2 H), 2.95 (m, 1 H), 3.614 (m, 3 H), 3.755 (m, 1 H), 4.322 (s, 2 H), 6.730 (d, J=9.0 Hz, 2 H), 6.873 (d, J=9.0 Hz, 2 H), 7.308 (m, 4 H), 7.516 (d, J=7.8 Hz, 2 H). Anal. Calcd for C₁₉H₂₄ClNO₃: C, 65.23; H, 6.91; N, 4.00. Found: C, 65.43; H, 7.10; N, 3.90.

EXAMPLE 127

1-[2-(4-Hydroxyphenoxy)ethyl]-4-phenylpiperidine hydrochloride

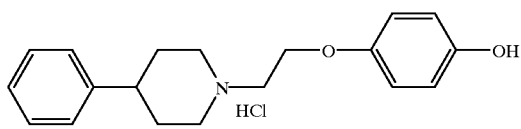

The title compound was prepared from 2-(4-benzyloxyphenoxy)ethyl bromide (0.377 g, 1.23 mmol), 4-phenylpiperidne hydrochloride (0.20 g, 1.23 mmol) and potassium carbonate (0.423 g, 3.07 mmol) in two steps as a white solid (180 mg), mp 198–200° C. ¹H NMR (CD₃OD) 2.114 (m, 4 H), 2.85 (m, 1 H), 3.295 (m, 2 H), 3.588 (m, 2 H), 3.767 (d, J=10.5 Hz, 2 H), 4.314 (d, J=5.1 Hz, 2 H), 6.730 (d, J=8.7 Hz, 2 H), 6.872 (d, J=8.7 Hz, 2 H), 7.292(m, 5 H). Anal. Calcd for C₁₉H₂₄ClNO₂.0.3H₂O: C, 67.26; H, 7.31; N, 4.13. Found: C, 67.32; H, 7.34; N, 4.04.

EXAMPLE 128

1-[2-(4-Hydroxyphenoxy)ethyl]-4-(2-fluorobenzyl) piperidine hydrochloride

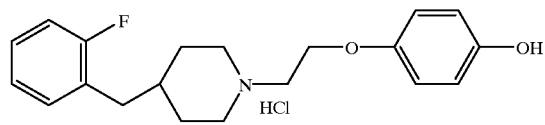

The title compound was prepared from 2-(4-benzyloxyphenoxy)ethyl bromide (0.393 g, 1.28 mmol), 4-(2-fluorobenzyl)piperidine hydrochloride (0.294 g, 1.28 mmol) and potassium carbonate (0.442 g, 3.2 mmol) in two steps as an off white solid (0.237 g), mp 196–198° C. ¹H NMR (CD₃OD) 1.629 (m, 2 H), 1.900 (m, 3 H), 2.704 (m, 2 H), 3.052 (m, 2 H), 3.500 (m, 2 H), 3.612 (m, 2 H), 4.252 (m, 2 H), 6.703 (d, J=9. 0 Hz, 2 H), 6.825 (6, J=9.0 Hz, 2 H), 7.057–7.248 (m, 2 H), 7.248 (m, 2 H). Anal. Calcd for C₂₀H₂₅ClFNO₂.1.2H₂O: C, 61.70; H, 7.15; N, 3.60. Found: C, 61.45; H, 6.90; N, 3.53.

EXAMPLE 129

1-[2-(4-Hydroxyphenoxy)ethyl]-4-(4-trifluorobenzyl)piperidine hydrochloride

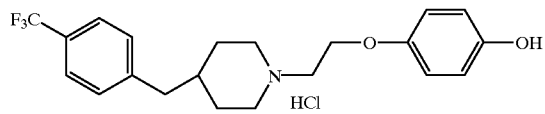

A) 4-(4-Trifluoromethylbenzyl)piperidine hydrochloride was prepared from triphenylphosphine and 4-trifluoromethylbenzyl bromide in four steps as white solid, mp 208–210° C. ¹H NMR (CHCl₃) 1.760–1.846 (m, 5 H), 2.662 (s, 4 H), 2.792 (s, 2 H), 3.454 (d, J=11.7 Hz, 2 H), 7.226 (d, J=7.8 Hz, 2 H), 7.539 (d, J=7.8 Hz, 2 H), 9.410 (s, 1 H), 9.660 (s, 1 H). Anal. Calcd for C₁₃H₁₇ClF₃N: C, 55.82; H, 6.13; N, 5.01. Found: C, 55.46; H, 6.00; N, 5.07.

B) The title compound was prepared from 2-(4-benzyloxyphenoxy)ethyl bromide 4-(trifluoromethylbenzyl) piperidine hydrochloride and potassium carbonate in two steps as an off white solid, mp 200–202° C. ¹H NMR (CD₃OD) 1.60 (m, 2 H), 1.893 (m, 3 H), 2.721 (d, J=6.3 Hz, 2 H), 3.08 (m, 2 H), 3.498 (m, 2 H), 3.629 (m, 2 H), 4.251 (t, J=5.1 Hz, 2 H), 6.719 (m, 2 H), 6.841 (m, 2 H), 7.398 (d, J=8.1 Hz, 2 H), 7.591 (d, J=8.1 Hz, 2 H). Anal. Calcd for C₂₁H₂₅ClF₃NO₂: C, 60.65; H, 6.06; N, 3.37. Found: C, 60.27; H, 5.80; N, 3.31.

EXAMPLE 130

4-Cyano-1-(2-(4-hydroxyphenoxy)ethyl)-4-phenylpiperidine hydrochloride

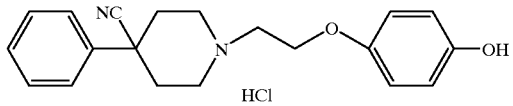

The title compound was prepared from 4-cyano-4-phenylpiperidine hydrochloride (600 mg, 2.69 mmol), 2-(4- methoxyphenoxy)ethyl bromide (653 mg, 2.82 mmol) and K₂CO₃ (761 mg, 5.51 mmol) in two steps as a colorless solid (28 mg, 60%), mp 199–200° C.; ¹H NMR (CD₃OD) 2.48–2.64 (m, 4H), 3.48–3.64 (m, 2H), 3.73 (t, J=4.8 Hz, 2H), 3.95 (d, J=12 Hz, 2H), 4.36 (t, J=4.5 Hz, 2H), 6.74 (d, J=8.7 Hz, 2H), 6.90 (d, J=9.0 Hz, 2H), 7.38–7.64 (m, 5H); HRMS calcd for C₂₀H₂₂N₂O₂ 322.1681, found 322.1678.

EXAMPLE 131

1-[2-(4-Hydroxyphenoxy)ethyl]-4-(4-isopropylbenzyl)piperidine hydrochloride

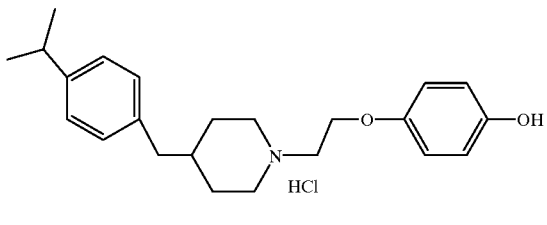

A) 4-(4-Isopropylbenzyl)piperidine hydrochloride was prepared from 4-isopropylbenzyl alcohol in five steps as white solid, mp 183–185° C. ¹H NMR (CHCl₃) 1.221 (d, J=7.2 Hz, 6 H), 1.709 (m, 2 H), 1.832 (m, 3 H), 2.552 (m, 2 H), 2.777–2.875 (m, 3 H), 3.434 (d, J=11.7 Hz, 2 H), 7.025 (d, J=7.8 Hz, 2 H), 7.135 (d, J=7.8 Hz, 2 H), 9.30 (s, 1 H), 9.60 (s, 1 H). Anal. Calcd for C₁₅H₂₄ClN.0.2H₂O: C, 69.98; H, 9.55; N, 5.44. Found: C, 70.06; H, 9.30; N, 5.29.

B) The title compound was prepared from 2-(4-benzyloxyphenoxy)ethyl bromide (0.393 g, 1.28 mmol), 4-isopropylbenzylpiperidine hydrochloride (0.325 g, 1.28 mmol) and potassium carbonate (0.444 g, 3.2 mmol) in two steps as white-off solid (385 mg), mp 168–170° C. ¹H NMR (CD₃OD) 1.207 (d, J=6.6 Hz, 6 H), 1.577 (m, 2 H), 1.893 (m, 3 H), 2.586 (d, J=6.3 Hz, 2 H), 2.859 (hepta, J=6.6 Hz, 1 H), 3.038 (brs, 2 H), 3.499 (m, 2 H), 3.607 (m, 2 H), 4.250 (s, 2 H), 6.734 (m, 2 H), 6.821 (m, 2 H), 7.087 (d, J=7.4 Hz, 2 H), 7.146 (m, 2 H). Anal. Calcd for C₂₃H₃₂ClNO₂: C, 70.84; H, 8.27; N, 3.59. Found: C, 71.03; H, 7.99; N, 3.56.

EXAMPLE 132

1-[2-(4-Hydroxyphenoxy)ethyl]-4-(4-t-butylbenzyl)piperidine hydrochloride

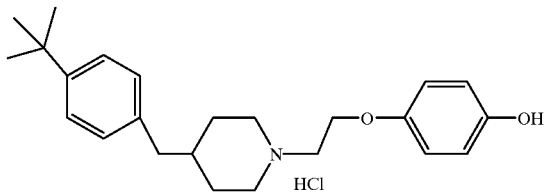

A) 4-(4-t-Butylbenzyl)piperidine hydrochloride was prepared from 4-t-butylbenzyl alcohol in five steps as white solid, mp 208–210° C. ¹H NMR (CHCl₃, 300 MHz) δ 1.303 (s, 9 H), 1.681 (m, 3 H), 1.841 (m, 2 H), 2.554 (m, 2 H), 2.798 (m, 2 H), 3.435 (d, J=12.3 Hz, 2 H), 7.036 (d, J=8.1 Hz, 2 H), 7.293 (d, J=8.1 Hz, 2 H), 9.30 (s, 1 H), 9.61 (s, 1 H). Anal. Calcd for C₁₆H₂₆ClN.0.3H₂O: C, 70.33; H, 9.81; N, 5.13. Found: C, 70.20; H, 9.62; N, 5.03.

B) The title compound was prepared from 2-(4-benzyloxyphenoxy)ethyl bromide (0.393 g, 1.28 mmol), 4-t-butylbenzylpiperidine hydrochloride (0.359 g, 1.5 mmol) and potassium carbonate (0.444 g, 3.2 mmol) in two steps as white-off solid (385 mg), mp 178–180° C. ¹H NMR (CD₃OD) 1.292 (s, 9 H), 1.516 (m, 2 H), 1.899 (m, 3 H), 2.582 (d, J=6.0 Hz, 2 H), 3.023 (m, 2 H), 3.484 (m, 2 H), 3.622 (d, J=11.7 Hz, 2 H), 4.248 (t, J=5.4 Hz, 2 H), 6.712 (d, J=9.0 Hz, 2 H), 6.832 (d, J=9.0 Hz, 2 H), 7.098 (d, J=8.1 Hz, 2 H), 7.315 (d, J=8.1 Hz, 2 H). Anal. Calcd for C₂₃H₃₂ClNO₂: C, 71.35; H. 8.48; N, 3.47. Found: C, 71.10; H, 8.21; N, 3.42.

EXAMPLE 133

4-(2-Fluoro-4-methylbenzyl)-1-(2-(4-fluorophenoxy)ethyl)piperidine hydrochloride

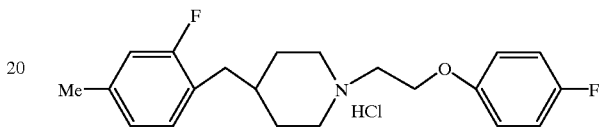

A) 4-(2-Fluoro-4-methylbenzyl)piperidine hydrochloride was prepared from 4-bromo-3-fluorotoluene, n-butyl lithium anid 4-cyanopyridine in three steps as a colorless powder, mp 211–213° C.; ¹H NMR (D₂O) 1.34–1.52 (m, 2H), 1.78–1.98 (m, 3H), 2.30 (s, 3H), 2.60 (d, J=6.6 Hz, 2H), 2.90 (td, J=13 and 2.7 Hz, 2H), 3.32–3.43 (m, 2H), 6.93–7.01 (m, 2H), 7.11–7.19 (m, 1H).

B) The title compound was prepared from 4-(2-fluoro-4-methylbenzyl)piperidine hydrochloride (375 mg, 1.54 mmol), 2-(4-fluorophenoxy)ethyl bromide (355 mg, 1.62 mmol) and K₂CO₃ (437 mg, 3.16 mmol) as a colorless crystalline solid (362 mg), mp 167–168° C.; ¹H NMR (CDCl₃) 1.60–1.80 (m, 3H), 1.95–2.15 (m, 2H), 2.30 (s, 3H), 2.61 (d, J=6.6 Hz, 2H), 2.65–2.83 (m, 2H), 3.20–3.70 (m, 4H), 4.51 (d, J=4.2 Hz, 2H), 6.78–7.00 (m, 7H), 12.60 (bs, 1H); Anal. Calcd for C₂₁H₂₆ClF₂NO: C, 66.05; H, 6.86; N, 3.67. Found: C, 66.09; H, 6.78; N, 3.46.

EXAMPLE 134

4-(2-Fluoro-4-methylbenzyl)-1-(2-(4-hydroxyphenoxy)ethyl)piperidine hydrochloride

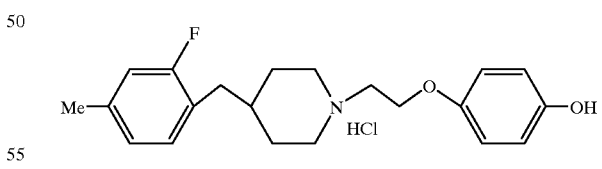

The title compound was prepared from 4-(2-fluoro-4-methylbenzyl)piperidine hydrochloride (375 mg, 1.54 mmol), 2-(4-hydroxyphenoxy)ethyl bromide (352 mg, 1.62 mmol) and NaHCO₃ (265 mg, 3.16 mmol) as a near colorless powder (430 mg): mp 164–165° C.; ¹H NMR (CD₃OD) 1.51–1.70 (m, 2H), 1.84–2.00 (m, 3H), 2.31 (s, 3H), 2.63 (d, J=5.7 Hz, 2H), 2.94–3.12 (m, 2H), 3.44–3.70 (m, 4H), 4.26 (t, J=4.8 Hz, 2H), 6.74 (d, J=9.3 Hz, 2H), 6.82–6.96 (m, 4H), 7.07–7.14 (m, 1H); Anal. Calcd for C₂₁H₂₇ClFNO₂: C, 66.39; H. 7.16; N, 3.69. Found: C, 66.62; H, 6.99; N, 3.54.

EXAMPLE 135

3,4-Dichloro-4-(4-chlorobenzyl)-1(2-(4-fluorophenoxy)ethyl)piperidine hydrochloride

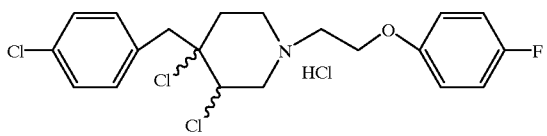

To a stirred solution of 4-(4-chlorobenzyl)-1-(2-(4-fluorophenoxy)ethyl)-1,2,5,6-tetrahydropyridine hydrochloride (70 mg, 136 μmol) in $CHCl_3$ (10 mL) a dilute solution of $Cl_2$ in $CCl_4$ was added in portions. After each addition the reaction was checked by TLC (1% $MeOH/CHCl_3$). $Cl_2$ addition was continued until all the starting material was converted to the much higher $R_f$ product spot. The reaction mixture was washed with dilute $NH_4OH$ and the organic portion was filtered (cotton). Solvent removal gave a yellow oil. The oil was purified on silica gel with $CHCl_3$ elution to give the free base of the title compound as a pale yellow oil (37 mg, 49%). The free base was converted to hydrochloride as a pale beige powder (40 mg): mp 78–83° C. (foams), $^1$H NMR ($CDCl_3$) 1.98 (d, J=15 Hz, 1H), 2.95–4.00 (m, 9H), 4.10–4.20 (m, 1H), 4.38–4.75 (m, 2H), 6.79–7.02 (m, 2H), 7.27–7.37 (m, 2H), 12.48 (bs, 1H); HRMS calcd for $C_{20}H_{21}Cl_3FNO$ 415.0673, found 415.0664.

EXAMPLE 136

1-(2-(4-Fluorophenoxy)ethyl)-4-(2-picolyl)piperidine dimaleic acid salt

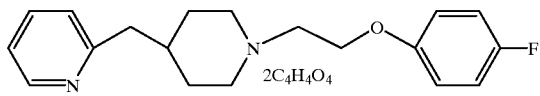

The title compound was prepared from isonipecotamide, 2-(4-fluorophenoxy)ethyl bromide, and $K_2CO_3$ in four steps as a pale yellow solid, mp 114–115° C.; $^1$H NMR ($CDCl_3$) 1.56–1.75 (m, 2H), 1.94 (d, J=15 Hz, 2H), 2.08–2.25 (m, 1H), 2.96–3.18 (m, 4H), 3.33–3.56 (m, 2H), 3.62–3.73 (m, 2H), 4.32 (d, J=4.8 Hz, 2H), 6.26 (s, 4H), 6.91–7.12 (m, 4H), 7.84–7.94 (m, 2H), 8.48 (td, J=7.8 and 1.5 Hz, 1H), 8.63 (d, J=6.0 Hz, 1H); Anal. Calcd for $C_{27}H_{31}FN_2O_9$: C, 59.33; H, 5.71; N, 5.12. Found: C, 59.36; H, 5.68; N, 4.94.

EXAMPLE 137

1-(2-(4-Fluorophenoxy)ethyl)-4-(4-picolyl)piperidine dimaleic acid salt

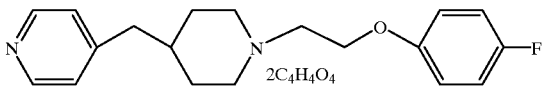

The title compound was prepared from 4-bromopyridine hydrochloride, n-BuLi and 4-cyano-1-(2-(4-fluorophenoxy)ethyl)piperidine in two steps as a near colorless solid: mp 108–109° C.; $^1$H NMR ($D_2O$) 1.52–1.70 (m, 2H), 1.92 (d, J=14 Hz, 2H), 2.04–2.20 (m, 1H), 2.94 (d, J=7.2 Hz, 2H), 3.04 (td, J=11 and 2.1 Hz, 2H), 3.32–3.56 (m, 2H), 3.60–3.72 (m, 2H), 4.32 (t, J=4.8 Hz, 2H), 6.26 (s, 4H), 6.90–7.12 (m, 4H), 7.90 (d, J=6.6 Hz, 2H), 8.64 (d, J=6.9 Hz, 2H); Anal. Calcd for $C_{27}H_{31}FN_2O_9$: C, 59.33; H, 5.71; N, 5.12. Found: C, 59.37; H, 5.75; N, 5.01.

EXAMPLE 138

4-(2-Fluoro-4-methylbenzyl)-1-(2-(2,4-difluorophenoxy)ethyl)piperidine hydrochloride

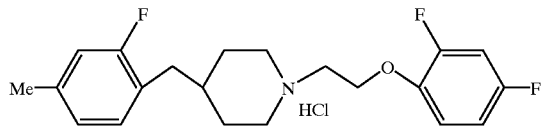

The title compound was prepared from 4-(2-fluoro-4-methylbenzyl)piperidine hydrochloride (300 mg, 1.23 mmol), 2-(2,4-difluorophenoxy)ethyl bromide (321 mg, 1.35 mmol) and $K_2CO_3$ (357 mg, 2.58 mmol) as colorless flakes (326 mg): mp 180–182° C.; $^1$H NMR ($CDCl_3$) 1.65–1.90 (m, 3H), 1.95–2.13 (m, 2H), 2.30 (s, 3H), 2.61 (d, J=6.9 Hz, 2H), 2.65–2.87 (m, 2H), 3.30–3.55 (m, 2H), 3.69 (d, J=12 Hz, 2H), 4.59 (t, J=4.2 Hz, 2H), 6.75–7.02 (m, 6H), 12.61 (bs, 1H); Anal Calcd. for $C_{21}H_{25}ClF_3NO$: C, 63.08; H, 6.30; N, 3.50. Found: C, 62.94; H, 6.34; N, 3.36.

EXAMPLE 139

4-((5,6,7,8-Tetrahydro-2-naphthyl)methyl)-1-(2-(4-hydroxyphenoxy) ethyl)piperidine hydrochloride

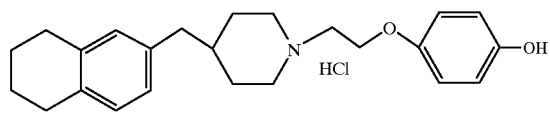

A) 4-((2-Naphthyl)methyl)pyridine was prepared from 2-bromonaphthalene, n-BuLi and 4-cyanopyridine in two steps as a yellow solid: mp 66–67° C., $^1$H NMR ($CDCl_3$) 4.13 (s, 2H), 7.14 (d, J=6.0 Hz, 2H), 7.27 (dd, J=5.7 and 1.8 Hz, 1H), 7.42–7.52 (m, 2H), 7.64 (s, 1H), 7.74–7.86 (m, 3H), 8.51 (dd, 4.8 and 1.5 Hz, 2H).

B) 4-((5,6,7,8-Tetrahydro-2-naphthyl)methyl)piperidine hydrochloride. A mixture of 4-((2-naphthyl)methyl)pyridine (1.50 g, 6.84 mmol), $PtO_2$ (100 mg) in MeOH (50 mL) and concd HCl (1 mL) was allowed to shake under $H_2$ (Parr, 20–30 psig) for 4 days to give the title compound as a colorless, crystalline solid (1.39 g, 76%): mp 213–214° C.; $^1$H NMR ($D_2O$) 1.30–1.48 (m, 2H), 1.68–1.90 (m, 7H), 2.53 (d, J=6.6 Hz, 2H), 2.64–2.76 (m, 4H), 2.90 (td, J=13 and 2.4 Hz, 2H), 3.31–3.42 (m, 2H), 6.96–7.01 (m, 2H), 7.08 (d, J=8.1 Hz, 1H).

C) The title compound was prepared from 4-((5,6,7,8-tetrahydro-2-naphthyl)methyl)piperidine hydrochloride (250 mg, 940 μmol), 2-(4-hydroxyphenoxy)ethyl bromide (204 mg, 940 μmol) and $NaHCO_3$ (162 mg, 1.93 mmol) as a pale beige solid (152 mg): $^1$H NMR ($CD_3OD$) 1.55–1.65 (m, 2H), 1.70–1.96 (m, 7H), 2.54 (d, J=6.3 Hz, 2H), 2.62–2.78 (m, 4H), 3.05 (t, J=12 Hz, 2H), 3.43–3.68 (m, 4H), 4.25 (t, J=4.8 Hz, 2H), 6.72 (d, J=9.0 Hz, 2H), 6.80–6.90 (m, 4H), 6.95 (d, J=7.5 Hz, 1H); Anal. Calcd for $C_{24}H_{32}ClNO_2 \cdot H_2O$: C, 68.64; H, 8.16; N, 3.33. Found: C, 68.39; H, 7.99; N, 3.36.

EXAMPLE 140

1-(2-(4-Fluorophenoxy)ethyl)-4-((5,6,7,8-tetrahydro-2-naphthyl)methyl)piperidine hydrochloride

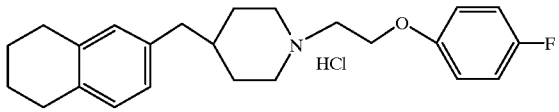

The title compound was prepared from 4-((5,6,7,8-tetrahydro-2-naphthyl)methyl)piperidine hydrochloride (250 mg, 940 μmol), 2-(4-fluorophenoxy)ethyl bromide (216 mg, 987 μmol) and $K_2CO_3$ (266 mg, 1.93 mmol) as a colorless solid (220 mg): mp 181–183° C.; $^1$H NMR (CDCl$_3$) 1.60–2.12 (m, 9H), 2.54 (d, J=7.2 Hz, 2H), 2.65–2.81 (m, 6H), 3.20–3.55 (m, 2H), 3.59–3.71 (m, 2H), 4.52 (t, J=4.2 Hz, 2H), 6.77–7.01 (m, 7H), 12.55 (bs, 1H); Anal. Calcd for $C_{24}H_{31}ClFNO$: C, 71.36; H, 7.74; N, 3.47. Found: C, 71.30; H, 7.78; N, 3.39.

EXAMPLE 141

1-(2-(4-Hydroxyphenoxy)ethyl)-4-((2-naphthyl)methyl)piperidine hydrochloride

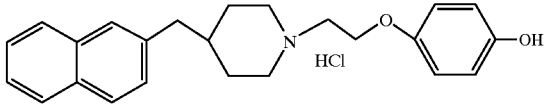

A) 4-((2-Naphthyl)methyl)piperidine hydrochloride. A mixture of 4-((2-naphthyl) methyl)pyridine (750 mg, 3.42 mmol) and PtO$_2$ (50 mg) in MeOH (25 mL) containing concd HCl (0.5 mL) was stirred under H$_2$ at ambient pressure (balloon) for 19 h to yield the title compound as a pale yellow granular solid (324 mg): mp 215–217° C.; $^1$H NMR (D$_2$O) 1.30–1.48 (m, 2H), 1.67–1.98 (m, 3H), 2.69 (d, J=6.9 Hz, 2H), 2.82 (td, J=13 and 3.0 Hz, 2H), 3.26–3.38 (m, 2H), 7.36 (d, J=8.4 Hz, 1H), 7.45–7.56 (m, 2H), 7.65 (s, 1H), 7.80–7.92 (m, 3H).

B) The title compound was prepared from 4-((2-naphthyl)methyl)piperidine hydrochloride (150 mg, 573 μmol), 2-(4-hydroxyphenoxy)ethyl bromide (130 mg, 602 μmol) and NaHCO$_3$ (97 mg, 1.17 mmol) as a pale yellow solid (182 mg): mp 221–222° C.; $^1$H NMR (CD$_3$OD) 1.53–1.72 (m, 2H), 1.87–2.12 (m, 3H), 2.81 (d, J=6.9 Hz, 2H), 2.92–3.18 (m, 2H), 3.43–3.70 (m, 4H), 4.25 (t, J=4.8 Hz, 2H), 6.73 (d, J=9.3 Hz, 2H), 6.85 (d, J=9.3 Hz, 2H), 7.32–7.49 (m, 3H), 7.66 (s, 1H), 7.76–7.85 (m, 3H); Anal. Calcd for $C_{24}H_{28}ClNO_2\cdot 0.4H_2O$: C, 71.15; H, 7.16; N, 3.46. Found: C, 71.17; H. 6.80; N, 3.11.

EXAMPLE 142

1-(2-(4-Fluorophenoxy)ethyl)-4-((2-naphthyl)methyl)piperidine hydrochloride

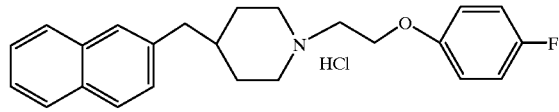

The title compound was prepared from 4-((2-naphthyl)methyl)piperidine hydrochloride (150 mg, 573 μmol), 2-(4-fluorophenoxy)ethyl bromide (132 mg, 602 μmol) and $K_2CO_3$ (162 mg, 1.17 mmol) as a colorless solid (126 mg): mp 170–172° C.; $^1$H NMR (CDCl$_3$) 1.60–1.92 (m, 3H), 2.02–2.41 (m, 2H), 2.65–2.90 (m, 4H), 3.45–3.55 (m, 2H), 3.60–3.71 (m, 2H), 4.51 (t, J=4.2 Hz, 2H), 6.77–7.01 (m, 4H), 7.25 (d, J=6.0 Hz, 1H), 7.40–7.51 (m, 2H), 7.57 (s, 1H), 7.72–7.84 (m, 3H) 12.64 (bs, 1H). Anal. Calcd for $C_{24}H_{27}ClFNO$: C, 72.08; H, 6.80; N, 3.50. Found: C, 71.73; H, 6.64; N, 3.34.

EXAMPLE 143

4-Benzyl-1-((2-(N-methyl-N-phenyl)amino)ethyl)piperidine dihydrochloride

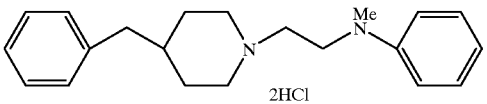

A) N-(Ethylcarboxy)methyl-N-methylaniline. From a mixture of N-methylaniline (2.00 g, 18.7 mmol), ethyl bromoacetate (3.12 g, 18.7 mmol) and $K_2CO_3$ (2.58 g, 18.7 mmol) in CH$_3$CN (50 mL) was obtained the title compound as a yellow liquid (2.70 g): $^1$H NMR (CDCl$_3$) 1.24 (t, J=7.2 Hz, 3H), 3.07 (s, 3H), 4.06 (s, 2H), 4.18 (q, J=7.2 Hz, 2H), 6.66–6.79 (m, 3H), 7.20–7.27 (m, 2H).

B) 4-Benzyl-1-((2-(N-methyl-N-phenyl)amino-1-oxo)ethyl)piperidine. A mixture of 4-benzylpiperidine (1.00 g, 5.7 mmol) and ethyl 2-(N-(N-methylanilino))acetate (500 mg, 2.59 mmol) was stirred at 150° C. under N$_2$ for 3 days to yield the title compound as a colorless oil (462 mg, 55%): $^1$H NMR (CDCl$_3$) 1.18 (qd, J=12 and 3.9 Hz, 2H), 1.62–1.85 (m, 3H), 2.45–2.62 (m, 3H), 2.90–3.05 (m, 4H), 3.82 (d, J=13 Hz, 1H), 4.06 (d, J=16 Hz, 1H), 4.13 (d, J=16 Hz, 1H), 4.58 (d, J=13 Hz, 1H), 6.65–6.76 (m, 3H), 7.10–7.33 (m, 7H).

C) 4-Benzyl-1-((2-(N-methyl-N-phenyl)amino)ethyl)piperidine dihydrochloride. A solution of 4-benzyl-1-((2-(N-methyl-N-phenyl)amino-1-oxo)ethyl)piperidine (270 mg, 837 μmol) in anhydrous THF (20 mL) with borane-THF complex in THF (~0.1 M, 19 mL, 1.9 mmol) was refluxed under N$_2$ for 1 h to yield the free base of the title compound as an amber oil (208 mg, 79%). The free base was converted to hydrochloride to yield the title compound as a fluffy colorless solid (97 mg): mp 205–206° C.; $^1$H NMR (CD$_3$OD) 1.62 (q, J=12 Hz, 2H), 1.80–1.96 (m, 3H), 2.60 (d, J=6.3 Hz, 2H), 2.98 (t, J=12 Hz, 2H), 3.26–3.40 (m, 5H), 3.61 (d, J=12 Hz, 2H), 4.10 (t, J=7.2 Hz, 2H), 7.14–7.68 (m, 10H); Anal. Calcd for $C_{21}H_{30}Cl_2N_2\cdot 0.1H_2O$: C, 65,82; H, 7.94; N, 7.31. Found: C, 65.72; H, 7.88; N, 7.16.

EXAMPLE 144

4-Benzyl-1-(2-thiophenoxyethyl)piperidine hydrochloride

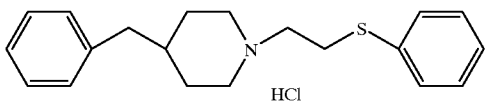

A) 2-Thiophenoxyethyl bromide. A mixture of NAOH (728 mg, 18.2 mmol) in absolute EtOH (40 mL) was stirred for 15 min while the reaction vessel was purged with $N_2$. Thiophenol (2.00 g, 1.86 mL, 18.2 mmol, MCB, used as received) was added. The mixture was stirred under $N_2$ until all the NaOH dissolved. Neat 1,2-dibromoethane (17.1 g, 7.84 mL, 91.0 mmol, Acros) was added in one portion with stirring under $N_2$. The reaction was allowed to stir for 3 days under $N_2$ at 25° C. The solution was added to a dilute NaCl solution (200 mL) and the resulting phases were separated. The aqueous portion was extracted with $CHCl_3$ (3×75 mL). The combined organic portion was washed with ice cold NaOH solution (1 M, 2×50 mL) and $H_2O$ (2×100 mL), was filtered through cotton and the solvent was removed to give a brown liquid. The remaining dibromide was removed by vacuum distillation ($H_2O$ aspirator, 80° C. oil bath) to give a brown liquid. The liquid was distilled (kugelrhor, OT=90–100° C., 0.06 Torr) to yield the title compound as a colorless liquid (3.10 g, 78%): $^1$H NMR ($CDCl_3$) 3.25–3.34 (m, 2H), 3.42–3.51 (m, 2H), 7.22–7.42 (m, 5H).

B) The title compound was prepared from 4-benzylpiperidine (500 mg, 2.85 mmol), 2-thiophenoxyethyl bromide (651 mg, 3.00 mmol) and $K_2CO_3$ (415 mg, 3.00 mmol) as a colorless solid (715 mg): mp 183–184° C.; $^1$H NMR ($CDCl_3$) 1.60–1.86 (m, 3H), 1.96–2.15 (m, 2H), 2.46–2.66 (m, 4H), 3.00–3.20 (m, 2H), 3.43–3.60 (m, 4H), 7.06–7.46 (m, 10H). Anal. Calcd for $C_{20}H_{26}ClNS$: C, 69.04; H, 7.53; N, 4.03. Found: C, 68.99; H, 7.43; N, 4.07.

EXAMPLE 145

4-(4-Chlorobenzyl)-1-[2-(2-chloro-4-(2-hydroxyethyl)phenoxy)ethyl]piperidine

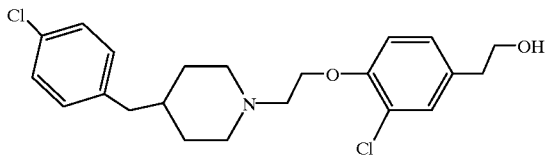

A) Ethyl 3-chloro-4-(2-bromoethoxy)phenylacetate. From a mixture of ethyl 3-chloro-4-hydroxyphenylacetate (6.43 g, 30 mmol), potassium carbonate (6.9 g, 50 mmol) and 10.4 mL of 1,2-dibromoethane was obtained 6.5 g (67%) of the title product as a white solid. $^1$H NMR ($CDCl_3$) 1.254 (t, J=7.2 Hz, 3 H), 3.526 (s, 2 H), 3.659 (t, J=6.6 Hz, 2 H), 4.161 (q, J=7.2 Hz, 2 H), 4.325 (t, J=6.6 Hz, 2 H), 6.872 (d, J=8.4 Hz, 1 H), 7.114 (d, J=8.4 Hz, 1 H), 7.315 (s, 1 H).

B) 1-[2-(2-Chloro-4-Ethoxycarbonylmethylphenoxy)ethyl]-4-(4-chlorobenzyl) piperidine. From a mixture of ethyl 3-chloro-4-(2-bromoethoxy)phenylacetate (1.93 g, 6.0 mmol), 4-chlorobenzylpiperidine hydrochloride (1.50 g, 6.0 mmol), potassium carbonate (4.14 g, 30 mmol) was obtained 2.62 g (100%) of the title compound as a pale yellow oil. $^1$H NMR ($CDCl_3$) 1.256 (t, J=6.9 Hz, 3 H), 1.50 (m, 1 H), 1.584 (m, 4 H), 2.529 (m, 2 H), 2.68 (m, 2 H), 3.001–3.177 (m, 4 H), 3.525 (s, 2 H), 4.139 (m, 4 H), 6.873 (d, J=8.4 Hz, 2 H), 7.084 (d, J=8.4 Hz, 2 H), 7.112–7.304 (m, 3H).

C) The title compound was prepared from reduction of 1-[2-(2-chloro-4-ethoxycarbonylmethylphenoxy)ethyl]-4-(4-chlorobenzyl)piperidine (450.3 mg, 1.0 mmol) by $LiAlH_4$ (38 mg, 1.0 mmol) as oily product (298 mg). $^1$H NMR ($CD_3OD$) 1.248 (m, 2 H), 1.374 (s, 1 H), 1.572 (m, 4 H), 2.530 (m, 2 H), 2.677 (m, 1 H), 2.782 (m, 2 H), 2.991–3.139 (m, 4 H), 3.828 (m, 2 H), 4.131 (m, 2 H), 6.868 (m, 1 H), 7.103 (m, 2 H), 7.233 (m, 4 H). HRMS Calcd for $C_{22}H_{27}{}^{35}Cl_2NO_2$: 407.1435; Found: 407.1427.

EXAMPLE 146

1-[2-(4-Hydroxyphenoxy)ethyl]-4-(2,6-difluorobenzyl)piperidine hydrochloride

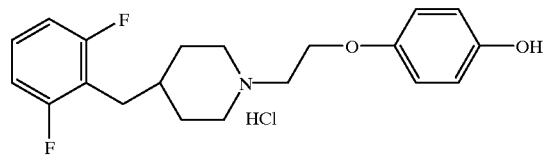

A) 4-(2,6-Difluorobenzyl)piperidine hydrochloride was prepared from triphenylphosphine and 2,6-difluorobenzyl bromide in 4 steps as white solid. mp 2216–218° C. $^1$H NMR ($CHCl_3$) 1.826 (m, 5 H), 2.679 (s, 2 H), 2.813 (m, 2 H), 3.455 (d, J=11.1 Hz, 2 H), 6.861 (m, 2 H), 7.177 (m, 1 H), 9.40 (s, 1 H), 9.62 (s, 1 H).

B) The title compound was prepared from 2-(4-benzyloxyphenoxy)ethyl bromide (0.393 g, 1.28 mmol), 4-(2,6-difluorobenzyl)piperidine hydrochloride (0.317 g, 1.28 mmol) and potassium carbonate (0.444 g, 3.2 mmol) in two steps as off white solid (0.240 g). mp 198–200° C. $^1$H NMR ($CD_3OD$) 1.595 (m, 2 H), 1.906 (m, 3 H), 2.705 (d, J=5.7 Hz, 2 H), 3.029 (t, J=12.3 Hz, 2 H), 3.303 (m, 2 H), 3.629 (d, J=12.6 Hz, 2 H), 4.238 (t, J=4.5 Hz, 2 H), 6.702 (d, J=9.0 Hz, 2 H), 6.825 (d, J=9.0 Hz, 2 H), 6.953 (m, 2 H), 7.277 (m, 1 H).

EXAMPLE 147

1-[2-(4-Hydroxy-3-methylphenoxy)ethyl]-4-(2-fluoro-4-methylbenzyl)piperidine hydrochloride

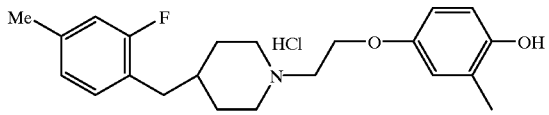

A) 4'-Benzyloxy-3'-methylacetophenone. From a mixture of 4'-hydroxy-3'-methylacetophenone (10 g, 66.6 mmol), benzyl bromide (11.4 g, 66.6 mmol), potassium carbonate (13.8 g, 99.9 mmol) was obtained 15.0 g (94%) of the title compound as a white solid. mp 64–66° C. $^1$H NMR ($CDCl_3$) 2.322 (s, 3 H), 2.552 (s, 3 H), 5.164 (s, 2 H), 6.892 (d, J=9.3 Hz, 1 H), 7.342–7.428 (m, 5 H), 7.790 (m, 2 H).

B) 4-Benzyloxy-3-methylphenol. A solution of 4'-benzyloxy-3'-methylacetophenone (6.0 g, 25 mmol) in 100 mL of dichloromethane containing 8.63 g (25.0 mmol)

of MCPBA was allowed to stir at rt for 6 days. The mixture was washed with saturated sodium thiosulfate solution and saturated sodium biocarbonate solution. Evaporation of dichloromethane gave a crude ester, which was dissolved into 250 mL of methanol. To this solution was added sodium methoxide (2.70 g, 50 mmol) and then stirred at rt for 1 hr. The methanol was evaporated and 50 mL of 2M HCl aqueous solution was added. The mixture was extracted with dichloromethane (3×50 mL), dried over sodium sulfate. Evaporation of solvent and further purification by flash chromatography gave 5 g (93%) of the phenol as a white solid. mp 69–71° C. $^1$H NMR (CDCl$_3$) 2.246 (s, 3 H), 4.398 (s, 1 H), 5.014 (s, 2 H), 6.604 (m, 1 H), 6.675 (m, 1 H), 6.771 (m, 1 H), 7.315–7.447 (m, 5 H).

C) 2-(4-Benzyloxy-3-methylphenoxy)ethyl bromide. From a mixture of 4-benzyloxy-3-methylphenol (5.0 g, 0.025 mol), potassium carbonate (8.63 g, 0.625 mol) and 25 mL of 1,2-dibromoethane was obtained 5.0 g (63%) of the title compound as a pale yellow oil, $^1$H NMR (CDCl$_3$) 2.263 (s, 3 H), 3.608 (t, J=5.7 Hz, 2 H), 4.230 (t, J=5.7 Hz, 2 H), 5.026 (s, 2 H), 6.655 (m, 1 H), 6.780 (m, 2 H), 7.313–7.443 (m, 5 H).

D) 4-Pyridyl-(2-fluoro-4-methylphenyl)methanol. To a slurry of sodium boronhydride (189 mg, 5,0 mmol) in 20 mL of ethanol was added a solution of 2-fluoro-4-methylphenyl 4-pyridyl ketone (1.075 g, 5.0 mmol) in 20 mL of ethanol at rt. The mixture was allowed to stir at rt for overnight. The mixture was poured into 200 mL of water and extracted with ethyl acetate (3×50 mL). The combined extracts were dried over Na$_2$SO$_4$. Evaporation of solvent gave 1.0 g (100%) of the product as a white solid. mp 131–133° C. $^1$H NMR (CDCl$_3$) 2.335 (s, 3 H), 2.858 (s, 1 H), 6.093 (s, 1 H), 6.861–6.967 (m, 2 H), 7.250 (m, 2 H), 7.325 (m, 2 H), 8.529 (m, 2 H).

E) 4-(2-Fluoro-4-methylbenzyl)piperidine hydrochloride. A mixture of 4-pyridyl-(2-fluoro-4-methylphenyl)methanol (1.09 g, 5.0 mmol) and 0.27 g of 30% Pd/C in 50 mL of methanol containing 1.0 mL of conc. HCl was hydrogenated at 55 psi for 3 days to give 1.1 g (90%) of the title compound as white solid. mp 196–198° C. $^1$H NMR (CHCl$_3$) 1.292 (m, 2 H), 1.679 (m, 3 H), 2.141 (m, 3 H), 2.443 (d, J=6.6 Hz, 2 H), 2.753 (m, 2 H), 3.207 (m, 2 H), 6.795 (m, 2 H), 6.970 (m, 1 H).

F) The title compound was prepared from 4-(2-fluoro-4-methylbenzyl)piperidine hydrochloride (311.7 mg, 1.28 mmol), 2-(4-benzyloxy-3-methylphenoxy)ethyl bromide (411 mg, 1.28 mmol) and potassium carbonate (444 mg, 3.2 mmol) in two steps as white-off solid (244 mg), mp 165–167° C. $^1$H NMR (CD$_3$OD) 1.503 (m, 2 H), 1.848 (m, 3 H), 2.076 (s, 3 H), 2.223 (s, 3 H), 2.560 (m, 2 H), 2.932 (m, 2 H), 3.389 (m, 2 H), 3.526 (m, 2 H), 4.141 (t, J=5.1 Hz, 2 H), 6.758 (s, 1 H), 6.667 (s, 1 H), 6.788–6.858 (m, 3 H), 7.109 (m, 1 H). Anal. Calcd for C$_{22}$H$_{29}$ClFNO$_2$: C, 67.08; H, 7.42; N, 3.98. Found: C, 66.85; H, 7.44; N, 3.46.

EXAMPLE 148

1-[2-(3,4-Methylenedioxyphenoxy)ethyl]-4-benzylpiperidine hydrochloride

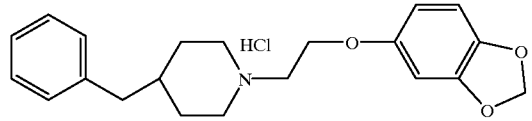

A) 2-(3,4-Methylenedioxyphenoxy)ethyl bromide. From a mixture of sesamol (4.14 g, 0.03 mol), potassium carbonate (10.35 g, 0.075 mol) and 13 mL of 1,2-dibromoethane was obtained 4.8 g (65%) of the title compound as a white solid. mp 70–72° C. $^1$H NMR (CDCl$_3$) 3.603 (t, J=6.3 Hz, 2 H), 4.216 (t, J=6.3 Hz, 2 H), 5.931 (s, 2 H), 6.350 (m, 1 H), 6.517 (m, 1 H), 6.697 (m, 1 H).

B) The title compound was prepared from 4-benzylpiperidine (1.02 g, 5.8 mmol), 2-(3,4-methylenedioxyphenoxy)ethyl bromide (1.43 g, 5.8 mmol) and potassium carbonate (2.0 g, 14.5 mmol) as a white solid (1.66 g): mp 153–155° C. $^1$H NMR (CDCl$_3$) 1.70 (m, 1 H), 1.86 (m, 2 H), 2.051 (m, 2 H), 2.614 (d, J=7.2 Hz, 2 H), 2.766 (m, 2 H), 3.344 (s, 2 H), 3.635 (d, J=12.3 Hz, 2 H), 4.466 (s, 2 H), 5.912 (s, 2 H), 6.312 (m, 1 H), 6.429 (m, 1 H), 6.674 (d, J=8.4 Hz, 1 H), 7.132 (m, 2 H), 7.260 (m, 3 H), 12.5 (brs, 1 H).

EXAMPLE 149

1-[2-(4-Hydroxy-3-fluorophenoxy)ethyl]-4-(2-fluoro-4-methylbenzyl)piperidine hydrochloride

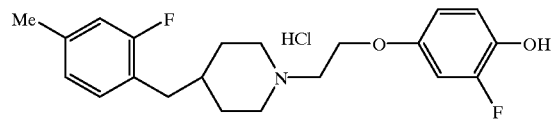

A) 1-Acetyloxy-2-fluorobenzene. A solution of 2-fluorophenol (22.4 g, 0.20 mol) in acetyl chloride (18.8 g, 0.24 mol) was allowed to stir at 80° C. for 5 h. Evaporation of excess acetyl chloride gave 30 g (98%) of the title compound as a colorless oil. $^1$H NMR (CDCl$_3$) 2.405 (s, 3 H), 7.181–7.260 (m, 4 H).

B) 3'-Fluoro-4'-hydroxyacetophenone. A mixture of 1-acetyloxy-2-fluorobenzene (30 g, 0.2 mol) and anhydrous aluminum chloride (33.35 g, 0.25 mol) in 80 mL of carbon disulfide was refluxed for 24 h until evolution of hydrogen chloride had ceased. The mixture was hydrolyzed by adding 4N HCl aqueous solution (200 mL). A brown solid was filtered off and purified by recrystallization from toluene, giving 20 g (67%) of the title compound as brown solid. mp 125–127° C. $^1$H NMR (CDCl$_3$) 2.564 (s, 3 H), 6.182 (s, 1 H), 7.070 (m, 1 H), 7.682–7.753 (m, 2 H).

C) 4-Benzyloxy-3-fluorophenol was obtained from 3'-fluoro-4'-hydroxyacetophenone, benzyl bromide and potassium carbonate in two steps as a white solid: mp 80–82° C. $^1$H NMR (CDCl$_3$) 4.616 (s, 1 H), 5.065 (s, 2 H), 6.466 (m, 1 H), 6.629 (dd, J$_1$=12.0 Hz, J$_2$=3.0 Hz, 1 H), 6.860 (m, 1 H), 7.316–7.437 (m, 5 H).

D) 2-(4-Benzyloxy-3-fluorophenoxy)ethyl bromide was prepared from 4-benzyloxy-3-fluorophenol (5.45 g, 0.025 mol), potassium carbonate (8.63 g, 0.625 mol) and 25 mL of 1,2-dibromoethane as a pale yellow solid (6.6 g, 81%): mp 63–65° C. $^1$H NMR (CDCl$_3$) 3.606 (t, J=6.3 Hz, 2 H), 4.218 (t, J=6.3 Hz, 2 H), 5.082 (s, 2 H), 6.582 (m, 1 H), 6.699 (m, 1 H), 6.914 (m, 1 H), 7.318–7.440 (m, 5 H).

E) The title compound was prepared from 4-(2-fluoro-4-methylbenzyl)piperidine hydrochloride (311.7 mg, 1.28 mmol), 2-(4-benzoxy-3-fluorophenoxy)ethyl bromide (411 mg, 1.28 mmol), potassium carbonate (444 mg, 3.2 mmol) in two steps as white-off solid (270 mg), mp 128–130° C. $^1$H NMR (CD$_3$OD) 1.40 (m, 2 H), 1.704 (m, 3 H), 2.114 (s, 3 H), 2.422 (d, J=6.3 Hz, 2 H), 2.837 (m, 2 H), 3.303 (m, 2 H), 3.430 (d, J=11.4 Hz, 2 H), 4.072 (m, 2 H), 6.50 (m, 1 H), 6.632–6.750 (m, 4 H), 6.90 (m, 1 H). Anal. Calcd for C$_{21}$H$_{26}$ClF$_2$NO$_2$.0.4H$_2$O: C, 62.25; H, 6.67; N, 3.46. Found: C, 62.20; H, 6.61; N, 3.22.

EXAMPLE 150

1-[2-(4-Hydroxy-3-fluorophenoxy)ethyl]-4-(4-fluorobenzyl)piperidine hydrochloride

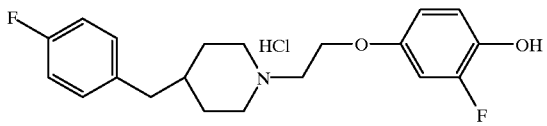

The title compound was prepared from 4-(4-fluorobenzyl)piperidine hydrochloride (344 mg, 1.50 mmol), 2-(4-benzoxy-3-fluorophenoxy)ethyl bromide (487 mg, 1.50 mmol), potassium carbonate (518 mg, 3.75 mmol) in two steps as white-off solid (277 mg), mp 184–186° C. $^1$H NMR (CD$_3$OD) 1.40 (m, 2 H), 1.709 (m, 3 H), 2.424 (d, J=4.8 Hz, 2 H), 2.850 (m, 2 H), 3.319 (m, 2 H), 3.443 (d, J=12.0 Hz, 2 H), 4.087 (s, 2 H), 6.50 (m, 1 H), 6.642 (m, 2 H), 6.833 (m, 2 H), 7.021 (m, 2 H).

EXAMPLE 151

1-[2-(4-Hydroxy-3-fluorophenoxy)ethyl]-4-(4-methylbenzyl)piperidine hydrochloride

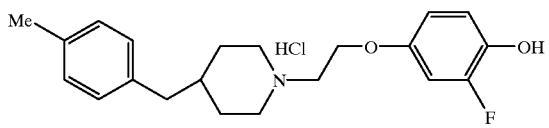

The title compound was prepared from 4-(4-methylbenzyl)piperidine hydrochloride (347 mg, 1.54 mmol), 2-(4-benzoxy-3-fluorophenoxy)ethyl bromide (499 mg, 1.54 mmol) and potassium carbonate (531 mg, 3.85 mmol) in two steps as white-off solid (272 mg): mp 148–150° C. $^1$H NMR (CD$_3$OD) 1.38 (m, 2 H), 1.699 (m, 3 H), 2.100 (s, 3 H), 2.375 (d, J=6.3 Hz, 2 H), 2.834 (m, 2 H), 3.307 (m, 2 H), 3.427 (d, J=11.7 Hz, 2 H), 4.078 (t, J=4.8 Hz, 2 H), 6.48 (m, 1 H), 6.638 (m, 2 H), 6.844 (m, 4 H). Anal. Calcd for C$_{21}$H$_{27}$ClFNO$_2$.0.3H$_2$O: C, 65.45; H, 7.22; N, 3.64. Found: C, 65.54; H, 7.15; N, 3.60.

EXAMPLE 152

1-[2-(4-Hydroxy-3-methylphenoxy)ethyl]-4-(4-fluorobenzyl)piperidine hydrochloride

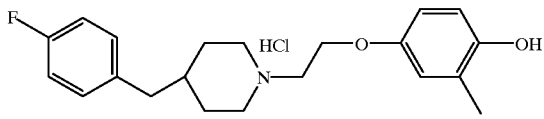

The title compound was prepared from 4-(4-fluorobenzyl)piperidine hydrochloride (344 mg, 1.5 mmol), 2-(4-benzoxy-3-methylphenoxy)ethyl bromide (482 mg, 1.5 mmol) and potassium carbonate (518 mg, 3.8 mmol) in two steps as white-off solid (240 mg): mp 118–120° C. $^1$H NMR (CD$_3$OD) 1.40 (m, 2 H), 1.699 (m, 3 H), 1.975 (s, 3 H), 2.441 (t, 2 H), 2.82 (m, 2 H), 3.310 (m, 2 H), 3.45 (m, 2 H), 4.054 (s, 2 H), 6.481 (s, 2 H), 6.753 (s, 1 H), 6.83 (m, 2 H), 7.021 (m, 2 H). Anal. Calcd for C$_{21}$H$_{27}$ClFNO$_2$.0.7H$_2$O: C, 64.25; H, 7.29; N, 3.57. Found: C, 64.24; H, 7.02; N, 3.91.

EXAMPLE 153

1-[2-(4-Hydroxy-3-methylphenoxy)ethyl]-4-(4-methylbenzyl)piperidine hydrochloride

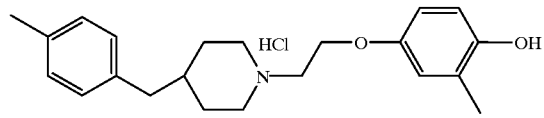

The title compound was prepared from 4-(4-methylbenzyl)piperidine hydrochloride (339 mg, 1.5 mmol), 2-(4-benzoxy-3-methylphenoxy)ethyl bromide (482 mg, 1.5 mmol) and potassium carbonate (518 mg, 3.8 mmol) in two steps as white-off solid (250 mg): mp 161–163° C. $^1$H NMR (CD$_3$OD) 1.328 (m, 2 H), 1.697 (m, 3 H), 1.964 (s, 3 H), 2.092 (s, 3 H), 2.384 (m, 2 H), 2.826 (m, 2 H), 3.279 (m, 2 H), 3.427 (m, 2 H), 4.037 (d, J=4.5 Hz, 2 H), 6.469 (m, 2 H), 6.563 (m, 1 H), 6.877 (m, 4 H). Anal. Calcd for C$_{22}$H$_{30}$ClNO$_2$.0.6H$_2$O: C, 68.31; H, 8.13; N, 3.62. Found: C, 68.52; H, 7.85; N, 3.65.

EXAMPLE 154

1-[2-(4-Hydroxyphenoxy)ethyl]-4-hydroxy-4-(4-methylbenzyl)piperidine hydrochloride

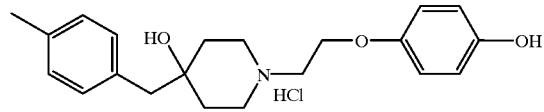

A) 1-Benzyl-4-hydroxy-4-(4-methylbenzyl)piperidine. To a 250-ml three-necked round-bottomed flask was added 2.31 g of Mg turnings and 15 mL of anhydrous THF under N$_2$. To which was added dropwise a solution of 1,2-dibromoethane (0.489 g, 2.65 mmol) in 5 mL of THF at rt. After addition, THF was removed and the residue was rinsed with THF (2×5 mL). To this residue was added dropwise a solution of 4-methylbenzyl chloride (13.0 g, 92.6 mmol) in 50 mL of THF at 0° C. After addition, the solution was allowed to stir at rt for 2 h and another 50 mL of THF was added. After cooling down to −35° C.—−40° C., a solution of 4-benzylpiperidone (5.0 g, 26.5 mmol) in 20 mL of THF was added dropwise. After the addition was complete, the reaction mixture was allowed to stir at rt for 3 h and stand overnight. To this reaction mixture was added 100 mL of saturated NH₄Cl aqueous solution at 0° C. and then extracted with dichloromethane (2×50 mL). The combined organic phase was evaporated in vacuo to give an oil, which was redissolved into 200 mL of dichloromethane and washed with saturated NH₄Cl aqueous solution (2×30 mL) and brine (50 mL), and then dried over sodium sulfate. Evaporation of solvent followed by flash chromatography (EtOAc $R_f$=0.25), giving 7.5 g (96%) of the product as a pale yellow oil. $^1$H NMR (CDCl₃) 1.476 (m, 2 H), 1.725 (m, 2 H), 2.046 (s, 1 H), 2.323 (m, 5 H), 2.611 (m, 2 H), 2.713 (s, 2 H), 3.505 (s, 2 H), 7.086 (m, 4 H), 7.299 (m, 5 H).

B) 4-Hydroxy-4-(4-methylbenzyl)piperidine hydrochloride. A mixture of 1-benzyl-4-(4-methylbenzyl)-4-hydroxypiperidine (2.8 g, 9.5 mmol) and 700 mg of 10% Pd/C in 100 mL of 95% ethanol was hydrogenated at 50 psi for overnight. The catalyst was removed through a short column of celite (10 g) and washed with methanol (3×15 mL). To the filtrate was added 12 mL of 1M HCl in methanol. Evaporation of methanol gave a residue, to which was added 30 mL of ether. The mixture was stirred at rt for 2 days. A white solid was collected by filtration, giving 2.1 g (92%) of the title product. mp 183–185° C. $^1$H NMR (CDCl₃) 1.680 (m, 2 H), 2.097 (m, 2 H), 2.338 (s, 3 H), 2.783 (s, 2 H), 3.241 (m, 5 H), 7.049 (d, J=7.5 Hz, 2 H), 7.142 (d, J=7.5 Hz, 2 H), 9.30 (brs, 1 H), 9.515 (brs, 1 H).

C) 1-[2-(4-Benzyloxyphenoxy)ethyl]-4-hydroxy-4-(4-methylbenzyl)piperidine hydrochloride. A mixture of 2-(4-benzyloxyphenoxy)ethyl bromide (368 mg, 1.2 mmol), 4-(4-methylbenzyl)-4-hydroxypiperidine hydrochloride (290 mg, 1.2 mmol), potassium carbonate (414 mg, 3 mmol) in 30 mL of acetonitrile was allowed to reflux for 12 h. The inorganic salt was removed through a short column of silica gel and washed with ethyl acetate (3×25 mL). The combined flitrate was evaporated in vacuo to give a crude mixture, which was purified by flash chromatography (5% methanol in ethyl acetate), giving a pale yellow oil, which was disolved into methanol (10 mL), to which was added 4 mL of 1 M HCl in methanol. The resulting solution was allowed to stir at rt for 10 min, and methanol was evaporated in vacuo to give a residue, to which 50 mL of ether was added. The resulting mixture was stirred overnight. A white solid was collected by filtration and dried in vacuo, giving 420 mg (75%) of the title product: mp 179–181° C. $^1$H NMR (CDCl₃) 1.605 (s, 2 H), 1.725 (d, J=14.1 Hz, 2 H), 2.332 (s, 3 H), 2.453 (m, 2 H), 2.809 (s, 2 H), 3.221 (m, 2 H), 3.361 (s, 1 H), 3.464 (d, J=8.4 Hz, 2 H), 4.488 (s, 2 H), 5.005 (s, 2 H), 6.820 (d, J=9.0 Hz, 2 H), 6.904 (d, J=9.0 Hz, 2 H), 7.077 (d, J=7.5 Hz, 2 H), 7.166 (d, J=7.5 Hz, 2 H), 7.376 (m, 5 H), 12.4 (bs, 1 H).

D) 1-[2-(4-hydroxyphenoxy)ethyl]-4-hydroxy-4-(4-methylbenzyl)piperidine hydrochloride. To a solution of 1-[2-(4-benzyloxyphenoxy)ethyl]-4-hydroxy-4-(4-methylbenzyl)piperidine hydrochloride (0.25 g, 0.53 mmol) in 30 mL of methanol was added 62.5 mg of 20% Pd(OH)₂. The resulting mixture was hydrogenated at 20 psi of hydrogen for 3 h. The catalyst was removed through a short column of celite (5 g) and washed with methanol (3×15 mL). Methanol was evaporated in vacuo to give a residue, to which 50 mL of ether was added. The resulting mixture was stirred overnight. A white solid was collected by filtration and dried in vacuo, giving 200 mg (100%) of the title product. mp 133–135° C. $^1$H NMR (CD₃OD) 1.58 (m, 2 H), 1.75 (m, 2 H), 2.119 (s, 3 H), 2.615 (s, 2 H), 3.20–3.30 (m, 6 H), 4.056 (m, 2 H), 6.528 (d, J=9.0 Hz, 2 H), 6.645 (d, J=9.0 Hz, 2 H), 6.938 (s, 4 H).

EXAMPLE 155

1-[2-(4-hydroxy-3-methylphenoxy)ethyl]-4-hydroxy-4-(4-methylbenzyl)piperidine hydrochloride

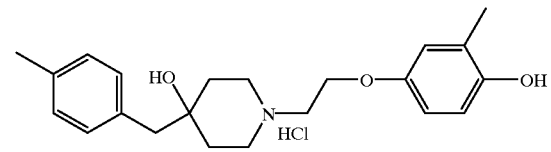

The title compound was prepared from 2-(4-benzyloxy-3-methylphenoxy)ethyl bromide (385 mg, 1.2 mmol), 4-(4-ethylbenzyl)-4-hydroxypiperidine hydrochloride (290 g, 1.2 mmol) and potassium carbonate (414 mg, 3 mmol) in two steps as white solid (200 mg): mp 90–94° C. (dec.). $^1$H NMR (CD₃OD) 1.641 (m, 2 H), 1.859 (m, 2 H), 2.083 (S, 3 H), 2.224 (s, 3 H), 2.718 (s, 2 H), 3.260–3.423 (m, 6 H), 4.133 (m, 2 H), 6.585 (s, 2 H), 6.668 (s, 1 H), 7.035 (m, 4 H).

EXAMPLE 156

4-Benzyl-1-[2-(2-hydroxyphenoxy)ethyl]piperidine hydrochloride

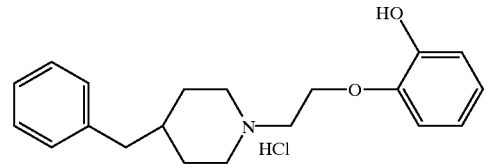

The title compound was prepared from 4-benzylpiperidine (228 mg, 1.30 mmol), 2-(2-benzyloxyphenoxy)ethyl bromide (399 mg, 1.3 mmol) and potassium carbonate (449 mg, 3.2 mmol) in two steps as white-off solid (120 mg): mp 220–222° C. (dec.). $^1$H NMR (CD₃OD) 1.412 (m, 2 H), 1.726 (d, J=13.2 Hz, 2 H), 2.453 (d, J=6.6 Hz, 2 H), 2.868 (m, 2 H), 3.347 (m, 2 H), 3.460 (d, J=12.3 Hz, 2 H), 4.133 (t, J=5.4 Hz, 2 H), 6.623–6.695 (m, 3 H), 6.779 (m, 1 H), 6.995–7.123 (m, 5 H).

EXAMPLE 157

4-Benzyl-1-[2-(3-hydroxyphenoxy)ethyl]piperidine hydrochloride

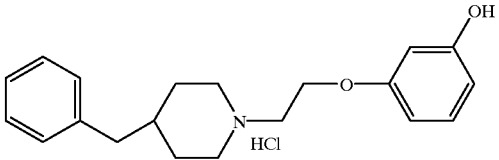

The title compound was prepared from 4-benzylpiperidine (228 mg, 1.30 mmol), 2-(3-benzyloxyphenoxy)ethyl bromide (399 mg, 1.3 mmol) and potassium carbonate (449 mg, 3.2 mmol) in two steps as white-off solid (112 mg): mp 168–170° C. (dec.). $^1$H NMR (CD$_3$OD) 1.40 (m, 2 H), 1.703 (d, J=12.9 Hz, 2 H), 2.435 (d, J=6.0 Hz, 2 H), 2.90 (m, 2 H), 3.334 (m, 2 H), 3.406 (m, 2 H), 4.108 (s, 2 H), 6.240–6.292 (m, 3 H), 6.906 (m, 1 H), 6.989–7.096 (m, 5 H).

EXAMPLE 158

4-(4-Fluorobenzyl)-1-[2-(2-hydroxyphenoxy)ethyl] piperidine hydrochloride

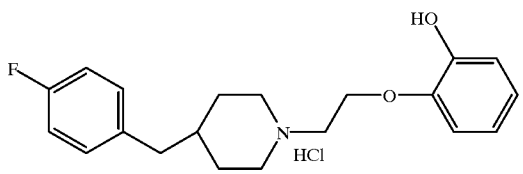

The title compound was prepared from 4-(4-fluorobenzyl) piperidine hydrochloride (298 mg, 1.30 mmol), 2-(2-benzyloxyphenoxy)ethyl bromide (399 mg, 1.3 mmol) and potassium carbonate (449 mg, 3.2 mmol) in two steps as white-off solid (240 mg): mp 233–235° C. (dec.). $^1$H NMR (CD$_3$OD) 1.532 (m, 2 H), 1.848 (d, J=13.2 Hz, 3 H), 2.571 (d, J=6.3 Hz, 2 H), 3.0 (m, 2 H), 3.483 (m, 2 H), 3.603 (d, J=10.5 Hz, 2 H), 4.262 (t, J=5.1 Hz, 2 H), 6.752–6.825 (m, 3 H), 6.909–6.986 (m, 3 H), 7.126–7.173 (m, 2 H).

EXAMPLE 159

4-(4-Fluorobenzyl)-1-[2-(3-Hydroxyphenoxy)ethyl] piperidine hydrochloride

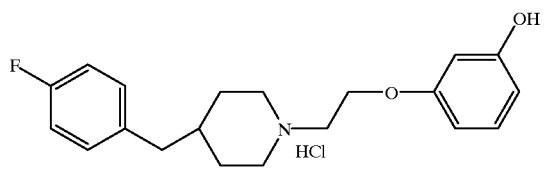

The title compound was prepared from 4-(4-fluorobenzyl) piperidine hydrochloride (298 mg, 1.30 mmol), 2-(3-benzyloxyphenoxy)ethyl bromide (399 mg, 1.3 mmol) and potassium carbonate (449 mg, 3.2 mmol) in two steps as white-off solid (250 mg): mp 145–147° C. $^1$H NMR (CD$_3$OD) 1.529 (m, 2 H), 1.821 (d, J=12.9 Hz, 2 H), 2.551 (d, J=6.3 Hz, 2 H), 3.003 (m, 2 H), 3.468 (m, 2 H), 3.541 (m, 2 H), 4.243 (t, J=5.4 Hz, 2 H), 6.369–6.422 (m, 3 H), 6.924–7.034 (m, 3 H), 7.120–7.167 (m, 2 H).

EXAMPLE 160

1-[2-(3-Hydroxyphenoxy)ethyl]-4-(4-methylbenzyl) piperidine hydrochloride

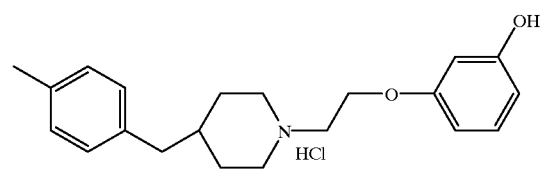

The title compound was prepared from 4-(4-methylbenzyl)piperidine hydrochloride (294 mg, 1.30 mmol), 2-(3-benzyloxyphenoxy)ethyl bromide (399 mg, 1.3 mmol) and potassium carbonate (449 mg, 3.2 mmol) in two steps as white-off solid (230 mg): mp 163–165° C. $^1$H NMR (CD$_3$OD) 1.421 (m, 2 H), 1.733 (m, 2 H), 2.135 (s, 3 H), 2.424 (d, J=5.7 Hz, 2 H), 2.9 (m, 2 H), 3.370 (m, 2 H), 3.448 (m, 2 H), 4.147 (t, J=4.8 Hz, 2 H), 6.302 (m, 3 H), 6.937 (m, 5 H).

EXAMPLE 161

1-[2-(2-Hydroxyphenoxy)ethyl]-4-(4-methylbenzyl) piperidine hydrochloride

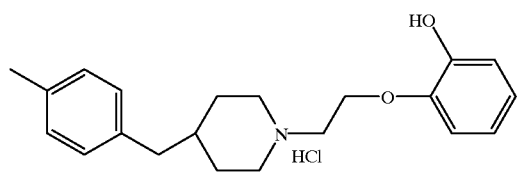

The title compound was prepared from 4-(4-methylbenzyl)piperidine hydrochloride (294 mg, 1.30 mmol), 2-(2-benzyloxyphenoxy)ethyl bromide (399 mg, 1.3 mmol) and potassium carbonate (449 mg, 3.2 mmol) in two steps as white-off solid (240 mg): mp 225–227° C. $^1$H NMR (CD$_3$OD) 1.436 (m, 2 H), 1.758 (d, J=12.9 Hz, 3 H), 2.135 (s, 3 H), 2.443 (d, J=6.3 Hz, 2 H), 2.900 (m, 2 H), 3.388 (m, 2 H), 3.503 (m, 2 H), 4.172 (t, J=5.7 Hz, 2 H), 6.651–6.739 (m, 3 H), 6.818 (m, 1 H), 6.928 (m, 4 H).

EXAMPLE 162

4-(4-Fluorobenzyl)-1-[2-(1,2,3,4-tetrahydro-1-oxo-naphth-7-oxy)ethyl]piperidine hydrochloride

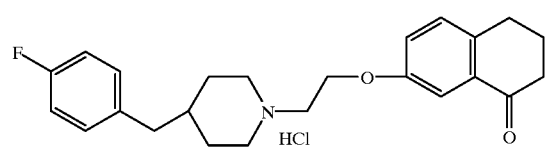

A) 7-(2-Bromoethoxy)-1-tetralone. From 7-hydroxy-1-tetralone (0.175 g, 1.08 mmol), 1,2-dibromoethane (0.50 mL, 5.80 mmol) and anhyd K$_2$O$_3$ (0.802 g, 5.80 mmol) in acetone (7.0 mL) was obtained 0.165 g (57%) of the title compound as yellow oil. $^1$H NMR (CDCl$_3$) 2.12 (p, 2H, J=6.0 Hz), 2.64 (t, 2H, J=6.0 Hz), 2.91 (t, 2H, J=6.0 Hz), 3.65 (t, 2H, J=6.0 Hz), 4.33 (t, 2H, J=6.0 Hz), 7.09 (d of d, 1H, J$_1$=3.0 Hz, J$_2$=8.4 Hz), 7.19 (d, 1H, J=8.4 Hz), 7.50 (d, 1H, J=3.0 Hz).

B) From 7-(2-bromoethoxy)-1-tetralone (0.136 g, 0.505 mmol), 4-fluorobenzylpiperidine hydrochloride (0.116 g, 0.505 mmol) and anhyd K$_2$CO$_3$ (0.175 g, 1.27 mmol) in acetonitrile (10 mL) was obtained the title compound as yellow flakes; mp 216–18° C. $^1$H NMR (CD$_3$OD) 1.54–1.59 (m, 2H), 1.89–1.94 (m, 3H), 2.11 (p, 2H, J=6.0 Hz), 2.61–2.66 (m, 4H), 2.94 (d, 2H, J=6.0 Hz), 3.06 (br t, 2H, J=12.0 Hz), 3.57–3.68 (m, 4H), 4.39 (t, 2H, J=6.0 Hz), 6.99–7.05 (m, 2H), 7.19–7.23 (m, 3H), 7.31 (d, 1H, J=8.4 Hz), 7.54 (d, 1H, J=3.0 Hz).

EXAMPLE 163

4-Benzyl-1-(2-(N-methyl-4-hydroxyanilino)ethyl)piperidine dihydrochloride

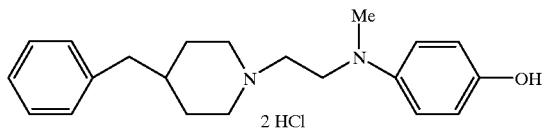

A) Ethyl 2-(N-(4-hydroxyphenyl)N-methyl)aminoacetate. From a mixture of 4-methylamimophenol sulfate (5.00 g, 14.5 mmol), ethyl bromoacetate (4.84 g, 29.0 mmol) and NaHCO$_3$ (4.87 g, 58.0 mmol) in CH$_3$CN (100 mL) was obtained the title compound as an amber oil (5.70 g, 94%): $^1$H NMR (CDCl$_3$) 1.23 (t, J=7.2 Hz, 3 H), 2.99 (s, 3 H), 3.99 (s, 2 H), 4.16 (q, J=7.2 Hz, 2 H), 5.48 (bs, 1 H), 6.59 (d, J=9.0 Hz, 2 H), 6.70 (d, J=8.4 Hz, 2 H).

B) The title compound was prepared from 4-benzylpiperidine (1.99 g, 11.4 mmol) and ethyl 2-(N-(4-hydroxyphenyl)N-methyl)aminoacetate (1.00 g, 4.78 mmol) in two steps as a beige solid: mp 190–192° C. (dec); $^1$H NMR (CD$_3$OD) 1.55–1.72 (q, J=13 Hz, 2 H), 1.82–1.95 (m, 3 H), 2.60 (d, J=6.6 Hz, 2 H), 2.92–3.08 (m, 2 H), 3.24–3.38 (m, 5 H), 3.58 (d, J=12 Hz, 2 H), 4.06 (t, J=7.2 Hz, 2 H), 6.96 (d, J=9.0 Hz, 2 H), 7.14–7.31 (m, 5 H), 7.56 (d, J=9.0 Hz, 2 H).

EXAMPLE 164

4-Benzyl-4-hydroxy-1-[2-(4-hydroxyphenoxy)ethyl]piperidine hydrochloride

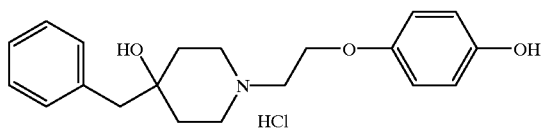

The title compound was prepared from 4-benzyl-4-hydroxypiperidine (383 mg, 2.00 mmol), 2-(4-benzoxyphenoxy)ethyl bromide (614 mg, 2.00 mmol) and potassium carbonate (490 mg, 5.0 mmol) in two steps as white-off solid (240 mg): mp 155–156° C. $^1$H NMR (CD$_3$OD) 1.567 (m, 2 H), 1.782 (m, 3 H), 2.665 (s, 2 H), 3.332 (m, 4 H), 4.075 (s, 2 H), 6.535 (m, 2 H), 6.654 (m, 2 H), 7.079 (m, 5 H).

EXAMPLE 165

4-(4-Fluorobenzyl)-1-(2-(4-hydroxythiophenoxy)ethyl)piperidine hydrochloride

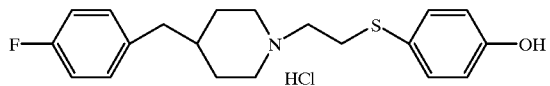

A) 4-Hydroxythiophenoxyacetaldehyde diethyl acetal. From a mixture of NaOH (1.58 g, 39.6 mmol) in absolute EtOH (100 mL) with 4-hydroxythiophenol (5.00 g, 39.6 mmol) and Bromoacetaldehyde diethyl acetal (9.80 g, 5.00 mmol) was obtained the title compound as a very pale yellow liquid (6.80 g, 71%): $^1$H NMR (CDCl$_3$) 1.19 (t, J=7.2 Hz, 3H), 3.02 (d, J=5.7 Hz, 2H), 3.48–3.72 (m, 4H), 4.61 (t, J=5.7 Hz, 1H), 6.06 (bs, 1H), 6.74 (d, J=8.7 Hz, 2H), 7.30 (d, J=9.0 Hz, 2 H).

B) 4-Hydroxythiophenoxyacetaldehyde. A stirred solution of 4-hydroxythiophenoxy acetaldehyde diethyl acetal (1.00 g, 4.12 mmol) in EtOH (20 mL) was heated to reflux. Water (50 mL) was added to the solution so as to maintain reflux. Concd HCl (1 mL) was added to the refluxing solution and reflux was maintained for 10 min. The reaction was diluted with ice water (100 mL) and was extracted with CHCl$_3$ (3×50 mL). The extract was washed with saturated NaCl solution (100 mL), was filtered (cotton) and the solvent was removed. The residue was dried in vacuo (rt, 0.005 Torr) to yield the title compound as a pale beige solid (570 mg, 82%): $^1$H NMR (CDCl$_3$) 3.47 (d, J=3.6 Hz, 2H), 5.84 (s, 1 H), 6.69 (d, J=8.7 Hz, 2H), 7.27 (d, J=9.0 Hz, 2H), 9.50 (t, J=3.6 Hz, 1H).

C) The title compound was prepared from 4-(4-fluorobenzyl)piperidine (from 804 mg of the hydrochloride), 4-hydroxythiophenoxyacetaldehyde (560 mg, 3.33 mmol) and NaCNH$_3$B (416 mg, 6.66 mmol) in MeOH (100 mL) as a colorless crystalline solid (430 mg): mp 177–178° C.; $^1$H NMR (CD$_3$OD) 1.40–1.60 (m, 2H), 1.76–1.92 (m, 3H), 2.59 (d, J=6.3 Hz, 2H), 2.81–3.00 (m, 2H), 3.08–3.26 (m, 4H), 3.42–3.58 (m, 2H), 6.78 (d, J=8.7 Hz, 2H), 6.96–7.22 (m, 4 H), 7.36 (d, J=8.7 Hz, 2H).

EXAMPLE 166

4-(4-Methoxyphenyl)-1-(4-phenylbutyl)piperidine

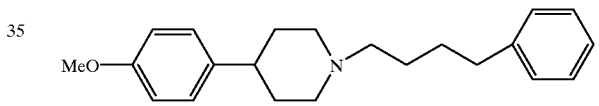

The title compound was prepared from 4-(4-methoxyphenyl)piperidine hydrochloride (1.00 g, 4.39 mmol), 4-phenyl-p-tosylbutane (1.40 g, 4.61 mmol) and K$_2$CO$_3$ (1.24 g, 9.00 mmol) in CH$_3$CN (25 mL) as a beige solid (979 mg, 69%): mp 48–50° C.; $^1$H NMR (CDCl$_3$) 1.52–1.86 (m, 8H), 2.01 (td, J=11 and 3.6 Hz, 2H), 2.34–2.50 (m, 3H), 2.65 (t, J=7.2 Hz, 2H), 2.98–3.08 ((m, 2H), 3.79 (J, 3H), 6.85 (d, J=8.7 Hz, 2H), 7.12–7.32 (m, 7H).

EXAMPLE 167

4-(4-Hydroxyphenyl)-1-(4-phenylbutyl)piperidine

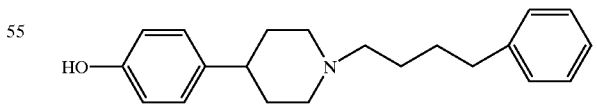

The title compound was prepared from BBr$_3$ in CH$_2$Cl$_2$ (1 M, 3.75 mL) and 4-(4-methoxyphenyl)-1-(4-phenylbutyl)piperidine (323 mg, 1.00 mmol) in dry CH$_2$Cl$_2$ (20 mL) as a colorless crystalline solid (85 mg, 26%): mp 210–211° C., $^1$H NMR (CD$_3$OD) 1.66–2.12 (m, 8H), 2.66–2.87 (m, 3H), 3.00–3.20 (m, 4H), 3.54–3.66 (m, 2H), 6.75 (d, J=8.4 Hz, 2H), 7.08 (d, J=8.4 Hz, 2H), 7.14–7.32 (m, 5H).

EXAMPLE 168

1-(2-(4-Chlorophenoxy)ethyl)-4-(4-methylbenzyl) piperidine hydrochloride

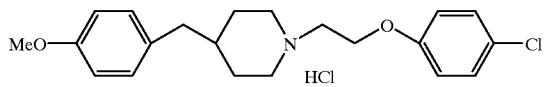

The title compound was prepared from 4-(4-methylbenzyl)piperidine hydrochloride (600 mg, 2.66 mmol), 2-(4-chlorophenoxy)ethyl bromide (658 mg, 2.79 mmol) and $K_2CO_3$ (754 mg, 5.45 mmol) in $CH_3CN$ (50 mL) as colorless flakes (661 mg): mp 201–203° C.; $^1$H NMR (CDCl$_3$) 1.60–2.12 (m, 5H), 2.31 (s, 3H), 2.58 (d, J=7.2 Hz, 2H), 2.63–2.82 (m, 2H), 3.20–3.50 (m, 2H), 3.58–3.70 (m, 2H), 4.53 (t, J=4.2 Hz, 2H), 6.80 (d, J=9.3 Hz, 2H), 7.00 (d, J=7.5 Hz, 2H), 7.09 (d, J=7.8 Hz, 2H), 7.24 (d, J=8.7 Hz, 2H), 12.60 (b, 1H).

EXAMPLE 169

1-[3-(4-Amino-3-nitrophenoxy)propyl]-4-benzylpiperidine

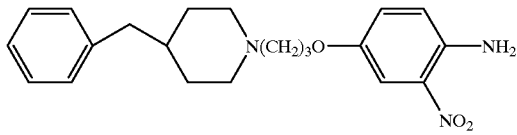

a) From a mixture of 4-amino-3-nitrophenol (3.08 g, 20.0 mmol), $K_2CO_3$ (5.52 g, 40.0 mmol), 1-chloro-3-iodopropane (12.24 g, 60.0 mmol) and 18-Crown-6 (20 mg) in THF (60 mL) was obtained 2.34 g (51%) of 3-(4-Amino-3-nitrophenoxy)propyl chloride as short red needles, mp 61–2° C. $^1$H NMR (CDCl$_3$): 2.20–2.28 (m, 2H), 3.743 (t, 2H, J=6), 4.097 (t, 2H, J=6), 5.892 (bs, 2H, NH$_2$), 6.769 (t, 1H, J=9), 7.067 (dd, 1H, J=9; 3), 7.587 (d, 1H, J=3).

b) From a mixture of 4-benzylpiperidine (715 mg, 4.08 mmol), 3-(4-amino-3-nitrophenoxy)propyl chloride (462 mg, 2.0 mmol) and NaI (360 mg) in toluene (20 mL) was obtained 528 mg (71%) of the title compound as a yellow powder, mp 108–9° C. $^1$H NMR (CDCl$_3$): 1.53–1.60 (m, 2H), 1.84–1.93 (m, 3H), 2.18–2.21 (m, 2H), 2.657 (d, 2H, J=7), 3.16–3.22 (m, 2H), 3.64–3.68 (m, 2H), 4.044 (t, 2H, J=6), 6.778 (d, 1H, J=9), 7.053 (dd,1H, J=9; 3), 7.13–7.33 (m, 5H), 7.522 (d, 1H, J=3).

EXAMPLE 170

4-Benzyl-1-[3-(2-oxobenzimidazol-5-oxy)propyl] piperidine

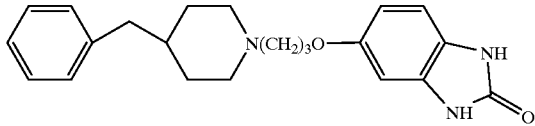

a) From a mixture of 1-[3-(4-Amino-3-nitrophenoxy) propyl]-4-benzylpiperidine (226 mg, 0.61 mmol) and stannous dihydrate (690 mg, 3.06 mmol) in EtOH (25 mL) was obtained 140 mg (67.6%) of 4-benzyl-1-[(3,4-diamino-phenoxy)propyl]piperidine as a yellowish viscous oil. $^1$H NMR (CDCl$_3$): 1.24–1.37 (m, 2H), 1.46–1.58 (m, 1H), 1.58–1.70 (m, 2H), 1.81–1.97 (m, 4H), 2.458 (t, 2H, J=7.5), 2.536 (d, 2H, J=7), 2.90–2.93 (m, 2H), 3.063 (bs, 2H, NH$_2$), 3.503 (bs, 2H, NH$_2$), 3.904 (t, 2H, J=6.5), 6.250 (dd, 1H, J=8; 2.5), 6.319 (d, 1H, J=2.5), 6.619 (d, 1H, J=8), 7.13–7.30 (m, 5H).

b) From a mixture of 4-benzyl-1-[(3,4-diaminophenoxy) propyl]piperidine (140 mg, 0.41 mmol) and CDI (130 mg, 0.8 mmol) in toluene (15 mL) was obtained 89 mg (59%) of the title compound as a white powder. $^1$H NMR (DMSO-d$_6$): 1.14–1.22 (m, 2H), 1.43–1.51 (m, 3H), 1.75–1.82 (m, 4H), 2.531 (d, 2H, J=7), 2.80– 2.83 (m, 2H), 3.893 (t, 2H, J=7), 6.490 (bs, 2H), 6.771 (d, 1H, J=9), 7.13–7.29 (m, 5H), 10.353 (s, 1H), 10.476 (s, 1H). The hydrochloride, mp. 220–2° C. Analysis, Calcd. for (C$_{22}$H$_{28}$ClN$_3$O$_2$+0.3 HCl): C 64.00, H 6.91, N 10.18; Found: C 64.09, H 6.92, N 9.92.

EXAMPLE 171

4-Benzyl-1-(2-(2-thioxobenzimidazol-5-oxy)ethyl) piperidine

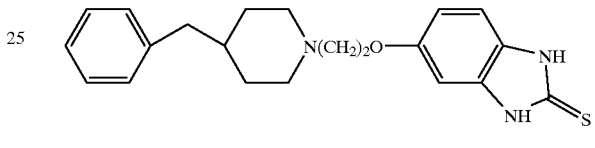

A mixture of 4-benzyl-1-[(3,4-diaminophenoxy)ethyl] piperidine (326 mg, 1.0 mmol), KOH (66 mg, 1.1 mmol) and CS$_2$ (66 μL, 1.1 mmol) in 95% EtOH (1.5 mL) and H$_2$O (0.2 mL) was refluxed for 3 h, then evaporated, and the residue was purified by chromatography over silica gel (CHCl$_3$—MeOH, 4:1) to give 250 mg (68%) of the title compound as a foam solid. $^1$H NMR (DMSO-d$_6$): 1.40–1.48 (m, 2H), 1.54–1.61 (m, 1H), 1.67–1.71 (m, 2H), 2.09–2.18 (m, 2H), 2.517 (d, 2H, J=6), 2.841 (t, 2H, J=5), 3.17–3.20 (m,2H), 4.139 (t, 2H, J=5), 6.551 (d, 1H, J=2), 6.605 (dd, 1H, J=8.5; 2), 6.950 (d, 1H, J=8.5), 7.11–7.28 (m, 5H). The hydrochloride, mp. 273–5° C. Analysis, Calcd. for C$_{21}$H$_{26}$ClN$_3$OS: C 62.44, H 6.49, N 10.40; Found: C 62.28, H 6.42, N 10.21.

EXAMPLE 172

4-Benzyl-1-(2-(2-iminobenzimidazol-5-oxy)ethyl) piperidine

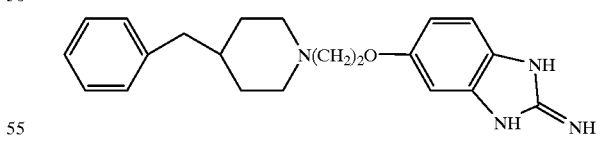

To a solution of 4-benzyl-1-[(3,4-diaminophenoxy)ethyl] piperidine (202 mg, 0.62 mmol) in MeOH (1.5 mL) was added 130 μL of 5.0 M solution of cyanogen bromide in acetonitrile. The resulting mixture was stirred at r.t. under N$_2$ for 24 h, then evaporated, and the residue was purified by chromatography over silica gel (CHCl$_3$—MeOH, 4:1) to give 174 mg (80%) of the title compound as a viscous oil. $^1$H NMR (CDCl$_3$): 1.35–1.46 (m, 2H), 1.50–1.67 (m, 3H), 2.04–2.12 (m, 2H), 2.539 (d, 2H, J=7), 2.773 (t, 2H, J=6), 3.00–3.03 (m, 2H), 3.50 (bs, 1H), 4.035 (t, 2H, J=6), 6.243

(dd, 1H, J=8; 3), 6.317 (d, 1H, J=3), 6.614 (d, 1H, J=8), 7.12–7.30 (m, 5H).

EXAMPLE 173

4-Benzyl-1-(2-(2-oxo-2,1,3-benzothiadiazol-5-oxy)ethyl)piperidine

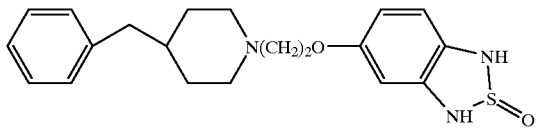

a) From a mixture of 2-(4-amino-3-nitrophenoxy)ethyl bromide (1.30 g, 5.0 mmol) and stannouschloride dihydrate (5.65 g, 25 mmol) in 95% EtOH (35 mL) was obtained 960 mg (83%) of 2-(3,4-diaminophenoxy)ethyl bromide as a pale powder. $^1$H NMR (CDCl$_3$): 3.597 (t, 2H, J=6), 4.210 (t, 2H, J=6), 6.273 (dd, 1H, J=8; 3), 6.359 (d, 1H, J=3), 6.637 (d, 1H, J=8).

b) To a cooled (ice-water) solution of 2-(3,4-diaminophenoxy)ethyl bromide (2.03 g, 8.8 mmol) in pyridine (40 mL) was added dropwise 0.65 mL (8.9 mml) of SOCl$_2$ with stirring. The resulting mixture was stirred at r.t for 2 h, then 4N H$_2$SO$_4$ was added dropwise with cooling. The acidic (pH 5) mixture was extracted with CHCl$_3$ (4×50 mL). The CHCl$_3$ solution was washed with brine, dried (Na$_2$SO$_4$), then evaporated to give 420 mg (17%) of 5-(2-bromoethoxy)-2,1,3-benzothiadiazol-2-one as an orange-yellow powder. $^1$H NMR (CDCl$_3$): 3.737 (t, 2H, J=6), 4.407 (t, 2H, J=6), 7.195 (d, 1H, J=2), 7.341 (dd, 1H, J=9; 2), 7.874 (d, 1H, J=9).

c) From a mixture of 4-benzylpiperidine (800 mg, 4.56 mmol), 5-(2-bromoethoxy)-2,1,3-benzothiadiazol-2-one (420 mg, 1.5 mmol) and K$_2$CO$_3$ (200 mg, 1.45 mmol) in toluene (35 mL) was obtained 420 mg (78%) of the title compound as a dark brown oil. $^1$H NMR (CDCl$_3$): 1.35–1.43 (m, 2H), 1.52–1.60 (m, 1H), 1.65–1.69 (m, 2H), 2.05–2.13 (m, 2H), 2.552 (d, 2H, J=7), 2.867 (t, 2H, J=6), 2.99–3.03 (m, 2H), 4.197 (t, 2H, J=6), 7.13–7.21 (m, 4H), 7.26–7.32 (m, 3H), 7.824 (d, 1H, J=9). The hydrochloride, mp. 225–6° C.

EXAMPLE 174

4-(4-Methylbenzyl)-1-(2-(2-thioxobenzimidazol-5-oxy)ethyl)piperidine

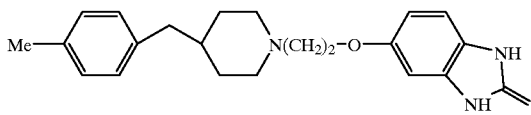

The title compound was prepared from 4-(4-methylbenzyl)piperidine hydrochloride (451 mg, 2.0 mmol), (4-amino-3-nitro-phenoxy)ethyl bromide (522 mg, 2.0 mmol) and K$_2$CO$_3$ (300 mg) in three steps as a pale powder. $^1$H NMR (CDCl$_3$): 1.36–1.70 (m, 5H), 2.08–2.15 (m, 2H), 2.038 (s, 3H), 2.488 (d, 2H, J=7), 2.839 (t, 2H, J=5), 3.09–3.12 (m, 2H), 4.127 (t, 2H, J=5), 6.64–6.72 (m, 2H), 6.99–7.09 (m, 5H). The hydrochloride, mp. 271–3° C. Analysis, Calcd. for C$_{22}$H$_{28}$ClN$_3$OS: C 63.22, H 6.75, N 10.05; Found: C 62.92, H 6.68, N 9.97.

EXAMPLE 175

4-(4-Fluorobenzyl)-1-(2-(2-thioxobenzimidazol-5-oxy)ethyl)piperidine

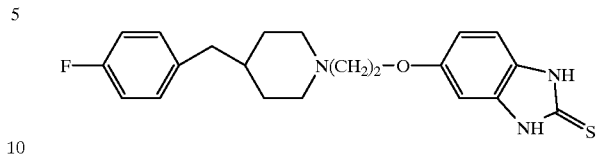

The title compound was prepared from (4-amino-3-nitrophenoxy)ethylbromide (960 mg, 3.68 mmol), 4-(4-fluorobenzyl)piperidine (860 mg, 4.46 mmol) and K$_2$CO$_3$ (1.46 g) in three steps as a foam solid. $^1$H NMR (CDCl$_3$): 1.39–1.56 (m, 3H), 1.65–1.70 (m, 2H), 2.13–2.20 (m, 2H), 2.508 (d, 2H, J=6.5), 2.890 (t, 2H, J=5), 3.16–3.20 (m, 2H), 4.61 (t, 2H, J=5), 6.633 (bs, 1H), 6.698 (d, 1H, J=8.5), 6.92–7.10 (m, 5H). The hydrochloride, mp. 278–80° C.

EXAMPLE 176

4-(4-Chlorobenzyl)-1-(2-(2-thioxobenzimidazol-5-oxy)ethyl)piperidine

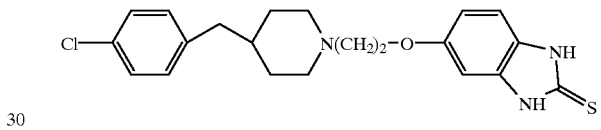

From a mixture of 1-[2-(3,4-diaminophenoxy)ethyl]-4-(4-chlorobenzyl)piperidine (1.30 g, 3.67 mmol), KOH (240 mg, 4.28 mmol) and CS$_2$ (250 μL, 4.16 mmol) in EtOH (5 mL) and water (0.8 mL) was obtained 1.28 g (88%) of the title compound as a foam solid. $^1$H NMR (CDCl$_3$): 1.38–1.68 (m, 5H), 2.09–2.17 (m, 2H), 2.481 (d, 2H, J=6.5), 2.851 (t, 2H, J=4.5), 3.18–3.21 (m, 2H), 4.142 (t, 2H, J=4.5), 6.561 (bs, 1H), 6.596 (d, 1H, J=8.5), 6.936 (d, 1H, J=8.5), 7.036 (d, 2H, J=8), 7.029 (d, 2H, J=8). $^1$H NMR (DMSO-d$_6$): 12.360 (s, 1H), 12.402 (s, 1H). The hydrochloride, mp. 291–3° C. Analysis, Calcd. for C$_{21}$H$_{25}$ClN$_3$OS: C 57.53, H 5.75, N 9.58; Found: C 57.82, H 5.65, N 9.44.

EXAMPLE 177

4-Benzyl-1-(2-(2-oxobenzimidazol-5-oxy)ethyl)-1,2,5,6-tetrahydropyridine

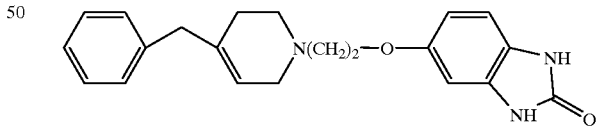

The title compound was prepared from (4-amino-3-nitrophenoxy)ethyl bromide (1.31 g, 5.0 mmol), 4-benzyl-1,2,5,6-tetrahydropyridine (870 mg, 5.02 mmol), K$_2$CO$_3$ (700 g) and KI (80 mg) in three steps as a slightly grey powder, mp. 202–3° C. $^1$H NMR (DMSO-d$_6$): 1.952 (bs, 2H), 2.50–2.56 (m, 4H), 2.686 (t, 2H, J=6), 2.973 (bs, 2H), 3.241 (s, 2H), 3.988 (t, 2H, J=6), 5.381 (s, 1H), 6.48–6.50 (m, 2H), 6.768 (d, 1H, J=9), 7.14–7.30 (m, 5H). The hydrochloride, mp. 256–7° C. Analysis, Calcd. for (C$_{21}$H$_{24}$ClN$_3$O$_2$+0.2 HCl): C 64.44, H 6.12, N 10.61; Found: C 64.15, H 6.20, N 10.68.

EXAMPLE 178

4-(2,3-Dihydrobenzofuran-2-yl)-1-(3-phenoxypropyl)piperidine

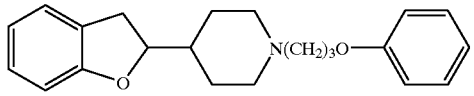

From a mixture of 4-[2-(2,3-dihydrobenzofuran-2-yl)]piperidine hydrochloride (194 mg, 0.81 mmol), 3-phenoxypropyl chloride (476 mg, 2.22 mmol), NaI (80 mg) and $K_2CO_3$ (138 mg) in toluene (15 mL) was obtained 60 mg (71%) of the title compound as a pale solid, $^1$H NMR ($CDCl_3$): 1.87–2.29 (m, 10H), 2.63–2.68 (m, 2H), 2.80–2.87 (m, 1H), 3.08–3.12 (m, 2H), 4.050 (t, 2H, J=6), 6.410 (s, 1H), 6.90–7.51 (m, 9H). The hydrochloride, mp 221–3° C. Analysis, Calcd. for ($C_{22}H_{28}ClNO_2$+0.35 HCl): C 68.75, H 7.39, N 3.62; Found: C 68.33, H 6.96, N 3.37.

EXAMPLE 179

4-(2-Oxo-2,3-dihydroindol-3-yl)-1-(3-phenoxypropyl)piperidine

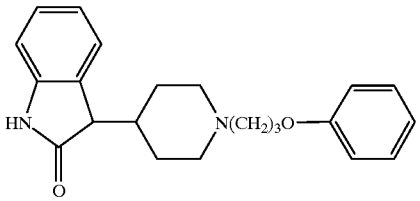

From a mixture of 4-[2-oxo-2,3-dihydroindol-3-yl)piperidine hydrochloride (198 mg, 0.73 mmol), 3-phenoxypropyl chloride (476 mg, 2.22 mmol) and $K_2CO_3$ (138 mg) in toluene (15 mL) was obtained 170 mg (70%) of the title compound as a yellow oil, $^1$H NMR ($CDCl_3$): 1.42–1.50 (m, 2H), 1.79–2.03 (m, 6H), 2.10–2.15 (m, 1H), 2.47–2.52 (m, 2H), 2.90–3.04 (m, 2H), 3.408 (d, 1H, J=3.5), 7.001 (t, 1H, J=7.5), 7.022 (t, 1H, J=7.5), 7.23–7.29 (m, 3H), 7.909 (s, 1H). The hydrochloride mp 182–3° C.

EXAMPLE 180

4-(4-Methybenzyl)-1-(2-(4-methylphenoxy)ethyl)piperidine

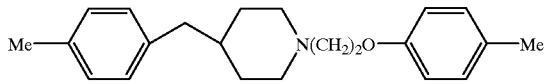

From a mixture of 4-(4-methylbenzyl)piperidine (1.14 g, 6.02 mmol), 2-(4-methylphenoxy)ethyl bromide (630 mg, 3.01 mmol) and KI (90 mg) in toluene (20 mL) was obtained 800 mg (85%) of the title compound as a yellow oil, $^1$H NMR ($CDCl_3$): 1.26–1.38 (m, 2H), 1.45–1.53 (m, 1H), 1.61–1.66 (m, 2H), 1.99–2.07 (m, 2H), 2.277 (s, 3H), 2.317 (s, 3H), 2.494 (d, 2H, J=7), 2.761 (t, 2H, J=6), 2.95–2.99 (m, 2H), 4.067 (t, 2H, J=6), 6.792 (d, 2H, J=78), (d, 2H, J=8), 7.01–7.10 (m, 6H). The hydrocloride, mp 170–1° C.

EXAMPLE 181

4-Benzyl-1-(2-(2-oxobenzoxazol-5-oxy)ethyl)piperidine

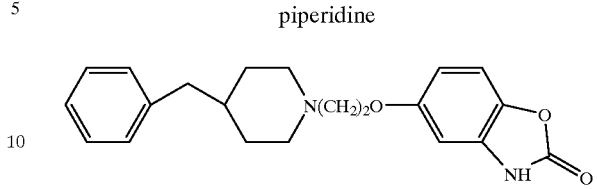

a) From a solution of 4-benzyloxy-3-nitrophenyl acetate (10.48 g, 42.7 mmol) in 70 mL of 20% solution of KOH in MeOH—$H_2O$ (7:3) was obtained 8.50 g (956) of 4-benzyloxy-3-nitrophenol as a yellow powder, mp. 137–8° C. $^1$H NMR ($CDCl_3$): 5.044 (s, 1H), 5.187 (s, 2H), 7.018 (s, 2H), 7.33–7.46 (m, 6H).

b) From a mixture of 4-benzyloxy-3-nitrophenol (4.91 g, 20 mmol), KOH (1.39 g, 21.0 mmol) in EtOH (50 mL) and 1,2-dibromoethane (11.3 g, 60.0 mmol) was obtained 2.75 g (37%.) of 2-(4-benzyloxy-3-nitrophenoxy)ethyl bromide as a solid, mp. 53–4° C. $^1$H NMR ($CDCl_3$): 3.639 (t, $2H_1$, J=6), 4.291 (t, 2H, J=6), 5.200 (s, 2H), 7.08–7.10 (m, 2H), 7.40–7.44 (m, $6H_1$).

c) From a mixture of 4-benzylpiperidine (2.68 9, 15.1 mmol), 2-(4-benzyloxy-3-nitrophenoxy)ethyl bromide (2.65 g, 7.52 mmol) and KI (110 mg) in toluene (25 mL) was obtained 2.59 g (77%) of 4-benzyl-1-(2-(4-benzyloxy-3-nitrophenoxy)ethyl)piperidine as an orange-yellow oil. $^1$H NMR ($CDCl_3$): 1.30–1.42 (m, 2H), 1.50–1.60 (m, 1H), 1.64–1.68 (m, 2H), 2.02–2.10 (m, 2H), 2.547 (d, 2H, J=7), 2.777 (t, 2H, T=6), 2.95–3.00 (m, 2H), 4.085 (t, 2H, J=6), 5.181 (s, 2H), 7.02–7.46 (m, 8H).

d) A mixture of 4-benzyl-1-(2-(4-benzyloxy-3-nitrophenoxy)ethyl)piperidine (1.40 g, 3.1 mmol) and 10% pd/C (about 500 mg) in MeOH (30 mL) was hydrogenated to give 1.0 g (98%) of 1-(2-(3-amino-4-hydroxyphenoxy)ethyl)-4-benzylpiperidine as a viscous oil. $^1$H NMR ($CDCl_3$): 1.40–1.68 (m, 5H), 2.06–2.13 (m, 2H), 2.530 (t, 2H, J=5.5), 6.000 (d, 2H, J=8), 6.242 (bs, 1H), 6.534 (d, 1H, J=8), 7.12–7.19 (m, 5H).

e) A mixture of 1-(3-amino-4-hydroxyphenoxy)ethyl-4-benzylpiperidine (1.0 g, 3.06 mmol) and CDI (650 mg, 4.0 mmol) in toluene (25 mL) was refluxed for 20 h, then evaporated. The residue was purified by chromatography over silica gel ($CHCl_3$—MeOH, 85:15) to give 600 mg (56%) of the title compound as a slightly pink colored powder, mp. 176–7° C. $^1$H NMR (DMSO-$d_6$): 1.14–1.23 (m, 2H), 1.40–1.54 (m, 3H), 1.91–1.98 (m, 2H), 2.47–2.50 (m, 3H), 2.620 (t, 2H, J=6), 2.86–2.90 (m, 2H), 4.010 (t, 2H, J=6), 6.603 (dd, 1H, J=9; 2), 6.654 (d, 1H, J=2), 7.13–7.29 (m, 6H). The hydrochloride, mp. 256–8° C. Analysis, Calcd. for $C_{21}H_{25}ClNO_3$: C 64.86, H 6.48, N 7.20; Found: C 64.73, H 6.51, N 7.04.

EXAMPLE 182

4-Benzyl-1-(2-(2-oxobenzoxazol-6-oxy)ethyl)piperidine

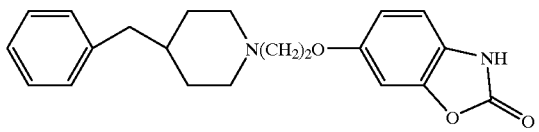

a) From a mixture of 4-nitroresorcinol (1.55 g, 10 mmol) and 85% KOH (720 mg, 12.8 mmol) in EtOH (25 mL) and 1,2-dibromoethane (3.8 g, 20.2 mmol) was obtained 570 mg (23%) of 2-(3-hydroxy-4-nitrophenoxy)ethyl bromide as a yellow powder, mp. 108–9° C. $^1$H NMR (CDCl$_3$): 3.669 (t, 2H, J=6), 4.363 (t, 2H, J=6), 6.54–6.57 (s, 2H), 8.069 (d, 1H, J=9), 10.010 (s, 1H).

b) From a mixture of 4-benzylpiperidine (820 mg, 4.68 mmol), 2-(3-hydroxy-4-nitrophenoxy)ethyl bromide (556 g, 2.26 mmol) and KI (180 mg) in toluene (25 mL) was obtained 750 g (97%) of 4-benzyl-1-(2-(3-hydroxy-4-nitrophenoxy)ethyl)piperidine as a yellow powder, mp. 136–7° C. $^1$H NMR (CDCl$_3$): 1.28–1.40 (m, 2H), 1.50–1.68 (m, 1H), 2.02–2.10 (m, 2H), 2.545 (d, 2H, J=7), 2.792 (t, 2H, J=6), 2.93–2.97 (m, 2H), 4.151 (t, 2H, J=6), 6.50–6.53 (m, 2H), 7.13–7.31 (m, 5H), 8.027 (d, 1H, J=10).

c) A mixture of 4-benzyl-1-(3-hydroxy-4-nitrophenoxy)ethylpiperidine (740 mg, 2.17 mmol) and 5% pd/C (100 mg) in MeOH (20 mL) was hydrogenated to give 621 mg (98%) of 1-(2-(4-amino-3-hydroxyphenoxy)ethyl)-4-benzylpiperidine as a viscous oil.

d) From a mixture of 1-(2-(4-amino-3-hydroxyphenoxy)ethyl)-4-benzylpiperidine (620 mg, 2.0 mmol) and CDI (440 mg, 2.7 mmol) in toluene (25 mL) was obtained 590 mg (65%) of the title compound as a grey colored powder. $^1$H NMR (DMSO-d$_6$): 1.20–1.42 (m, 2H), 1.50–1.58 (m, 1H), 1.64–1.68 (m, 2H), 2.02–2.10 (m, 2H), 2.543 (d, 2H, J=7), 2.784 (t, 2H, J=6), 2.98–3.02 (m, 2H), 4.072 (t, 2H, J=6), 6.669 (dd, 1H, J=9; 2), 6.809 (d, 1H, J=2), 6.888 (d, 1H, J=9), 7.13–7.30 (m, 5H). The hydrochloride, mp. 205–6° C. Analysis, Calcd. for C$_{21}$H$_{25}$ClNO$_3$: C 64.86, H 6.48, N 7.20; Found: C 65.14, H 6.40, N 6.96.

EXAMPLE 183

4-(-4-Methylbenzyl)-1-(2-(4-methylaminophenoxy)ethyl)piperidine

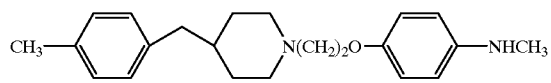

From a mixture of 4-(4-methylbenzyl)piperidine (1.42 mg, 7.5 mmol), 2-(4-methylphenoxy)ethyl bromide (860 mg, 3.74 mmol), K$_2$CO$_3$ (260 mg) and KI (180 mg) in toluene (25 mL) was obtained 720 g (57%) of the title compound as a yellow powder, mp. 136–7° C. $^1$H NMR (CDCl$_3$): 1.24–1.36 (m, 2H), 1.50–1.52 (m, 1H), 1.65–1.70 (m, 2H), 1.95–2.05 (m, 2H), 2.319 (s, 3H), 2.499 (d, 2H, J=7), 6.334 (bs, 1H), 6.59–6.62 (m, 2H), 6.70–6.74 (m, 2H), 7.054 (m, 4H, J=7).

EXAMPLE 184

4-(-4-Methylbenzyl)-1-(2-(4-nitrophenoxy)ethyl)piperidine

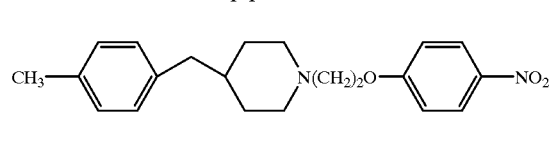

From a mixture of 4-(4-methylbenzyl)piperidine (2.27 g, 12.0 mmol), 2-(4-nitrophenoxy)ethyl bromide (1.42 g, 6.0 mmol), K$_2$CO$_3$ (130 mg) and KI (120 mg) in toluene (25 mL) was obtained 2.02 g (100%) of the title compound as a viscous oil. $^1$H NMR (CDCl$_3$): 1.25–1.38 (m, 2H), 1.46–1.56 (m, 1H), 1.63–1.67 (m, 2H), 2.01–2.09 (m, 2H), 2.314 (s, 3H), 2.498 (d, 2H, J=7), 2.797 (t, 2H, J=6), 2.94–2.98 (m, 2H), 4.171 (t, 21, J=6), 6.950 (d, 26, J=9), 7.059 (AB, 4H, J=8), 8.191 (d, 2H, J=9). The hydrochloride, mp. 180–1° C.

EXAMPLE 185

1-[2-(4-Aminophenoxy)ethyl]-4-(4-methylbenzyl)piperidine

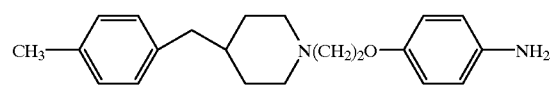

From a mixture of 4-(4-methylbenzyl)-1-[2-(4-nitrophenoxy)ethyl]piperidine (1.80 g, 5.2 mmol), stannous chloride dihydrate (7.40 g, 32.8 mmol) in EtOH (50 mL) was obtained 1.43 g (84%) of the title compound as a viscous oil. $^1$H NMR (CDCl$_3$): 1.25–1.38 (m, 2H), 1.36–1.56 (m, 1H), 1.61–1.65 (m, 2H), 1.98–2.05 (m, 2H), 2.315 (s, 3H), 2.490 (d, 2H, J=7), 2.726 (t, 2H, J=6), 2.94–2.98 (m, 2H), 3.316 (bs, 2H), 4.015 (t, 2H, J=6), 6.681 (AB, 2H, J=9), 7.056 (AB, 4H, J=9).

EXAMPLE 186

1-[2-(4-Acetamidophenoxy)ethyl]-4-(4-methylbenzyl)piperidine

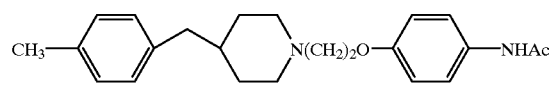

From a solution of 1-[2-(4-aminophenoxy)ethyl]-4-(4-methylbenzyl)piperidine (1.22 g, 3.72 mmol) in CH$_2$Cl$_2$ (20 mL) with acetic anhydride (2 mL) at r.t. was obtained 1.27 g (85%) of the title compound as a white powder. $^1$H NMR (CDCl$_3$): 1.25–1.38 (m, 2H), 1.42–1.55 (m, 1H), 1.62–1.66 (m, 2H), 2.00–2.07 (m, 2H), 2.152 (s, 3H), 2.315 (s, 3H), 2.493 (d, 2H, J=7), 2.754 (t, 2H, J=6), 2.94–2.98 (m, 2H), 4.065 (t, 2H, J=6), 6.847 (d, 2H, J=9), 7.055 (AB, 4H, J=9), 7.363 (d, 2H, J=9).

EXAMPLE 187

1-(2-(3-Amino-4-hydroxyphenoxy)ethyl)-4-(4-methylbenzyl)piperidine

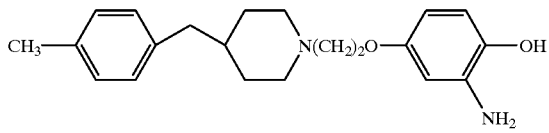

a) From a mixture of 4-(4-methylbenzyl)piperidine (1.96 g, 30.36 mmol), 2-(4-benzyloxy-3-nitrophenoxy)ethyl bromide (1.825 g, 5.18 mmol) and KI (100 mg) in toluene (50 mL) was obtained 1.965 g (80%) of 4-(4-methylbenzyl)-1-(2-(4-benzyloxy-3-nitrophenoxy)ethyl)piperidine as yellow solid, mp. 176–7° C. $^1$H NMR (CDCl$_3$) 1.25–1.39 (m, 2H), 1.46–1.54 (m, 1H), 1.60–1.66 (m, 2H), 2.00–2.07 (m, 2H), 2.320 (s, 3H), 2.500 (d, 2H, J=9), 2.754 (t, 2H, J=6), 2.93–2.97 (m, 2H), 4.068 (t, 2H, J=6), 5.179 (s, 2H), 7.02–7.10 (m, 4H), 7.33–7.46 (m, 3H).

b) A mixture of 4-benzyl-1-(4-benzyloxy-3-nitrophenoxy)ethylpiperidine (1.46 g, 3.17 mmol) and 10% pd/C (200 mg) in MeOH (25 mL) was hydrogenated to give 1.0 g (92%) of 1-(2-(3-amino-4-hydroxyphenoxy)ethyl)-4-(4-methylbenzyl)piperidine as a viscous oil. $^1$H NMR (CDCl$_3$): 1.32–1.45(m, 2H), 1.49–1.55 (m, 1H), 1.63–1.67 (m, 2H), 2.03–2.11 (m, 2H), 2.319 (s, 3H), 2.491 (t, 2H, J=7), 2.724 (t, 2H, J=6), 3.02–3.06 (m, 2H), 3.942 (t, 2H, J=6), 5.997 (dd, 1H, J=8.5; 2), 6.245 (d, 1H, J=2), 6.536 (d, 1H, J=8.5), 7.056 (AB, 4H, J=8).

EXAMPLE 188

1-(3-Acetamido-4-hydroxyphenoxy)ethyl-4-(4-methylbenzyl)piperidine

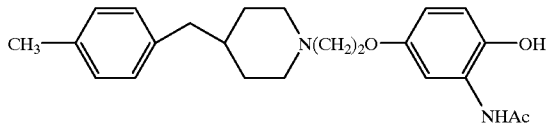

From a solution of 1-(2-(3-amino-4-hydroxyphenoxy) ethyl)-4-(4-methylbenzyl)piperidine (950 mg, 2.8 mmol) in CH$_2$Cl$_2$ (20 mL) with acetic anhydride (2 mL) was obtained 930 mg (87%) of 1-(2-(3-acetarmido-4-hydroxy-phenoxy) ethyl)-4-(4-methylbenzyl)piperidine as a viscous oil. $^1$H NMR (CDCl$_3$): 1.30–1.42 (m, 2H), 1.48–1.56 (m, 1H), 1.64–1.68 (m, 2H), 2.02–2.09 (m, 2H), 2.246 (s, 3H), 2.320 (s, 3H), 2.500 (d, 2H, J=7), 2.731 (t, 2H, J=6), 2.99–3.03 (m, 2H), 3.956 (t, 2H, J=6), 6.530 (dd, 1H, J=9; 3), 6.76–6.79 (m, 2H), 7.027 (d, 2H, J=8), 7.090 (d, 2H, J=8), 7.830 (bs, 1H).

EXAMPLE 189

4-Benzyl-1-(2-(2-hydroxynaphth-6-oxy)ethyl) piperidine

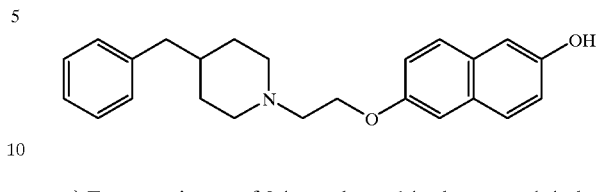

a) From a mixture of 2-benzyloxy-6-hydroxy-naphthalene (0.50 g, 2.00 mmol), 1-(4-benzyl-piperidin-1-yl)-2-bromo-ethanone (0.60 g, 2.02 mmol) and potassium carbonate (0.55 g, 3.98 mmol) in tetrahydofuran (40 ml) were obtained 0.76 g (75%) of 2-(6-benzyloxy-naphthalen-2-yloxy)-1-(4-benzyl-piperidin-1-yl)-ethanone. $^1$H NMR (CDCl$_3$) 7.64 (2H, dd, J=8.6, 6.5), 7.48 (2H, d, J=7.23), 7.42–7.38 (2H, m), 7.35–7.11 (10H, m), 5.16 (2H, s), 4.75 (2H, s), 4.56 (1H, d, J=13), 4.02 (1H, d, J=13.7), 3.08 (1H, td, J=13.7, 2.4), 2.56 (1H, td, J=12.8, 2.9), 2.53 (2H, d, J=7.2)1.8–1.68 (3H, m), 1.26–1.12 (2H, m).

b) To 2-(6-benzyloxy-naphthalen-2-yloxy)-1-(4-benzyl-piperidin-1-yl)-ethanone (0.71 g, 1.53 mmol) in anhydrous tetrahydofuran (25 ml) was added BH$_3$•SMe$_2$ (0.62 ml, 6.20 mmol) and diisopropyl amine (0.214 ml, 1.53 mmol), and the solution was refluxed for 18 h under N$_2$. The reaction was cooled in an ice bath and quenched with dropwise addition of methanol (15 ml). The solvent was evaporated, the solid washed with hexanes and evaporated. The solid was washed with hexanes, filtered, and air dried to give 0.69 g (100%) of 4-benzyl-1-[2-(6-benzyloxy-naphthalen-2-yloxy)-ethyl]-piperidine. $^1$H NMR (CDCl$_3$) 7.64–7.56 (2H, m), 7.45 (2H, d, J=7.3), 7.39–7.003 (12H, m), 5.12 (2H, d, J=3.6), 4.55 (1H, t, J=5.4), 4.51 (1H, t, J=5.4), 3.62 (1H, t, J=5.4), 3.18–3.14 (3H, m), 2.92 (1H, m), 2.60–2.54 (3H, m), 2.15–2.0 (1H, m), 1.66–1.51 (4H, m).

c) A mixture of of 4-benzyl-1-[2-(6-benzyloxy-naphthalen-2-yloxy)-ethyl]-piperidine (0.67 g, 1.48 mmol) and 20% palladium on carbon (0.06 g) in methanol (8 ml) and tetrahydrofuran (8 ml) was shaken on a Parr hydrogenation apparatus under a hydrogen atmosphere (50 psi) for 20 h. After removal of the catalyst, the filtrate was evaporated and the white solid (0.51 g, 95%) was dissolved in tetrahydofuran (5 ml). A solution of isethionic acid in methanol (4.6 ml, 1.28 mmol) was added, and the solid precipitate was filtered off. The solid was washed with tetrahydofuran, and dried in vacuo overnight to give the title compound (0.51 g, 82%), mp139–141° C. Analysis calculated for C$_{24}$H$_{27}$NO$_2$•C$_2$H$_6$O$_4$S: C, 64.04; H, 6.82; N, 2.87; S, 6.58. Found: C, 63.88; H, 6.77; N, 2.70; S, 6.60.

EXAMPLE 190

4-Benzyl-1-(2-(3-hydroxynaphth-6-oxy)ethyl) piperidine

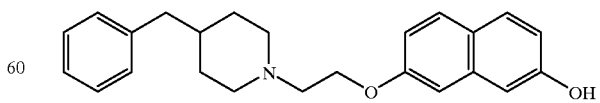

The title compound was prepared from 7-benzyloxy-naphthalen-2-ol (1.00 g, 4.00 mmol), 1-(4-benzyl-piperidin-1-yl)-2-bromo-ethanone (1.20 g, 4.05 mmol) and potassium carbonate (1.10 g, 7.96 mmol) in tetrahydofuran (40 ml) in three steps as a solid, mp 159–160° C. Analysis calculated for C₂₄H₂₇NO₂•0.16H₂O: C, 79.11; H, 7.56; N, 3.85. Found: C, 79.11; H. 7.63; N, 3.83.

EXAMPLE 191

4-(4-Fluorobenzyl)-1-(2-(2-hydroxynaphth-6-oxy)ethyl)piperidine

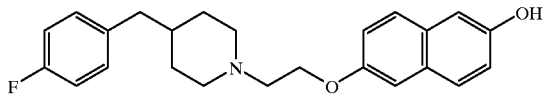

a) From a suspension of 6-benzyloxy-naphthalen-2-ol (1.00 g, 4.00 mmol), 1,2-dibromoethane (1.72 ml, 20.00 mmol), and potassium carbonate (1.10 g, 7.96 mmol) in acetonitrile (25 ml) was obtained 2-benzyloxy-6-(2-bromo-ethoxy)-naphthalene (0.64 g, 45%) as a white solid. ¹H NMR (CDCl₃) 7.61 (2H, d, J=8.79), 7.45 (d, 2H, J=7.32), 7.37 (2H, t, J=7.25), 7.32–7.29 (1H, m), 7.20–7.15 (2H, m), 7.11 (1H, dd, J=8.79, 2.44), 7.06 (1H, d, J=2.44), 5.12 (2H, s), 4.35 (2H, t, J=6.22), 3.66 (2H, t, J=6.35)

b) The title compound was prepared from 4-(4-Fluoro-benzyl)-piperidine and 2-benzyloxy-6-(2-bromo-ethoxy)-naphthalene and potassium carbonate in two steps as a solid, mp184–185° C. Analysis calculated for C₂₄H₂₆FNO₂: C, 75.96; H, 6.91; N, 3.69; F, 5.01. Found: C, 75.52; H, 6.86; N, 3.50; F, 5.15.

EXAMPLE 192

4-(4-Methylbenzyl)-1-(2-(2-hydroxynaphth-6-oxy)ethyl)piperidine

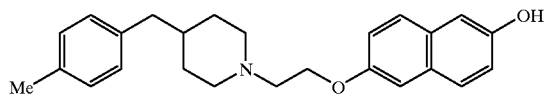

The title compound was prepared from 4-(4-Methylbenzyl)-piperidine and and 2-benzyloxy-6-(2-bromo-ethoxy)-naphthalene and potassium carbonate in two steps as a solid, mp 164–166° C. Analysis calculated for CH₂₅H₂₉O₂: C, 79.96; H, 7.78; N, 3.73. Found: C, 79.63; H, 7.84; N, 3.67.

EXAMPLE 193

4-Benzyl-1-(2-(3-methyl-2-oxobenzamidazol-5-oxy)ethyl)piperidine

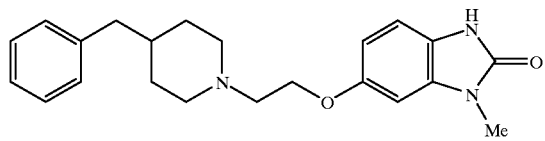

a) To a solution of methyl 5-hydroxy-2-nitro-benzoate (7.97 g, 40.43 mmol), triphenylphosphine (12.73 g, 48.53 mmol), and 2-benzyloxyethanol (5.86 ml, 41.24 mmol) in tetrahydofuran (100 ml) was added DEAD (8.04 ml, 95%, 48.51 mmol) dropwise. After addition of the DEAD, the reaction was stirred under nitrogen for 18 h. The solvent was evaporated, benzene was added, and the triphenylphosphine oxide was filtered off. The solid was washed with some benzene, and the filtrate evaporated. The yellow oil was dissolved in minimal benzene, and chromatographed on silica gel eluting with 25% ethyl acetate/hexanes to give methyl 5-(2-benzyloxy-ethoxy)-2-nitro-benzoate (12.47 g, 93%) as a light yellow oil. Analysis calculated for C₁₇H₁₇NO₆: C, 61.63; H, 5.17; N, 4.23. Found: C, 61.46; H, 5.02; N, 4.28.

b) To a solution of methyl 5-(2-benzyloxy-ethoxy)-2-nitro-benzoate (8.26 g, 24.93 mmol) in methanol (200 ml) was added LiOH (1N, 80 ml), and the reaction mixture was heated to 50° C. for 2 h. The solvent was evaporated, water was added (100 ml), and the solution was cooled in an ice bath. 3N HCl was added slowly to pH=2.5. The aqueous layer was salted with NaCl and extracted with ethyl acetate (4×75 ml). The aqueous layer was reacidified and extracted with ethyl acetate (100 ml). The combined organic extracts were washed with brine (100 ml), dried over MgSO₄, filtered and evaporated to give an oil that solidified upon standing. The solid was washed with ether (30 ml), filtered and air dried to give 5-(2-benzyloxy-ethoxy)-2-nitro-benzoic acid (5.99 g, 75%). ¹H NMR (CDCl₃) 7.96 (1H, d, J=9.0), 7.36–7.25 (5H, m), 7.17 (1H, d, J=2.7), 7.05 (1H, dd, J=9.0, 2.7), 4.62 (2H, s), 4.22 (2H, m), 3.84 (2H, m).

c) To a solution of 5-(2-benzyloxy-ethoxy)-2-nitro-benzoic acid (5.98 g, 18.85 mmol) in benzene (100 ml) and anhydrous tetrahydofuran (25 ml) was added triethyl amine (3.07 ml, 22 mmol) followed by diphenylphosphoryl azide (4.74 ml, 22 mmol). The reaction was stirred at room temp for 15 min, and then refluxed under nitrogen for 4 h. methanol (3 ml, 74.06 mmol) was added, and the reaction was refluxed for 18 h. The solvent was evaporated, and the oil chromatographed on silica gel eluting with 25% ethyl acetate/hexanes to give [5-(2-benzyloxy-ethoxy)-2-nitro-phenyl]-carbamic acid methyl ester (6.12 g, 94%) as an oil. Analysis calculated for C₁₇H₁₈N₂O₆: C, 58.96; H, 5.24; N, 8.09. Found: C, 58.94; H, 5.11; N, 7.87 d) To a solution of [5-(2-benzyloxy-ethoxy)-2-nitro-phenyl]-carbamic acid methyl ester (2.03 g, 5.86 mmol) in anhydrous dimethylformamide (20 ml) was added iodomethane (1.82 ml, 29.3 mmol), followed by portion wise addition of NaH (0.35 g, 60%, 8.79 mmol). The reaction was stirred under nitrogen for 2 h. The reaction was quenched with NH₄Cl (sat) (10 ml) and brine (10 ml), and the aqueous layer was extracted with ether (3×30 ml). The combined organics were dried over MgSO₄, filtered and evaporated. The residue was chromatographed on silica gel eluting with hexanes, then 30% ethyl acetate/hexanes to give [5-(2-benzyloxy-ethoxy)-2-nitro-phenyl]-methyl-carbamic acid methyl ester (0.93 g, 89%) as an oil. Analysis calculated for C₁₈H₂₀N₂O₆: C, 59.99; H, 5.59; N, 7.77. Found: C, 59.30; H, 5.34; N, 7.62.

e) To a solution of [5-(2-benzyloxy-ethoxy)-2-nitro-phenyl]-methyl-carbamic acid methyl ester (0.93 g, 2.58 mmol) in methanol (50 ml) and tetrahydofuran (50 ml) was added Raney Ni and the mixture was stirred under a hydrogen atmosphere (1 atm) until all starting material was consumed as indicated by TLC. The catalyst was filtered, washed generously with tetrahydofuran, and the filtrate evaporated. The residue was washed with anhydrous tetrahydofuran and evaporated (2×15 ml). The oil was dissolved in anhydrous tetrahydofuran (30 ml) and NaH was added (0.31 g, 60%, 7.75 mmol), and the reaction mixture was heated to reflux under nitrogen for 3.5 h. The reaction was quenched with NH₄Cl (sat) (20 ml), water (20 ml) and ethyl acetate (20 ml). The layers were separated, and the aqueous layer was extracted with ethyl acetate (2×25 ml).

The combined organics were washed with brine (25 ml), dried over MgSO$_4$, filtered, and evaporated to give 6-(2-benzyloxy-ethoxy)-1-methyl-1,3-dihydro-benzoimidazol-2-one (0.75 g, 97%) as a solid. Analysis calculated for C$_{17}$H$_{18}$N$_2$O$_3$: C, 68.44; H, 6.08; N, 9.39. Found: C, 68.64; H, 6.13; N, 8.96.

f) A mixture of 6-(2-benzyloxy-ethoxy)-1-methyl-1,3-dihydro-benzoimidazol-2-one (0.69 g, 2.31 mmol) and 20% palladium on carbon (0.10 g) in methanol (10 ml) and tetrahydrofuran (10 ml) was stirred under a hydrogen atmosphere (1 atm) for 2 h. After removal of the catalyst, the catalyst was washed with boiling methanol (50 ml). The filtrate was evaporated to give 6-(2-hydroxy-ethoxy)-1-methyl-1,3-dihydro-benzoimidazol-2-one (0.46 g, 96%) as a solid. $^1$H NMR (DMSO) 10.54 (1H, s), 6.78 (1H, d, J=8.3), 6.70 (H, d, J=632.2), 6.50 (1H, dd, J=8.3, 2.4), 4.79 (1H, t, J=5.6), 3.90 (2H, t, J=5.0), 3.64 (2H, q, J=5.2), 3.18 (3H, s).

g) To a solution of 6-(2-hydroxy-ethoxy)-1-methyl-1,3-dihydro-benzoimidazol-2-one (0.41 g, 1.97 mmol) in anhydrous pyridine (30 ml) and cooled in 0° C. in an ice bath was added p-toluenesulfonic anhydride (0.86 g, 97%, 2.56 mmol), and the reaction was allowed to warm to rt while stirring under nitrogen overnight. The solvent was evaporated, and ethyl acetate (100 ml) and 1N HCl (100 ml) was added. The resulting emulsion was filtered, and the solid was washed with tetrahydofuran. The filtrate layers were seoarated. The organic layer was washed with brine (75 ml), dried over MgSO$_4$, filtered and evaporated to give toluene-4-sulfonic acid 2-(3-methyl-2-oxo-2,3-dihydro-1H-benzoimidazol-5-yloxy)-ethyl ester (0.52 g, 73%), which was used without further purification.

h) A suspension of toluene-4-sulfonic acid 2-(3-ethyl-2-oxo-2,3-dihydro-1H-benzoimidazol-5-yloxy)-ethyl ester (0.52 g, 1.43 mmol), 4-benzylpiperidine (0.31 ml, 1.76 ml), and potassium carbonate (0.39 g, 2.99 mmol) in acetonitrile (100 ml) was refluxed under nitrogen for 8 h. Dimethylformamide (10 ml) was added, and refluxing was continued for 36 h. The solid was filtered off and washed with methanol. The filtrate was evaporated, and the solid was chromatographed on silica gel eluting with 10% methanol/ethyl acetate to give the title compound (0.21 g, 40%) as a solid. $^1$H NMR (CDCL$_3$) 9.63 (1H, s), 7.30–7.25 (2H, m), 7.19 (1H, d, J=6.7), 7.13 (2H, d, J=7.3), 6.94 (1H, d, J=8.5), 6.59 (1H, d, J=8.6), 6.56 (1H, s), 4.15–4.03 (3H, m), 3.37 (3H, s), 3.08 (2H, d, J=11.3), 2.86 (2H, t, J=5.8), 2.54 (2H, d, J=6.8), 2.13 (2H, t, J=11.2), 1.67 (2H, d, J=13.3), 1.60–1.53 (1H, m), 1.40 (2H, m). The free base (0.21 g, 0.57 mmol) was dissolved in ethyl acetate (3 ml). Oxalylic acid was dissolved in ethanol (1 ml) and added to the ethyl acetate solution. The solid was filtered, washed with ethyl acetate, and dried in vacuo at 70° C. overnight to give the salt (0.21 g, 81%), mp 193–197° C. Analysis calculated for C$_{22}$H$_{27}$N$_3$O$_2$·1.3 C$_2$H$_2$O$_4$·0.07 H$_2$O: C, 61.07; H, 6.20; N, 8.69. Found: C, 61.12; H, 6.20; N, 8.69.

EXAMPLE 194

4-Benzyl-1-(2-(2-oxo-1,3-dihydroindol-5-oxy)ethyl)piperidine

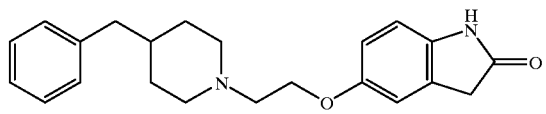

a) From 4-methyl-3-nitrophenol (9.48 g, 61.90 mmol), triphenylphosphine (19.60 g, 74.73 mmol), and 2-benzyloxyethanol (9.83 g, 64.59 mmol) in tetrahydofuran (130 ml) with DEAD (12.4 ml, 95%, 74.81 mmol) was obtained 2-methyl-1-nitro-4-[2-(phenylmethoxy)ethoxy]benzene (14.06 g, 79%) as a yellow oil. $^1$H NMR (CDCl$_3$) 8.04 (1H, d, J=9.77), 7.35–7.25 (5H, m), 6.80–6.77 (2H, m), 4.59 (2H, s), 4.17 (2H, m), 3.82 (2H, m), 2.58 (3H, s).

b) To a suspension of sodium hydride (1.62 g, 60%, 40.5 mmol) in 20 ml of anhydrous THF at room temperature was added ethanol (2.5 ml) slowly. Diethyl oxalate (5.5 ml, 40.50 mmol) and 2-methyl-1-nitro-4-[2-(phenylmethoxy)ethoxy]benzene (10.19 g, 35.49 mmol) was added to the solution slowly after hydrogen evolution subsided. The reaction was heated at 60° C. for 2 h. The deep red solution was cooled to 0° C. and quenched with 50 ml of 3N HCl solution. Brine (50 ml) was added and the mixture was extracted with EtOAc (2×100 ml). The combined organic layers was dried with MgSO$_4$, filtered and concentrated. The brown oil was chromatographed on silica gel with 20% ethyl acetate in hexanes to elute out starting material and then with 35% ethyl acetate in hexanes to give 9.93 g (72%) of 3-[5-(2-benzyloxy-ethoxy)-2-nitro-phenyl]-2-oxo-propionic acid ethyl ester as a yellow oil. $^1$H NMR (CDCl$_3$) 8.18 (1H, d, J=9.29), 7.35–7.25 (5H, m), 6.91 (1H, dd, J=9.29, 2.69), 6.77 (1H, d, J=2.69), 4.59 (2H, s), 4.44 (2H, s), 4.35 (2H, q, J=7.32), 4.19 (2H, m), 3.81 (2H, m), 1.37 (3H, t, J=7.32).

c) To a solution of 3-[5-(2-benzyloxy-ethoxy)-2-nitro-phenyl]-2-oxo-propionic acid ethyl ester(37.77 g, 97.50 mmol) in methanol (370 ml) was added 1 N lithium hydroxide solution (230 ml, 0.23 mol). The deep red reaction mixture was stirred at 55° C. for 30 min and worked up to give [5-(2-benzyloxy-ethoxy)-2-nitro-phenyl]-acetic acid (22.42 g, 69%) as an off-white solid. Analysis calculated for C$_{17}$H$_{17}$NO$_6$: C, 61.63; H, 5.17; N, 4.23. Found: C, 61.66; H, 5.08; N, 4.18.

d) A mixture of [5-(2-benzyloxy-ethoxy)-2-nitro-phenyl]-acetic acid (0.58 g, 1751 mmol), 5% palladium on carbon (0.05 g) and triethylamine (0.37 ml, 2.66 mmol) in methanol (35 ml) was stirred under a hydrogen atmosphere (1 atm) for 3 h. After removal of the catalyst by filtration, the filtrate was evaporated to give a yellow oil. The oil was dissolved in 10 ml of acetic acid and the solution was stirred at 80° C. under argon for 3 h. The acetic acid was removed on a rotavap. The residue was dissolved in a small amount of methylene chloride and chromatographed on silica gel eluted with 30% ethyl acetate in methylene chloride to give 5-(2-benzyloxy-ethoxy)-1,3-dihydro-indol-2-one (0.39 g, 79%) as a white solid. Analysis calculated for C$_{17}$H$_{17}$NO$_3$: C, 72.07; H, 6.05; N, 4.85. Found: C, 72.09; H, 6.01; N, 4.85.

e) A mixture of 5-(2-benzyloxy-ethoxy)-1,3-dihydro-indol-2-one (3.20 g, 11.29 mmol), 20% palladium on carbon (0.38 g) and 8 drops of 1 N HCl solution in methanol (360 ml) was stirred under a hydrogen atmosphere (1 atm) overnight. After removal of the catalyst by filtration, the filtrate was evaporated to give a pale yellow solid. The solid was triturated with ethyl acetate and collected by filtration. 5-(2-Hydroxy-ethoxy)-1,3-dihydro-indol-2-one (1.52 g, 70%) was collected after air dried as an off-white solid. Analysis calculated for C$_{10}$H$_{11}$NO$_3$: C, 62.17; H, 5.74; N, 7.25. Found: C, 61.90; H, 5.82; N, 7.15.

f) 5-(2-Hydroxy-ethoxy)-1,3-dihydro-indol-2-one (0.70 g, 3.62 mmol) was dissolved in anhydrous pyridine (15 ml) and cooled to 0°C. in an ice bath. p-Toluenesulfonic anhydride (1.42 g, 97%, 4.22 mmol) was added, and the reaction was allowed to stir at 0°C. for 40 min. Ethyl acetate (100 ml) was added to precipitate pyridinium tosylate. The solid material was removed by filtration. The filtrate was washed with ice cold 3N HCl (2×30 ml) and then with brine. The organic layer was dried over MgSO$_4$, filtered and evaporated to give a pale brown solid. The solid was triturated with a mixture of EtOAc (6 ml) and Et$_2$O (40 ml) to give toluene-4-sulfonic acid 2-(2-oxo-2,3-dihydro-1H-indol-5-yloxy)-ethyl ester (0.77 g, 61%) after air-dried, which was used without further purification.

g) A suspension of toluene-4-sulfonic acid 2-(2-oxo-2,3-dihydro-1H-indol-5-yloxy)-ethyl ester (0.84 g, 2.42 mmol), 4-benzylpiperidine (1.32 ml, 7.53 ml), and potassium carbonate (2.70 g, 19.54 mmol) in acetonitrile (84 ml) was refluxed overnight under argon. The reaction mixture was cooled to room temperature and the solid was filtered off and washed with THF (3×60 ml). The filtrate was evaporated, and the red colored oil was chromatographed on silica gel eluting with 35% methanol/ethyl acetate to give a tan solid (0.51 g, 60%). This material was dissolved in a mixture of methanol (3 ml) and ethyl acetate (6 ml). A solution of oxalic acid (0.19 g) in methanol (1 ml) was added slowly. The mixture was stirred at room temperature for 5 min then at 0° C. for 5 min. The precipitates was collected and washed with ethyl acetate (3×5 ml). The solid was dried overnight in a vacuum oven at 70° C. to give the oxalate salt of the title compound (0.55 g, 55%) as a tan solid, mp 210–211° C. Analysis calculated for $C_{22}H_{26}N_2O_2 \cdot 1.1\ C_2H_2O_4$: C, 64.66; H, 6.32; N, 6.23. Found: C, 64.66; H, 6.40; N, 6.19.

EXAMPLE 195

4-(4-Fluorobenzyl)-1-(2-(2-oxo-1,3-dihydroindol-5-oxy)ethyl)piperidine

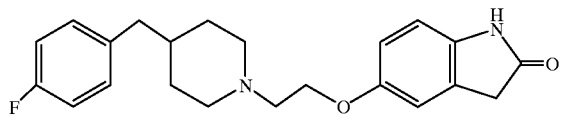

A suspension of toluene-4-sulfonic acid 2-(2-oxo-2,3-dihydro-1H-indol-5-yloxy)-ethyl ester (0.77 g, 2.22 mmol), 4-(4-fluorobenzyl)piperidine (1.1 g, 5.63 mmol), and potassium carbonate (2.2 g, 15.92 mmol) in acetonitrile (75 ml) was refluxed overnight under argon. The reaction mixture was cooled to room temperature and the solid was filtered off and washed with THF (3×20 ml). The filtrate was evaporated, and the solid chromatographed on silica gel eluting with 35% methanol/ethyl acetate to give the title compound (0.62 g, 76%) as a solid, mp 149–150° C. Analysis calculated for $C_{22}H_{25}FN_2O_2 \cdot 0.14H_2O$: C, 71.21; H, 6.87; N, 7.55; F, 5.12. Found: C, 71.21; H, 6.68; N, 7.49; F, 5.26.

EXAMPLE 196

4-Benzyl-1-(2-(1H-benzotriazol-5-oxy)ethyl)piperidine

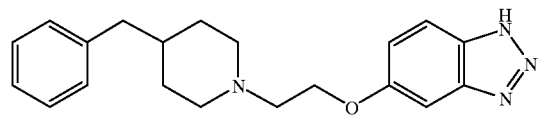

a) Raney nickel (10.95 g) was washed with water (4×300 ml) then with methanol (4×300 ml). The catalyst was suspended in 450 ml of methanol and 4-(2-bromoethoxy)-6-nitroaniline (5.08 g, 19.46 mmol) was added. The reaction mixture was stirred under a hydrogen atmosphere (1 atm) at room temperature for 1.5 h. After removal of the catalyst by filtration, the filtrate was evaporated to give a black residue. The black residue was redissolved in a mixture of ethyl acetate (200 ml) and methanol (50 ml). Etheral HCl solution (1N, 40 ml) was added slowly to precipitate the diamine as the hydrochloride salt. The purple solid was collected and dissolved in a mixture of acetic acid (25 ml) and water (50 ml). The reaction mixture was cooled to 5° C. in an ice-bath. A solution of sodium nitrite (1.75 g, 25.36 mmol) in 10 ml water was added slowly into the reaction mixture. The mixture was heated at 80° C. for 3 h. The solid was collected by filtration and washed with water (3×30 ml). The solid was dissolved in THF and dried over magnesium sulphate, filtered and concentrated. The residue was chromatographed on silica gel eluted with 50% ethyl acetate in hexanes to give 2.15 g of 6-(2-bromoethoxy)-1H-benzotriazole as a white solid. $^1$H NMR (CDCl$_3$) 7.86 (1h, d, J=9.03), 7.11–7.05 (2H, m), 4.34 (2H, t, J=6.10), 3.67 (2H, t, J=6.10).

b) A suspension of 6-(2-bromoethoxy)-1H-benzotriazole (0.31 g, 1.28 mmol), 4-benzylpiperidine (0.45 g, 2.57 mmol), triethyl amine (0.75 ml, 5.38 mmol), 18-C-6 (cat. amount) and potassium iodide (cat. amount) in THF (50 ml) was refluxed overnight under argon. The reaction mixture was cooled to room temperature and concentrated on a rotavap. The residue was chromatographed on silica gel eluting with 35% methanol/ethyl acetate to give a tan solid (0.47 g). This material was dissolved in ethyl acetate (15 ml). A solution of oxalic acid (0.18 g) in methanol (2 ml) was added slowly. The mixture was stirred at room temperature for 5 min. then at 0° C. for 5 min. The precipitate was collected and washed with ethyl acetate (3×5 ml). The solid was dried overnight in a vacuum oven at 70° C. to give the oxalate salt of the title compound (0.37 g) as a tan solid: mp 164–166° C. Analysis calculated for $C_{20}H_{24}N_4O \cdot 1.28\ C_2H_2O_4$: C, 60.00; H, 5.93; N, 12.41 Found: C, 60.00; H, 5.88; N, 12.68.

Other exemplary compounds of this invention are set forth below in Tables 1 and 2.

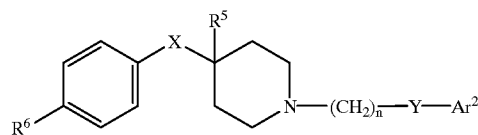

TABLE 1
| Example | R⁶ | X | R5 | n | Y | Ar² |
|---|---|---|---|---|---|---|
| 197 | H | CH₂ | H | 2 | O | 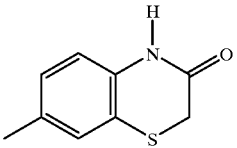 |
| 198 | F | S | H | 2 | O | 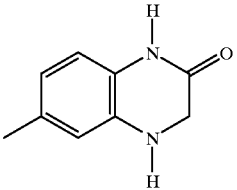 |
| 199 | Me | O | H | 3 | S | 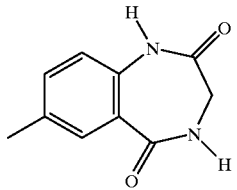 |
| 200 | Cl | NH | H | 3 | NH | 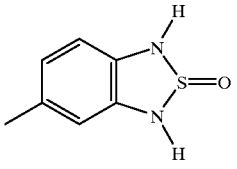 |
| 201 | MeO | CH₂ | OH | 2 | O | 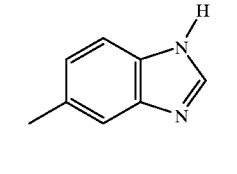 |
| 202 | F | CH₂ | H | 4 | NMe | 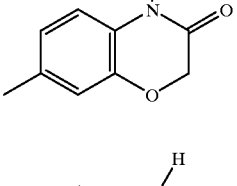 |
| 203 | Et | O | H | 2 | S | 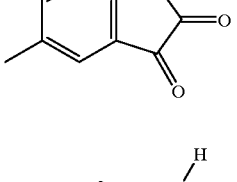 |
| 204 | Cl | NMe | H | 3 | O | 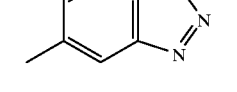 |

TABLE 1-continued

| Example | R⁶ | X | R5 | n | Y | Ar² |
|---|---|---|---|---|---|---|
| 205 | Me | CH₂ | H | 2 | NAc | 5-methyl-1H-indazole |
| 206 | H | S | H | 4 | O | 7-methyl-1,2,3,4-tetrahydroquinoxaline |
| 207 | MeO | CH₂ | OH | 3 | NH | 6-methyl-1,4-dihydro-2H-benzo[d][1,3]oxazin-2-one |
| 208 | F | O | H | 2 | O | 6-methylquinolin-4(1H)-one |
| 209 | F | CH₂ | H | 3 | S | 7-methyl-3,4-dihydroquinazolin-2(1H)-one |
| 210 | Cl | CH₂ | H | 2 | O | 5-methyl-7-methyl-1H-benzo[e][1,4]diazepin-2(3H)-one |
| 211 | i-Pr | CH₂ | OH | 3 | S | 8-methyl-1H-benzo[b][1,4]diazepine-2,4(3H,5H)-dione |
| 212 | Me | S | H | 4 | O | 7-methyl-1,3,4,5-tetrahydro-2H-benzo[d][1,3]diazepin-2-one |

TABLE 1-continued

| Example | R⁶ | X | R5 | n | Y | Ar² |
|---|---|---|---|---|---|---|
| 213 | OH | CH₂ | H | 3 | NMe | |
| 214 | H | CH₂ | OH | 2 | O | |
| 215 | Cl | O | H | 2 | NAc | |
| 216 | F | CH₂ | H | 3 | O | |
| 217 | H | CH₂ | H | 2 | O | |
| 218 | F | S | H | 3 | HN | |
| 219 | MeO | NH | H | 2 | NBz | |
| 220 | Cl | O | H | 4 | NAc | |
| 221 | H | CH₂ | OH | 3 | NMe | |

TABLE 1-continued

| Example | R⁶ | X | R5 | n | Y | Ar² |
|---|---|---|---|---|---|---|
| 222 | Cl | S | H | 2 | O | 3-methyl-1H-pyrazole |
| 223 | MeO | O | H | 3 | NH | 4-methyl-1H-pyrazolo[3,4-d]pyrimidine |
| 224 | F | CH₂ | H | 4 | S | 1,6-dimethylpyrimidine-2,4(1H,3H)-dione |
| 225 | H | CH₂ | OH | 4 | NAc | 7-methyl-4,5-dihydro-1H-benzo[b]azepin-2(3H)-one |
| 226 | F | CH₂ | OH | 2 | O | 5-(3-methylphenyl)-1H-tetrazole |
| 227 | HO | CH₂ | H | 3 | O | 4-hydroxy-6-methylquinolin-2(1H)-one |
| 228 | Cl | O | H | 2 | O | 1-hydroxy-5-methylindolin-2-one |
| 229 | H | CH₂ | OH | 4 | NH | 6-methylphthalazine-1,4(2H,3H)-dione |

TABLE 1-continued
| Example | R⁶ | X | R5 | n | Y | Ar² |
|---|---|---|---|---|---|---|
| 230 | MeO | CH₂ | H | 3 | O | 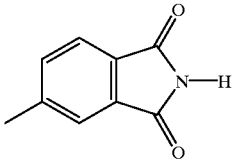 |
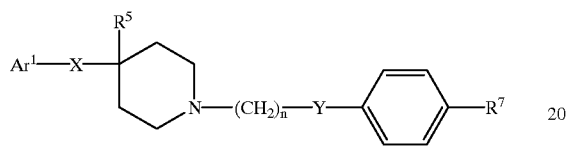
TABLE 2
| Example | Ar¹ | X | R⁵ | n | Y | R⁷ |
|---|---|---|---|---|---|---|
| 231 | 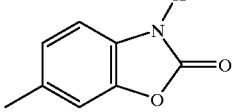 | CH₂ | H | 2 | O | H |
| 232 | 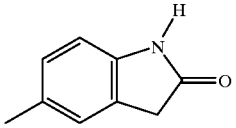 | S | H | 2 | O | F |
| 233 | 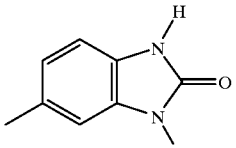 | O | H | 3 | S | Me |
| 234 | 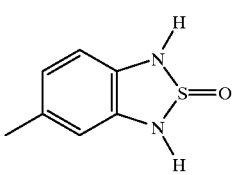 | NH | H | 3 | NH | Cl |
| 235 | 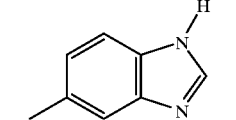 | CH₂ | OH | 2 | O | MeO |
| 236 | 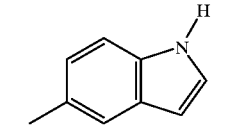 | CH₂ | H | 4 | NMe | F |

TABLE 2-continued

| Example | Ar¹ | X | R⁵ | n | Y | R⁷ |
|---|---|---|---|---|---|---|
| 237 | 7-methyl-benzoxazol-2(3H)-one | O | H | 2 | S | Et |
| 238 | 5-methyl-1H-benzotriazole | NMe | H | 3 | O | Cl |
| 239 | 5-methyl-1H-indazole | CH₂ | H | 2 | NAc | Me |
| 240 | 6-methyl-1,2,3,4-tetrahydroquinoxaline | S | H | 4 | O | H |
| 241 | 6-methyl-quinoxaline-2,3(1H,4H)-dione | CH₂ | OH | 3 | NH | MeO |
| 242 | 6-methyl-quinolin-4(1H)-one | — | H | 2 | O | F |
| 243 | 6-methyl-3,4-dihydroquinazolin-2(1H)-one | CH₂ | H | 3 | S | F |
| 244 | 7-methyl-5-methyl-1,3-dihydro-2H-1,4-benzodiazepin-2-one | CH₂ | H | 2 | O | Cl |

TABLE 2-continued

| Example | Ar¹ | X | R⁵ | n | Y | R⁷ |
|---|---|---|---|---|---|---|
| 245 | (7-methyl-1H-1,5-benzodiazepine-2,4(3H,5H)-dione) | — | OH | 3 | S | i-Pr |
| 246 | (7-methyl-1,3,4,5-tetrahydro-2H-1,3-benzodiazepin-2-one) | S | H | 4 | O | Me |
| 247 | (5-methyl-1,3-dihydro-2,1,3-benzothiadiazole 2,2-dioxide) | — | H | 3 | NMe | OH |
| 248 | (1-methyl-3-amino-1H-benzimidazol-2(3H)-one) | CH₂ | OH | 2 | O | H |
| 249 | (2-amino-5-methylpyridine) | O | H | 2 | NAc | Cl |
| 250 | (2-amino-5-methylthiazole) | CH₂ | H | 3 | O | F |
| 251 | (2-amino-5-methylthiazole) | — | OH | 2 | O | H |
| 252 | (4-methylphenol) | — | H | 2 | O | Cl |
| 253 | (N-methyl-4-methylaniline) | O | H | 3 | NH | MeO |
| 254 | (6-methyl-3,4-dihydroquinolin-2(1H)-one) | CH₂ | H | 3 | NH | F |

TABLE 2-continued

| Example | Ar¹ | X | R⁵ | n | Y | R⁷ |
|---|---|---|---|---|---|---|
| 255 | (7-methyl-2,3,4,5-tetrahydro-1H-1-benzazepin-2-one) | — | H | 2 | O | OH |
| 256 | (6-methyl-3,4-dihydroisoquinolin-1(2H)-one) | S | H | 4 | Nac | Me |

The binding data for certain compounds described above in the expressed cloned NMDA subtypes as well as MES data is shown below in Table 3.

TABLE 3

| Compound | Subunits (IC$_{50}$ ($\mu$M)) | | | MES ED$_{50}$ (mg/kg) |
|---|---|---|---|---|
|  | 1A/2A | 1A/2B | 1A/2C |  |
| Ex. 1 | >100 | 0.8 | >100 | 2 |
| Ex. 2 | 89 | 1.1 | >100 | 3 |
| Ex. 3 | 35 | 2.8 | >100 | 2 |
| Ex. 4 | >100 | 9 | >100 | — |
| Ex. 7 | >100 | 10 | >100 | — |
| Ex. 9 | >100 | 10 | >100 | — |
| Ex. 11 | >100 | 10 | >100 | — |
| Ex. 12 | >100 | 6 | >100 | — |
| Ex. 13 | 90 | 1.3 | >100 | 6 |
| Ex. 14 | >100 | 3 | >100 | — |
| Ex. 15 | 100 | 1.2 | >100 | 100 |
| Ex. 16 | 100 | 0.5 | >100 | 2.5 |
| Ex. 17 | 100 | 3 | >100 | — |
| Ex. 18 | 60 | 0.4 | >100 | 6 |
| Ex. 19 | >100 | 0.35 | — | 6 |
| Ex. 20 | 5.5 | 0.7 | >100 | — |
| Ex. 21 | 45 | 2.5 | >100 | — |
| Ex. 22 | 90 | 0.9 | >100 | 4 |
| Ex. 24 | 70 | 1 | 100 | 2 |
| Ex. 25 | 60 | 1 | 80 | 4 |
| Ex. 26 | >100 | 12 | >100 | — |
| Ex. 27 | >100 | 5 | >100 | 5 |
| Ex. 28 | 38 | 0.4 | >100 | 5 |
| Ex. 29 | >100 | 0.5 | >100 | — |
| Ex. 30 | 50 | 0.8 | 100 | 6 |
| Ex. 31 | 34 | 0.9 | 60 | 7.5 |
| Ex. 33 | >100 | 2 | >100 | 4 |
| Ex. 34 | >100 | 15 | >100 | — |
| Ex. 35 | >100 | 4 | >100 | — |
| Ex. 36 | 40 | 22 | >100 | — |
| Ex. 37 | 14 | 10 | >100 | — |
| Ex. 38 | 75 | 45 | >100 | 10 |
| Ex. 39 | >100 | 60 | >100 | — |
| Ex. 40 | 80 | 3 | 100 | 2.5 |
| Ex. 41 | 90 | 5.0 | >100 | — |
| Ex. 46 | >100 | 1.5 | >100 | — |
| Ex. 47 | 85 | 3 | >100 | 3.2 |
| Ex. 48 | >100 | 22 | >100 | — |
| Ex. 49 | >100 | 5 | >100 | — |
| Ex. 50 | 75 | 5 | >100 | — |
| Ex. 51 | 80 | 5 | >100 | — |
| Ex. 52 | 60 | 9.5 | >100 | — |
| Ex. 53 | 100 | 0.31 | >100 | 2.5 |
| Ex. 54 | 60 | 3.6 | >100 | — |
| Ex. 55 | 50 | 0.11 | >100 | 6 |
| Ex. 56 | 90 | 1.1 | >100 | — |
| Ex. 57 | 100 | 0.3 | >100 | 6.5 |
| Ex. 58 | 25 | 0.1 | >100 | 5.1 |
| Ex. 59 | 75 | 0.024 | >100 | 1 |
| Ex. 60 | >100 | 6 | >100 | — |
| Ex. 61 | 100 | 0.3 | >100 | 2.5 |
| Ex. 62 | 80 | 6 | >100 | — |
| Ex. 63 | 100 | 0.5 | >100 | 3 |
| Ex. 64 | >100 | 6 | >100 | — |
| Ex. 65 | 90 | 1.3 | >100 | 6 |
| Ex. 66 | >100 | 10 | >100 | — |
| Ex. 67 | >100 | 0.32 | >100 | 6 |
| Ex. 68 | >100 | 5 | >100 | — |
| Ex. 69 | 20 | 0.43 | >100 | — |
| Ex. 70 | >100 | 1 | >100 | 1.5 |
| Ex. 71C | >100 | 8 | >100 | — |
| Ex. 71A | >100 | 20 | >100 | — |
| Ex. 73 | 30 | 8 | 100 | 8 |
| Ex. 74 | 60 | 3 | >100 | 3.5 |
| Ex. 77 | 50 | 0.11 | >100 | 6 |
| Ex. 80 | 16 | 0.025 | 70 | — |
| Ex. 83 | >100 | 1.0 | >100 | 2 |
| Ex. 84 | >100 | 2.2 | >100 | — |
| Ex. 90 | >100 | 5 | >100 | 5 |
| Ex. 91 | >100 | 22 | >100 | — |
| Ex. 96 | >100 | 17 | >100 | 3.5 |
| Ex. 98 | 80 | 100 | 80 | |
| Ex. 99 | >300 | 0.03 | >300 | 2.0 |
| Ex. 101 | 55 | 0.05 | 240 | 3.0 |
| Ex. 102 | 60 | 0.02 | 290 | 3.0 |
| Ex. 103 | 95 | 1 | >300 | 3.0 |
| Ex. 104 | 50 | 0.2 | >300 | 3.0 |
| Ex. 106 | 90 | 0.02 | 260 | |
| Ex. 107 | 60 | 0.03 | 270 | |
| Ex. 108 | 62 | 0.25 | >300 | |
| Ex. 112 | 30 | 0.08 | 280 | 4.5 |
| Ex. 113 | 200 | 30 | 200 | |
| Ex. 115 | 75 | 0.03 | 220 | 0.7 |
| Ex. 116 | 70 | 4.5 | 150 | 3.0 |
| Ex. 120 | 55 | 0.02 | >300 | 2.0 |
| Ex. 121 | 110 | 0.05 | >300 | 2.5 |
| Ex. 122 | 55 | 0.18 | 280 | 5.0 |
| Ex. 123 | 50 | 0.07 | >300 | 3.0 |
| Ex. 125 | 75 | 3.3 | >300 | 15 |
| Ex. 127 | 70 | 5.0 | >300 | |
| Ex. 128 | 110 | 0.04 | >300 | 1.0 |
| Ex. 129 | 170 | 0.05 | 170 | 2.0 |
| Ex. 131 | 50 | 0.05 | >300 | 1.5 |
| Ex. 132 | 23 | 0.16 | 230 | 1.0 |
| Ex. 133 | 80 | 0.21 | 150 | 2.5 |
| Ex. 134 | 60 | 0.03 | 140 | 1.5 |

TABLE 3-continued

| Compound | Subunits ($IC_{50}$ ($\mu M$)) 1A/2A | 1A/2B | 1A/2C | MES $ED_{50}$ (mg/kg) |
|---|---|---|---|---|
| Ex. 139 | 70 | 0.25 | | 4.5 |
| Ex. 140 | 80 | 28 | | |
| Ex. 141 | 100 | 0.1 | 90 | |
| Ex. 143 | 190 | 0.4 | >300 | 0.5 |
| Ex. 144 | >300 | 1.6 | >300 | |
| Ex. 146 | 30 | 0.01 | 160 | 0.8 |
| Ex. 147 | 40 | 0.1 | 210 | 3.0 |
| Ex. 148 | 105 | 3.8 | 135 | |
| Ex. 149 | 50 | 0.04 | 140 | 2.0 |
| Ex. 150 | 100 | 0.02 | >300 | 3.0 |
| Ex. 151 | 52 | 0.02 | 100 | 2.5 |
| Ex. 152 | 90 | 0.04 | 200 | |
| Ex. 153 | 65 | 0.04 | 70 | |
| Ex. 154 | 250 | 0.02 | 230 | 1.5 |
| Ex. 155 | 170 | 0.03 | >300 | |
| Ex. 158 | 100 | 0.3 | 190 | |
| Ex. 159 | 130 | 0.5 | 140 | |
| Ex. 160 | 60 | 0.2 | 120 | |
| Ex. 161 | 85 | 0.04 | 170 | |
| Ex. 163 | 35 | 0.1 | >300 | |
| Ex. 164 | 100 | 0.12 | >300 | |
| Ex. 165 | 65 | 0.05 | 301 | 0.5 |
| Ex. 166 | 270 | 170 | >300 | 0.7 |
| Ex. 167 | 110 | 0.02 | 301 | 0.3 |
| Ex. 168 | >300 | 9.5 | >300 | 4.0 |
| Ex. 170 | 62 | 0.04 | 230 | 10 |
| Ex. 171 | 72 | 0.04 | 170 | 5.0 |
| Ex. 172 | 140 | 0.11 | 50 | |
| Ex. 174 | 35 | 0.03 | 45 | 5.0 |
| Ex. 175 | 48 | 0.02 | 70 | 8.0 |
| Ex. 176 | 25 | 0.03 | 50 | 7.5 |
| Ex. 177 | 35 | 0.1 | 210 | 5.0 |
| Ex. 181 | 110 | 1.0 | 140 | 6.0 |
| Ex. 182 | 43 | 1.0 | 210 | >20 |
| Ex. 189 | 7.0 | 0.1 | 130 | 7.0 |
| Ex. 191 | 25 | 0.1 | >300 | |
| Ex. 192 | >300 | 0.1 | >300 | |
| Ex. 193 | | 0.2 | >300 | |
| Ex. 194 | >300 | 0.06 | >300 | 2.5 |
| Ex. 195 | >300 | 0.07 | >300 | |

The data shows that 4-substituted piperidine analogs of this invention exhibit selectivity for 2B subtype receptors compared to 2A and 2C subtype receptors, and many of these compounds are active as anticonvulsants in the MES assay.

In vivo data is presented below. The compound of Example 1(4-benzyl-1-(2-phenoxyethyl)piperidine) was administered (2.5 mg/Kg i.v. bolus, 0.5 mg/ml solution) to rats immediately after MCA-0. The compound was then administered continuously at a rate of 1.75 mg/Kg for 22 hours. The results shown in table 4 and FIG. 1 show that the compound gave significant protection from ischemia.

TABLE 4

| Region in the Brain | Mean Infarct Volume in $mm^3$ Vehicle n = 13 | Drug n = 12 | % of Ischemia Protection |
|---|---|---|---|
| Cortex | 120.450 ± 20.166 | 50.450 ± 11.428 | 58%*(p = 0.0071) |
| Subcortex | 74.462 ± 7.481 | 67.400 ± 6.775 | 9.5%(p = 0.4936) |

*Statistically significant p ≦ 0.05
All numerical values of the parameters in the above table are expressed as the mean ± S.E.M.

Figure 2:
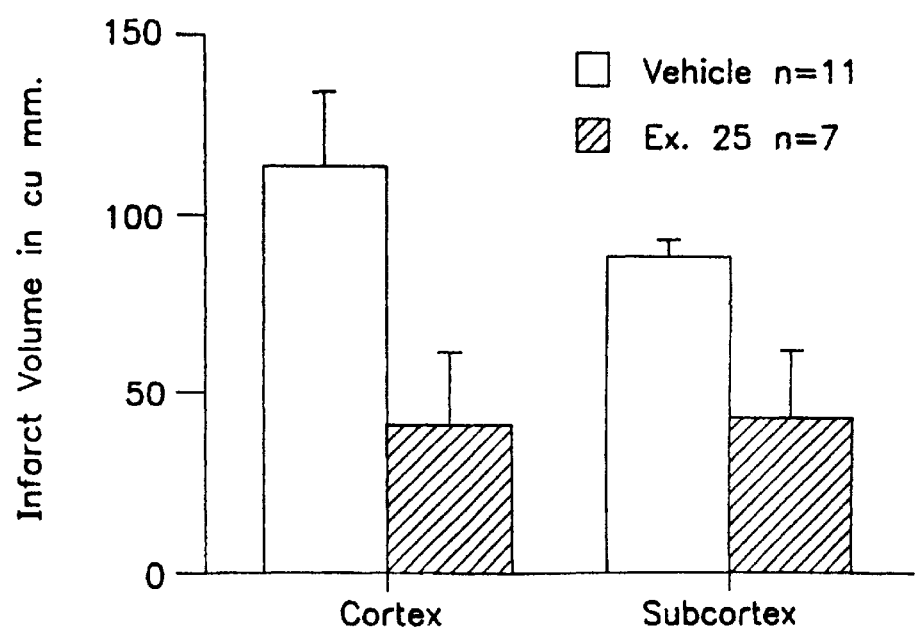

The compound of Example 25 (4-(4-chlorobenzyl)-1-(2-(4-fluorophenoxy)ethyl)piperidine hydrobromide was administered (10 mg/Kg i.v. bolus, 2.5 mg/ml solution) immediately after MCA-O. The results shown in Table 5 and FIG. 2 show that the compound gave significant protection from ischemia.

TABLE 5

| Region in the Brain | Mean Infarct Volume in $mm^3$ Vehicle n = 11 | Drug n = 7 | % of Ischemia Protection |
|---|---|---|---|
| Cortex | 114.936 ± 22.3 | 41.857 ± 19.984 | 64%*(p = 0.0381) |
| Subcortex | 81.564 ± 5675 | 43.343 ± 17.37 | 47%(p = .0320) |

*Statistically significant p ≦ 0.05
All numerical values of the parameters in the above table are expressed as the mean ± S.E.M.

Other variations and modifications of this invention will be obvious to those skilled in this art. This invention is not limited except as set forth in the following claims.

What is claimed is:

1. A compound represented by the formula:

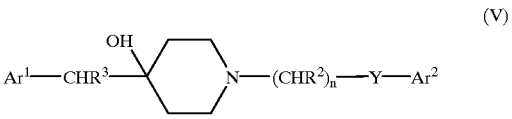

(V)

or a pharmaceutically acceptable salt thereof wherein:

$Ar^1$ and $Ar^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ and $R^3$ are independently hydrogen, hydroxy or a lower alkyl group having 1 to 6 carbon atoms;

n is 0, 1, 2, 3 or 4; and

Y is O, S, or is a single bond provided that $R^2$ cannot be hydroxy in a position alpha to $Ar^2$.

2. A compound represented by the formula:

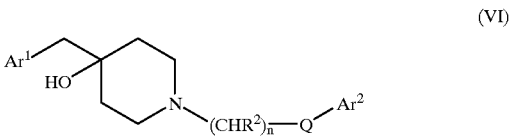

(VI)

or a pharmaceutically acceptable salt thereof wherein:

$Ar^1$ and $Ar^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ is independently hydrogen, hydroxy or a lower alkyl group having 1 to 6 carbon atoms;

n is 0, 1, 2, 3 or 4; and

Q is O, S, or is a single bond.

3. A compound represented by the formula:

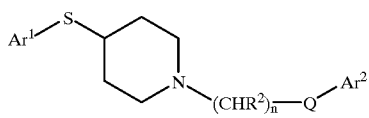

(VII)

or a pharmaceutically acceptable salt thereof, wherein:
Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each R$^2$ is independently hydrogen, hydroxy or a lower alkyl group having 1 to 6 carbon atoms;

n is 0, 1,2,3 or 4; and

Q is O, S, or is a single bond.

4. A compound represented by the formula:

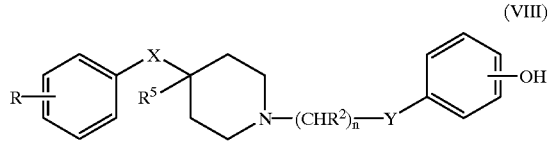

(VIII)

or a pharmaceutically acceptable salt thereof wherein:
R is hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each R$^2$ is independently hydrogen, hydroxy or a lower alkyl group having 1 to 6 carbon atoms;

n is 0, 1, 2, 3 or 4;

R$^5$ is hydroxy;

Y is O, S, or is a single bond; and

X is —(CHR$^3$)$_m$—, O, S or NR$^4$, wherein each R$^3$ is independently hydrogen, hydroxy or a lower alkyl group having 1 to 6 carbon atoms, R$^4$ is hydrogen or a lower alkyl group having 1 to 6 carbon atoms and m is 0, 1 or 2.

5. A pharmaceutical composition comprising:
(a) a compound represented by the formula:

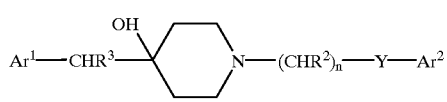

(V)

or a pharmaceutically acceptable salt thereof wherein:
Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each R$^2$ and R$^3$ are independently hydrogen, hydroxy or a lower alkyl group having 1 to 6 carbon atoms;

n is 0, 1, 2, 3 or 4; and

Y is O, S, or is a single bond provided that R$^2$ cannot be hydroxy in a position alpha to Ar$^2$; and (b) a pharmaceutically acceptable carrier.

6. A pharmaceutical composition comprising:
(a) a compound represented by the formula:

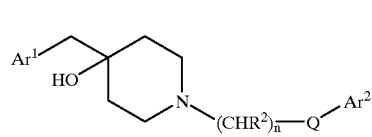

(VI)

or a pharmaceutically acceptable salt thereof wherein:
Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each 2 is independently hydrogen, hydroxy or a lower alkyl group having 1 to 6 carbon atoms;

n is 0, 1, 2, 3 or 4; and

Q is O, S, or is a single bond; and (b) a pharmaceutically acceptable carrier.

7. A pharmaceutical composition comprising:
(a) a compound represented by the formula:

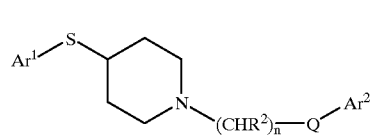

(VII)

or a pharmaceutically acceptable salt thereof, wherein:
Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each R$^2$ is independently hydrogen, hydroxy or a lower alkyl group having 1 to 6 carbon atoms;

n is 0, 1,2,3 or 4; and

Q is O, S, or is a single bond; and (b) a pharmaceutically acceptable carrier.

8. A pharmaceutical composition comprising;
(a) a compound represented by the formula:

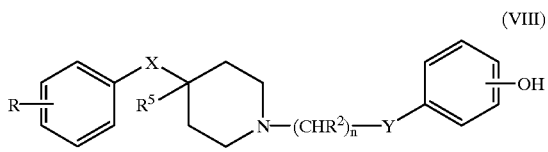

(VIII)

or a pharmaceutically acceptable salt thereof wherein:
R is hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;
each $R^2$ is independently hydrogen, hydroxy or a lower alkyl group having 1 to 6 carbon atoms;
n is 0, 1, 2, 3 or 4;
$R^5$ is hydroxy;
Y is O, S, or is a single bond; and
X is —$(CHR^3)_m$—, O, S or $NR^4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2; and
(b) a pharmaceutically acceptable carrier.

9. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

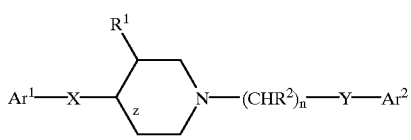

(I)

or a pharmaceutically acceptable salt thereof wherein
$Ar^1$ and $Ar^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;
z is a single or double bond;
X is —$(CHR^3)_m$—, O, S or $NR^4$, wherein $R^3$ is hydrogen, hydroxy or a lower alkyl group having 1 to 6 carbon atoms, $R^4$ is hydrogen or a lower alkyl group having 1 to 6 carbon atoms and m is 0, 1 or 2, provided that when z is a double bond then X is not O or $NR^4$;
$R^1$ is hydroxy;
each $R^2$ is independently hydrogen, hydroxy or a lower alkyl group having 1 to 6 carbon atoms;
n is 0, 1, 2, 3 or 4; and
Y is O, S, or is a single bond.

10. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

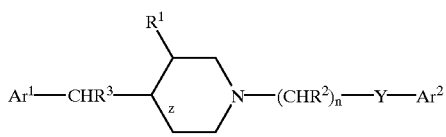

(II)

or a pharmaceutically acceptable salt thereof wherein:
$Ar^1$ and $Ar^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;
z is a single or double bond;
$R^1$ is hydroxy;
each $R^2$ is independently hydrogen, hydroxy or a lower alkyl group having 1 to 6 carbon atoms;
n is 0, 1, 2, 3 or 4; and
Y is O, S, or is a single bond.

11. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

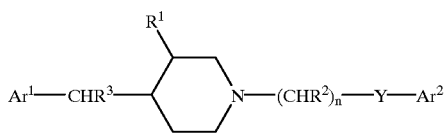

(III)

or a pharmaceutically acceptable salt thereof wherein;
$Ar^1$ and $Ar^2$ are aryl, either of which may be independently substituted by hydrogen, alkyl, hydroxy, halogen, nitro, cyano, carboxaldehyde, benzaldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;
$R^1$ is hydroxy;
$R^2$ and $R^3$ are independently hydrogen, hydroxy or a lower alkyl group having 1 to 6 carbon atoms;

n is 0, 1, 2, 3 or 4; and

Y is O, S, or is a single bond.

12. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

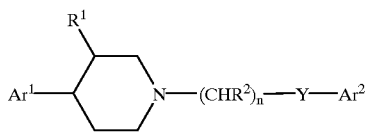

(IV)

or a pharmaceutically acceptable salt thereof, wherein:

Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

R$^1$ is hydroxy;

each R$^2$ is independently hydrogen, hydroxy or a lower alkyl group having 1 to 6 carbon atoms;

n is 1, 2, 3 or 4; and

Y is O, S, or is a single bond.

13. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

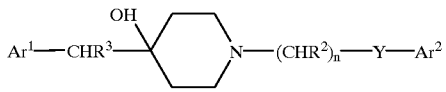

(V)

or a pharmaceutically acceptable salt thereof, wherein:

Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each R$^2$ and R$^3$ are independently hydrogen, hydroxy or a lower alkyl group having 1 to 6 carbon atoms;

n is 0, 1, 2, 3 or 4; and

Y is O, S, or is a single bond.

14. The method of claim 13, wherein said disorder is selected from the group consisting of stroke, cerebral ischemia, centeral nervous system trauma, hypoglycemia, psychosis, anxiety, convulsions, chronic pain, neurodegenerative, migraine headache, opioid tolerance, opioid withdrawal, glaucoma, CMV retinitis, Parkinson's disease, urinary incontinence, and aminoglycoside antibiotics-induced hearing loss.

15. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

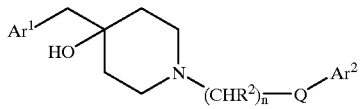

(VI)

or a pharmaceutically acceptable salt thereof wherein:

Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each R$^2$ is independently hydrogen, hydroxy or a lower alkyl group having 1 to 6 carbon atoms;

n is 0, 1, 2, 3 or 4; and

Q is O, S, or is a single bond.

16. The method of claim 15, wherein said disorder is selected from the group consisting of stroke, cerebral ischemia, centeral nervous system trauma, hypoglycemia, psychosis, anxiety, convulsions, chronic pain, neurodegenerative, migraine headache, opioid tolerance, opioid withdrawal, glaucoma, CMV retinitis, Parkinson's disease, urinary incontinence, and aminoglycoside antibiotics-induced hearing loss.

17. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

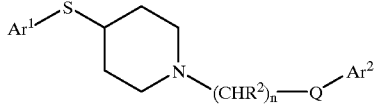

(VII)

or a pharmaceutically acceptable salt thereof, wherein:

Ar$^1$ and Ar$^2$ are aryl, either of which may be independently substituted by hydrogen, alkyl, hydroxy, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower aikyl amino group or a lower alkoxy group;

each $R^2$ is independently hydrogen, hydroxy or a lower alkyl group having 1 to 6 carbon atoms;

n is 0, 1,2,3 or 4; and

Q is O, S, or is a single bond.

18. The method of claim 17, wherein said disorder is selected from the group consisting of stroke, cerebral ischemia, centeral nervous system trauma, hypoglycemia, psychosis, anxiety, convulsions, chronic pain, neurodegenerative, migraine headache, opioid tolerance, opioid withdrawal, glaucoma, CMV retinitis, Parkinson's disease, urinary incontinence, and aminoglycoside antibiotics-induced hearing loss.

19. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

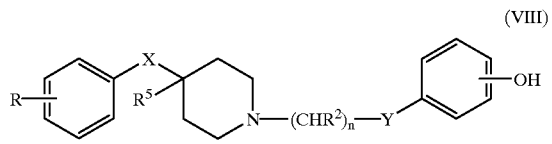

(VIII)

or a pharmaceutically acceptable salt thereof wherein:
R is hydrogen, alkyl, hydroxy, halogen, nitro, cyano, carboxaldehyde, aldehyde oxine, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ is independently hydrogen, hydroxy or a lower alkyl group having 1 to 6 carbon atoms;

n is 0, 1, 2, 3 or 4;

$R^5$ is hydroxy;

Y is O, S, or is a single bond; and

X is —$(CHR^3)_m$—, O, S or $NR^4$, wherein each $R^3$ is independently hydrogen, hydroxy or a lower alkyl group having 1 to 6 carbon atoms, $R^4$ is hydrogen or a lower alkyl group having 1 to 6 carbon atoms and m is 0, 1 or 2.

20. The method of claim 19, wherein said disorder is selected from the group consisting of stroke, cerebral ischemia, central nervous system trauma, hypoglycemia, psychosis, anxiety, convulsions, chronic pain, neurodegenerative, migraine headache, opioid tolerance, opioid withdrawal, glaucoma, CMV retinitis, Parkinson's disease, urinary incontinence, and aminoglycoside antibiotics-induced hearing loss.

21. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-methyl-D-aspartate receptor subtype antagonist compound represented by the formula:

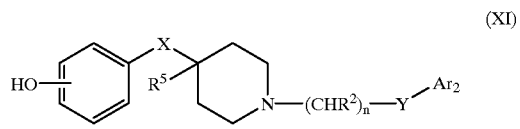

(XI)

or a pharmaceutically acceptable salt thereof wherein:
$Ar^2$ is aryl which may be independently substituted by hydrogen, alkyl, hydroxy, halogen, nitro, cyano, carboxaldehyde, aldehyde oxiine, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

each $R^2$ is independently hydrogen, hydroxy or a lower alkyl group having 1 to 6 carbon atoms;

n is 0, 1, 2, 3 or 4;

X is —$(CHR^3)_m$—, O, S or $NR^4$, wherein each $R^3$ is independently hydrogen, hydroxy or a lower alkyl group having 1 to 6 carbon atoms, Rd is hydrogen or a lower alkyl group having 1 to 6 carbon atoms and m is 0, 1 or 2;

$R^5$ is hydroxy; and

Y is O, S, or is a single bond.

22. A method for treating disorders responsive to the selective blockade of N-methyl-D-aspartate receptor subtypes in an animal suffering thereof, wherein said disorder is selected from the group consisting of migraine headache, opioid tolerance, opioid withdrawal, glaucoma, CMV retinitis, Parkinson's disease, urinary incontinence, and aminoglycoside antibiotics-induced hearing loss, which comprises administering in unit dosage form of at least one selective N-inethyl-D-aspartate receptor subtype antagonist compound selected from the group consisting of:

4-(4-Chlorophenyl)-4-hydroxy-1-(2-phenoxyethyl) piperidine;

4-(4-Chlorophenyl)-4-hydroxy-1-(3-phenoxypropyl) piperidine;

3-Hydroxy-1-(2-phenoxyethyl)-4-(3-trifluoromethylphenyl)-piperidine;

3-Hydroxy-1-(3-phenoxypropyl)-4-(3-trifluoromethyl phenyl)-piperidine;

4-(4-Chlorophenyl)-4-hydroxyl-1-(3-phenylpropyl) piperidine;

4-(4-Chlorophenyl)-4-hydroxy-1-(4-phenylbutyl) piperidine;

3-Hydroxy-1-(4-phenylbutyl)-4-(3-trifluoromethylphenyl)piperidine;

4-Benzyl-4-hydroxy-1-(2-phenylethyl)piperidine;

1,4-Dibenzyl-4-hydroxypiperidine;

1-Benzyl-4-(4-fluorobenzyl)-4-hydroxypiperidine;

4-(4-Fluorobenzyl)-1-[2-(4-fluorophenyl)ethyl]-4-hydroxy piperidine;

3-Hydroxy-4-(3-trifluoromethylphenyl)-1-[3-(3-aminophenoxy)propyl]piperidine;

3-Hydroxy-4-(4-fluorophenyl)-1-[3-(3-amino-1-naphthyloxy)propyl]piperidine;

4-(4-Fluorobenzyl)-4-hydroxy-1-(2-(4-hydroxyphenoxy)ethyl)piperidine;

4-Behzyl-4-hydroxy-1-(2-(4-hydroxyphenoxy)ethyl) piperidine; and a pharmaceutically acceptable salt of any thereof.

* * * * *

UNITED STATES PATENT AND TRADEMARK OFFICE
CERTIFICATE OF CORRECTION

PATENT NO.   : 6,124,323
DATED        : September 26, 2000
INVENTOR(S)  : Christopher F. Bigge et al.

It is certified that error appears in the above-identified patent and that said Letters Patent is hereby corrected as shown below:

Column 3,
Line 29, "their" should read -- there --.

Column 4,
Line 26, "a" should read -- $\alpha$ --.

Column 5,
Line 61, "Ar(CH$_2$)1-4" should read -- Ar(CH$_2$)$_{1-4'}$ --.

Column 9,
Line 65, "al," should read -- al., --; and
Line 66, "al," (both occurrences) should read -- al., --.

Column 11,
Line 26, "phenoxanthiinyl," should read -- phenoxanthenyl --.

Column 12,
Line 66, "NR$_4$, should read -- NR$^4$, --.

Column 13,
Line 4, "NR$_4$;" should read -- NR$^4$, --; and
Line 50, "NR$_4$" should read -- NR$^4$ --.

Column 14,
Line 37, "NR$_4$" should read -- NR$^4$ --; and
Line 56, "NR$_4$" should read -- NR$^4$ --.

Column 15,
Line 6, "NR$_4$" should read -- NR$^4$ --; and
Line 65, "NR$_4$," should read -- NR$^4$, --.

Column 16,
Line 3, "indepenently" should read -- independently --; and
Line 30, "NR$_4$," should read -- NR$^4$, --.

Column 21,
Line 21, "(3,4-bisacet amidophenoxy)" should read -- (3,4-bisacetamidophenoxy) --.

Column 28,
Line 39, "toleranfce" should read -- tolerance --.

UNITED STATES PATENT AND TRADEMARK OFFICE
CERTIFICATE OF CORRECTION

PATENT NO. : 6,124,323
DATED : September 26, 2000
INVENTOR(S) : Christopher F. Bigge et al.

It is certified that error appears in the above-identified patent and that said Letters Patent is hereby corrected as shown below:

Column 42,
Line 2, "was" (2nd occurrence) should be deleted.

Column 46,
Line 17, "and" should read -- an --.

Column 48,
Line 25, "was" should be deleted.

Column 50,
Line 60, "2." should read -- 2% --.

Column 51,
Line 42, "J. = 8" should read -- $J_1$ = 8.1 --; and
Line 43, "1" should be deleted.

Column 61,
Line 20, "7,47" should read -- 7.47 --.

Column 63,
Line 29, "zoles" should read -- zole --.

Column 69,
Line 17, "((, 4M)," should read -- (m, 4M), --.

Column 72,
Line 60, "flitrate" should read -- filtrate --.

Column 73,
Line 60, "4-chlorobenzylpiperidne" should read -- 4-chlorobenzylpiperidine --.

Column 75,
Line 2, "was" should read -- were --; and
Line 37, "obtained 4:0g" should read -- obtained, 4.0g --.

Column 77,
Line 46, "as ectracted" should read -- was extracted --; and
Line 49, "(960)" should read -- (96%) --.

UNITED STATES PATENT AND TRADEMARK OFFICE
CERTIFICATE OF CORRECTION

PATENT NO.  : 6,124,323
DATED       : September 26, 2000
INVENTOR(S) : Christopher F. Bigge et al.

It is certified that error appears in the above-identified patent and that said Letters Patent is hereby corrected as shown below:

Column 80,
Line 58, "piperidne" should read -- piperidine --.

Column 82,
Line 1, "piperidne" should read -- piperidine --.

Column 83,
Line 23, "101" should read -- 10% --; and
Line 26, "10." should read -- 10% --.

Column 86,
Line 3, "white-off" should read -- off-white --.

Column 88,
Line 67, "dihydrochloride" should read -- dihydrochloride. --

Column 89,
Line 31, "phenylpiperidne" should read -- phenylpiperidine --; and
Line 60, "phenylpiperidne" should read -- phenylpiperidine --.

Column 91,
Line 35, "white-off" should read -- off-white --.

Column 92,
Line 27, "anid" should read -- and --.

Column 94,
Line 26, "$C_{21}H, 25C1F_3NO:$" should read -- $C_{21}H_{25}C1F_3NO:$ --.

Column 97,
Line 28, "Kugelrhor," should read -- Kugelrohr, --.

Column 99,
Line 60, "white-off" should read -- off-white --

Column 102,
Line 16, "white-off" should read -- off-white --.

Column 103,
Line 38, "flitrate" should read -- filtrate --.

UNITED STATES PATENT AND TRADEMARK OFFICE
CERTIFICATE OF CORRECTION

PATENT NO. : 6,124,323
DATED : September 26, 2000
INVENTOR(S) : Christopher F. Bigge et al.

It is certified that error appears in the above-identified patent and that said Letters Patent is hereby corrected as shown below:

Column 105,
Line 47, "white-off" should read -- off-white --.

Column 106,
Line 3, "white-off" should read -- off-white --;
Line 28, "white-off" should read -- off-white --; and
Line 50, "$K_2O_3$" should read -- $K_2CO_3$ --.

Column 107,
Line 47, "white-off" should read -- off-white --.

Column 108,
Line 47, "((m," should read -- (m, --; and
Line 48, "J,3H)," should read -- s, 3H), --.

Column 111,
Line 17, "stannouschloride" should read -- stannous chloride --.

Column 117,
Column 59, "(3-acetarmido" should read -- 3-acetamido --.

Column 119,
Line 46, "$CH_{25}H_{29}O_2$:" should read -- $CH_{25}H_{29}NO_2$: --.

Column 121,
Line 15, "(H,d,J=632.2)," should read -- (1H,d,J=2.2), --; and
Line 27, "seorated." should read -- separated. --

Column 122,
Line 16, "was" should read -- were --.

Column 123,
Line 6, "after" should read -- after being --; and
Line 25, "$c_{22}$" should read -- $C_{22}$ --.

Column 144,
Line 33, "2" should read -- $R^2$ --.

UNITED STATES PATENT AND TRADEMARK OFFICE
CERTIFICATE OF CORRECTION

PATENT NO. : 6,124,323
DATED : September 26, 2000
INVENTOR(S) : Christopher F. Bigge et al.

It is certified that error appears in the above-identified patent and that said Letters Patent is hereby corrected as shown below:

Column 145,
Line 52, "oxine," should read -- oxime, --.

Column 148,
Line 1, "centeral" should read -- central --; and
Line 3, "neurodegenerative," should read -- neurodegenerative disorders, --.

Column 149,
Line 14, "neurodegenerative," should read -- neurodegenerative disorders, --;
Line 42, "oxine," should read -- oxime, --; and
Line 64, "neurodegenerative," should read -- neurodegenerative disorders, --.

Column 150,
Line 25, "oxiine," should read -- oxime, --.

Column 152,
Line 5, "4-Behzyl" should read -- 4-Benzyl --.

Signed and Sealed this

Twenty-second Day of January, 2002

Attest:

JAMES E. ROGAN
*Director of the United States Patent and Trademark Office*

*Attesting Officer*